US012516373B2

(12) United States Patent

Askary et al.

(10) Patent No.: US 12,516,373 B2

(45) Date of Patent: *Jan. 6, 2026

(54) IN SITU READOUT OF DNA BARCODES

(71) Applicant: California Institute of Technology, Pasadena, CA (US)

(72) Inventors: Amjad Askary, Pasadena, CA (US); Michael B. Elowitz, Los Angeles, CA (US); Mark W. Budde, Arcadia, CA (US); Carlos Lois, South Pasadena, CA (US); Luis Sanchez Guardado, Pasadena, CA (US); Long Cai, Pasadena, CA (US); James Linton, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 662 days.

This patent is subject to a terminal disclaimer.

(21) Appl. No.: 17/817,516

(22) Filed: Aug. 4, 2022

(65) Prior Publication Data

US 2022/0396833 A1 Dec. 15, 2022

Related U.S. Application Data

(63) Continuation of application No. 16/701,087, filed on Dec. 2, 2019, now Pat. No. 11,421,273.

(60) Provisional application No. 62/936,307, filed on Nov. 15, 2019, provisional application No. 62/774,754, filed on Dec. 3, 2018.

(51) Int. Cl.

*C12Q 1/6874* (2018.01)
*C12Q 1/6818* (2018.01)
*C12Q 1/6876* (2018.01)
*G01N 1/30* (2006.01)

(52) U.S. Cl.

CPC ......... *C12Q 1/6874* (2013.01); *C12Q 1/6818* (2013.01); *C12Q 1/6876* (2013.01); *G01N 1/30* (2013.01)

(58) Field of Classification Search

CPC ................ C12Q 1/6874; C12Q 1/6818; C12Q 1/6876; C12Q 1/6841; G01N 1/30

See application file for complete search history.

(56) References Cited

U.S. PATENT DOCUMENTS 11,421,273 B2 * 8/2022 Askary .................... G01N 1/30
2012/0190835 A1 * 7/2012 Pierce .................... C12Q 1/682 536/23.1
2014/0073520 A1 3/2014 Cai et al.
2015/0148239 A1 5/2015 Peter et al.
2015/0167003 A1 * 6/2015 Naldini .................. A61P 31/00 435/325
2015/0267251 A1 9/2015 Cai et al.
2016/0289740 A1 10/2016 Fu et al.
2019/0094115 A1 3/2019 Bhakdi

FOREIGN PATENT DOCUMENTS

WO WO2016/007063 1/2016
WO WO2017/044893 3/2017
WO WO2018/218150 11/2018

OTHER PUBLICATIONS

Alemany et al., "Whole-organism clone tracing using single-cell sequencing, "Nature 2018, 556, 108-112.
Askary et al., "In situ readout of DNA barcodes and single base edits facilitated by in vitro transcription," Nature Biotechnology 2020, 38(1), 66-75.
Baker et al., "Transneuronal Regulation of Tyrosine Hydroxylase Expression in Olfactory Bulb of Mouse and Rat," The Journal of Neuroscience 1983, 3(1), 69-78.
Bhang et al., "Studying clonal dynamics in response to cancer therapy using high complexity barcoding," Nature Medicine 2015, 21(5), 440-448.
Biddy et al., "Single-cell mapping of lineage and identity in direct reprogramming," Nature 2018, 564(7735), 219-224.
Boutros et al., "Microscopy-Based High-Content Screening," Cell 2015, 163, 1314-1325.
Cai et al., "Improved tools for the Brainbow toolbox," Nature Methods 2013, 10(6), 540-547.
Chan et al., "Molecular recording of mammalian embryogenesis," bioRxiv 2018, 384925, in 32 pages. https://doi.org/10.1101/384925.
Chen et al., "A Barcoding Strategy Enabling Higher-Throughput Library Screening by Microscopy," ACS Snyth. Biol. 2015, 4, 1205-1216.
Chen et al., "Spatially resolved, highly multiplexed RNA profiling in single cells," Science 2015, 348(6233), aaa6090, 1-36.
Chen et al., "Efficient in situ barcode sequencing using padlock probe-based BaristaSeq," Nucleic Acids Research 2018, 46(4), e22, 1-10.
Choi et al., "Programmable in situ amplification for multiplexed imaging of mRNA expression," Nat Biotechnol. 2010, 28(11), 1208-1212.
Choi et al., "Mapping a multiplexed zoo of mRNA expression," Development 2016, 143, 3632-3637.
Choi et al., "Third-generation in situ hybridization chain reaction: multiplexed, quantitative, sensitive, versatile, robust," Development 2018, 145, 1-10.
Cong et al., "Multiplex Genome Engineering Using CRISPR/Cas Systems," Science 2013, 339(6121), 819-823.
Ding et al., "Constitutive splicing and economies of scale in gene expression," Nat. Struct. Mol. Biol. 2019, 26, 424-432.
Dixit et al., "Perturb-Seq: Dissecting Molecular Circuits with Scalable Single-Cell RNA Profiling of Pooled Genetic Screens," Cell 2016, 167, 1853-1866.

(Continued)

*Primary Examiner* — Cynthia B Wilder

(57) ABSTRACT

Disclosed herein include systems, methods, compositions, and kits for in situ readout of barcodes, such as DNA barcodes. Barcode constructs containing a promoter (e.g., a phage promoter) that is inactive in live cells can be integrated in the genomes of cells. Cells can be fixed, and phage RNA polymerase can be used for transcription of the barcode to RNA transcripts. The RNA transcripts can be detected using, for example, fluorescent imaging and used to determine barcode sequences.

20 Claims, 35 Drawing Sheets

(33 of 35 Drawing Sheet(s) Filed in Color)

Specification includes a Sequence Listing.

(56) References Cited

OTHER PUBLICATIONS

Doench et al., "Optimized sgRNA design to maximize activity and minimize off-target effects of CRISPR-Cas9," Nat Biotechnol. 2016, 34(2), 184-191.
Emanuel et al., "High-throughput, image-based screening of pooled genetic variant libraries," Nat Methods. 2017, 14(12), 1159-1162.
Eng et al., "Transcriptome-scale super-resolved imaging in tissues by RNA seqFISH+," Nature 2019, 568(7751), 235-239.
Extended European Search Report dated Aug. 10, 2022 in European Application No. 19893008.3.
Faedo et al., "Developmental expression of the T-box transcription factor T-bet/Tbx21 during mouse embryogenesis," Mechanisms of Development 2002, 116, 157-160.
Farzadfard et al., "Single-Nucleotide-Resolution Computing and Memory in Living Cells, " bioRxiv 2018, 263657, in 51 pages. https://doi.org/10.1101/263657.
Farzadfard et al., "Emerging applications for DNA writers and molecular recorders," Science 2018, 361, 870-875.
Feldman et al., "Pooled optical screens in human cells," bioRxiv 2018, 383943, in 23 pages. https://doi.org/10.1101/383943.
Freida et al., "Synthetic recording and in situ readout of lineage information in single cells," Nature 2017, 541, 107-111.
Gaudelli et al., "Programmable base editing of A·T to G·C in genomic DNA without DNA cleavage," Nature 2017, 551(7681), 464-471.
Gehrke et al., "An APOBEC3A-Cas9 base editor with minimized bystander and off-target activities," Nat Biotechnol. 2018, 36(10), 977-982.
Hamburger et al., "A Series of Normal Stages in the Development of the Chick Embryo," J. Morphol. 1951, 88, 49-92.
International Search Report and Written Opinion dated Mar. 20, 2020 in PCT Patent Application No. PCT/US2019/064071.
Kalhor et al., "Rapidly evolving homing CRISPR barcodes," Nat Methods. 2017, 14(2), 195-200.
Kalhor et al., "Developmental barcoding of whole mouse via homing CRISPR," Science 2018, 361(6405), 1-27.
Ke et al., "In situ sequencing for RNA analysis in preserved tissue and cells," Nature Methods 2013, 10(9), 857-860.
Kebschull et al., "High-Throughput Mapping of Single-Neuron Projections by Sequencing of Barcoded RNA," Neuron 2016, 91, 975-987.
Kebschull et al., "Cellular barcoding: lineage tracing, screening and beyond," Nature Methods 2018, 15, 871-879.
Komor et al., "Improved base excision repair inhibition and bacteriophage Mu Gam protein yields C:G-to-T:A base editors with higher efficiency and product purity," Sci. Adv. 2017, 3(eaao4774), 1-9.
Komor et al., "Programmable editing of a target base in genomic DNA without double-stranded DNA cleavage," Nature 2016, 533(7603), 420-424.
Lee et al., "Fluorescent in situ sequencing (FISSEQ) of RNA for gene expression profiling in intact cells and tissues," Nat Protoc 2015, 10, 442-458.
Lee et al., "Highly multiplexed subcellular RNA sequencing in situ, " Science 2014, 343(6177), 1360-1363.
Levesque et al., "Visualizing SNVs to quantify allele-specific expression in single cells," Nat Methods. 2013, 10(9), 865-867.
Li et al., "Base editing with a Cpf1—cytidine deaminase fusion," Nature Biotechnology 2018, 36(4), 324- 327.
Li et al., "Aligning sequence reads, clone sequences and assembly contigs with BWA-MEM," arXiv [q-bio.GN] 2013, 1-3.
Listgarten et al., "Prediction of off-target activities for the end-to-end design of CRISPR guide RNAs," Nature Biomedical Engineering 2, 38-47.
Livet et al., "Transgenic strategies for combinatorial expression of fluorescent proteins in the nervous system," Nature 2007, 450, 56-62.
Lois et al., "Germline Transmission and Tissue-Specific Expression of Transgenes Delivered by Lentiviral Vectors," Science 2002, 295(5556), 868-872.
Lois et al., "Long-Distance Neuronal Migration in the Adult Mammalian Brain," Science 1994, 264(5162), 1145-1148.
Lu et al., "Tracking single hematopoietic stem cells in vivo using high-throughput sequencing in conjunction with viral genetic barcoding," Nature Biotechnology 2011, 29(10), 928-933.
Marras et al., "High-fidelity amplified FISH for the detection and allelic discrimination of single mRNA molecules," PNAS 2019, 116(28), 13921-13926.
Mathews et al., "Expanded Sequence Dependence of Thermodynamic Parameters Improves Prediction of RNA Secondary Structure," J. Mol. Biol. 1999, 288, 911-940.
Mckenna et al., "Whole organism lineage tracing by combinatorial and cumulative genome editing," Science 2016, 353(6298), aaf7907, 1-27.
Mitra et al., "Fluorescent in situ sequencing on polymerase colonies," Analytical Biochemistry 2003, 320, 55-65.
Moffitt et al., "High-throughput single-cell gene-expression profiling with multiplexed error-robust fluorescence in situ hybridization," PNAS 2016, 113(39), 11046-11051.
Naik et al., "Diverse and heritable lineage imprinting of early haematopoietic progenitors," Nature 2013, 496, 229-232.
Non-Final Office Action dated Sep. 16, 2021 in U.S. Appl. No. 16/701,087.
Notice of Allowance dated Apr. 14, 2022 in U.S. Appl. No. 16/701,087.
Pei et al., "Polylox barcoding reveals haematopoietic stem cell fates realized in vivo," Nature 2017, 548(7668), 456-460.
Press et al., "Numerical Recipes in C: The Art of Scientific Computing," Cambridge University Press 1992, in 1,018 pages.
Raj et al., "Imaging individual mRNA molecules using multiple singly labeled probes," Nature Methods 2008, 5(10), 877-879.
Raj et al., "Simultaneous single-cell profiling of lineages and cell types in the vertebrate brain," Nat Biotechnol. 2018, 36(5), 442-450.
Rees et al., "Base editing: precision chemistry on the genome and transcriptome of living cells," Nature Reviews Genetics 2018, 19, 770-788.
Rouhanifard et al., "ClampFISH detects individual nucleic-acid molecules using click chemistry based amplification," Nat Biotechnol. 2019, 1-17.
Santalucia, "A unified view of polymer, dumbbell, and oligonucleotide DNA nearest-neighbor thermodynamics," Proc. Natl. Acad. Sci. USA 1998, 95, 1460-1465.
Satija et al., "Spatial reconstruction of single-cell gene expression," Nat Biotechnol. 2015, 33(5), 495-502.
Schindelin et al., "Fiji: an open-source platform for biological-image analysis," Nature Methods 2012, 9, 676-682.
Shah et al., "Single-molecule RNA detection at depth by hybridization chain reaction and tissue hydrogel embedding and clearing," Development 2016, 143, 2862-2867.
Shah et al., "seqFISH Accurately Detects Transcripts in Single Cells and Reveals Robust Spatial Organization in the Hippocampus," Neuron 2017, 94, 752-758.
Shah et al., "Dynamics and Spatial Genomics of the Nascent Transcriptome by Intron seqFISH," Cell 2018, 174, 363-376.
Sousa et al., "T7 RNA Polymerase," Progress in Nucleic Acid Research and Molecular Biology 2003, 73, 1-41.
Spanjaard et al., "Simultaneous lineage tracing and cell-type identification using CRISPR/Cas9-induced genetic scars," Nat Biotechnol. 2018, 36(5), 469-473,.
Sternberg et al., "Exquisite Sequence Selectivity with Small Conditional RNAs, "Nano Lett. 2014, 14, 4568-4572.
Symmons et al., "Allele-specific RNA imaging shows that allelic imbalances can arise in tissues through transcriptional bursting," bioRxiv 2018, 386359, in 49 pages. https://doi.org/10.1101/386359.
Tang et al., "Rewritable multi-event analog recording in bacterial and mammalian cells," Science 2018, 360(6385), 1-23.
Vieregg et al., "Selective Nucleic Acid Capture with Shielded Covalent Probes," J. Am. Chem. Soc. 2013, 135, 9691-9699.

(56) References Cited

OTHER PUBLICATIONS

Walsh et al., "Widespread Dispersion of Neuronal Clones Across Functional Regions of the Cerebral Cortex," Science 1992, 255(5043), 434-440.
Wang et al., "Three-dimensional intact-tissue sequencing of single-cell transcriptional states," Science 2018, 1-18.
Weinreb et al., "Lineage tracing on transcriptional landscapes links state to fate during differentiation," bioRxiv 2018, 467886, in 40 pages. https://doi.org/10.1101/467886.
Weistein et al., "DNA microscopy: Optics-free spatio-genetic imaging by a stand-alone chemical reaction," bioRxiv 2018, 471219, in 41 pages. https://doi.org/10.1101/471219.
Wu et al., "Continuously Tunable Nucleic Acid Hybridization Probes," Nat Methods 2015, 12(12), 1191-1196.
Zheng et al., "Massively parallel digital transcriptional profiling of single cells," Nature Communications 2017, 8(14049), 1-12.

* cited by examiner

Polymerase
Promoter
T7
SP6
T3
zBC CFP DAPI

"Z3" construct
barcode 3
barcode 2
barcode 1
T3 T7 SP6

Possible
Interactions
(schematic)
probability of detection
P(BC$_i$)
P(BC$_i$| BC$_j$)
P(BC1)
P(BC1|BC2)
P(BC1|BC3)
P(BC2)
P(BC2|BC1)
P(BC2|BC3)
P(BC3)
P(BC3|BC1)
P(BC3|BC2)

% cells with no active site
Number of barcodes

FIG. 5A
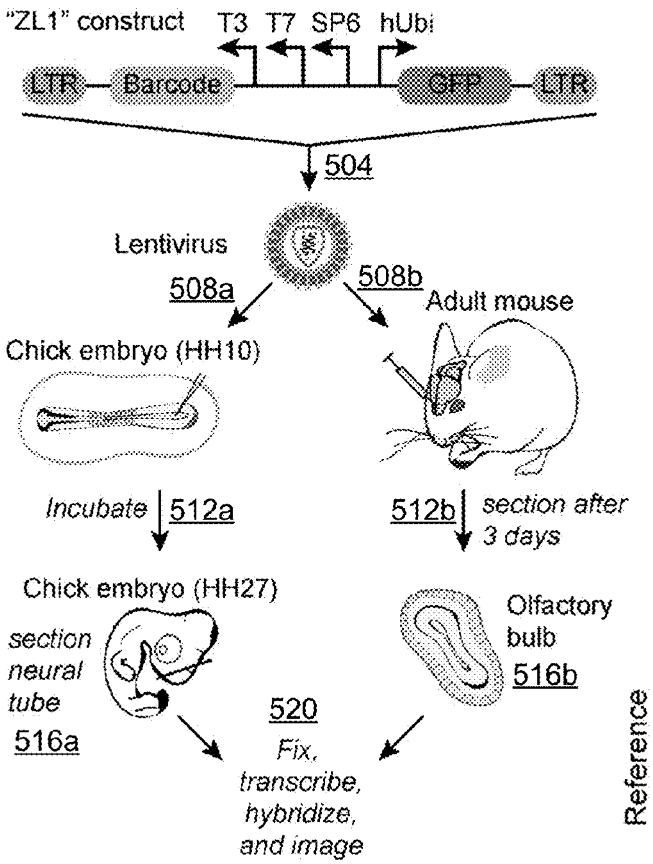
FIG. 5C
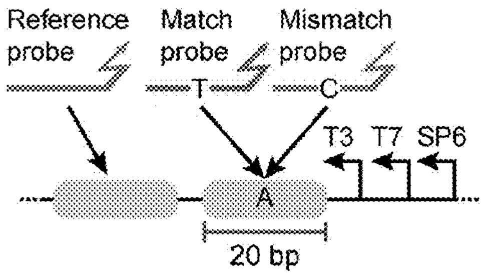
FIG. 5D
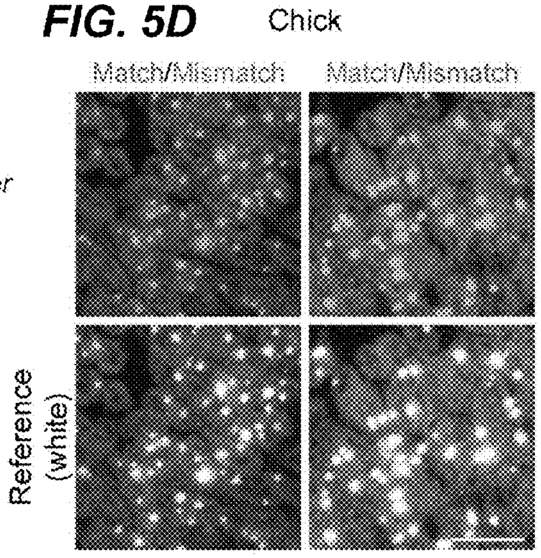
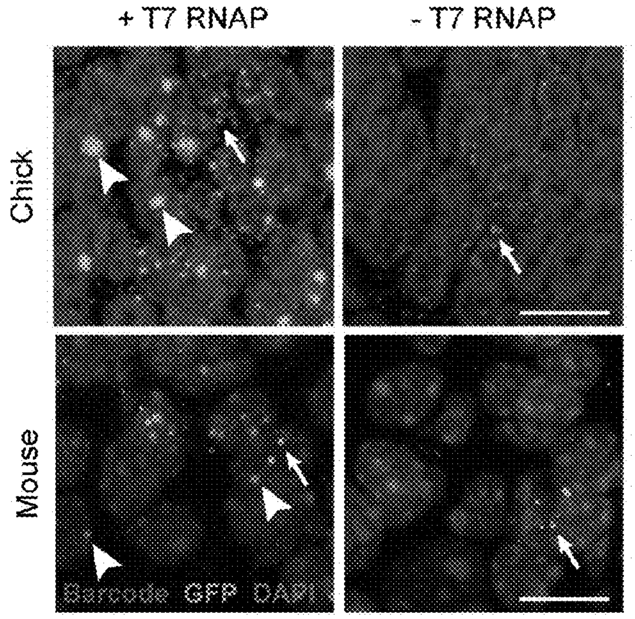
FIG. 5B
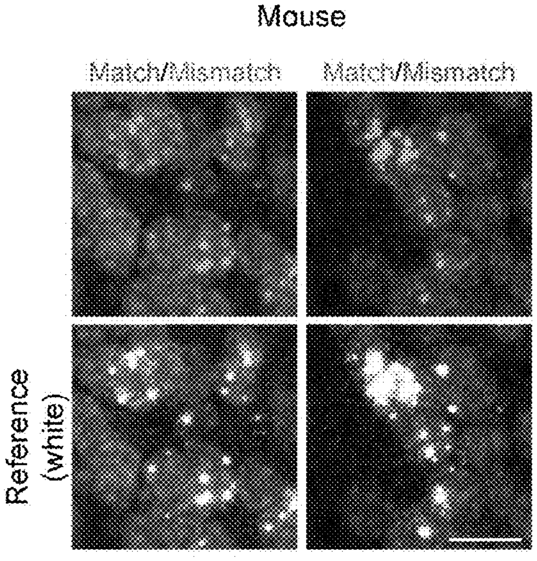
FIG. 5E Distinct barcode combinations are labeled in arbitrary colors; no relation to colors in C.

Detection with HCR

Design 2: frequency of classification change upon bootstrap resampling (%)

SEQUENCE LISTING

```
Sequence total quantity: 304
SEQ ID NO: 1           moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 1
caggacaacg cccacacacc                                              20

SEQ ID NO: 2           moltype = DNA  length = 916
FEATURE                Location/Qualifiers
misc_feature           1..916
                       note = Synthetic Polynucleotide
source                 1..916
                       mol_type = other DNA
                       organism = synthetic construct
SEQUENCE: 2
taacaggaaa cagctatgac gggcccccta ggtaagcagt atcttcgaca gcttgtctct  60
ccagatgctc ttgggccatc ttccacatcg tccgtagcag ccttggcaat ttgccatcac  120
tggcaaatac acataaatcc aatgaatacg gttaccacca tcacattacc atgcaggtac  180
acagcaagaa ttgacgttgg catatcacat ggtgtaataa ccccacttgt gaaacaaccc  240
agaataaggt acaaggcgga aatgtcgtca ttctaaaata aaaggcatgg ccaggaattt  300
gtctaatacc gggaacttaa attcagcttg aacaccagtc gcaaaaaatt caaagaaagt  360
gattcaggtt cgggttcgtg gattggaaca gcttcttttg tttcagtgat gagagaatcc  420
tcctgtcact cgagaaagaa tcaaagaggc caacaacgca gaacaggaaa cagctatgac  480
gggcccccta ggtaagcagt atcttcgaca gcttgtctct ccagatgctc ttgggccatc  540
ttccacatcg tccgtagcag ccttggcaat ttgccatcac tggcaaatac acataaatcc  600
aatgaatacg gttaccacca tcacattacc atgcaggtac acagcaagaa ttgacgttgg  660
catatcacat ggtgtaataa ccccacttgt gaaacaaccc agaataaggt acaaggcgga  720
aatgtcgtca ttctaaaata aaaggcatgg ccaggaattt gtctaatacc gggaacttaa  780
attcagcttg aacaccagtc gcaaaaaatt caaagaaagt gattcaggtt cgggttcgtg  840
gattggaaca gcttcttttg tttcagtgat gagagaatcc tcctgtcact cgagaaagaa  900
tcaaagaggc caacaa                                                  916

SEQ ID NO: 3           moltype = DNA  length = 916
FEATURE                Location/Qualifiers
misc_feature           1..916
                       note = Synthetic Polynucleotide
source                 1..916
                       mol_type = other DNA
                       organism = synthetic construct
SEQUENCE: 3
taacaggaaa cagctatgac gggcccccta ggtaagcagt atcttcgaca gcttgtctct  60
ccagatgctc ttgggccatc ttccacatcg tccgtagcag ccttggcaat ttgccatcac  120
tggcaaatac acataaatcc aatgaatacg gttaccacca tcacattacc atgcaggtac  180
acagcaagaa ttgacgttgg catatcacat ggtgtaataa ccccacttgt gaaacaaccc  240
agaataaggt acaaggcgga aatgtcgtca ttctaaaata aaaggcatgg ccaggaattt  300
gtctaatacc gggaacttaa attcagcttg aacaccagtc gcaaaaaatt caaagaaagt  360
gattcaggtt cgggttcgtg gattggaaca gcttcttttg tttcagtgat gagagaatcc  420
tcctgtcact cgagaaagaa tcaaagaggc caacaacgca gaacaggaaa cagctatgac  480
gggcccccta ggtaagcagt atcttcgaca gcttgtctct ccagatgctc ttgggccatc  540
ttccacatcg tccgtagcag ccttggcaat ttgccatcac tggcaaatac acataaatcc  600
aatgaatacg gttaccacca tcacattacc atgcaggtac acagcaagaa ttgacgttgg  660
catatcacat ggtgtaataa ccccacttgt gaaacaaccc agaataaggt acaaggcgga  720
aatgtcgtca ttctaaaata aaaggcatgg ccaggaattt gtctaatacc gggaacttaa  780
attcagcttg aacaccagtc gcaaaaaatt caaagaaagt gattcaggtt cgggttcgtg  840
gattggaaca gcttcttttg tttcagtgat gagagaatcc tcctgtcact cgagaaagaa  900
tcaaagaggc caacaa                                                  916

SEQ ID NO: 4           moltype = DNA  length = 916
FEATURE                Location/Qualifiers
misc_feature           1..916
                       note = Synthetic Polynucleotide
source                 1..916
                       mol_type = other DNA
                       organism = synthetic construct
SEQUENCE: 4
taacaggaaa cagctatgac gggcccccta gggggttctg acttcttacg aaaatgtggc  60
tagcattcca ttctctgacg ttcaaagaat cggaataagt catggtaatg gtgggaaatc  120
taatagaagc gactcccata acctccatat ttcttggcaa ataattctgt ctgggttacc  180
gttcacgagc cttcagagat ctacgacgtg tagtgggtgg gcttgccctc cagggtgtag  240
tttgtaatta gaatgggatt tcctgtttta agtacccaaa tacgaaaatt gctcttgatg  300
tttaacggct cacttttaag taaagtttgt gccaataccg tgcatgggag taagttattg  360
ccaatcttcg agaatttagg caattttggt atactcaact gggtctaata tggtggacgg  420
aatgatttct cgagaaagaa tcaaagaggc caacaacgca gaacaggaaa cagctatgac  480
gggcccccta gggggttctg acttcttacg aaaatgtggc tagcattcca ttctctgacg  540
```

```
ttcaaagaat cggaataagt catggtaatg gtgggaaatc taatagaagc gactcccata  600
acctccatat ttcttggcaa ataattctgt ctgggttacc gttcacgagc cttcagagat  660
ctacgacgtg tagtgggtgg gcttgccctc cagggtgtag tttgtaatta gaatgggatt  720
tcctgtttta agtacccaaa tacgaaaatt gctcttgatg tttaacggct cacttttaag  780
taaagtttgt gccaataccg tgcatgggag taagttattg ccaatcttcg agaatttagg  840
caattttggt atactcaact gggtctaata tggtggacgg aatgatttct cgagaaagaa  900
tcaaagaggc caacaa                                                  916

SEQ ID NO: 5            moltype = DNA  length = 916
FEATURE                 Location/Qualifiers
misc_feature            1..916
                        note = Synthetic Polynucleotide
source                  1..916
                        mol_type = other DNA
                        organism = synthetic construct
SEQUENCE: 5
taacaggaaa cagctatgac gggcccccta ggcacattgc gtctttataa acttactaaa  60
ggttttggat agttttgaac ccattgtttg acgaatattc catattaaaa actctaaaat  120
aaaccccagc caccaacatt tgaaccagcg ttccccccat ctccgctgtg atcattctag  180
atctgtatta tggcatcgac tatgggaata cagggttatt ctcccatttt attgaggtat  240
atggccagtt gcgcaacttc tttgatgaaa ttttatttgt ccgttgcatg attgaaatcc  300
taccagtagt tatatatatg tctttttcat tgttgtactt tggataaagc tgcttcttca  360
gaacgctccc tactatgctt taaacgctta ttttcggaag aaatcatgtg ggtcatattt  420
ttttgcttct cgagaaagaa tcaaagaggc caacaacgca gaacaggaaa cagctatgac  480
gggcccccta ggcacattgc gtctttataa acttactaaa ggttttggat agttttgaac  540
ccattgtttg acgaatattc catattaaaa actctaaaat aaaccccagc caccaacatt  600
tgaaccagcg ttccccccat ctccgctgtg atcattctag atctgtatta tggcatcgac  660
tatgggaata cagggttatt ctcccatttt attgaggtat atggccagtt gcgcaacttc  720
tttgatgaaa ttttatttgt ccgttgcatg attgaaatcc taccagtagt tatatatatg  780
tctttttcat tgttgtactt tggataaagc tgcttcttca gaacgctccc tactatgctt  840
taaacgctta ttttcggaag aaatcatgtg ggtcatattt ttttgcttct cgagaaagaa  900
tcaaagaggc caacaa                                                  916

SEQ ID NO: 6            moltype = DNA  length = 9711
FEATURE                 Location/Qualifiers
misc_feature            1..9711
                        note = Synthetic Polynucleotide
source                  1..9711
                        mol_type = other DNA
                        organism = synthetic construct
SEQUENCE: 6
agacacctcg agacccaata aaagatcttt attttcatta gatctgtgtg ttggtttttt  60
gtgtgtctag agtgtgggtg tgggcgttgt cctgcagggg aattgaacag gtgtaaaatt  120
ggagggacaa gacttcccac agattttcgg ttttgtcggg aagttttttta atagggggcaa  180
ataaggaaaa tgggaggata ggtagtcatc tggggtttta tgcagcaaaa ctacaggtta  240
ttattgcttg tgatccgcct cggagtattt tccatcgagg tagattaaag acatgctcac  300
ccgagtttta tactctcctg cttgagatcc ttactacagt atgaaattac agtgtcgcga  360
gttagactat gtaagcagaa ttttaatcat ttttaaagag cccagtactt catatccatt  420
tctcccgctc cttctgcagc cttatcaaaa ggtattttag aacactcatt ttagccccat  480
tttcatttat tatactggct tatccaaccc ctagacagag cattggcatt ttccctttcc  540
tgatcttaga agtctgatga ctcatgaaac cagacagatt accctgttat ccctagaatt  600
cagcttggga taaaaagcta tggcataggc ggtaatacgg ttatccacag aatcagggga  660
taacgcagga aagaacatgt gagcaaaagg ccagcaaaag gccaggaacc gtaaaaaggc  720
cgcgttgctg gcgtttttcc ataggctccg cccccctgac gagcatcaca aaaatcgacg  780
ctcaagtcag aggtggcgaa acccgacagg actataaaga taccaggcgt ttccccctgg  840
aagctccctc gtgcgctctc ctgttccgac cctgccgctt accggatacc tgtccgcctt  900
tctcccttcg ggaagcgtgg cgctttctca tagctcacgc tgtaggtatc tcagttcggt  960
gtaggtcgtt cgctccaagc tgggctgtgt gcacgaaccc cccgttcagc ccgaccgctg  1020
cgccttatcc ggtaactatc gtcttgagtc caacccggta agacacgact tatcgccact  1080
ggcagcagcc actggtaaca ggattagcag agcgaggtat gtaggcggtg ctacagagtt  1140
cttgaagtgg tggcctaact acggctacac tagaagaaca gtatttggta tctgcgctct  1200
gctgaagcca gttaccttcg gaaaaagagt tggtagctct tgatccggca aacaaaccac  1260
cgctggtagc ggtggttttt ttgtttgcaa gcagcagatt acgcgcagaa aaaaaggatc  1320
tcaagaagat cctttgatct tttctacggg gtctgacgct cagtggaacg aaaactcacg  1380
ttaagggatt ttggtcatga gattatcaaa aaggatcttc acctagatcc ttttaaatta  1440
aaaatgaagt tttaaatcaa tctaaagtat atatgagtaa acttggtctg acagttacca  1500
atgcttaatc agtgaggcac ctatctcagc gatctgtcta tttcgttcat ccatagttgc  1560
ctgactcccc gtcgtgtaga taactacgat acgggagggc ttaccatctg gccccagtgc  1620
tgcaatgata ccgcgagatc cacgctcacc ggctccagat ttatcagcaa taaaccagcc  1680
agccggaagg gccgagcgca gaagtggtcc tgcaacttta tccgcctcca tccagtctat  1740
taattgttgc cgggaagcta gagtaagtag ttcgccagtt aatagtttgc gcaacgttgt  1800
tgccattgct acaggcatcg tggtgtcacg ctcgtcgttt ggtatggctt cattcagctc  1860
cggttcccaa cgatcaaggc gagttacatg atcccccatg ttgtgcaaaa aagcggttag  1920
ctccttcggt cctccgatcg ttgtcagaag taagttggcc gcagtgttat cactcatggt  1980
tatggcagca ctgcataatt ctcttactgt catgccatcc gtaagatgct tttctgtgac  2040
tggtgagtac tcaaccaagt cattctgaga atagtgtatg cggcgaccga gttgctcttg  2100
cccggcgtca atacgggata ataccgcgcc acatagcaga actttaaaag tgctcatcat  2160
tggaaaacgt tcttcggggc gaaaactctc aaggatctta ccgctgttga gatccagttc  2220
gatgtaaccc actcgtgcac ccaactgatc ttcagcatct tttactttca ccagcgtttc  2280
```

-continued

```
tgggtgagca aaaacaggaa ggcaaaatgc cgcaaaaaag ggaataaggg cgacacggaa  2340
atgttgaata ctcatactct tcctttttca atattattga agcatttatc agggttattg  2400
tctcatgagc ggatacatat ttgaatgtat ttagaaaaat aaacaaatag gggtgattta  2460
atctgtatca ggggcgtata gtggagcaaa gcgaattcta actataacgg tcctaaggta  2520
gcgaaggccc tcccctcggc cccgcgccgc agagtctggc cgcgcgcccc tgcgcaacgt  2580
ggcaggaagc gcgcgctggg ggcggggacg ggcagtaggg ctgagcggct gcggggcggg  2640
tgcaagcacg tttccgactt gagttgcctc aagaggggcg tgctgagcca gacctccatc  2700
gcgcactccg gggagtggag ggaaggagcg agggctcagt tgggctgttt tggaggcagg  2760
aagcacttgc tctcccaaag tcgctctgag ttgttatcag taagggagct gcagtggagt  2820
aggcggggag aaggccgcac ccttctccgg aggggggagg ggagtgttgc aatacctttc  2880
tgggagttct ctgctgcctc ctggcttctg aggaccgccc tgggcctggg agaatccctt  2940
ccccctcttc cctcgtgatc tgcaactcca gtctttctag aagatgggcg ggagtctttt  3000
gggcaggctt aaaggctaac ctggttaggg cgcagtagtc cagggtttcc ttgatgatgt  3060
catacttatc ctgtcccttt tttttccaca gctcgcggtt gaggacaaac tcttcgcggt  3120
ctttccagtg ttgacaatta atcatcggca tagtatatcg gcatagtata atacgacaag  3180
gtgaggaacg ccaccatgat tgaacaagat ggattgcacg caggttctcc ggccgcttgg  3240
gtggagaggc tattcggcta tgactgggca caacagacaa tcggctgctc tgatgccgcc  3300
gtgttccggc tgtcagcgca ggggcgcccg gttctttttg tcaagaccga cctgtccggt  3360
gccctgaatg aactgcaaga cgaggcagcg cggctatcgt ggctggccac gacgggcgtt  3420
ccttgcgcag ctgtgctcga cgttgtcact gaagcgggaa gggactggct gctattgggc  3480
gaagtgccgg ggcaggatct cctgtcatct caccttgctc ctgccgagaa agtatccatc  3540
atggctgatg caatgcggcg gctgcatacg cttgatccgg ctacctgccc attcgaccac  3600
caagcgaaac atcgcatcga gcgagcacgt actcggatgg aagccggtct tgtcgatcag  3660
gatgatctgg acgaagagca tcaggggctc gcgccagccg aactgttcgc caggctcaag  3720
gcgagcatgc ccgacggcga ggatctcgtc gtgacccatg gcgatgcctg cttgccgaat  3780
atcatggtgg aaaatggccg cttttctgga ttcatcgact gtggccggct gggtgtggcg  3840
gaccgctatc aggacatagc gttggctacc cgtgatattg ctgaagagct tggcggcgaa  3900
tgggctgacc gcttcctcgt gctttacggt atcgccgctc ccgattcgca gcgcatcgcc  3960
ttctatcgcc ttcttgacga gttcttctga tgtacaagta aagcggccgc gactctagat  4020
cataatcagc cataccacat ttgtagaggt tttacttgct ttaaaaaacc tcccacacct  4080
ccccctgaac ctgaaacata aaatgaatgc aattgttgtt gttaacttgt ttattgcagc  4140
ttataatggt tacaaataaa gcaatagcat cacaaatttc acaaataaag catttttttc  4200
actgcattct agttgtggtt tgtccaaact catcaatgta tcttaggtct cgcgtactgt  4260
aggtcctttc agcaaaaaac ccctcaagac ccgtttagag gccccaaggg gttatgctag  4320
ttattgctca gcggtggcag cagccaactc agcttccttt cgggctttgt tagcagccgg  4380
atctcagtgg tggtggtggt ggtgctccca tctgacttgc aagaaaacag atggcaagca  4440
tgacaatcat ttcgagtgcg gccgcagcga caaacaacag ataaaacgaa aggcccagtc  4500
tttcgactga gcctttcgtt ttatttgaag cttctttcag caaaaaaccc cgcaggaccc  4560
ccgaagaggc cccgcggggt tatgctaggt cgactacgca gacgtaacag gaaacagcta  4620
tgacgggccc cctaggtaag cagtatcttc gacagcttgt ctctccagat gctcttgggc  4680
catcttccac atcgtccgta gcagccttgg caatttgcca tcactggcaa atacacataa  4740
atccaatgaa tacggttacc accatcacat taccatgcag gtacacagca agaattgacg  4800
ttggcatatc acatggtgta ataaccccac ttgtgaaaca acccagaata aggtacaagg  4860
cggaaatgtc gtcattctaa aataaaaggc atggccagga atttgtctaa taccgggaac  4920
ttaaattcag cttgaacacc agtcgcaaaa aattcaaaga aagtgattca ggttcgggtt  4980
cgtggattgg aacagcttct tttgtttcag tgatgagaga atcctcctgt cactcgagaa  5040
agaatcaaag aggccaacaa cgcagaacag gaaacagcta tgacgggccc cctaggtaag  5100
cagtatcttc gacagcttgt ctctccagat gctcttgggc catcttccac atcgtccgta  5160
gcagccttgg caatttgcca tcactggcaa atacacataa atccaatgaa tacggttacc  5220
accatcacat taccatgcag gtacacagca agaattgacg ttggcatatc acatggtgta  5280
ataaccccac ttgtgaaaca acccagaata aggtacaagg cggaaatgtc gtcattctaa  5340
aataaaaggc atggccagga atttgtctaa taccgggaac ttaaattcag cttgaacacc  5400
agtcgcaaaa aattcaaaga aagtgattca ggttcgggtt cgtggattgg aacagcttct  5460
tttgtttcag tgatgagaga atcctcctgt cactcgagaa agaatcaaag aggccaacaa  5520
cgacctgtag aggtcctccc tttagtgagg gttaattctc gagtctccct atagtgagtc  5580
gtattaattc cgtgtattct atagtgtcac ctaaatcgtt acgggttcgt aaattctgca  5640
ggacttctag ttattaatag taatcaatta cggggtcatt agttcatagc ccatatatgg  5700
agttccgcgt tacataactt acggtaaatg gcccgcctgg ctgaccgccc aacgaccccc  5760
gcccattgac gtcaataatg acgtatgttc ccatagtaac gccaataggg actttccatt  5820
gacgtcaatg ggtggagtat ttacggtaaa ctgcccactt ggcagtacat caagtgtatc  5880
atatgccaag tacgccccct attgacgtca atgacggtaa atggcccgcc tggcattatg  5940
cccagtacat gaccttatgg gactttccta cttggcagta catctacgta ttagtcatcg  6000
ctattaccat ggtcgaggtg agccccacgt tctgcttcac tctccccatc tcccccccct  6060
ccccaccccc aattttgtat ttatttattt tttaattatt ttgtgcagcg atgggggcgg  6120
gggggggggg ggggcgcgcg ccaggcgggg cggggcgggg cgaggggcgg ggcggggcga  6180
ggcggagagg tgcggcggca gccaatcaga gcggcgcgct ccgaaagttt cctttatgg  6240
cgaggcggcg gcggcggcgg ccctataaaa agcgaagcgc gcggcgggcg ggagtcgctg  6300
cgcgctgcct tcgccccgtg ccccgctccg ccgccgcctc gcgccgcccg ccccggctct  6360
gactgaccgc gttactccca caggtgagcg ggcgggacgg cccttctcct ccgggctgta  6420
attagcgctt ggtttaatga cggcttgttt cttttctgtg gctgcgtgaa agccttgagg  6480
ggctccggga gggccctttg tgcgggggga gcggctcggg gggtgcgtgc gtgtgtgtgt  6540
gcgtggggag cgccgcgtgc ggctccgcgc tgcccggcgg ctgtgagcgc tgcgggcgcg  6600
gcgcggggct ttgtgcgctc cgcagtgtgc gcgaggggag cgcggccggg ggcggtgccc  6660
cgcggtgcgg ggggggctgcg aggggaacaa aggctgcgtg cggggtgtgt gcgtgggggg  6720
gtgagcaggg ggtgtgggcg cgtcggtcgg gctgcaaccc cccccctgcac ccccctcccc  6780
gagttgctga gcacggcccg gcttcgggtg cggggctccg tacggggcgt ggcgcggggc  6840
tcgccgtgcc gggcgggggg tggcggcagg tgggggtgcc gggcggggcg gggccgcctc  6900
gggccgggga gggctcgggg gaggggcgcg gcggcccccg gagcgccggc ggctgtcgag  6960
gcgcggcgag ccgcagccat tgccttttat ggtaatcgtg cgagagggcg cagggacttc  7020
```

```
ctttgtccca aatctgtgcg gagccgaaat ctgggaggcg ccgccgcacc ccctctagcg  7080
ggcgcggggc gaagcggtgc ggcgccggca ggaaggaaat gggcggggag ggccttcgtg  7140
cgtcgccgcg ccgccgtccc cttctccctc tccagcctcg gggctgtccg cggggggacg  7200
gctgccttcg ggggggacgg ggcagggcgg ggttcggctt ctggcgtgtg accggcggct  7260
ctagagcctc tgctaaccat gttcatgcct tcttcttttt cctacagctc ctgggcaacg  7320
tgctggttat tgtgctgtct catcattttg gcaaagaatt gatttgatac cgcgggcccg  7380
ggatcccctc gagggaatta cctttggcgt agccgccacc atgccagagc cagcgaagtc  7440
tgctcccgcc ccgaaaaagg gctccaagaa ggcggtgact aaggcgcaga agaaaggcgg  7500
caagaagcgc aagcgcagcc gcaaggagag ctattccatc tatgtgtaca aggttctgaa  7560
gcaggtccac cctgacaccg gcatttcgtc caaggccatg ggcatcatga attcgtttgt  7620
gaacgacatt ttcgagcgca tcgctggtga ggcttcccgc ctggcgcatt acaacaagcg  7680
ctcgaccatc acctccaggg agatccagac ggccgtgcgc ctgctgctgc ctggggagtt  7740
ggccaagcac gccgtgtccg agggtactaa ggccatcacc aagtacacca gcgctaagga  7800
tccccgggta ccggtcgcca ccatggtgag caagggcgag gagctgttca ccggggtggt  7860
gcccatcctg gtcgagctgg acggcgacgt aaacggccac aagttcagcg tgtccggcga  7920
gggcgagggc gatgccacct acggcaagct gaccctgaag ttcatctgca ccaccggcaa  7980
gctgcccgtg ccctggccca ccctcgtgac caccctgacc tggggcgtgc agtgcttcgc  8040
ccgctacccc gaccacatga agcagcacga cttcttcaag tccgccatgc ccgaaggcta  8100
cgtccaggag cgcaccatct tcttcaagga cgacggcaac tacaagaccc gcgccgaggt  8160
gaagttcgag ggcgacaccc tggtgaaccg catcgagctg aagggcatcg acttcaagga  8220
ggacggcaac atcctggggc acaagctgga gtacaacgcc atcagcgaca acgtctatat  8280
caccgccgac aagcagaaga acggcatcaa ggccaacttc aagatccgcc acaacatcga  8340
ggacggcagc gtgcagctcg ccgaccacta ccagcagaac acccccatcg gcgacggccc  8400
cgtgctgctg cccgacaacc actacctgag cacccagtcc aagctgagca aagaccccaa  8460
cgagaagcgc gatcacatgg tcctgctgga gttcgtgacc gccgccggga tcactctcgg  8520
catggacgag ctgtacaagt gaacctgagt cgtaacagga aacagctatg acgggccccc  8580
taggacgttc ccatagctcc ttttgatgtc ttaatgtagg ttcaacagat atgcggcttc  8640
ttcgcattct gatggcgtca gctacgatag gcgagagctg aatagttgaa aatttttagc  8700
agatgcctga gaaaattaaa cttgatttga ttccagtaat ttaccaaaat acgcacagtt  8760
gccttcttcg atgtaatctt ttcaatcgta ctatgtcgta tgcagttagc aaatgaaagt  8820
agcaacacca atttgcgcca gaatttcacg tcgaaaatat ccttaaacct tgcaagccaa  8880
gttacggagt tgaaatttcc gtaagctacg gttatcttcc aatggcccat acttggctaa  8940
atcagagttc cctttcgtgg aaactgcaat agccaaattc ctcgagaaag aatcaaagag  9000
gccaacaacg cagaacagga aacagctatg acgggccccc taggacgttc ccatagctcc  9060
ttttgatgtc ttaatgtagg ttcaacagat atgcggcttc ttcgcattct gatggcgtca  9120
gctacgatag gcgagagctg aatagttgaa aatttttagc agatgcctga gaaaattaaa  9180
cttgatttga ttccagtaat ttaccaaaat acgcacagtt gccttcttcg atgtaatctt  9240
ttcaatcgta ctatgtcgta tgcagttagc aaatgaaagt agcaacacca atttgcgcca  9300
gaatttcacg tcgaaaatat ccttaaacct tgcaagccaa gttacggagt tgaaatttcc  9360
gtaagctacg gttatcttcc aatggcccat acttggctaa atcagagttc cctttcgtgg  9420
aaactgcaat agccaaattc ctcgagaaag aatcaaagag gccaacaacg acctgctaag  9480
gtctgtgcct tctagttgcc agccatctgt tgtttgcccc tcccccgtgc cttccttgac  9540
cctggaaggt gccactccca ctgtcctttc ctaataaaat gaggaaattg catcgcattg  9600
tctgagtagg tgtcattcta ttctgggggg tggggtgggg caggacagca agggggagga  9660
ttgggaagag aatagcaggc atgctgggga tgcggtgggc tctatggtac g           9711
```

```
SEQ ID NO: 7           moltype = DNA  length = 9614
FEATURE                Location/Qualifiers
misc_feature           1..9614
                       note = Synthetic Polynucleotide
source                 1..9614
                       mol_type = other DNA
                       organism = synthetic construct
SEQUENCE: 7
agacacctcg agacccaata aaagatcttt attttcatta gatctgtgtg ttggtttttt  60
gtgtgtctag agtgtgggtg tgggcgttgt cctgcagggg aattgaacag gtgtaaaatt  120
ggagggacaa gacttcccac agattttcgg ttttgtcggg aagtttttta ataggggcaa  180
ataaggaaaa tgggaggata ggtagtcatc tggggtttta tgcagcaaaa ctacaggtta  240
ttattgcttg tgatccgcct cggagtattt tccatcgagg tagattaaag acatgctcac  300
ccgagtttta tactctcctg cttgagatcc ttactacagt atgaaattac agtgtcgcga  360
gttagactat gtaagcagaa ttttaatcat ttttaaagag cccagtactt catatccatt  420
tctcccgctc cttctgcagc cttatcaaaa ggtattttag aacactcatt ttagccccat  480
tttcatttat tatactggct tatccaaccc ctagacagag cattggcatt ttccctttcc  540
tgatcttaga agtctgatga ctcatgaaac cagacagatt accctgttat ccctagaatt  600
cagcttggga taaaaagcta tggcataggc ggtaatacgg ttatccacag aatcagggga  660
taacgcagga aagaacatgt gagcaaaagg ccagcaaaag gccaggaacc gtaaaaaggc  720
cgcgttgctg gcgtttttcc ataggctccg cccccctgac gagcatcaca aaaatcgacg  780
ctcaagtcag aggtggcgaa acccgacagg actataaaga taccaggcgt ttccccctgg  840
aagctccctc gtgcgctctc ctgttccgac cctgccgctt accggatacc tgtccgcctt  900
tctcccttcg ggaagcgtgg cgctttctca tagctcacgc tgtaggtatc tcagttcggt  960
gtaggtcgtt cgctccaagc tgggctgtgt gcacgaaccc cccgttcagc ccgaccgctg  1020
cgccttatcc ggtaactatc gtcttgagtc caacccggta agacacgact tatcgccact  1080
ggcagcagcc actggtaaca ggattagcag agcgaggtat gtaggcggtg ctacagagtt  1140
cttgaagtgg tggcctaact acggctacac tagaagaaca gtatttggta tctgcgctct  1200
gctgaagcca gttaccttcg gaaaaagagt tggtagctct tgatccggca aacaaaccac  1260
cgctggtagc ggtggttttt ttgtttgcaa gcagcagatt acgcgcagaa aaaaaggatc  1320
tcaagaagat cctttgatct tttctacggg gtctgacgct cagtggaacg aaaactcacg  1380
ttaagggatt ttggtcatga gattatcaaa aaggatcttc acctagatcc ttttaaatta  1440
aaaatgaagt tttaaatcaa tctaaagtat atatgagtaa acttggtctg acagttacca  1500
```

```
atgcttaatc agtgaggcac ctatctcagc gatctgtcta tttcgttcat ccatagttgc  1560
ctgactcccc gtcgtgtaga taactacgat acgggagggc ttaccatctg gccccagtgc  1620
tgcaatgata ccgcgagatc cacgctcacc ggctccagat ttatcagcaa taaaccagcc  1680
agccggaagg gccgagcgca gaagtggtcc tgcaacttta tccgcctcca tccagtctat  1740
taattgttgc cgggaagcta gagtaagtag ttcgccagtt aatagtttgc gcaacgttgt  1800
tgccattgct acaggcatcg tggtgtcacg ctcgtcgttt ggtatggctt cattcagctc  1860
cggttcccaa cgatcaaggc gagttacatg atcccccatg ttgtgcaaaa aagcggttag  1920
ctccttcggt cctccgatcg ttgtcagaag taagttggcc gcagtgttat cactcatggt  1980
tatggcagca ctgcataatt ctcttactgt catgccatcc gtaagatgct tttctgtgac  2040
tggtgagtac tcaaccaagt cattctgaga atagtgtatg cggcgaccga gttgctcttg  2100
cccggcgtca atacgggata ataccgcgcc acatagcaga actttaaaag tgctcatcat  2160
tggaaaacgt tcttcggggc gaaaactctc aaggatctta ccgctgttga gatccagttc  2220
gatgtaaccc actcgtgcac ccaactgatc ttcagcatct tttactttca ccagcgtttc  2280
tgggtgagca aaaacaggaa ggcaaaatgc cgcaaaaaag ggaataaggg cgacacggaa  2340
atgttgaata ctcatactct tcctttttca atattattga agcatttatc agggttattg  2400
tctcatgagc ggatacatat ttgaatgtat ttagaaaaat aaacaaatag gggtgattta  2460
atctgtatca ggggcgtata gtggagcaaa gcgaattcta actataacgg tcctaaggta  2520
gcgaaggccc tcccctcggc cccgcgccgc agagtctggc cgcgcgcccc tgcgcaacgt  2580
ggcaggaagc gcgcgctggg ggcggggacg ggcagtaggg ctgagcggct gcggggcggg  2640
tgcaagcacg tttccgactt gagttgcctc aagaggggcg tgctgagcca gacctccatc  2700
gcgcactccg gggagtggag ggaaggagcg agggctcagt tgggctgttt tggaggcagg  2760
aagcacttgc tctcccaaag tcgctctgag ttgttatcag taagggagct gcagtggagt  2820
aggcggggag aaggccgcac ccttctccgg aggggggagg ggagtgttgc aatacctttc  2880
tgggagttct ctgctgcctc ctggcttctg aggaccgccc tgggcctggg agaatccctt  2940
ccccctcttc cctcgtgatc tgcaactcca gtctttctag aagatgggcg ggagtctttt  3000
gggcaggctt aaaggctaac ctggttaggg cgcagtagtc cagggtttcc ttgatgatgt  3060
catacttatc ctgtcccttt tttttccaca gctcgcggtt gaggacaaac tcttcgcggt  3120
ctttccagtg ttgacaatta atcatcggca tagtatatcg gcatagtata atacgacaag  3180
gtgaggaacg ccaccatgat tgaacaagat ggattgcacg caggttctcc ggccgcttgg  3240
gtggagaggc tattcggcta tgactgggca caacagacaa tcggctgctc tgatgccgcc  3300
gtgttccggc tgtcagcgca ggggcgcccg gttctttttg tcaagaccga cctgtccggt  3360
gccctgaatg aactgcaaga cgaggcagcg cggctatcgt ggctggccac gacgggcgtt  3420
ccttgcgcag ctgtgctcga cgttgtcact gaagcgggaa gggactggct gctattgggc  3480
gaagtgccgg ggcaggatct cctgtcatct caccttgctc ctgccgagaa agtatccatc  3540
atggctgatg caatgcggcg gctgcatacg cttgatccgg ctacctgccc attcgaccac  3600
caagcgaaac atcgcatcga gcgagcacgt actcggatgg aagccggtct tgtcgatcag  3660
gatgatctgg acgaagagca tcaggggctc gcgccagccg aactgttcgc caggctcaag  3720
gcgagcatgc ccgacggcga ggatctcgtc gtgacccatg gcgatgcctg cttgccgaat  3780
atcatggtgg aaaatggccg cttttctgga ttcatcgact gtggccggct gggtgtggcg  3840
gaccgctatc aggacatagc gttggctacc cgtgatattg ctgaagagct tggcggcgaa  3900
tgggctgacc gcttcctcgt gctttacggt atcgccgctc ccgattcgca gcgcatcgcc  3960
ttctatcgcc ttcttgacga gttcttctga tgtacaagta aagcggccgc gactctagat  4020
cataatcagc cataccacat ttgtagaggt tttacttgct ttaaaaaacc tcccacacct  4080
ccccctgaac ctgaaacata aaatgaatgc aattgttgtt gttaacttgt ttattgcagc  4140
ttataatggt tacaaataaa gcaatagcat cacaaatttc acaaataaag cattttttc  4200
actgcattct agttgtggtt tgtccaaact catcaatgta tcttaggtct cgcgtactgt  4260
aggtcctttc agcaaaaaac ccctcaagac ccgtttagag gccccaaggg gttatgctag  4320
ttattgctca gcggtggcag cagccaactc agcttccttt cgggctttgt tagcagccgg  4380
atctcagtgg tggtggtggt ggtgctccca tctgacttgc aagaaaacag atggcaagca  4440
tgacaatcat ttcgagtgcg gccgcagcga caaacaacag ataaaacgaa aggcccagtc  4500
tttcgactga gcctttcgtt ttatttgaag cttctttcag caaaaaaccc cgcaggaccc  4560
ccgaagaggc cccgcggggt tatgctaggt cgactacgca gacgtaacag gaaacagcta  4620
tgacgggccc cctaggtaag cagtatcttc gacagcttgt ctctccagat gctcttgggc  4680
catcttccac atcgtccgta gcagccttgg caatttgcca tcactggcaa atacacataa  4740
atccaatgaa tacggttacc accatcacat taccatgcag gtacacagca agaattgacg  4800
ttggcatatc acatggtgta ataaccccac ttgtgaaaca acccagaata aggtacaagg  4860
cggaaatgtc gtcattctaa aataaaaggc atggccagga atttgtctaa taccgggaac  4920
ttaaattcag cttgaacacc agtcgcaaaa aattcaaaga aagtgattca ggttcgggtt  4980
cgtggattgg aacagcttct tttgtttcag tgatgagaga atcctcctgt cactcgagaa  5040
agaatcaaag aggccaacaa cgcagaacag gaaacagcta tgacgggccc cctaggtaag  5100
cagtatcttc gacagcttgt ctctccagat gctcttgggc catcttccac atcgtccgta  5160
gcagccttgg caatttgcca tcactggcaa atacacataa atccaatgaa tacggttacc  5220
accatcacat taccatgcag gtacacagca agaattgacg ttggcatatc acatggtgta  5280
ataaccccac ttgtgaaaca acccagaata aggtacaagg cggaaatgtc gtcattctaa  5340
aataaaaggc atggccagga atttgtctaa taccgggaac ttaaattcag cttgaacacc  5400
agtcgcaaaa aattcaaaga aagtgattca ggttcgggtt cgtggattgg aacagcttct  5460
tttgtttcag tgatgagaga atcctcctgt cactcgagaa agaatcaaag aggccaacaa  5520
cgacctgtag cgtaaattct gcaggacttc tagttattaa tagtaatcaa ttacggggtc  5580
attagttcat agcccatata tggagttccg cgttacataa cttacggtaa atggcccgcc  5640
tggctgaccg cccaacgacc cccgcccatt gacgtcaata atgacgtatg ttcccatagt  5700
aacgccaata gggactttcc attgacgtca atgggtggag tatttacggt aaactgccca  5760
cttggcagta catcaagtgt atcatatgcc aagtacgccc cctattgacg tcaatgacgg  5820
taaatggccc gcctggcatt atgcccagta catgacctta tgggactttc ctacttggca  5880
gtacatctac gtattagtca tcgctattac catggtcgag gtgagcccca cgttctgctt  5940
cactctcccc atctcccccc cctccccacc cccaattttg tatttattta tttttaatt  6000
attttgtgca gcgatggggg cgggggggggg gggggggcgc gcgccaggcg gggcggggcg  6060
gggcgagggg cggggcgggg cgaggcggag aggtgcggcg gcagccaatc agagcggcgc  6120
gctccgaaag tttcctttta tggcgaggcg gcggcggcgg cggccctata aaaagcgaag  6180
cgcgcggcgg gcgggagtcg ctgcgcgctg ccttcgcccc gtgccccgct ccgccgccgc  6240
```

```
ctcgcgccgc ccgccccggc tctgactgac cgcgttactc ccacaggtga gcgggcggga  6300
cggcccttct cctccgggct gtaattagcg cttggtttaa tgacggcttg tttcttttct  6360
gtggctgcgt gaaagccttg aggggctccg ggagggccct ttgtgcgggg ggagcggctc  6420
ggggggtgcg tgcgtgtgtg tgtgcgtggg gagcgccgcg tgcggctccg cgctgcccgg  6480
cggctgtgag cgctgcgggc gcggcgcggg gctttgtgcg ctccgcagtg tgcgcgaggg  6540
gagcgcggcc gggggcggtg ccccgcggtg cggggggggct gcgaggggaa caaaggctgc  6600
gtgcggggtg tgtgcgtggg ggggtgagca gggggtgtgg gcgcgtcggt cgggctgcaa  6660
ccccccctg caccccccctc cccgagttgc tgagcacggc ccggcttcgg gtgcggggct  6720
ccgtacgggg cgtggcgcgg ggctcgccgt gccgggcggg gggtggcggc aggtgggggt  6780
gccgggcggg gcggggccgc ctcgggccgg ggagggctcg gggggagggc gcggcggccc  6840
ccggagcgcc ggcggctgtc gaggcgcggc gagccgcagc cattgccttt tatggtaatc  6900
gtgcgagagg gcgcagggac ttcctttgtc ccaaatctgt gcggagccga aatctgggag  6960
gcgccgccgc acccccctcta gcgggcgcgg ggcgaagcgg tgcggcgccg gcaggaagga  7020
aatgggcggg gagggccttc gtgcgtcgcc gcgccgccgt ccccttctcc ctctccagcc  7080
tcggggctgt ccgcgggggg acggctgcct tcggggggga cggggcaggg cggggttcgg  7140
cttctggcgt gtgaccggcg gctctagagc ctctgctaac catgttcatg ccttcttctt  7200
tttcctacag ctcctgggca acgtgctggt tattgtgctg tctcatcatt ttggcaaaga  7260
attgatttga taccgcgggc ccgggatccc ctcgagggaa ttacctggtt cgtagccgcc  7320
accatgccag agccagcgaa gtctgctccc gccccgaaaa agggctccaa gaaggcggtg  7380
actaaggcgc agaagaaagg cggcaagaag cgcaagcgca gccgcaagga gagctattcc  7440
atctatgtgt acaaggttct gaagcaggtc caccctgaca ccggcatttc gtccaaggcc  7500
atgggcatca tgaattcgtt tgtgaacgac attttcgagc gcatcgctgg tgaggcttcc  7560
cgcctggcgc attacaacaa gcgctcgacc atcacctcca gggagatcca gacggccgtg  7620
cgcctgctgc tgcctgggga gttggccaag cacgccgtgt ccgagggtac taaggccatc  7680
accaagtaca ccagcgctaa ggatccccgg gtaccggtcg ccaccatggt gagcaagggc  7740
gaggagctgt tcaccggggt ggtgcccatc ctggtcgagc tggacggcga cgtaaacggc  7800
cacaagttca gcgtgtccgg cgagggcgag ggcgatgcca cctacggcaa gctgaccctg  7860
aagttcatct gcaccaccgg caagctgccc gtgccctggc ccaccctcgt gaccaccctg  7920
acctggggcg tgcagtgctt cgcccgctac cccgaccaca tgaagcagca cgacttcttc  7980
aagtccgcca tgcccgaagg ctacgtccag gagcgcacca tcttcttcaa ggacgacggc  8040
aactacaaga cccgcgccga ggtgaagttc gagggcgaca ccctggtgaa ccgcatcgag  8100
ctgaagggca tcgacttcaa ggaggacggc aacatcctgg ggcacaagct ggagtacaac  8160
gccatcagcg acaacgtcta tatcaccgcc gacaagcaga agaacggcat caaggccaac  8220
ttcaagatcc gccacaacat cgaggacggc agcgtgcagc tcgccgacca ctaccagcag  8280
aacaccccca tcggcgacgg ccccgtgctg ctgcccgaca accactacct gagcacccag  8340
tccaagctga gcaaagaccc caacgagaag cgcgatcaca tggtcctgct ggagttcgtg  8400
accgccgccg ggatcactct cggcatggac gagctgtaca agtgaacctt tggcgtaaca  8460
ggaaacagct atgacgggcc ccctaggacg ttcccatagc tcctttgat gtcttaatgt  8520
aggttcaaca gatatgcggc ttcttcgcat tctgatggcg tcagctacga taggcgagag  8580
ctgaatagtt gaaaattttt agcagatgcc tgagaaaatt aaacttgatt tgattccagt  8640
aatttaccaa aatacgcaca gttgccttct tcgatgtaat cttttcaatc gtactatgtc  8700
gtatgcagtt agcaaatgaa agtagcaaca ccaatttgcg ccagaatttc acgtcgaaaa  8760
tatccttaaa ccttgcaagc caagttacgg agttgaaatt tccgtaagct acggttatct  8820
tccaatggcc catacttggc taaatcagag ttccctttcg tggaaactgc aatagccaaa  8880
ttcctcgaga aagaatcaaa gaggccaaca acgcagaaca ggaaacagct atgacgggcc  8940
ccctaggacg ttcccatagc tcctttgat gtcttaatgt aggttcaaca gatatgcggc  9000
ttcttcgcat tctgatggcg tcagctacga taggcgagag ctgaatagtt gaaaattttt  9060
agcagatgcc tgagaaaatt aaacttgatt tgattccagt aatttaccaa aatacgcaca  9120
gttgccttct tcgatgtaat cttttcaatc gtactatgtc gtatgcagtt agcaaatgaa  9180
agtagcaaca ccaatttgcg ccagaatttc acgtcgaaaa tatccttaaa ccttgcaagc  9240
caagttacgg agttgaaatt tccgtaagct acggttatct tccaatggcc catacttggc  9300
taaatcagag ttccctttcg tggaaactgc aatagccaaa ttcctcgaga aagaatcaaa  9360
gaggccaaca acgacctgag taggtctgtg ccttctagtt gccagccatc tgttgtttgc  9420
ccctcccccg tgccttcctt gaccctggaa ggtgccactc ccactgtcct ttcctaataa  9480
aatgaggaaa ttgcatcgca ttgtctgagt aggtgtcatt ctattctggg gggtggggtg  9540
gggcaggaca gcaaggggga ggattgggaa gagaatagca ggcatgctgg ggatgcggtg  9600
ggctctatgg tacg                                                    9614
```

```
SEQ ID NO: 8            moltype = DNA  length = 11977
FEATURE                 Location/Qualifiers
misc_feature            1..11977
                        note = Synthetic Polynucleotide
source                  1..11977
                        mol_type = other DNA
                        organism = synthetic construct
SEQUENCE: 8
agacacctcg agacccaata aaagatcttt attttcatta gatctgtgtg ttggtttttt  60
gtgtgtctag agtgtgggtg tgggcgttgt cctgcagggg aattgaacag gtgtaaaatt  120
ggagggacaa gacttcccac agattttcgg ttttgtcggg aagtttttta ataggggcaa  180
ataaggaaaa tgggaggata ggtagtcatc tggggtttta tgcagcaaaa ctacaggtta  240
ttattgcttg tgatccgcct cggagtattt tccatcgagg tagattaaag acatgctcac  300
ccgagtttta tactctcctg cttgagatcc ttactacagt atgaaattac agtgtcgcga  360
gttagactat gtaagcagaa ttttaatcat ttttaaagag cccagtactt catatccatt  420
tctcccgctc cttctgcagc cttatcaaaa ggtattttag aacactcatt ttagccccat  480
tttcatttat tatactggct tatccaaccc ctagacagag cattggcatt ttccctttcc  540
tgatcttaga agtctgatga ctcatgaaac cagacagatt accctgttat ccctagaatt  600
cagcttggga taaaaagcta tggcataggc ggtaatacgg ttatccacag aatcagggga  660
taacgcagga aagaacatgt gagcaaaagg ccagcaaaag gccaggaacc gtaaaaaggc  720
cgcgttgctg gcgtttttcc ataggctccg ccccctgac gagcatcaca aaaatcgacg  780
```

```
ctcaagtcag aggtggcgaa acccgacagg actataaaga taccaggcgt ttccccctgg  840
aagctccctc gtgcgctctc ctgttccgac cctgccgctt accggatacc tgtccgcctt  900
tctcccttcg ggaagcgtgg cgctttctca tagctcacgc tgtaggtatc tcagttcggt  960
gtaggtcgtt cgctccaagc tgggctgtgt gcacgaaccc cccgttcagc ccgaccgctg  1020
cgccttatcc ggtaactatc gtcttgagtc caacccggta agacacgact tatcgccact  1080
ggcagcagcc actggtaaca ggattagcag agcgaggtat gtaggcggtg ctacagagtt  1140
cttgaagtgg tggcctaact acggctacac tagaagaaca gtatttggta tctgcgctct  1200
gctgaagcca gttaccttcg gaaaaagagt tggtagctct tgatccggca aacaaaccac  1260
cgctggtagc ggtggttttt ttgtttgcaa gcagcagatt acgcgcagaa aaaaaggatc  1320
tcaagaagat cctttgatct tttctacggg gtctgacgct cagtggaacg aaaactcacg  1380
ttaagggatt ttggtcatga gattatcaaa aaggatcttc acctagatcc ttttaaatta  1440
aaaatgaagt tttaaatcaa tctaaagtat atatgagtaa acttggtctg acagttacca  1500
atgcttaatc agtgaggcac ctatctcagc gatctgtcta tttcgttcat ccatagttgc  1560
ctgactcccc gtcgtgtaga taactacgat acgggagggc ttaccatctg gccccagtgc  1620
tgcaatgata ccgcgagatc cacgctcacc ggctccagat ttatcagcaa taaaccagcc  1680
agccggaagg gccgagcgca gaagtggtcc tgcaacttta tccgcctcca tccagtctat  1740
taattgttgc cgggaagcta gagtaagtag ttcgccagtt aatagtttgc gcaacgttgt  1800
tgccattgct acaggcatcg tggtgtcacg ctcgtcgttt ggtatggctt cattcagctc  1860
cggttcccaa cgatcaaggc gagttacatg atcccccatg ttgtgcaaaa aagcggttag  1920
ctccttcggt cctccgatcg ttgtcagaag taagttggcc gcagtgttat cactcatggt  1980
tatggcagca ctgcataatt ctcttactgt catgccatcc gtaagatgct tttctgtgac  2040
tggtgagtac tcaaccaagt cattctgaga atagtgtatg cggcgaccga gttgctcttg  2100
cccggcgtca atacgggata ataccgcgcc acatagcaga actttaaaag tgctcatcat  2160
tggaaaacgt tcttcggggc gaaaactctc aaggatctta ccgctgttga gatccagttc  2220
gatgtaaccc actcgtgcac ccaactgatc ttcagcatct tttactttca ccagcgtttc  2280
tgggtgagca aaaacaggaa ggcaaaatgc cgcaaaaaag ggaataaggg cgacacggaa  2340
atgttgaata ctcatactct tcctttttca atattattga agcatttatc agggttattg  2400
tctcatgagc ggatacatat ttgaatgtat ttagaaaaat aaacaaatag gggtgattta  2460
atctgtatca ggggcgtata gtggagcaaa gcgaattcta actataacgg tcctaaggta  2520
gcgaaggccc tcccctcggc cccgcgccgc agagtctggc cgcgcgcccc tgcgcaacgt  2580
ggcaggaagc gcgcgctggg ggcggggacg ggcagtaggg ctgagcggct gcggggcggg  2640
tgcaagcacg tttccgactt gagttgcctc aagaggggcg tgctgagcca gacctccatc  2700
gcgcactccg gggagtggag ggaaggagcg agggctcagt tgggctgttt tggaggcagg  2760
aagcacttgc tctcccaaag tcgctctgag ttgttatcag taagggagct gcagtggagt  2820
aggcggggag aaggccgcac ccttctccgg aggggggagg ggagtgttgc aatacctttc  2880
tgggagttct ctgctgcctc ctggcttctg aggaccgccc tgggcctggg agaatccctt  2940
ccccctcttc cctcgtgatc tgcaactcca gtctttctag aagatgggcg ggagtctttt  3000
gggcaggctt aaaggctaac ctggttaggg cgcagtagtc cagggtttcc ttgatgatgt  3060
catacttatc ctgtcccttt tttttccaca gctcgcggtt gaggacaaac tcttcgcggt  3120
ctttccagtg ttgacaatta atcatcggca tagtatatcg gcatagtata atacgacaag  3180
gtgaggaacg ccaccatgat tgaacaagat ggattgcacg caggttctcc ggccgcttgg  3240
gtggagaggc tattcggcta tgactgggca caacagacaa tcggctgctc tgatgccgcc  3300
gtgttccggc tgtcagcgca ggggcgcccg gttctttttg tcaagaccga cctgtccggt  3360
gccctgaatg aactgcaaga cgaggcagcg cggctatcgt ggctggccac gacgggcgtt  3420
ccttgcgcag ctgtgctcga cgttgtcact gaagcgggaa gggactggct gctattgggc  3480
gaagtgccgg ggcaggatct cctgtcatct caccttgctc ctgccgagaa agtatccatc  3540
atggctgatg caatgcggcg gctgcatacg cttgatccgg ctacctgccc attcgaccac  3600
caagcgaaac atcgcatcga gcgagcacgt actcggatgg aagccggtct tgtcgatcag  3660
gatgatctgg acgaagagca tcaggggctc gcgccagccg aactgttcgc caggctcaag  3720
gcgagcatgc ccgacggcga ggatctcgtc gtgacccatg gcgatgcctg cttgccgaat  3780
atcatggtgg aaaatggccg cttttctgga ttcatcgact gtggccggct gggtgtggcg  3840
gaccgctatc aggacatagc gttggctacc cgtgatattg ctgaagagct tggcggcgaa  3900
tgggctgacc gcttcctcgt gctttacggt atcgccgctc ccgattcgca gcgcatcgcc  3960
ttctatcgcc ttcttgacga gttcttctga tgtacaagta aagcggccgc gactctagat  4020
cataatcagc cataccacat ttgtagaggt tttacttgct ttaaaaaacc tcccacacct  4080
ccccctgaac ctgaaacata aaatgaatgc aattgttgtt gttaacttgt ttattgcagc  4140
ttataatggt tacaaataaa gcaatagcat cacaaatttc acaaataaag catttttttc  4200
actgcattct agttgtggtt tgtccaaact catcaatgta tcttaggtct cgcgtactgt  4260
cgtactgtcg taggtttgtc tggtcaacca ccgcgttctc agtggtgtac ggtacaaacc  4320
acctcagaag gtggtttgta ccgtacacca ctgagaacgc ggtggttgac cagacaaacc  4380
tacggtagcg taacaggaaa cagctatgac gggcccccta ggcacattgc gtctttataa  4440
acttactaaa ggttttggat agttttgaac ccattgtttg acgaatattc catattaaaa  4500
actctaaaat aaaccccagc caccaacatt tgaaccagcg ttccccccat ctccgctgtg  4560
atcattctag atctgtatta tggcatcgac tatgggaata cagggttatt ctcccatttt  4620
attgaggtat atggccagtt gcgcaacttc tttgatgaaa ttttatttgt ccgttgcatg  4680
attgaaatcc taccagtagt tatatatatg tctttttcat tgttgtactt tggataaagc  4740
tgcttcttca gaacgctccc tactatgctt taaacgctta ttttcggaag aaatcatgtg  4800
ggtcatattt ttttgcttct cgagaaagaa tcaaagaggc caacaacgca gaacaggaaa  4860
cagctatgac gggcccccta ggcacattgc gtctttataa acttactaaa ggttttggat  4920
agttttgaac ccattgtttg acgaatattc catattaaaa actctaaaat aaaccccagc  4980
caccaacatt tgaaccagcg ttccccccat ctccgctgtg atcattctag atctgtatta  5040
tggcatcgac tatgggaata cagggttatt ctcccatttt attgaggtat atggccagtt  5100
gcgcaacttc tttgatgaaa ttttatttgt ccgttgcatg attgaaatcc taccagtagt  5160
tatatatatg tctttttcat tgttgtactt tggataaagc tgcttcttca gaacgctccc  5220
tactatgctt taaacgctta ttttcggaag aaatcatgtg ggtcatattt ttttgcttct  5280
cgagaaagaa tcaaagaggc caacaacgac ctggttcgta ggcttgtcga cgacggcgtt  5340
ctccgtcgtc aggatcatac ctagacacct cagaaggtcc tccctttagt gagggttaat  5400
tctcgagtct ccctatagtg agtcgtatta attccgtgta ttctatagtg tcacctaaat  5460
cgttacggta gcgtactgtc gtaggtttgt ctggtcaacc accgcgctct cagtggtgta  5520
```

-continued

```
cggtacaaac cacctcagaa ggtggtttgt accgtacacc actgagagcg cggtggttga  5580
ccagacaaac ctacggtagc gtaacaggaa acagctatga cgggcccccct agggggttct  5640
gacttcttac gaaaatgtgg ctagcattcc attctctgac gttcaaagaa tcggaataag  5700
tcatggtaat ggtgggaaat ctaatagaag cgactcccat aacctccata tttcttggca  5760
aataattctg tctgggttac cgttcacgag ccttcagaga tctacgacgt gtagtgggtg  5820
ggcttgccct ccagggtgta gtttgtaatt agaatgggat ttcctgtttt aagtacccaa  5880
atacgaaaat tgctcttgat gtttaacggc tcacttttaa gtaaagtttg tgccaatacc  5940
gtgcatggga gtaagttatt gccaatcttc gagaatttag gcaattttgg tatactcaac  6000
tgggtctaat atggtggacg gaatgatttc tcgagaaaga atcaaagagg ccaacaacgc  6060
agaacaggaa acagctatga cgggcccccct agggggttct gacttcttac gaaaatgtgg  6120
ctagcattcc attctctgac gttcaaagaa tcggaataag tcatggtaat ggtgggaaat  6180
ctaatagaag cgactcccat aacctccata tttcttggca aataattctg tctgggttac  6240
cgttcacgag ccttcagaga tctacgacgt gtagtgggtg ggcttgccct ccagggtgta  6300
gtttgtaatt agaatgggat ttcctgtttt aagtacccaa atacgaaaat tgctcttgat  6360
gtttaacggc tcacttttaa gtaaagtttg tgccaatacc gtgcatggga gtaagttatt  6420
gccaatcttc gagaatttag gcaattttgg tatactcaac tgggtctaat atggtggacg  6480
gaatgatttc tcgagaaaga atcaaagagg ccaacaacga cctggttcgt aggcttgtcg  6540
acgacggcgc tctccgtcgt caggatcata cctagacacc tggttaggtc ctccctttag  6600
tgagggttaa ttctcgagtc tccctatagt gagtcgtatt aattccgtgt attctatagt  6660
gtcacctaaa tcgttacgtt ggcgtactgt cgtaggtttg tctggtcaac caccgcgcac  6720
tcagtggtgt acggtacaaa ccacctcaga aggtggtttg taccgtacac cactgagtgc  6780
gcggtggttg accagacaaa cctacggtag cgtaacagga aacagctatg acgggccccc  6840
taggtaagca gtatcttcga cagcttgtct ctccagatgc tcttgggcca tcttccacat  6900
cgtccgtagc agccttggca atttgccatc actggcaaat acacataaat ccaatgaata  6960
cggttaccac catcacatta ccatgcaggt acacagcaag aattgacgtt ggcatatcac  7020
atggtgtaat aaccccactt gtgaaacaac ccagaataag gtacaaggcg gaaatgtcgt  7080
cattctaaaa taaaaggcat ggccaggaat ttgtctaata ccgggaactt aaattcagct  7140
tgaacaccag tcgcaaaaaa ttcaaagaaa gtgattcagg ttcgggttcg tggattggaa  7200
cagcttcttt tgtttcagtg atgagagaat cctcctgtca ctcgagaaag aatcaaagag  7260
gccaacaacg cagaacagga aacagctatg acgggccccc taggtaagca gtatcttcga  7320
cagcttgtct ctccagatgc tcttgggcca tcttccacat cgtccgtagc agccttggca  7380
atttgccatc actggcaaat acacataaat ccaatgaata cggttaccac catcacatta  7440
ccatgcaggt acacagcaag aattgacgtt ggcatatcac atggtgtaat aaccccactt  7500
gtgaaacaac ccagaataag gtacaaggcg gaaatgtcgt cattctaaaa taaaaggcat  7560
ggccaggaat ttgtctaata ccgggaactt aaattcagct tgaacaccag tcgcaaaaaa  7620
ttcaaagaaa gtgattcagg ttcgggttcg tggattggaa cagcttcttt tgtttcagtg  7680
atgagagaat cctcctgtca ctcgagaaag aatcaaagag gccaacaacg acctggttcg  7740
taggcttgtc gacgacggcg cactccgtcg tcaggatcat acctagacac ctgagtaggt  7800
cctcccttta gtgagggtta attctcgagt ctccctatag tgagtcgtat taattccgtg  7860
tattctatag tgtcacctaa atcgttacgg ctacgtaaat tctgcaggac ttctagttat  7920
taatagtaat caattacggg gtcattagtt catagcccat atatggagtt ccgcgttaca  7980
taacttacgg taaatggccc gcctggctga ccgcccaacg acccccgccc attgacgtca  8040
ataatgacgt atgttcccat agtaacgcca atagggactt tccattgacg tcaatgggtg  8100
gagtatttac ggtaaactgc ccacttggca gtacatcaag tgtatcatat gccaagtacg  8160
ccccctattg acgtcaatga cggtaaatgg cccgcctggc attatgccca gtacatgacc  8220
ttatgggact ttcctacttg gcagtacatc tacgtattag tcatcgctat taccatggtc  8280
gaggtgagcc ccacgttctg cttcactctc cccatctccc ccccctcccc acccccaatt  8340
ttgtatttat ttatttttta attattttgt gcagcgatgg gggcgggggg gggggggggg  8400
cgcgcgccag gcggggcggg gcggggcgag gggcggggcg gggcgaggcg gagaggtgcg  8460
gcggcagcca atcagagcgg cgcgctccga aagtttcctt ttatggcgag gcggcggcgg  8520
cggcggccct ataaaaagcg aagcgcgcgg cgggcgggag tcgctgcgcg ctgccttcgc  8580
cccgtgcccc gctccgccgc cgcctcgcgc cgcccgcccc ggctctgact gaccgcgtta  8640
ctcccacagg tgagcgggcg ggacggccct tctcctccgg gctgtaatta gcgcttggtt  8700
taatgacggc ttgtttcttt tctgtggctg cgtgaaagcc ttgaggggct ccgggagggc  8760
cctttgtgcg gggggagcgg ctcggggggt gcgtgcgtgt gtgtgtgcgt ggggagcgcc  8820
gcgtgcggct ccgcgctgcc cggcggctgt gagcgctgcg ggcgcggcgc ggggctttgt  8880
gcgctccgca gtgtgcgcga ggggagcgcg gccgggggcg gtgccccgcg gtgcgggggg  8940
gctgcgaggg gaacaaaggc tgcgtgcggg gtgtgtgcgt gggggggtga gcagggggtg  9000
tgggcgcgtc ggtcgggctg caaccccccc ctgcaccccc ctccccgagt tgctgagcac  9060
ggcccggctt cgggtgcggg gctccgtacg gggcgtggcg cggggctcgc cgtgccgggc  9120
ggggggtggc ggcaggtggg ggtgccgggc ggggcggggc cgcctcgggc cggggagggc  9180
tcgggggagg ggcgcggcgg cccccggagc gccggcggct gtcgaggcgc ggcgagccgc  9240
agccattgcc ttttatggta atcgtgcgag agggcgcagg gacttccttt gtcccaaatc  9300
tgtgcggagc cgaaatctgg gaggcgccgc cgcacccccct ctagcgggcg cggggcgaag  9360
cggtgcggcg ccggcaggaa ggaaatgggc ggggagggcc ttcgtgcgtc gccgcgccgc  9420
cgtccccttc tccctctcca gcctcggggc tgtccgcggg gggacggctg ccttcggggg  9480
ggacggggca gggcggggtt cggcttctgg cgtgtgaccg gcggctctag agcctctgct  9540
aaccatgttc atgccttctt ctttttccta cagctcctgg gcaacgtgct ggttattgtg  9600
ctgtctcatc attttggcaa agaattgatt tgataccgcg ggcccgggat cccctcgagg  9660
gaattacctg aaccgtagcc gccaccatgc cagagccagc gaagtctgct cccgccccga  9720
aaaagggctc caagaaggcg gtgactaagg cgcagaagaa aggcggcaag aagcgcaagc  9780
gcagccgcaa ggagagctat tccatctatg tgtacaaggt tctgaagcag gtccaccctg  9840
acaccggcat ttcgtccaag gccatgggca tcatgaattc gtttgtgaac gacatttttcg  9900
agcgcatcgc tggtgaggct tcccgcctgg cgcattacaa caagcgctcg accatcacct  9960
ccagggagat ccagacggcc gtgcgcctgc tgctgcctgg ggagttggcc aagcacgccg  10020
tgtccgaggg tactaaggcc atcaccaagt acaccagcgc taaggatccc cgggtaccgg  10080
tcgccaccat ggtgagcaag ggcgaggagc tgttcaccgg ggtggtgccc atcctggtcg  10140
agctggacgg cgacgtaaac ggccacaagt tcagcgtgtc cggcgagggc gagggcgatg  10200
ccacctacgg caagctgacc ctgaagttca tctgcaccac cggcaagctg cccgtgccct  10260
```

```
ggcccaccct cgtgaccacc ctgacctggg gcgtgcagtg cttcgcccgc taccccgacc  10320
acatgaagca gcacgacttc ttcaagtccg ccatgcccga aggctacgtc caggagcgca  10380
ccatcttctt caaggacgac ggcaactaca agacccgcgc cgaggtgaag ttcgagggcg  10440
acaccctggt gaaccgcatc gagctgaagg gcatcgactt caaggaggac ggcaacatcc  10500
tggggcacaa gctggagtac aacgccatca gcgacaacgt ctatatcacc gccgacaagc  10560
agaagaacgg catcaaggcc aacttcaaga tccgccacaa catcgaggac ggcagcgtgc  10620
agctcgccga ccactaccag cagaacaccc ccatcggcga cggccccgtg ctgctgcccg  10680
acaaccacta cctgagcacc cagtccaagc tgagcaaaga ccccaacgag aagcgcgatc  10740
acatggtcct gctggagttc gtgaccgccg ccgggatcac tctcggcatg gacgagctgt  10800
acaagtgaac ctccttcgta acaggaaaca gctatgacgg gcccccctagg acgttcccat  10860
agctcctttt gatgtcttaa tgtaggttca acagatatgc ggcttcttcg cattctgatg  10920
gcgtcagcta cgataggcga gagctgaata gttgaaaatt tttagcagat gcctgagaaa  10980
attaaacttg atttgattcc agtaatttac caaaatacgc acagttgcct tcttcgatgt  11040
aatcttttca atcgtactat gtcgtatgca gttagcaaat gaaagtagca acaccaattt  11100
gcgccagaat ttcacgtcga aaatatcctt aaaccttgca agccaagtta cggagttgaa  11160
atttccgtaa gctacggtta tcttccaatg gcccatactt ggctaaatca gagttccctt  11220
tcgtggaaac tgcaatagcc aaattcctcg agaaagaatc aaagaggcca acaacgcaga  11280
acaggaaaca gctatgacgg gcccccctagg acgttcccat agctcctttt gatgtcttaa  11340
tgtaggttca acagatatgc ggcttcttcg cattctgatg gcgtcagcta cgataggcga  11400
gagctgaata gttgaaaatt tttagcagat gcctgagaaa attaaacttg atttgattcc  11460
agtaatttac caaaatacgc acagttgcct tcttcgatgt aatcttttca atcgtactat  11520
gtcgtatgca gttagcaaat gaaagtagca acaccaattt gcgccagaat ttcacgtcga  11580
aaatatcctt aaaccttgca agccaagtta cggagttgaa atttccgtaa gctacggtta  11640
tcttccaatg gcccatactt ggctaaatca gagttccctt tcgtggaaac tgcaatagcc  11700
aaattcctcg agaaagaatc aaagaggcca acaacgacct cttgaggtct gtgccttcta  11760
gttgccagcc atctgttgtt tgcccctccc ccgtgccttc cttgaccctg gaaggtgcca  11820
ctcccactgt cctttcctaa taaaatgagg aaattgcatc gcattgtctg agtaggtgtc  11880
attctattct ggggggtggg gtggggcagg acagcaaggg ggaggattgg gaagagaata  11940
gcaggcatgc tggggatgcg gtgggctcta tggtacg                          11977

SEQ ID NO: 9            moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 9
cgtggattgg aacagcttct                                           20

SEQ ID NO: 10           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 10
agcttgaaca ccagtcgcaa                                           20

SEQ ID NO: 11           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 11
gcatggccag gaatttgtct                                           20

SEQ ID NO: 12           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 12
cgtggattgg aacagcttct tatagcattc tttcttgagg agggcagcaa acgggaagag  60

SEQ ID NO: 13           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 13
agcttgaaca ccagtcgcaa tataagctca gtccatcctc gtaaatcctc atcaatcatc  60
```

```
SEQ ID NO: 14          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 14
gcatggccag gaatttgtct tataaaagtc taatccgtcc ctgcctctat atctccactc  60

SEQ ID NO: 15          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 15
cgtggattgg aacagcttct tatagcattc tttcttgagg agggcagcaa acgggaagag  60

SEQ ID NO: 16          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 16
cgtggatcgg aacagcttct tataagctca gtccatcctc gtaaatcctc atcaatcatc  60

SEQ ID NO: 17          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 17
cgtggatggg aacagcttct tataaaagtc taatccgtcc ctgcctctat atctccactc  60

SEQ ID NO: 18          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 18
cgtggatagg aacagcttct tatacacatt tacagacctc aacctacctc caactctcac  60

SEQ ID NO: 19          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 19
cgtggattgg aacagcttct tataagctca gtccatcctc gtaaatcctc atcaatcatc  60

SEQ ID NO: 20          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 20
cgtggatcgg aacagcttct tataaaagtc taatccgtcc ctgcctctat atctccactc  60

SEQ ID NO: 21          moltype = DNA  length = 60
FEATURE                Location/Qualifiers
misc_feature           1..60
                       note = Synthetic Polynucleotide
source                 1..60
                       mol_type = other DNA
                       organism = synthetic construct
```

```
SEQUENCE: 21
cgtggatggg aacagcttct tatacacatt tacagacctc aacctacctc caactctcac  60

SEQ ID NO: 22          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 22
cgtggatagg aacagcttct tatagcattc tttcttgagg agggcagcaa acgggaagag  60

SEQ ID NO: 23          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 23
cgtggattgg aacagcttct tataaaagtc taatccgtcc ctgcctctat atctccactc  60

SEQ ID NO: 24          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 24
cgtggatcgg aacagcttct tatacacatt tacagacctc aacctacctc caactctcac  60

SEQ ID NO: 25          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 25
cgtggatggg aacagcttct tatagcattc tttcttgagg agggcagcaa acgggaagag  60

SEQ ID NO: 26          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 26
cgtggatagg aacagcttct tataagctca gtccatcctc gtaaatcctc atcaatcatc  60

SEQ ID NO: 27          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 27
cgtggattgg aacagcttct tatacacatt tacagacctc aacctacctc caactctcac  60

SEQ ID NO: 28          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 28
cgtggatcgg aacagcttct tatagcattc tttcttgagg agggcagcaa acgggaagag  60

SEQ ID NO: 29          moltype = DNA  length = 60
FEATURE                Location/Qualifiers
misc_feature           1..60
                       note = Synthetic Polynucleotide
```

```
source                  1..60
                        mol_type = other DNA
                        organism = synthetic construct
SEQUENCE: 29
cgtggatggg aacagcttct tataagctca gtccatcctc gtaaatcctc atcaatcatc  60

SEQ ID NO: 30           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 30
cgtggatagg aacagcttct tataaaagtc taatccgtcc ctgcctctat atctccactc  60

SEQ ID NO: 31           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 31
cgtggattgg aacagcttct tatagcattc tttcttgagg agggcagcaa acgggaagag  60

SEQ ID NO: 32           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 32
cgtggattgc aacagcttct tataagctca gtccatcctc gtaaatcctc atcaatcatc  60

SEQ ID NO: 33           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 33
cgtggattgt aacagcttct tataaaagtc taatccgtcc ctgcctctat atctccactc  60

SEQ ID NO: 34           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 34
cgtggattga aacagcttct tatacacatt tacagacctc aacctacctc caactctcac  60

SEQ ID NO: 35           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 35
cgtggattgg aacagcttct tataagctca gtccatcctc gtaaatcctc atcaatcatc  60

SEQ ID NO: 36           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 36
cgtggattgc aacagcttct tataaaagtc taatccgtcc ctgcctctat atctccactc  60

SEQ ID NO: 37           moltype = DNA  length = 60
FEATURE                 Location/Qualifiers
```

```
misc_feature           1..60
                       note = Synthetic Polynucleotide
source                 1..60
                       mol_type = other DNA
                       organism = synthetic construct
SEQUENCE: 37
cgtggattgt aacagcttct tatacacatt tacagacctc aacctacctc caactctcac  60

SEQ ID NO: 38          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 38
cgtggattga aacagcttct tatagcattc tttcttgagg agggcagcaa acgggaagag  60

SEQ ID NO: 39          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 39
cgtggattgg aacagcttct tataaaagtc taatccgtcc ctgcctctat atctccactc  60

SEQ ID NO: 40          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 40
cgtggattgc aacagcttct tatacacatt tacagacctc aacctacctc caactctcac  60

SEQ ID NO: 41          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 41
cgtggattgt aacagcttct tatagcattc tttcttgagg agggcagcaa acgggaagag  60

SEQ ID NO: 42          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 42
cgtggattga aacagcttct tataagctca gtccatcctc gtaaatcctc atcaatcatc  60

SEQ ID NO: 43          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 43
cgtggattgg aacagcttct tatacacatt tacagacctc aacctacctc caactctcac  60

SEQ ID NO: 44          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 44
cgtggattgc aacagcttct tatagcattc tttcttgagg agggcagcaa acgggaagag  60

SEQ ID NO: 45          moltype = DNA  length = 60
```

```
FEATURE                Location/Qualifiers
misc_feature           1..60
                       note = Synthetic Polynucleotide
source                 1..60
                       mol_type = other DNA
                       organism = synthetic construct
SEQUENCE: 45
cgtggattgt aacagcttct tataagctca gtccatcctc gtaaatcctc atcaatcatc  60

SEQ ID NO: 46          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 46
cgtggattga aacagcttct tataaaagtc taatccgtcc ctgcctctat atctccactc  60

SEQ ID NO: 47          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 47
cgtggattgg aacagcttct tatagcattc tttcttgagg agggcagcaa acgggaagag  60

SEQ ID NO: 48          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 48
cgtggattgg aaaagcttct tataagctca gtccatcctc gtaaatcctc atcaatcatc  60

SEQ ID NO: 49          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 49
cgtggattgg aagagcttct tataaaagtc taatccgtcc ctgcctctat atctccactc  60

SEQ ID NO: 50          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 50
cgtggattgg aatagcttct tatacacatt tacagacctc aacctacctc caactctcac  60

SEQ ID NO: 51          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 51
cgtggattgg aacagcttct tataagctca gtccatcctc gtaaatcctc atcaatcatc  60

SEQ ID NO: 52          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 52
cgtggattgg aaaagcttct tataaaagtc taatccgtcc ctgcctctat atctccactc  60
```

-continued

```
SEQ ID NO: 53          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 53
cgtggattgg aagagcttct tatacacatt tacagacctc aacctacctc caactctcac  60

SEQ ID NO: 54          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 54
cgtggattgg aatagcttct tatagcattc tttcttgagg agggcagcaa acgggaagag  60

SEQ ID NO: 55          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 55
cgtggattgg aacagcttct tataaaagtc taatccgtcc ctgcctctat atctccactc  60

SEQ ID NO: 56          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 56
cgtggattgg aaaagcttct tatacacatt tacagacctc aacctacctc caactctcac  60

SEQ ID NO: 57          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 57
cgtggattgg aagagcttct tatagcattc tttcttgagg agggcagcaa acgggaagag  60

SEQ ID NO: 58          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 58
cgtggattgg aatagcttct tataagctca gtccatcctc gtaaatcctc atcaatcatc  60

SEQ ID NO: 59          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 59
cgtggattgg aacagcttct tatacacatt tacagacctc aacctacctc caactctcac  60

SEQ ID NO: 60          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 60
cgtggattgg aaaagcttct tatagcattc tttcttgagg agggcagcaa acgggaagag  60
```

```
SEQ ID NO: 61          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 61
cgtggattgg aagagcttct tataagctca gtccatcctc gtaaatcctc atcaatcatc  60

SEQ ID NO: 62          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 62
cgtggattgg aatagcttct tataaaagtc taatccgtcc ctgcctctat atctccactc  60

SEQ ID NO: 63          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 63
cgtggattgg aacagcttct tatagcattc tttcttgagg agggcagcaa acgggaagag  60

SEQ ID NO: 64          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 64
cgtggattgg cacagcttct tataagctca gtccatcctc gtaaatcctc atcaatcatc  60

SEQ ID NO: 65          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 65
cgtggattgg gacagcttct tataaaagtc taatccgtcc ctgcctctat atctccactc  60

SEQ ID NO: 66          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 66
cgtggattgg tacagcttct tatacacatt tacagacctc aacctacctc caactctcac  60

SEQ ID NO: 67          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 67
cgtggattgg aacagcttct tataagctca gtccatcctc gtaaatcctc atcaatcatc  60

SEQ ID NO: 68          moltype = DNA  length = 60
FEATURE                Location/Qualifiers
misc_feature           1..60
                       note = Synthetic Polynucleotide
source                 1..60
                       mol_type = other DNA
                       organism = synthetic construct
```

```
SEQUENCE: 68
cgtggattgg cacagcttct tataaaagtc taatccgtcc ctgcctctat atctccactc  60

SEQ ID NO: 69           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 69
cgtggattgg gacagcttct tatacacatt tacagacctc aacctacctc caactctcac  60

SEQ ID NO: 70           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 70
cgtggattgg tacagcttct tatagcattc tttcttgagg agggcagcaa acgggaagag  60

SEQ ID NO: 71           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 71
cgtggattgg aacagcttct tataaaagtc taatccgtcc ctgcctctat atctccactc  60

SEQ ID NO: 72           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 72
cgtggattgg cacagcttct tatacacatt tacagacctc aacctacctc caactctcac  60

SEQ ID NO: 73           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 73
cgtggattgg gacagcttct tatagcattc tttcttgagg agggcagcaa acgggaagag  60

SEQ ID NO: 74           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 74
cgtggattgg tacagcttct tataagctca gtccatcctc gtaaatcctc atcaatcatc  60

SEQ ID NO: 75           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 75
cgtggattgg aacagcttct tatacacatt tacagacctc aacctacctc caactctcac  60

SEQ ID NO: 76           moltype = DNA  length = 60
FEATURE                 Location/Qualifiers
misc_feature            1..60
                        note = Synthetic Polynucleotide
```

```
source                  1..60
                        mol_type = other DNA
                        organism = synthetic construct
SEQUENCE: 76
cgtggattgg cacagcttct tatagcattc tttcttgagg agggcagcaa acgggaagag  60

SEQ ID NO: 77           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 77
cgtggattgg gacagcttct tataagctca gtccatcctc gtaaatcctc atcaatcatc  60

SEQ ID NO: 78           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 78
cgtggattgg tacagcttct tataaaagtc taatccgtcc ctgcctctat atctccactc  60

SEQ ID NO: 79           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 79
agtggattgg aacagcttct tataagctca gtccatcctc gtaaatcctc atcaatcatc  60

SEQ ID NO: 80           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 80
cctggattgg aacagcttct tataagctca gtccatcctc gtaaatcctc atcaatcatc  60

SEQ ID NO: 81           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 81
cgcggattgg aacagcttct tataagctca gtccatcctc gtaaatcctc atcaatcatc  60

SEQ ID NO: 82           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 82
cgtcgattgg aacagcttct tataagctca gtccatcctc gtaaatcctc atcaatcatc  60

SEQ ID NO: 83           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 83
cgtgcattgg aacagcttct tataagctca gtccatcctc gtaaatcctc atcaatcatc  60

SEQ ID NO: 84           moltype = DNA  length = 60
FEATURE                 Location/Qualifiers
```

```
misc_feature            1..60
                        note = Synthetic Polynucleotide
source                  1..60
                        mol_type = other DNA
                        organism = synthetic construct
SEQUENCE: 84
cgtggcttgg aacagcttct tataagctca gtccatcctc gtaaatcctc atcaatcatc  60

SEQ ID NO: 85           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 85
cgtggactgg aacagcttct tataagctca gtccatcctc gtaaatcctc atcaatcatc  60

SEQ ID NO: 86           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 86
ggtggattgg aacagcttct tataaaagtc taatccgtcc ctgcctctat atctccactc  60

SEQ ID NO: 87           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 87
cttggattgg aacagcttct tataaaagtc taatccgtcc ctgcctctat atctccactc  60

SEQ ID NO: 88           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 88
cggggattgg aacagcttct tataaaagtc taatccgtcc ctgcctctat atctccactc  60

SEQ ID NO: 89           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 89
cgttgattgg aacagcttct tataaaagtc taatccgtcc ctgcctctat atctccactc  60

SEQ ID NO: 90           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 90
cgtgtattgg aacagcttct tataaaagtc taatccgtcc ctgcctctat atctccactc  60

SEQ ID NO: 91           moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 91
cgtggtttgg aacagcttct tataaaagtc taatccgtcc ctgcctctat atctccactc  60

SEQ ID NO: 92           moltype = DNA  length = 60
```

```
FEATURE                Location/Qualifiers
misc_feature           1..60
                       note = Synthetic Polynucleotide
source                 1..60
                       mol_type = other DNA
                       organism = synthetic construct
SEQUENCE: 92
cgtggagtgg aacagcttct tataaaagtc taatccgtcc ctgcctctat atctccactc  60

SEQ ID NO: 93          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 93
tgtggattgg aacagcttct tatacacatt tacagacctc aacctacctc caactctcac  60

SEQ ID NO: 94          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 94
catggattgg aacagcttct tatacacatt tacagacctc aacctacctc caactctcac  60

SEQ ID NO: 95          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 95
cgaggattgg aacagcttct tatacacatt tacagacctc aacctacctc caactctcac  60

SEQ ID NO: 96          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 96
cgtagattgg aacagcttct tatacacatt tacagacctc aacctacctc caactctcac  60

SEQ ID NO: 97          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 97
cgtgaattgg aacagcttct tatacacatt tacagacctc aacctacctc caactctcac  60

SEQ ID NO: 98          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 98
cgtgggttgg aacagcttct tatacacatt tacagacctc aacctacctc caactctcac  60

SEQ ID NO: 99          moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 99
cgtggaatgg aacagcttct tatacacatt tacagacctc aacctacctc caactctcac  60
```

```
SEQ ID NO: 100         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 100
tgtggattgg aacagcttct tatagcattc tttcttgagg agggcagcaa acgggaagag  60

SEQ ID NO: 101         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 101
catggattgg aacagcttct tatagcattc tttcttgagg agggcagcaa acgggaagag  60

SEQ ID NO: 102         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 102
cgaggattgg aacagcttct tatagcattc tttcttgagg agggcagcaa acgggaagag  60

SEQ ID NO: 103         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 103
cgtagattgg aacagcttct tatagcattc tttcttgagg agggcagcaa acgggaagag  60

SEQ ID NO: 104         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 104
cgtgaattgg aacagcttct tatagcattc tttcttgagg agggcagcaa acgggaagag  60

SEQ ID NO: 105         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 105
cgtgggttgg aacagcttct tatagcattc tttcttgagg agggcagcaa acgggaagag  60

SEQ ID NO: 106         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 106
cgtggaatgg aacagcttct tatagcattc tttcttgagg agggcagcaa acgggaagag  60

SEQ ID NO: 107         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 107
agtggattgg aacagcttct tataaaagtc taatccgtcc ctgcctctat atctccactc  60
```

```
SEQ ID NO: 108          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 108
cctggattgg aacagcttct tataaaagtc taatccgtcc ctgcctctat atctccactc  60

SEQ ID NO: 109          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 109
cgcggattgg aacagcttct tataaaagtc taatccgtcc ctgcctctat atctccactc  60

SEQ ID NO: 110          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 110
cgtcgattgg aacagcttct tataaaagtc taatccgtcc ctgcctctat atctccactc  60

SEQ ID NO: 111          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 111
cgtgcattgg aacagcttct tataaaagtc taatccgtcc ctgcctctat atctccactc  60

SEQ ID NO: 112          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 112
cgtggcttgg aacagcttct tataaaagtc taatccgtcc ctgcctctat atctccactc  60

SEQ ID NO: 113          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 113
cgtggactgg aacagcttct tataaaagtc taatccgtcc ctgcctctat atctccactc  60

SEQ ID NO: 114          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 114
ggtggattgg aacagcttct tatacacatt tacagacctc aacctacctc caactctcac  60

SEQ ID NO: 115          moltype = DNA  length = 60
FEATURE                 Location/Qualifiers
misc_feature            1..60
                        note = Synthetic Polynucleotide
source                  1..60
                        mol_type = other DNA
                        organism = synthetic construct
```

```
SEQUENCE: 115
cttggattgg aacagcttct tatacacatt tacagacctc aacctacctc caactctcac  60

SEQ ID NO: 116         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 116
cggggattgg aacagcttct tatacacatt tacagacctc aacctacctc caactctcac  60

SEQ ID NO: 117         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 117
cgttgattgg aacagcttct tatacacatt tacagacctc aacctacctc caactctcac  60

SEQ ID NO: 118         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 118
cgtgtattgg aacagcttct tatacacatt tacagacctc aacctacctc caactctcac  60

SEQ ID NO: 119         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 119
cgtggtttgg aacagcttct tatacacatt tacagacctc aacctacctc caactctcac  60

SEQ ID NO: 120         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 120
cgtggagtgg aacagcttct tatacacatt tacagacctc aacctacctc caactctcac  60

SEQ ID NO: 121         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 121
ggtggattgg aacagcttct tatagcattc tttcttgagg agggcagcaa acgggaagag  60

SEQ ID NO: 122         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 122
cttggattgg aacagcttct tatagcattc tttcttgagg agggcagcaa acgggaagag  60

SEQ ID NO: 123         moltype = DNA  length = 60
FEATURE                Location/Qualifiers
misc_feature           1..60
                       note = Synthetic Polynucleotide
```

```
source                  1..60
                        mol_type = other DNA
                        organism = synthetic construct
SEQUENCE: 123
cggggattgg aacagcttct tatagcattc tttcttgagg agggcagcaa acgggaagag  60

SEQ ID NO: 124          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 124
cgttgattgg aacagcttct tatagcattc tttcttgagg agggcagcaa acgggaagag  60

SEQ ID NO: 125          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 125
cgtgtattgg aacagcttct tatagcattc tttcttgagg agggcagcaa acgggaagag  60

SEQ ID NO: 126          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 126
cgtggtttgg aacagcttct tatagcattc tttcttgagg agggcagcaa acgggaagag  60

SEQ ID NO: 127          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 127
cgtggagtgg aacagcttct tatagcattc tttcttgagg agggcagcaa acgggaagag  60

SEQ ID NO: 128          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 128
tgtggattgg aacagcttct tataagctca gtccatcctc gtaaatcctc atcaatcatc  60

SEQ ID NO: 129          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 129
catggattgg aacagcttct tataagctca gtccatcctc gtaaatcctc atcaatcatc  60

SEQ ID NO: 130          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 130
cgaggattgg aacagcttct tataagctca gtccatcctc gtaaatcctc atcaatcatc  60

SEQ ID NO: 131          moltype = DNA  length = 60
FEATURE                 Location/Qualifiers
```

```
misc_feature          1..60
                      note = Synthetic Polynucleotide
source                1..60
                      mol_type = other DNA
                      organism = synthetic construct
SEQUENCE: 131
cgtagattgg aacagcttct tataagctca gtccatcctc gtaaatcctc atcaatcatc  60

SEQ ID NO: 132        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 132
cgtgaattgg aacagcttct tataagctca gtccatcctc gtaaatcctc atcaatcatc  60

SEQ ID NO: 133        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 133
cgtgggttgg aacagcttct tataagctca gtccatcctc gtaaatcctc atcaatcatc  60

SEQ ID NO: 134        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 134
cgtggaatgg aacagcttct tataagctca gtccatcctc gtaaatcctc atcaatcatc  60

SEQ ID NO: 135        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 135
agtggattgg aacagcttct tatacacatt tacagacctc aacctacctc caactctcac  60

SEQ ID NO: 136        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 136
cctggattgg aacagcttct tatacacatt tacagacctc aacctacctc caactctcac  60

SEQ ID NO: 137        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 137
cgcggattgg aacagcttct tatacacatt tacagacctc aacctacctc caactctcac  60

SEQ ID NO: 138        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 138
cgtcgattgg aacagcttct tatacacatt tacagacctc aacctacctc caactctcac  60

SEQ ID NO: 139        moltype = DNA  length = 60
```

```
FEATURE                Location/Qualifiers
misc_feature           1..60
                       note = Synthetic Polynucleotide
source                 1..60
                       mol_type = other DNA
                       organism = synthetic construct
SEQUENCE: 139
cgtgcattgg aacagcttct tatacacatt tacagacctc aacctacctc caactctcac  60

SEQ ID NO: 140         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 140
cgtggcttgg aacagcttct tatacacatt tacagacctc aacctacctc caactctcac  60

SEQ ID NO: 141         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 141
cgtggactgg aacagcttct tatacacatt tacagacctc aacctacctc caactctcac  60

SEQ ID NO: 142         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 142
agtggattgg aacagcttct tatagcattc tttcttgagg agggcagcaa acgggaagag  60

SEQ ID NO: 143         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 143
cctggattgg aacagcttct tatagcattc tttcttgagg agggcagcaa acgggaagag  60

SEQ ID NO: 144         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 144
cgcggattgg aacagcttct tatagcattc tttcttgagg agggcagcaa acgggaagag  60

SEQ ID NO: 145         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 145
cgtcgattgg aacagcttct tatagcattc tttcttgagg agggcagcaa acgggaagag  60

SEQ ID NO: 146         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 146
cgtgcattgg aacagcttct tatagcattc tttcttgagg agggcagcaa acgggaagag  60
```

```
SEQ ID NO: 147         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 147
cgtggcttgg aacagcttct tatagcattc tttcttgagg agggcagcaa acgggaagag  60

SEQ ID NO: 148         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 148
cgtggactgg aacagcttct tatagcattc tttcttgagg agggcagcaa acgggaagag  60

SEQ ID NO: 149         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 149
ggtggattgg aacagcttct tataagctca gtccatcctc gtaaatcctc atcaatcatc  60

SEQ ID NO: 150         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 150
cttggattgg aacagcttct tataagctca gtccatcctc gtaaatcctc atcaatcatc  60

SEQ ID NO: 151         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 151
cggggattgg aacagcttct tataagctca gtccatcctc gtaaatcctc atcaatcatc  60

SEQ ID NO: 152         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 152
cgttgattgg aacagcttct tataagctca gtccatcctc gtaaatcctc atcaatcatc  60

SEQ ID NO: 153         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 153
cgtgtattgg aacagcttct tataagctca gtccatcctc gtaaatcctc atcaatcatc  60

SEQ ID NO: 154         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 154
cgtggtttgg aacagcttct tataagctca gtccatcctc gtaaatcctc atcaatcatc  60
```

```
SEQ ID NO: 155          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 155
cgtggagtgg aacagcttct tataagctca gtccatcctc gtaaatcctc atcaatcatc  60

SEQ ID NO: 156          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 156
tgtggattgg aacagcttct tataaaagtc taatccgtcc ctgcctctat atctccactc  60

SEQ ID NO: 157          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 157
catggattgg aacagcttct tataaaagtc taatccgtcc ctgcctctat atctccactc  60

SEQ ID NO: 158          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 158
cgaggattgg aacagcttct tataaaagtc taatccgtcc ctgcctctat atctccactc  60

SEQ ID NO: 159          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 159
cgtagattgg aacagcttct tataaaagtc taatccgtcc ctgcctctat atctccactc  60

SEQ ID NO: 160          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 160
cgtgaattgg aacagcttct tataaaagtc taatccgtcc ctgcctctat atctccactc  60

SEQ ID NO: 161          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 161
cgtgggttgg aacagcttct tataaaagtc taatccgtcc ctgcctctat atctccactc  60

SEQ ID NO: 162          moltype = DNA  length = 60
FEATURE                 Location/Qualifiers
misc_feature            1..60
                        note = Synthetic Polynucleotide
source                  1..60
                        mol_type = other DNA
                        organism = synthetic construct
```

```
SEQUENCE: 162
cgtggaatgg aacagcttct tataaaagtc taatccgtcc ctgcctctat atctccactc  60

SEQ ID NO: 163         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 163
cgtggattgg aacagcttct tatagcattc tttcttgagg agggcagcaa acgggaagag  60

SEQ ID NO: 164         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 164
cgtggattgg aacagcttct tataagctca gtccatcctc gtaaatcctc atcaatcatc  60

SEQ ID NO: 165         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 165
cgtggattgg aacagcttct tataaaagtc taatccgtcc ctgcctctat atctccactc  60

SEQ ID NO: 166         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 166
cgtggattgg aacagcttct tatacacatt tacagacctc aacctacctc caactctcac  60

SEQ ID NO: 167         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 167
taaagaatgc gttggggcga tatagcattc tttcttgagg agggcagcaa acgggaagag  60

SEQ ID NO: 168         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 168
ttccacatcc ctctgcgatt tataagctca gtccatcctc gtaaatcctc atcaatcatc  60

SEQ ID NO: 169         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 169
taaagaacgc gttggggcga tataaaagtc taatccgtcc ctgcctctat atctccactc  60

SEQ ID NO: 170         moltype = DNA  length = 60
FEATURE                Location/Qualifiers
misc_feature           1..60
                       note = Synthetic Polynucleotide
```

```
source                  1..60
                        mol_type = other DNA
                        organism = synthetic construct
SEQUENCE: 170
ttccacaccc ctctgcgatt tatacacatt tacagacctc aacctacctc caactctcac  60

SEQ ID NO: 171          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 171
taaagaatgc gttggggcga tatagcattc tttcttgagg agggcagcaa acgggaagag  60

SEQ ID NO: 172          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 172
ttccacatcc ctctgcgatt tataagctca gtccatcctc gtaaatcctc atcaatcatc  60

SEQ ID NO: 173          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 173
taaagaacgc gttggggcga tataaaagtc taatccgtcc ctgcctctat atctccactc  60

SEQ ID NO: 174          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 174
ttccacaccc ctctgcgatt tatacacatt tacagacctc aacctacctc caactctcac  60

SEQ ID NO: 175          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 175
ataccaatcc cttcggcgat tataaaagtc taatccgtcc ctgcctctat atctccactc  60

SEQ ID NO: 176          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 176
ttagcgatac atccgaccca tatagcattc tttcttgagg agggcagcaa acgggaagag  60

SEQ ID NO: 177          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 177
ataccaaccc cttcggcgat tataagctca gtccatcctc gtaaatcctc atcaatcatc  60

SEQ ID NO: 178          moltype = DNA  length = 60
FEATURE                 Location/Qualifiers
```

```
misc_feature           1..60
                       note = Synthetic Polynucleotide
source                 1..60
                       mol_type = other DNA
                       organism = synthetic construct
SEQUENCE: 178
ttagcgacac atccgaccca tatacacatt tacagacctc aacctacctc caactctcac  60

SEQ ID NO: 179         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 179
ataccaatcc cttcggcgat tataaaagtc taatccgtcc ctgcctctat atctccactc  60

SEQ ID NO: 180         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 180
ttagcgatac atccgaccca tatagcattc tttcttgagg agggcagcaa acgggaagag  60

SEQ ID NO: 181         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 181
ataccaaccc cttcggcgat tataagctca gtccatcctc gtaaatcctc atcaatcatc  60

SEQ ID NO: 182         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 182
ttagcgacac atccgaccca tatacacatt tacagacctc aacctacctc caactctcac  60

SEQ ID NO: 183         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 183
ctccaactga atgaaggcga tataagctca gtccatcctc gtaaatcctc atcaatcatc  60

SEQ ID NO: 184         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 184
ttcaacatac gccaatgcgg tataaaagtc taatccgtcc ctgcctctat atctccactc  60

SEQ ID NO: 185         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 185
ctccaaccga atgaaggcga tatagcattc tttcttgagg agggcagcaa acgggaagag  60

SEQ ID NO: 186         moltype = DNA  length = 60
```

```
FEATURE                 Location/Qualifiers
misc_feature            1..60
                        note = Synthetic Polynucleotide
source                  1..60
                        mol_type = other DNA
                        organism = synthetic construct
SEQUENCE: 186
ttcaacacac gccaatgcgg tatacacatt tacagacctc aacctacctc caactctcac  60

SEQ ID NO: 187          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 187
ctccaactga atgaaggcga tataagctca gtccatcctc gtaaatcctc atcaatcatc  60

SEQ ID NO: 188          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 188
ttcaacatac gccaatgcgg tataaaagtc taatccgtcc ctgcctctat atctccactc  60

SEQ ID NO: 189          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 189
ctccaaccga atgaaggcga tatagcattc tttcttgagg agggcagcaa acgggaagag  60

SEQ ID NO: 190          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 190
ttcaacacac gccaatgcgg tatacacatt tacagacctc aacctacctc caactctcac  60

SEQ ID NO: 191          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 191
atcgcaatcc accaaagcag tatagcattc tttcttgagg agggcagcaa acgggaagag  60

SEQ ID NO: 192          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 192
gtcaacatac acgccctgat tataagctca gtccatcctc gtaaatcctc atcaatcatc  60

SEQ ID NO: 193          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 193
atcgcaaccc accaaagcag tataaaagtc taatccgtcc ctgcctctat atctccactc  60
```

```
SEQ ID NO: 194          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 194
gtcaacacac acgccctgat tatacacatt tacagacctc aacctacctc caactctcac  60

SEQ ID NO: 195          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 195
atcgcaatcc accaaagcag tatagcattc tttcttgagg agggcagcaa acgggaagag  60

SEQ ID NO: 196          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 196
gtcaacatac acgccctgat tataagctca gtccatcctc gtaaatcctc atcaatcatc  60

SEQ ID NO: 197          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 197
atcgcaaccc accaaagcag tataaaagtc taatccgtcc ctgcctctat atctccactc  60

SEQ ID NO: 198          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 198
gtcaacacac acgccctgat tatacacatt tacagacctc aacctacctc caactctcac  60

SEQ ID NO: 199          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 199
ttagagatga acgccaacgc tataaaagtc taatccgtcc ctgcctctat atctccactc  60

SEQ ID NO: 200          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 200
acacgactca actccgaaga tatagcattc tttcttgagg agggcagcaa acgggaagag  60

SEQ ID NO: 201          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 201
ttagagacga acgccaacgc tataagctca gtccatcctc gtaaatcctc atcaatcatc  60
```

```
SEQ ID NO: 202          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 202
acacgaccca actccgaaga tatacacatt tacagacctc aacctacctc caactctcac  60

SEQ ID NO: 203          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 203
ttagagatga acgccaacgc tataaaagtc taatccgtcc ctgcctctat atctccactc  60

SEQ ID NO: 204          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 204
acacgactca actccgaaga tatagcattc tttcttgagg agggcagcaa acgggaagag  60

SEQ ID NO: 205          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 205
ttagagacga acgccaacgc tataagctca gtccatcctc gtaaatcctc atcaatcatc  60

SEQ ID NO: 206          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 206
acacgaccca actccgaaga tatacacatt tacagacctc aacctacctc caactctcac  60

SEQ ID NO: 207          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 207
atccgcatca acggtagcaa tataagctca gtccatcctc gtaaatcctc atcaatcatc  60

SEQ ID NO: 208          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 208
atcagcgtga caactgtgct tataaaagtc taatccgtcc ctgcctctat atctccactc  60

SEQ ID NO: 209          moltype = DNA  length = 60
FEATURE                 Location/Qualifiers
misc_feature            1..60
                        note = Synthetic Polynucleotide
source                  1..60
                        mol_type = other DNA
                        organism = synthetic construct
```

```
SEQUENCE: 209
atccgcacca acggtagcaa tatagcattc tttcttgagg agggcagcaa acgggaagag  60

SEQ ID NO: 210         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 210
atcagcgcga caactgtgct tatacacatt tacagacctc aacctacctc caactctcac  60

SEQ ID NO: 211         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 211
atccgcatca acggtagcaa tataagctca gtccatcctc gtaaatcctc atcaatcatc  60

SEQ ID NO: 212         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 212
atcagcgtga caactgtgct tataaaagtc taatccgtcc ctgcctctat atctccactc  60

SEQ ID NO: 213         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 213
atccgcacca acggtagcaa tatagcattc tttcttgagg agggcagcaa acgggaagag  60

SEQ ID NO: 214         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 214
atcagcgcga caactgtgct tatacacatt tacagacctc aacctacctc caactctcac  60

SEQ ID NO: 215         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 215
ttacaactga ctctccgtcc tatagcattc tttcttgagg agggcagcaa acgggaagag  60

SEQ ID NO: 216         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 216
ttacaactga ctcctcctcg tataagctca gtccatcctc gtaaatcctc atcaatcatc  60

SEQ ID NO: 217         moltype = DNA  length = 60
FEATURE                Location/Qualifiers
misc_feature           1..60
                       note = Synthetic Polynucleotide
```

```
source                  1..60
                        mol_type = other DNA
                        organism = synthetic construct
SEQUENCE: 217
ttacaaccga ctctccgtcc tataaaagtc taatccgtcc ctgcctctat atctccactc  60

SEQ ID NO: 218          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 218
ttacaaccga ctcctcctcg tatacacatt tacagacctc aacctacctc caactctcac  60

SEQ ID NO: 219          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 219
ttacaactga ctcgtgcggt tataaaagtc taatccgtcc ctgcctctat atctccactc  60

SEQ ID NO: 220          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 220
ttacaactga ctctggggtg tatagcattc tttcttgagg agggcagcaa acgggaagag  60

SEQ ID NO: 221          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 221
ttacaaccga ctcgtgcggt tataagctca gtccatcctc gtaaatcctc atcaatcatc  60

SEQ ID NO: 222          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 222
ttacaaccga ctctggggtg tatacacatt tacagacctc aacctacctc caactctcac  60

SEQ ID NO: 223          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 223
ttacaactga cttgggcgtc tataagctca gtccatcctc gtaaatcctc atcaatcatc  60

SEQ ID NO: 224          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 224
ttacaactga ctgcgtcctg tataaaagtc taatccgtcc ctgcctctat atctccactc  60

SEQ ID NO: 225          moltype = DNA  length = 60
FEATURE                 Location/Qualifiers
```

```
misc_feature          1..60
                      note = Synthetic Polynucleotide
source                1..60
                      mol_type = other DNA
                      organism = synthetic construct
SEQUENCE: 225
ttacaaccga cttgggcgtc tatagcattc tttcttgagg agggcagcaa acgggaagag  60

SEQ ID NO: 226        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 226
ttacaaccga ctgcgtcctg tatacacatt tacagacctc aacctacctc caactctcac  60

SEQ ID NO: 227        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 227
ttacaactga ctgtcgccct tatagcattc tttcttgagg agggcagcaa acgggaagag  60

SEQ ID NO: 228        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 228
ttacaactga ctgtgcctgc tataagctca gtccatcctc gtaaatcctc atcaatcatc  60

SEQ ID NO: 229        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 229
ttacaaccga ctgtcgccct tataaaagtc taatccgtcc ctgcctctat atctccactc  60

SEQ ID NO: 230        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 230
ttacaaccga ctgtgcctgc tatacacatt tacagacctc aacctacctc caactctcac  60

SEQ ID NO: 231        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 231
ttacaactga ctggtcgctc tataaaagtc taatccgtcc ctgcctctat atctccactc  60

SEQ ID NO: 232        moltype = DNA  length = 60
FEATURE               Location/Qualifiers
misc_feature          1..60
                      note = Synthetic Polynucleotide
source                1..60
                      mol_type = other DNA
                      organism = synthetic construct
SEQUENCE: 232
ttacaactga ctgctgtccg tatagcattc tttcttgagg agggcagcaa acgggaagag  60

SEQ ID NO: 233        moltype = DNA  length = 60
```

```
FEATURE                Location/Qualifiers
misc_feature           1..60
                       note = Synthetic Polynucleotide
source                 1..60
                       mol_type = other DNA
                       organism = synthetic construct
SEQUENCE: 233
ttacaaccga ctggtcgctc tataagctca gtccatcctc gtaaatcctc atcaatcatc  60

SEQ ID NO: 234         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 234
ttacaaccga ctgctgtccg tatacacatt tacagacctc aacctacctc caactctcac  60

SEQ ID NO: 235         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 235
ttacaactga ctggctgtgg tataagctca gtccatcctc gtaaatcctc atcaatcatc  60

SEQ ID NO: 236         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 236
ttacaactga cttccctggc tataaaagtc taatccgtcc ctgcctctat atctccactc  60

SEQ ID NO: 237         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 237
ttacaaccga ctggctgtgg tatagcattc tttcttgagg agggcagcaa acgggaagag  60

SEQ ID NO: 238         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 238
ttacaaccga cttccctggc tatacacatt tacagacctc aacctacctc caactctcac  60

SEQ ID NO: 239         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 239
acgcattctt tatgacacgg                                              20

SEQ ID NO: 240         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 240
agggatgtgg aaacagaaca                                              20
```

```
SEQ ID NO: 241          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 241
agggattggt atctgaacag                                              20

SEQ ID NO: 242          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 242
atgtatcgct aacaacccag                                              20

SEQ ID NO: 243          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 243
attcagttgg aggataacgg                                              20

SEQ ID NO: 244          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 244
gcgtatgttg aatcacaggg                                              20

SEQ ID NO: 245          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 245
gtggattgcg atacataccg                                              20

SEQ ID NO: 246          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 246
gtgtatgttg acgaatcaca                                              20

SEQ ID NO: 247          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 247
gttcatctct aatagccgag                                              20

SEQ ID NO: 248          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 248
gttgagtcgt gtaagcagag                                              20
```

```
SEQ ID NO: 249         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 249
gttgatgcgg atacaatgtg                                            20

SEQ ID NO: 250         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 250
tgtcacgctg atgaatctgg                                            20

SEQ ID NO: 251         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 251
agtcagttgt aatcacaggg                                            20

SEQ ID NO: 252         moltype = DNA  length = 439
FEATURE                Location/Qualifiers
misc_feature           1..439
                       note = Synthetic Polynucleotide
source                 1..439
                       mol_type = other DNA
                       organism = synthetic construct
SEQUENCE: 252
gcctccagat tcatcagcgt gacaactgtg ctgtaggacc ccacattgta tccgcatcaa  60
cggtagcaag caatcccact ctgcttacac gactcaactc cgaagagtcg aaccgctcgg  120
ctattagaga tgaacgccaa cgcgtcggcc cctgtgattc gtcaacatac acgccctgat  180
aaatatcctc ggtatgtatc gcaatccacc aaagcagagc gacccaccct gtgattcaac  240
atacgccaat gcggacgcgg ccgccgttat cctccaactg aatgaaggcg acaaccaccc  300
ctgggttgtt agcgatacat ccgacccaat cataccgctg ttcagatacc aatcccttcg  360
gcgatttccc gccgtgttct gtttccacat ccctctgcga ttcgtggccc gccgtgtcat  420
aaagaatgcg ttggggcga                                             439

SEQ ID NO: 253         moltype = DNA  length = 10491
FEATURE                Location/Qualifiers
misc_feature           1..10491
                       note = Synthetic Polynucleotide
source                 1..10491
                       mol_type = other DNA
                       organism = synthetic construct
SEQUENCE: 253
gtcgacggat cgggagatct cccgatcccc tatggtgcac tctcagtaca atctgctctg  60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg ggccagatat acgcgttgac  240
attgattatt gactagttat taatagtaat caattacggg gtcattagtt catagcccat  300
atatggagtt ccgcgttaca taacttacgg taaatggccc gcctggctga ccgcccaacg  360
acccccgccc attgacgtca ataatgacgt atgttcccat agtaacgcca atagggactt  420
tccattgacg tcaatgggtg gagtatttac ggtaaactgc ccacttggca gtacatcaag  480
tgtatcatat gccaagtacg ccccctattg acgtcaatga cggtaaatgg cccgcctggc  540
attatgccca gtacatgacc ttatgggact ttcctacttg gcagtacatc tacgtattag  600
tcatcgctat taccatggtg atgcggtttt ggcagtacat caatgggcgt ggatagcggt  660
ttgactcacg gggatttcca agtctccacc ccattgacgt caatgggagt ttgttttggc  720
accaaaatca acgggacttt ccaaaatgtc gtaacaactc cgccccattg acgcaaatgg  780
gcggtaggcg tgtacggtgg gaggtctata taagcagcgc gttttgcctg tactgggtct  840
ctctggttag accagatctg agcctgggag ctctctggct aactagggaa cccactgctt  900
aagcctcaat aaagcttgcc ttgagtgctt caagtagtgt gtgcccgtct gttgtgtgac  960
tctggtaact agagatccct cagacccttt tagtcagtgt ggaaaatctc tagcagtggc  1020
gcccgaacag ggacttgaaa gcgaaaggga aaccagagga gctctctcga cgcaggactc  1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
```

```
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
gaaggtggag agagagacag agacagatcc attcgattag tgaacggatc ggcactgcgt  2400
gcgccaattc tgcagacaaa tggcagtatt catccacaat tttaaaagaa aaggggggat  2460
tggggggtac agtgcagggg aaagaatagt agacataata gcaacagaca tacaaactaa  2520
agaattacaa aaacaaatta caaaaattca aaattttcgg gtttattaca gggacagcag  2580
agatccagtt tggttaattt atagcctcca gattcatcag cgtgacaact gtgctgtagg  2640
accccacatt gtatccgcat caacggtagc aagcaatccc actctgctta cacgactcaa  2700
ctccgaagag tcgaaccgct cggctattag agatgaacgc caacgcgtcg gcccctgtga  2760
ttcgtcaaca tacacgccct gataaatatc ctcggtatgt atcgcaatcc accaaagcag  2820
agcgacccac cctgtgattc aacatacgcc aatgcggacg cggccgccgt tatcctccaa  2880
ctgaatgaag gcgacaacca cccctgggtt gttagcgata catccgaccc aatcataccg  2940
ctgttcagat accaatccct tcggcgattt cccgccgtgt tctgtttcca catccctctg  3000
cgattcgtgg cccgccgtgt cataaagaat gcgttggggc gaccctttag tgagggttaa  3060
ttctcgagtc tccctatagt gagtcgtatt aattccgtgt attctatagt gtcacctaaa  3120
tcgttacggg attaacccgt gtcggctcca gatctggcct ccgcgccggg ttttggcgcc  3180
tcccgcgggc gcccccctcc tcacggcgag cgctgccacg tcagacgaag ggcgcagcga  3240
gcgtcctgat ccttccgccc ggacgctcag gacagcggcc cgctgctcat aagactcggc  3300
cttagaaccc cagtatcagc agaaggacat tttaggacgg gacttgggtg actctagggc  3360
actggttttc tttccagaga gcggaacagg cgaggaaaag tagtcccttc tcggcgattc  3420
tgcggaggga tctccgtggg gcggtgaacg ccgatgatta tataaggacg cgccgggtgt  3480
ggcacagcta gttccgtcgc agccgggatt tgggtcgcgg ttcttgtttg tggatcgctg  3540
tgatcgtcac ttggtgagta gcgggctgct gggctggccg gggctttcgt ggccgccggg  3600
ccgctcggtg ggacggaagc gtgtggagag accgccaagg gctgtagtct gggtccgcga  3660
gcaaggttgc cctgaactgg gggttggggg gagcgcagca aaatggcggc tgttcccgag  3720
tcttgaatgg aagacgcttg tgaggcgggc tgtgaggtcg ttgaaacaag gtgggggca  3780
tggtgggcgg caagaaccca aggtcttgag gccttcgcta atgcgggaaa gctcttattc  3840
gggtgagatg ggctggggca ccatctgggg accctgacgt gaagtttgtc actgactgga  3900
gaactcggtt tgtcgtctgt tgcgggggcg gcagttatgg cggtgccgtt gggcagtgca  3960
cccgtacctt tgggagcgcg cgccctcgtc gtgtcgtgac gtcacccgtt ctgttggctt  4020
ataatgcagg gtggggccac ctgccggtag gtgtgcggta ggcttttctc cgtcgcagga  4080
cgcagggttc gggcctaggg taggctctcc tgaatcgaca ggcgccggac ctctggtgag  4140
gggagggata agtgaggcgt cagtttcttt ggtcggtttt atgtacctat cttcttaagt  4200
agctgaagct ccggttttga actatgcgct cggggttggc gagtgtgttt tgtgaagttt  4260
tttaggcacc ttttgaaatg taatcatttg ggtcaatatg taattttcag tgttagacta  4320
gtaaattgtc cgctaaattc tggccgtttt tggctttttt gttagacgaa gcttgggctg  4380
caggtcgact ctagaggatc cccgggtaag gatccccggg taccggtcgc caccatggtg  4440
agcaagggcg aggagctgtt caccggggtg gtgcccatcc tggtcgagct ggacggcgac  4500
gtaaacggcc acaagttcag cgtgtccggc gagggcgagg gcgatgccac ctacggcaag  4560
ctgaccctga agttcatctg caccaccggc aagctgcccg tgccctggcc caccctcgtg  4620
accaccctga cctggggcgt gcagtgcttc gcccgctacc ccgaccacat gaagcagcac  4680
gacttcttca agtccgccat gcccgaaggc tacgtccagg agcgcaccat cttcttcaag  4740
gacgacggca actacaagac ccgcgccgag gtgaagttcg agggcgacac cctggtgaac  4800
cgcatcgagc tgaagggcat cgacttcaag gaggacggca acatcctggg gcacaagctg  4860
gagtacaacg ccatcagcga caacgtctat atcaccgccg acaagcagaa gaacggcatc  4920
aaggccaact tcaagatccg ccacaacatc gaggacggca gcgtgcagct cgccgaccac  4980
taccagcaga acacccccat cggcgacggc cccgtgctgc tgcccgacaa ccactacctg  5040
agcacccagt ccaagctgag caaagacccc aacgagaagc gcgatcacat ggtcctgctg  5100
gagttcgtga ccgccgccgg gatcactctc ggcatggacg agctgtacaa gtgaacctga  5160
attcgatatc aagcttatcg ataatcaacc tctggattac aaaatttgtg aaagattgac  5220
tggtattctt aactatgttg ctccttttac gctatgtgga tacgctgctt taatgccttt  5280
gtatcatgct attgcttccc gtatggcttt cattttctcc tccttgtata aatcctggtt  5340
gctgtctctt tatgaggagt tgtggcccgt tgtcaggcaa cgtggcgtgg tgtgcactgt  5400
gtttgctgac gcaaccccca ctggttgggg cattgccacc acctgtcagc tcctttccgg  5460
gactttcgct ttccccctcc ctattgccac ggcggaactc atcgccgcct gccttgcccg  5520
ctgctggaca ggggctcggc tgttgggcac tgacaattcc gtggtgttgt cggggaaatc  5580
atcgtccttt ccttggctgc tcgcctgtgt tgccacctgg attctgcgcg ggacgtcctt  5640
ctgctacgtc ccttcggccc tcaatccagc ggaccttcct tcccgcggcc tgctgccggc  5700
tctgcggcct cttccgcgtc ttcgccttcg ccctcagacg agtcggatct ccctttgggc  5760
cgcctccccg catcgatacc gtcgacctcg agacctagaa aaacatggag caatcacaag  5820
tagcaataca gcagctacca atgctgattg tgcctggcta gaagcacaag aggaggagga  5880
ggtgggtttt ccagtcacac ctcaggtacc tttaagacca atgacttaca aggcagctgt  5940
agatcttagc cactttttaa aagaaaaggg gggactggaa gggctaattc actcccaacg  6000
aagacaagat atccttgatc tgtggatcta ccacacacaa ggctacttcc ctgattggca  6060
gaactacaca ccagggccag ggatcagata tccactgacc tttggatggt gctacaagct  6120
```

```
agtaccagtt gagcaagaga aggtagaaga agccaatgaa ggagagaaca cccgcttgtt  6180
acaccctgtg agcctgcatg ggatggatga cccggagaga gaagtattag agtggaggtt  6240
tgacagccgc ctagcatttc atcacatggc ccgagagctg catccggact gtactgggtc  6300
tctctggtta gaccagatct gagcctggga gctctctggc taactaggga acccactgct  6360
taagcctcaa taaagcttgc cttgagtgct tcaagtagtg tgtgcccgtc tgttgtgtga  6420
ctctggtaac tagagatccc tcagaccctt ttagtcagtg tggaaaatct ctagcagggc  6480
ccgtttaaac ccgctgatca gcctcgactg tgccttctag ttgccagcca tctgttgttt  6540
gcccctcccc cgtgccttcc ttgaccctgg aaggtgccac tcccactgtc ctttcctaat  6600
aaaatgagga aattgcatcg cattgtctga gtaggtgtca ttctattctg gggggtgggg  6660
tggggcagga cagcaagggg gaggattggg aagacaatag caggcatgct ggggatgcgg  6720
tgggctctat ggcttctgag gcggaaagaa ccagctgggg ctctaggggg tatccccacg  6780
cgccctgtag cggcgcatta agcgcggcgg gtgtggtggt tacgcgcagc gtgaccgcta  6840
cacttgccag cgccctagcg cccgctcctt tcgctttctt cccttccttt ctcgccacgt  6900
tcgccggctt tccccgtcaa gctctaaatc gggggctccc tttagggttc cgatttagtg  6960
ctttacggca cctcgacccc aaaaaacttg attagggtga tggttcacgt agtgggccat  7020
cgccctgata gacggttttt cgccctttga cgttggagtc cacgttcttt aatagtggac  7080
tcttgttcca aactggaaca acactcaacc ctatctcggt ctattctttt gatttataag  7140
ggattttgcc gatttcggcc tattggttaa aaaatgagct gatttaacaa aaatttaacg  7200
cgaattaatt ctgtggaatg tgtgtcagtt agggtgtgga aagtccccag gctccccagc  7260
aggcagaagt atgcaaagca tgcatctcaa ttagtcagca accaggtgtg gaaagtcccc  7320
aggctcccca gcaggcagaa gtatgcaaag catgcatctc aattagtcag caaccatagt  7380
cccgccccta actccgccca tcccgcccct aactccgccc agttccgccc attctccgcc  7440
ccatggctga ctaatttttt ttatttatgc agaggccgag gccgcctctg cctctgagct  7500
attccagaag tagtgaggag gcttttttgg aggcctaggc ttttgcaaaa agctcccggg  7560
agcttgtata tccattttcg gatctgatca gcacgtgttg acaattaatc atcggcatag  7620
tatatcggca tagtataata cgacaaggtg aggaactaaa ccatggccaa gttgaccagt  7680
gccgttccgg tgctcaccgc gcgcgacgtc gccggagcgg tcgagttctg gaccgaccgg  7740
ctcgggttct cccgggactt cgtggaggac gacttcgccg gtgtggtccg ggacgacgtg  7800
accctgttca tcagcgcggt ccaggaccag gtggtgccgg acaacaccct ggcctgggtg  7860
tgggtgcgcg gcctggacga gctgtacgcc gagtggtcgg aggtcgtgtc cacgaacttc  7920
cgggacgcct ccgggccggc catgaccgag atcggcgagc agccgtgggg gcgggagttc  7980
gccctgcgcg acccggccgg caactgcgtg cacttcgtgg ccgaggagca ggactgacac  8040
gtgctacgag atttcgattc caccgccgcc ttctatgaaa ggttgggctt cggaatcgtt  8100
ttccgggacg ccggctggat gatcctccag cgcggggatc tcatgctgga gttcttcgcc  8160
caccccaact tgtttattgc agcttataat ggttacaaat aaagcaatag catcacaaat  8220
ttcacaaata aagcattttt ttcactgcat tctagttgtg gtttgtccaa actcatcaat  8280
gtatcttatc atgtctgtat accgtcgacc tctagctaga gcttggcgta atcatggtca  8340
tagctgtttc ctgtgtgaaa ttgttatccg ctcacaattc cacacaacat acgagccgga  8400
agcataaagt gtaaagcctg gggtgcctaa tgagtgagct aactcacatt aattgcgttg  8460
cgctcactgc ccgctttcca gtcgggaaac ctgtcgtgcc agctgcatta atgaatcggc  8520
caacgcgcgg ggagaggcgg tttgcgtatt gggcgctctt ccgcttcctc gctcactgac  8580
tcgctgcgct cggtcgttcg gctgcggcga gcggtatcag ctcactcaaa ggcggtaata  8640
cggttatcca cagaatcagg ggataacgca ggaaagaaca tgtgagcaaa aggccagcaa  8700
aaggccagga accgtaaaaa ggccgcgttg ctggcgtttt tccataggct ccgcccccct  8760
gacgagcatc acaaaaatcg acgctcaagt cagaggtggc gaaacccgac aggactataa  8820
agataccagg cgtttccccc tggaagctcc ctcgtgcgct ctcctgttcc gaccctgccg  8880
cttaccggat acctgtccgc ctttctccct tcgggaagcg tggcgctttc tcatagctca  8940
cgctgtaggt atctcagttc ggtgtaggtc gttcgctcca agctgggctg tgtgcacgaa  9000
ccccccgttc agcccgaccg ctgcgcctta tccggtaact atcgtcttga gtccaacccg  9060
gtaagacacg acttatcgcc actggcagca gccactggta acaggattag cagagcgagg  9120
tatgtaggcg gtgctacaga gttcttgaag tggtggccta actacggcta cactagaaga  9180
acagtatttg gtatctgcgc tctgctgaag ccagttacct tcggaaaaag agttggtagc  9240
tcttgatccg gcaaacaaac caccgctggt agcggtggtt tttttgtttg caagcagcag  9300
attacgcgca gaaaaaaagg atctcaagaa gatcctttga tcttttctac ggggtctgac  9360
gctcagtgga acgaaaactc acgttaaggg attttggtca tgagattatc aaaaaggatc  9420
ttcacctaga tccttttaaa ttaaaaatga agttttaaat caatctaaag tatatatgag  9480
taaacttggt ctgacagtta ccaatgctta atcagtgagg cacctatctc agcgatctgt  9540
ctatttcgtt catccatagt tgcctgactc cccgtcgtgt agataactac gatacgggag  9600
ggcttaccat ctggccccag tgctgcaatg ataccgcgag acccacgctc accggctcca  9660
gatttatcag caataaacca gccagccgga agggccgagc gcagaagtgg tcctgcaact  9720
ttatccgcct ccatccagtc tattaattgt tgccgggaag ctagagtaag tagttcgcca  9780
gttaatagtt tgcgcaacgt tgttgccatt gctacaggca tcgtggtgtc acgctcgtcg  9840
tttggtatgg cttcattcag ctccggttcc caacgatcaa ggcgagttac atgatccccc  9900
atgttgtgca aaaaagcggt tagctccttc ggtcctccga tcgttgtcag aagtaagttg  9960
gccgcagtgt tatcactcat ggttatggca gcactgcata attctcttac tgtcatgcca  10020
tccgtaagat gcttttctgt gactggtgag tactcaacca agtcattctg agaatagtgt  10080
atgcggcgac cgagttgctc ttgcccggcg tcaatacggg ataataccgc gccacatagc  10140
agaactttaa aagtgctcat cattggaaaa cgttcttcgg ggcgaaaact ctcaaggatc  10200
ttaccgctgt tgagatccag ttcgatgtaa cccactcgtg cacccaactg atcttcagca  10260
tcttttactt tcaccagcgt ttctgggtga gcaaaaacag gaaggcaaaa tgccgcaaaa  10320
aagggaataa gggcgacacg gaaatgttga atactcatac tcttcctttt tcaatattat  10380
tgaagcattt atcagggtta ttgtctcatg agcggataca tatttgaatg tatttagaaa  10440
aataaacaaa taggggttcc gcgcacattt ccccgaaaag tgccacctga c           10491
```

```
SEQ ID NO: 254          moltype = DNA  length = 524
FEATURE                 Location/Qualifiers
misc_feature            1..524
                        note = Synthetic Polynucleotide
```

```
source                  1..524
                        mol_type = other DNA
                        organism = synthetic construct
SEQUENCE: 254
ctgtaggtta gcaaccaccc tgtgattaca actgactcct cctcgcgcaa gccaccctgt  60
gattacaact gactctccgt cctacgcaga aggtcctctt ccaccctgtg attacaactg  120
actctggggt gggtgctcca ccctgtgatt acaactgact cgtgcggtta cggtagaggt  180
ttgaccccac cctgtgatta caactgactg cgtcctgttg tatccaccct gtgattacaa  240
ctgacttggg cgtctacggg ttaggtctgg ggccaccctg tgattacaac tgactgtgcc  300
tgccactatc caccctgtga ttacaactga ctgtcgccct tacgttggag gtccatgccc  360
accctgtgat tacaactgac tgctgtccgt ccctcccacc ctgtgattac aactgactgg  420
tcgctctacg gagtaggtgt ctcaccaccc tgtgattaca actgacttcc ctggccacta  480
tccaccctgt gattacaact gactggctgt ggtacggcta aggt                   524

SEQ ID NO: 255          moltype = DNA  length = 10580
FEATURE                 Location/Qualifiers
misc_feature            1..10580
                        note = Synthetic Polynucleotide
source                  1..10580
                        mol_type = other DNA
                        organism = synthetic construct
SEQUENCE: 255
gtcgacggat cgggagatct cccgatcccc tatggtgcac tctcagtaca atctgctctg  60
atgccgcata gttaagccag tatctgctcc ctgcttgtgt gttggaggtc gctgagtagt  120
gcgcgagcaa aatttaagct acaacaaggc aaggcttgac cgacaattgc atgaagaatc  180
tgcttagggt taggcgtttt gcgctgcttc gcgatgtacg ggccagatat acgcgttgac  240
attgattatt gactagttat taatagtaat caattacggg gtcattagtt catagcccat  300
atatggagtt ccgcgttaca taacttacgg taaatggccc gcctggctga ccgcccaacg  360
acccccgccc attgacgtca ataatgacgt atgttcccat agtaacgcca atagggactt  420
tccattgacg tcaatgggtg gagtatttac ggtaaactgc ccacttggca gtacatcaag  480
tgtatcatat gccaagtacg ccccctattg acgtcaatga cggtaaatgg cccgcctggc  540
attatgccca gtacatgacc ttatgggact ttcctacttg gcagtacatc tacgtattag  600
tcatcgctat taccatggtg atgcggtttt ggcagtacat caatgggcgt ggatagcggt  660
ttgactcacg gggatttcca agtctccacc ccattgacgt caatgggagt ttgttttggc  720
accaaaatca acgggacttt ccaaaatgtc gtaacaactc cgccccattg acgcaaatgg  780
gcggtaggcg tgtacggtgg gaggtctata taagcagcgc gttttgcctg tactgggtct  840
ctctggttag accagatctg agcctgggag ctctctggct aactagggaa cccactgctt  900
aagcctcaat aaagcttgcc ttgagtgctt caagtagtgt gtgcccgtct gttgtgtgac  960
tctggtaact agagatccct cagacccttt tagtcagtgt ggaaaatctc tagcagtggc  1020
gcccgaacag ggacttgaaa gcgaaaggga aaccagagga gctctctcga cgcaggactc  1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
gaaggtggag agagagacag agacagatcc attcgattag tgaacggatc ggcactgcgt  2400
gcgccaattc tgcagacaaa tggcagtatt catccacaat tttaaaagaa aaggggggat  2460
tggggggtac agtgcagggg aaagaatagt agacataata gcaacagaca tacaaactaa  2520
agaattacaa aaacaaatta caaaaattca aaattttcgg gtttattaca gggacagcag  2580
agatccagtt tggttaatct gtaggttagc aaccaccctg tgattacaac tgactcctcc  2640
tcgcgcaagc caccctgtga ttacaactga ctctccgtcc tacgcagaag gtcctcttcc  2700
accctgtgat tacaactgac tctggggtgg gtgctccacc ctgtgattac aactgactcg  2760
tgcggttacg gtagaggttt gaccccaccc tgtgattaca actgactgcg tcctgttgta  2820
tccaccctgt gattacaact gacttgggcg tctacgggtt aggtctgggg ccaccctgtg  2880
attacaactg actgtgcctg ccactatcca ccctgtgatt acaactgact gtcgccctta  2940
cgttggaggt ccatgcccac cctgtgatta caactgactg ctgtccgtcc ctcccaccct  3000
gtgattacaa ctgactggtc gctctacgga gtaggtgtct caccaccctg tgattacaac  3060
tgacttccct ggccactatc caccctgtga ttacaactga ctggctgtgg tacggctaag  3120
gtcctcccct tagtgagggt taattctcga gtctccctat agtgagtcgt attaattccg  3180
tgtattctat agtgtcacct aaatcgttac gagacaccta ttaacccgtg tcggctccag  3240
atctggcctc cgcgccgggt tttggcgcct cccgcgggcg ccccccctcct cacggcgagc  3300
gctgccacgt cagacgaagg gcgcagcgag cgtcctgatc cttccgcccg gacgctcagg  3360
acagcggccc gctgctcata agactcggcc ttagaacccc agtatcagca gaaggacatt  3420
```

-continued

```
ttaggacggg acttgggtga ctctagggca ctggttttct ttccagagag cggaacaggc  3480
gaggaaaagt agtcccttct cggcgattct gcggagggat ctccgtgggg cggtgaacgc  3540
cgatgattat ataaggacgc gccgggtgtg gcacagctag ttccgtcgca gccgggattt  3600
gggtcgcggt tcttgtttgt ggatcgctgt gatcgtcact tggtgagtag cgggctgctg  3660
ggctggccgg ggctttcgtg gccgccgggc cgctcggtgg gacggaagcg tgtggagaga  3720
ccgccaaggg ctgtagtctg ggtccgcgag caaggttgcc ctgaactggg ggttgggggg  3780
agcgcagcaa aatggcggct gttcccgagt cttgaatgga agacgcttgt gaggcgggct  3840
gtgaggtcgt tgaaacaagg tgggggcat ggtgggcggc aagaacccaa ggtcttgagg  3900
ccttcgctaa tgcgggaaag ctcttattcg ggtgagatgg gctggggcac catctgggga  3960
ccctgacgtg aagtttgtca ctgactggag aactcggttt gtcgtctgtt gcgggggcgg  4020
cagttatggc ggtgccgttg ggcagtgcac ccgtaccttt gggagcgcgc gccctcgtcg  4080
tgtcgtgacg tcacccgttc tgttggctta taatgcaggg tggggccacc tgccggtagg  4140
tgtgcggtag gcttttctcc gtcgcaggac gcagggttcg ggcctagggt aggctctcct  4200
gaatcgacag gcgccggacc tctggtgagg ggagggataa gtgaggcgtc agtttctttg  4260
gtcggtttta tgtacctatc ttcttaagta gctgaagctc cggttttgaa ctatgcgctc  4320
ggggttggcg agtgtgtttt gtgaagtttt ttaggcacct tttgaaatgt aatcatttgg  4380
gtcaatatgt aattttcagt gttagactag taaattgtcc gctaaattct ggccgttttt  4440
ggcttttttg ttagacgaag cttgggctgc aggtcgactc tagaggatcc ccgggtaagg  4500
atccccgggt accggtcgcc accatggtga gcaagggcga ggagctgttc accggggtgg  4560
tgcccatcct ggtcgagctg gacggcgacg taaacggcca caagttcagc gtgtccggcg  4620
agggcgaggg cgatgccacc tacggcaagc tgaccctgaa gttcatctgc accaccggca  4680
agctgcccgt gccctggccc accctcgtga ccaccctgac ctggggcgtg cagtgcttcg  4740
cccgctaccc cgaccacatg aagcagcacg acttcttcaa gtccgccatg cccgaaggct  4800
acgtccagga gcgcaccatc ttcttcaagg acgacggcaa ctacaagacc cgcgccgagg  4860
tgaagttcga gggcgacacc ctggtgaacc gcatcgagct gaagggcatc gacttcaagg  4920
aggacggcaa catcctgggg cacaagctgg agtacaacgc catcagcgac aacgtctata  4980
tcaccgccga caagcagaag aacggcatca aggccaactt caagatccgc cacaacatcg  5040
aggacggcag cgtgcagctc gccgaccact accagcagaa cacccccatc ggcgacggcc  5100
ccgtgctgct gcccgacaac cactacctga gcacccagtc caagctgagc aaagacccca  5160
acgagaagcg cgatcacatg gtcctgctgg agttcgtgac cgccgccggg atcactctcg  5220
gcatggacga gctgtacaag tgaacctgaa ttcgatatca agcttatcga taatcaacct  5280
ctggattaca aaatttgtga aagattgact ggtattctta actatgttgc tccttttacg  5340
ctatgtggat acgctgcttt aatgcctttg tatcatgcta ttgcttcccg tatggctttc  5400
attttctcct ccttgtataa atcctggttg ctgtctcttt atgaggagtt gtggcccgtt  5460
gtcaggcaac gtggcgtggt gtgcactgtg tttgctgacg caacccccac tggttggggc  5520
attgccacca cctgtcagct cctttccggg actttcgctt tccccctccc tattgccacg  5580
gcggaactca tcgccgcctg ccttgcccgc tgctggacag gggctcggct gttgggcact  5640
gacaattccg tggtgttgtc ggggaaatca tcgtcctttc cttggctgct cgcctgtgtt  5700
gccacctgga ttctgcgcgg gacgtccttc tgctacgtcc cttcggccct caatccagcg  5760
gaccttcctt cccgcggcct gctgccggct ctgcggcctc ttccgcgtct tcgccttcgc  5820
cctcagacga gtcggatctc cctttgggcc gcctccccgc atcgataccg tcgacctcga  5880
gacctagaaa aacatggagc aatcacaagt agcaatacag cagctaccaa tgctgattgt  5940
gcctggctag aagcacaaga ggaggaggag gtgggttttc cagtcacacc tcaggtacct  6000
ttaagaccaa tgacttacaa ggcagctgta gatcttagcc actttttaaa agaaaagggg  6060
ggactggaag ggctaattca ctcccaacga agacaagata tccttgatct gtggatctac  6120
cacacacaag gctacttccc tgattggcag aactacacac cagggccagg gatcagatat  6180
ccactgacct ttggatggtg ctacaagcta gtaccagttg agcaagagaa ggtagaagaa  6240
gccaatgaag gagagaacac ccgcttgtta caccctgtga gcctgcatgg gatggatgac  6300
ccggagagag aagtattaga gtggaggttt gacagccgcc tagcatttca tcacatggcc  6360
cgagagctgc atccggactg tactgggtct ctctggttag accagatctg agcctgggag  6420
ctctctggct aactagggaa cccactgctt aagcctcaat aaagcttgcc ttgagtgctt  6480
caagtagtgt gtgcccgtct gttgtgtgac tctggtaact agagatccct cagacccttt  6540
tagtcagtgt ggaaaatctc tagcagggcc cgtttaaacc cgctgatcag cctcgactgt  6600
gccttctagt tgccagccat ctgttgtttg cccctccccc gtgccttcct tgaccctgga  6660
aggtgccact cccactgtcc tttcctaata aaatgaggaa attgcatcgc attgtctgag  6720
taggtgtcat tctattctgg ggggtggggt ggggcaggac agcaaggggg aggattggga  6780
agacaatagc aggcatgctg gggatgcggt gggctctatg gcttctgagg cggaaagaac  6840
cagctggggc tctagggggt atccccacgc gccctgtagc ggcgcattaa gcgcggcggg  6900
tgtggtggtt acgcgcagcg tgaccgctac acttgccagc gccctagcgc ccgctccttt  6960
cgctttcttc ccttcctttc tcgccacgtt cgccggcttt ccccgtcaag ctctaaatcg  7020
ggggctccct ttagggttcc gatttagtgc tttacggcac ctcgacccca aaaaacttga  7080
ttagggtgat ggttcacgta gtgggccatc gccctgatag acggtttttc gccctttgac  7140
gttggagtcc acgttcttta atagtggact cttgttccaa actggaacaa cactcaaccc  7200
tatctcggtc tattcttttg atttataagg gattttgccg atttcggcct attggttaaa  7260
aaatgagctg atttaacaaa aatttaacgc gaattaattc tgtggaatgt gtgtcagtta  7320
gggtgtggaa agtccccagg ctccccagca ggcagaagta tgcaaagcat gcatctcaat  7380
tagtcagcaa ccaggtgtgg aaagtcccca ggctccccag caggcagaag tatgcaaagc  7440
atgcatctca attagtcagc aaccatagtc ccgcccctaa ctccgcccat cccgccccta  7500
actccgccca gttccgccca ttctccgccc catggctgac taattttttt tatttatgca  7560
gaggccgagg ccgcctctgc ctctgagcta ttccagaagt agtgaggagg cttttttgga  7620
ggcctaggct tttgcaaaaa gctcccggga gcttgtatat ccattttcgg atctgatcag  7680
cacgtgttga caattaatca tcggcatagt atatcggcat agtataatac gacaaggtga  7740
ggaactaaac catggccaag ttgaccagtg ccgttccggt gctcaccgcg cgcgacgtcg  7800
ccggagcggt cgagttctgg accgaccggc tcgggttctc ccgggacttc gtggaggacg  7860
acttcgccgg tgtggtccgg gacgacgtga ccctgttcat cagcgcggtc caggaccagg  7920
tggtgccgga caacaccctg gcctgggtgt gggtgcgcgg cctggacgag ctgtacgccg  7980
agtggtcgga ggtcgtgtcc acgaacttcc gggacgcctc cgggccggcc atgaccgaga  8040
tcggcgagca gccgtggggg cgggagttcg ccctgcgcga cccggccggc aactgcgtgc  8100
acttcgtggc cgaggagcag gactgacacg tgctacgaga tttcgattcc accgccgcct  8160
```

```
tctatgaaag gttgggcttc ggaatcgttt tccgggacgc cggctggatg atcctccagc  8220
gcggggatct catgctggag ttcttcgccc accccaactt gtttattgca gcttataatg  8280
gttacaaata aagcaatagc atcacaaatt tcacaaataa agcatttttt tcactgcatt  8340
ctagttgtgg tttgtccaaa ctcatcaatg tatcttatca tgtctgtata ccgtcgacct  8400
ctagctagag cttggcgtaa tcatggtcat agctgtttcc tgtgtgaaat tgttatccgc  8460
tcacaattcc acacaacata cgagccggaa gcataaagtg taaagcctgg ggtgcctaat  8520
gagtgagcta actcacatta attgcgttgc gctcactgcc cgctttccag tcgggaaacc  8580
tgtcgtgcca gctgcattaa tgaatcggcc aacgcgcggg gagaggcggt ttgcgtattg  8640
ggcgctcttc cgcttcctcg ctcactgact cgctgcgctc ggtcgttcgg ctgcggcgag  8700
cggtatcagc tcactcaaag gcggtaatac ggttatccac agaatcaggg gataacgcag  8760
gaaagaacat gtgagcaaaa ggccagcaaa aggccaggaa ccgtaaaaag gccgcgttgc  8820
tggcgttttt ccataggctc cgcccccctg acgagcatca caaaaatcga cgctcaagtc  8880
agaggtggcg aaacccgaca ggactataaa gataccaggc gtttccccct ggaagctccc  8940
tcgtgcgctc tcctgttccg accctgccgc ttaccggata cctgtccgcc tttctccctt  9000
cgggaagcgt ggcgctttct catagctcac gctgtaggta tctcagttcg gtgtaggtcg  9060
ttcgctccaa gctgggctgt gtgcacgaac cccccgttca gcccgaccgc tgcgccttat  9120
ccggtaacta tcgtcttgag tccaacccgg taagacacga cttatcgcca ctggcagcag  9180
ccactggtaa caggattagc agagcgaggt atgtaggcgg tgctacagag ttcttgaagt  9240
ggtggcctaa ctacggctac actagaagaa cagtatttgg tatctgcgct ctgctgaagc  9300
cagttacctt cggaaaaaga gttggtagct cttgatccgg caaacaaacc accgctggta  9360
gcggtggttt ttttgtttgc aagcagcaga ttacgcgcag aaaaaaagga tctcaagaag  9420
atcctttgat cttttctacg gggtctgacg ctcagtggaa cgaaaactca cgttaaggga  9480
ttttggtcat gagattatca aaaaggatct tcacctagat ccttttaaat taaaaatgaa  9540
gttttaaatc aatctaaagt atatatgagt aaacttggtc tgacagttac caatgcttaa  9600
tcagtgaggc acctatctca gcgatctgtc tatttcgttc atccatagtt gcctgactcc  9660
ccgtcgtgta gataactacg atacgggagg gcttaccatc tggccccagt gctgcaatga  9720
taccgcgaga cccacgctca ccggctccag atttatcagc aataaaccag ccagccggaa  9780
gggccgagcg cagaagtggt cctgcaactt tatccgcctc catccagtct attaattgtt  9840
gccgggaagc tagagtaagt agttcgccag ttaatagttt gcgcaacgtt gttgccattg  9900
ctacaggcat cgtggtgtca cgctcgtcgt ttggtatggc ttcattcagc tccggttccc  9960
aacgatcaag gcgagttaca tgatccccca tgttgtgcaa aaaagcggtt agctccttcg  10020
gtcctccgat cgttgtcaga agtaagttgg ccgcagtgtt atcactcatg gttatggcag  10080
cactgcataa ttctcttact gtcatgccat ccgtaagatg cttttctgtg actggtgagt  10140
actcaaccaa gtcattctga gaatagtgta tgcggcgacc gagttgctct tgcccggcgt  10200
caatacggga taataccgcg ccacatagca gaactttaaa agtgctcatc attggaaaac  10260
gttcttcggg gcgaaaactc tcaaggatct taccgctgtt gagatccagt tcgatgtaac  10320
ccactcgtgc acccaactga tcttcagcat cttttacttt caccagcgtt tctgggtgag  10380
caaaaacagg aaggcaaaat gccgcaaaaa agggaataag ggcgacacgg aaatgttgaa  10440
tactcatact cttccttttt caatattatt gaagcattta tcagggttat tgtctcatga  10500
gcggatacat atttgaatgt atttagaaaa ataaacaaat aggggttccg cgcacatttc  10560
cccgaaaagt gccacctgac                                             10580

SEQ ID NO: 256         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 256
cgtggattgg aacagcttct tatagcattc tttcttgagg agggcagcaa acgggaagag  60

SEQ ID NO: 257         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 257
cgtggatcgg aacagcttct tataaaagtc taatccgtcc ctgcctctat atctccactc  60

SEQ ID NO: 258         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 258
agcttgaaca ccagtcgcaa tataagctca gtccatcctc gtaaatcctc atcaatcatc  60

SEQ ID NO: 259         moltype = DNA  length = 60
FEATURE                Location/Qualifiers
misc_feature           1..60
                       note = Synthetic Polynucleotide
source                 1..60
                       mol_type = other DNA
                       organism = synthetic construct
```

```
SEQUENCE: 259
cgtggattgg aacagcttct tataaaagtc taatccgtcc ctgcctctat atctccactc  60

SEQ ID NO: 260          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 260
cgtggatcgg aacagcttct tatagcattc tttcttgagg agggcagcaa acgggaagag  60

SEQ ID NO: 261          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 261
agcttgaaca ccagtcgcaa tataagctca gtccatcctc gtaaatcctc atcaatcatc  60

SEQ ID NO: 262          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 262
cgtggattgg aacagcttct tatagcattc tttcttgagg agggcagcaa acgggaagag  60

SEQ ID NO: 263          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 263
cgtggatcgg aacagcttct tataaaagtc taatccgtcc ctgcctctat atctccactc  60

SEQ ID NO: 264          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 264
ttccacatcc ctctgcgatt tataagctca gtccatcctc gtaaatcctc atcaatcatc  60

SEQ ID NO: 265          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 265
ttccacaccc ctctgcgatt tatacacatt tacagacctc aacctacctc caactctcac  60

SEQ ID NO: 266          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 266
ataccaatcc cttcggcgat tataaaagtc taatccgtcc ctgcctctat atctccactc  60

SEQ ID NO: 267          moltype = DNA  length = 60
FEATURE                 Location/Qualifiers
misc_feature            1..60
                        note = Synthetic Polynucleotide
```

```
source                  1..60
                        mol_type = other DNA
                        organism = synthetic construct
SEQUENCE: 267
ataccaaccc cttcggcgat tataagctca gtccatcctc gtaaatcctc atcaatcatc  60

SEQ ID NO: 268          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 268
ttcaacatac gccaatgcgg tatagcattc tttcttgagg agggcagcaa acgggaagag  60

SEQ ID NO: 269          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 269
ttcaacacac gccaatgcgg tatacacatt tacagacctc aacctacctc caactctcac  60

SEQ ID NO: 270          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 270
gtcaacatac acgccctgat tataagctca gtccatcctc gtaaatcctc atcaatcatc  60

SEQ ID NO: 271          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 271
gtcaacacac acgccctgat tataaaagtc taatccgtcc ctgcctctat atctccactc  60

SEQ ID NO: 272          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 272
ttagcgatac atccgaccca tatagcattc tttcttgagg agggcagcaa acgggaagag  60

SEQ ID NO: 273          moltype = DNA  length = 60
FEATURE                 Location/Qualifiers
misc_feature            1..60
                        note = Synthetic Polynucleotide
source                  1..60
                        mol_type = other DNA
                        organism = synthetic construct
SEQUENCE: 273
ttagcgacac atccgaccca tatacacatt tacagacctc aacctacctc caactctcac  60

SEQ ID NO: 274          moltype = DNA  length = 383
FEATURE                 Location/Qualifiers
misc_feature            1..383
                        note = Synthetic Polynucleotide
source                  1..383
                        mol_type = other DNA
                        organism = synthetic construct
SEQUENCE: 274
cgacagcttg tctctccaga tgctcttggg ccatcttcca catcgtccgt agcagccttg  60
gcaatttgcc atcactggca aatacacata aatccaatga atacggttac caccatcaca  120
ttaccatgca ggtacacagc aagaattgac gttggcatat cacatggtgt aataacccca  180
cttgtgaaac aacccagaat aaggtacaag gcggaaatgt cgtcattcta aaataaaagg  240
catggccagg aatttgtcta ataccgggaa cttaaattca gcttgaacac cagtcgcaaa  300
```

```
aaattcaaag aaagtgattc aggttcgggt tcgtggattg gaacagcttc ttttgtttca  360
gtgatgagag aatcctcctg tca                                           383

SEQ ID NO: 275         moltype = DNA  length = 50
FEATURE                Location/Qualifiers
misc_feature           1..50
                       note = Synthetic Polynucleotide
source                 1..50
                       mol_type = other DNA
                       organism = synthetic construct
SEQUENCE: 275
ttccacatcc ctctgcgatt cgtggcatcg tggattggaa cagcttcttt             50

SEQ ID NO: 276         moltype = DNA  length = 50
FEATURE                Location/Qualifiers
misc_feature           1..50
                       note = Synthetic Polynucleotide
source                 1..50
                       mol_type = other DNA
                       organism = synthetic construct
SEQUENCE: 276
ttccacaccc ctctgcgatt cgtggcatcg tggatcggaa cagcttcttt             50

SEQ ID NO: 277         moltype = DNA  length = 63
FEATURE                Location/Qualifiers
misc_feature           1..63
                       note = Synthetic Polynucleotide
source                 1..63
                       mol_type = other DNA
                       organism = synthetic construct
SEQUENCE: 277
ttcaacatac gccaatgcgg acgcggccgc tgttcagata ccaatccctt cggcgatttc  60
ccg                                                                 63

SEQ ID NO: 278         moltype = DNA  length = 63
FEATURE                Location/Qualifiers
misc_feature           1..63
                       note = Synthetic Polynucleotide
source                 1..63
                       mol_type = other DNA
                       organism = synthetic construct
SEQUENCE: 278
ttcaacacac gccaatgcgg acgcggccgc tgttcagata ccaacccctt cggcgatttc  60
ccg                                                                 63

SEQ ID NO: 279         moltype = DNA  length = 63
FEATURE                Location/Qualifiers
misc_feature           1..63
                       note = Synthetic Polynucleotide
source                 1..63
                       mol_type = other DNA
                       organism = synthetic construct
SEQUENCE: 279
ttagcgatac atccgaccca atcataccct gtgattcgtc aacatacacg ccctgataaa  60
tat                                                                 63

SEQ ID NO: 280         moltype = DNA  length = 63
FEATURE                Location/Qualifiers
misc_feature           1..63
                       note = Synthetic Polynucleotide
source                 1..63
                       mol_type = other DNA
                       organism = synthetic construct
SEQUENCE: 280
ttagcgacac atccgaccca atcataccct gtgattcgtc aacacacacg ccctgataaa  60
tat                                                                 63

SEQ ID NO: 281         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 281
agatgctcct gagccatctt                                               20

SEQ ID NO: 282         moltype = DNA  length = 20
FEATURE                Location/Qualifiers
```

```
misc_feature          1..20
                      note = Synthetic Oligonucleotide
source                1..20
                      mol_type = other DNA
                      organism = synthetic construct
SEQUENCE: 282
cgtggattgg aacagcttct                                                  20

SEQ ID NO: 283        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 283
gaaagtgatt caggttcggg                                                  20

SEQ ID NO: 284        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 284
agcttgaaca ccagtcgcaa                                                  20

SEQ ID NO: 285        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 285
gcatggccag gaatttgtct                                                  20

SEQ ID NO: 286        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 286
ggcggaaatg tcgtcattct                                                  20

SEQ ID NO: 287        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 287
ccacttgtga aacaacccag                                                  20

SEQ ID NO: 288        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 288
cgttggcata tcacatggtg                                                  20

SEQ ID NO: 289        moltype = DNA  length = 20
FEATURE               Location/Qualifiers
misc_feature          1..20
                      note = Synthetic Oligonucleotide
source                1..20
                      mol_type = other DNA
                      organism = synthetic construct
SEQUENCE: 289
accatgcagg tacacagcaa                                                  20

SEQ ID NO: 290        moltype = DNA  length = 20
```

```
FEATURE                Location/Qualifiers
misc_feature           1..20
                       note = Synthetic Oligonucleotide
source                 1..20
                       mol_type = other DNA
                       organism = synthetic construct
SEQUENCE: 290
ttccacatcc ctctgcgatt                                              20

SEQ ID NO: 291         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 291
ataccaatcc cttcggcgat                                              20

SEQ ID NO: 292         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 292
atcagcgtga caactgtgct                                              20

SEQ ID NO: 293         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 293
agatgctcct gagccatctt tatagcattc tttcttgagg agggcagcaa acgggaagag  60

SEQ ID NO: 294         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 294
cgtggattgg aacagcttct tataagctca gtccatcctc gtaaatcctc atcaatcatc  60

SEQ ID NO: 295         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 295
gaaagtgatt caggttcggg tatacacatt tacagacctc aacctacctc caactctcac  60

SEQ ID NO: 296         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 296
ttccacatcc ctctgcgatt tataaaagtc taatccgtcc ctgcctctat atctccactc  60

SEQ ID NO: 297         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 297
agcttgaaca ccagtcgcaa tatagcattc tttcttgagg agggcagcaa acgggaagag  60
```

```
SEQ ID NO: 298         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 298
gcatggccag gaatttgtct tataagctca gtccatcctc gtaaatcctc atcaatcatc  60

SEQ ID NO: 299         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 299
ggcggaaatg tcgtcattct tatacacatt tacagacctc aacctacctc caactctcac  60

SEQ ID NO: 300         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 300
ataccaatcc cttcggcgat tataaaagtc taatccgtcc ctgcctctat atctccactc  60

SEQ ID NO: 301         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 301
ccacttgtga aacaacccag tatagcattc tttcttgagg agggcagcaa acgggaagag  60

SEQ ID NO: 302         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 302
cgttggcata tcacatggtg tataagctca gtccatcctc gtaaatcctc atcaatcatc  60

SEQ ID NO: 303         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 303
accatgcagg tacacagcaa tatacacatt tacagacctc aacctacctc caactctcac  60

SEQ ID NO: 304         moltype = DNA  length = 60
FEATURE                Location/Qualifiers
misc_feature           1..60
                       note = Synthetic Polynucleotide
source                 1..60
                       mol_type = other DNA
                       organism = synthetic construct
SEQUENCE: 304
atcagcgtga caactgtgct tataaaagtc taatccgtcc ctgcctctat atctccactc  60
```

IN SITU READOUT OF DNA BARCODES

RELATED APPLICATIONS

The present application is a continuation application of U.S. application Ser. No. 16/701,087, filed Dec. 2, 2019, which claims priority under 35 U.S.C. § 119(e) to U.S. Provisional Application No. 62/774,754, filed Dec. 3, 2018, and U.S. Provisional Application No. 62/936,307, filed Nov. 15, 2019. The content of each of these related applications is incorporated herein by reference in its entirety.

STATEMENT REGARDING FEDERALLY SPONSORED R&D

This invention was made with government support under Grant No. MH116508 awarded by the National Institutes of Health. The government has certain rights in the invention.

REFERENCE TO SEQUENCE LISTING

The present application is being filed along with a Sequence Listing in electronic format. The Sequence Listing is provided as a file entitled 30KJ-302413-US_Sequence-Listing, created Aug. 3, 2022, which is 445 kilobytes in size. The information in the electronic format of the Sequence Listing is incorporated herein by reference in its entirety.

BACKGROUND

Field

The present disclosure relates generally to the field of barcoding cells, for example in situ readout of barcodes.

Description of the Related Art

Barcodes transcribed in living cells can be detected in cells. Detecting barcode expression across a diverse population of living cells can be challenging, for example, due to stochastic silencing, bursty expression, and unintended cell-type dependent promoter activity. Barcodes with large differences can be detected. There is a need to eliminate barcode expression in living cells and to detect single nucleotide variations in barcodes.

SUMMARY

Disclosed herein include embodiments of systems, methods, compositions, and kits for determining barcode sequences in situ. In some embodiments, the method of determining barcode sequences in situ comprises: providing a plurality of cells each comprising a barcode polynucleotide with a barcode sequence. The method can comprise: fixing the plurality of cells using a fixative to generate a plurality of fixed cells. The method can comprise: generating a plurality of barcode molecules comprising the barcode sequence of the barcode polynucleotide in each of the plurality of fixed cells. The method can comprise: contacting the plurality of fixed cells with a plurality of detection probes each comprising a barcode binding sequence and an initiator sequence, thereby each of the plurality of barcode molecules comprising the barcode sequence of the barcode polynucleotide in the fixed cell hybridizes to a detection probe, of the plurality of detection probes, comprising the barcode binding sequence reverse complementary to the barcode sequence, or a portion thereof. The method can comprise: contacting the plurality of fixed cells with pairs of amplifier probes, wherein the amplifier probes of each pair of amplifier probes comprise an identical fluorophore, thereby a first amplifier probe of a pair of amplifier probes hybridizes to (i) the initiator sequence of a detection probe of the plurality of detection probes hybridized to a barcode molecule in a fixed cell of the plurality of fixed cells and (ii) a second amplifier probe of the pair of amplifier probes. The method can comprise: detecting the fluorophore, or fluorescence thereof, of the pair of amplifier probes with the first amplifier probe hybridized to the detection probe hybridized to the barcode molecules in each of the plurality of fixed cells using fluorescence imaging. The method can comprise: determining the barcode sequence in each of the plurality of fixed cells using the fluorophore detected, wherein the fluorophore detected indicates the barcode sequence of the barcode polynucleotide in the one or more fixed cells.

In some embodiments, thereby the barcode sequence of each of the plurality of barcode molecules hybridizes to the barcode binding sequence of the detection probe that is reverse complementary to the barcode sequence of the barcode molecule. In some embodiments, contacting the plurality of fixed cells with the plurality of detection probes comprises: contacting the plurality of fixed cells with detection probe molecules of each of the plurality of detection probes, thereby each of the plurality of barcode molecules comprising the barcode sequence of the barcode polynucleotide in the fixed cell hybridizes to a detection probe molecule of the detection probe comprising the barcode binding sequence reverse complementary to the barcode sequence, or a portion thereof. In some embodiments, four, or at least two, detection probes of the plurality of detection probes comprise (i) barcode binding sequences that differ at one position and (ii) different initiator sequences.

In some embodiments, different pairs of amplifier probes comprise different fluorophores, and optionally the different fluorophores are spectrally distinct. In some embodiments, thereby a first amplifier probe molecule of the first amplifier probe of the pair of amplifier probes hybridizes to (i) a detection probe molecule of the detection probe hybridized to the barcode molecule in the fixed cell and (ii) a second amplifier probe molecule of the second amplifier probe of the pairs of amplifier probes, and first amplifier probe molecules of the first amplifier probe of the pair of amplifier probes hybridize to second amplifier probe molecules, comprising the second amplifier probe molecule hybridized to the first amplifier probe molecule, of the second amplifier probe of the pairs of amplifier probes in a chain reaction. In some embodiments, at least 10 first amplifier probe molecules hybridize to at least 10 second amplifier probe molecules in the chain reaction.

In some embodiments, (1) a first amplifier probe of the pair of amplifier probes comprises: (1a) a first amplifier probe subsequence reverse complementary to a first subsequence of the initiator sequence of the detection probe of the plurality of detection probes, (1b) a second amplifier probe subsequence reverse complementary to a second subsequence of the initiator sequence, (1c) a third amplifier probe subsequence, and (1d) a fourth amplifier probe subsequence comprising the second subsequence of the initiator sequence, and/or (2) a second amplifier probe of the pair of amplifier probes comprises: (2a) a first amplifier probe subsequence comprising a reverse complementary sequence of the third amplifier probe subsequence of the first amplifier probe, (2b) a second amplifier probe subsequence comprising the second amplifier probe subsequence, (2c) a third amplifier probe subsequence comprising the first subsequence of the initiator sequence, and (2d) a fourth amplifier probe subsequence comprising the second subsequence of the initiator sequence. In some embodiments, contacting the plurality of fixed cells with the pairs of amplifier probes comprises contacting the plurality of fixed cells with the pairs of amplifier probes each comprising the first amplifier probe and the second amplifier probe with hairpin structures formed by the second amplifier probe subsequence hybridizing with fourth amplifier probe subsequence of the first amplifier probe and by the second amplifier probe subsequence hybridizing with the fourth amplifier probe subsequence of the second amplifier probe. In some embodiments, thereby (1a) the first amplifier probe subsequence, of the first amplifier probe, reverse complementary to a first subsequence of the initiator sequence and (1b) the second amplifier probe subsequence, of the first amplifier probe, reverse complementary to a second subsequence of the initiator sequence of (1) the first amplifier probe hybridize to the first subsequence and the second subsequence, respectively, of the initiator sequence, respectively, and (1c) the third amplifier probe subsequence and (1d) the fourth amplifier probe subsequence of the second amplifier probe hybridize to (2a) the first amplifier probe subsequence and (2b) the fourth amplifier probe subsequence of the second amplifier probe, respectively.

Disclosed herein include embodiments of a method of determining barcode sequences in situ. In some embodiments, the method comprises: providing a plurality of cells each comprising a barcode polynucleotide with a barcode sequence. The method can comprise: fixing the plurality of cells using a fixative to generate a plurality of fixed cells. The method can comprise: generating a plurality of barcode molecules comprising the barcode sequence of the barcode polynucleotide in each of the plurality of fixed cells. The method can comprise: contacting the plurality of fixed cells with a plurality of detection probes each comprising a barcode binding sequence and an initiator sequence, thereby each of the plurality of barcode molecules comprising the barcode sequence of the barcode oligonucleotide in the fixed cell hybridizes to a detection probe, of the plurality of detection probes, comprising the barcode binding sequence reverse complementary to the barcode sequence, or a portion thereof. The method can comprise: contacting the plurality of fixed cells with a plurality of first amplifier probes each comprising a different fluorophore, thereby a first amplifier probe of the plurality of first amplifier probes hybridizes to (i) the initiator sequence of a detection probe of the plurality of detection probes hybridized to a barcode molecule in a fixed cell of the plurality of fixed cells. The method can comprise: detecting the fluorophore, or fluorescence thereof, of the first amplifier probe hybridized to the detection probe hybridized to the barcode molecules in each of the plurality of fixed cells using fluorescence imaging. The method can comprise: determining the barcode sequence in each of the plurality of fixed cells using the fluorophore detected, wherein the fluorophore detected indicates the barcode sequence of the barcode polynucleotide in the one or more fixed cells.

Disclosed herein include embodiments of a method of determining barcode sequences in situ. In some embodiments, the method comprises: providing a plurality of cells each comprising a barcode polynucleotide with a barcode sequence. The method can comprise: fixing the plurality of cells using a fixative to generate a plurality of fixed cells. The method can comprise: generating a plurality of barcode molecules comprising the barcode sequence of the barcode polynucleotide in each of the plurality of fixed cells. The method can comprise: contacting the plurality of fixed cells with a plurality of detection probes each comprising a barcode binding sequence and a fluorophore, thereby each of the plurality of barcode molecules comprising the barcode sequence of the barcode oligonucleotide in the fixed cell hybridizes to a detection probe, of the plurality of detection probes, comprising the barcode binding sequence reverse complementary to the barcode sequence of the barcode polynucleotide. The method can comprise: detecting the fluorophore, or fluorescence thereof, of the detection probe hybridized to the barcode molecules in each of the plurality of fixed cells using fluorescence imaging. The method can comprise: determining the barcode sequence in each of the plurality of fixed cells using the fluorophore detected, wherein the fluorophore detected indicates the barcode sequence of the barcode polynucleotide in the one or more fixed cells.

Disclosed herein include embodiments of a method of determining barcode sequences in situ. In some embodiments, the method comprises: providing a plurality of cells each comprising a barcode polynucleotide with a barcode sequence. The method can comprise: fixing cells of the plurality of cells using a fixative to obtain a plurality of fixed cells. The method can comprise: generating, for each of one or more fixed cells of the plurality of fixed cells, a plurality of barcode molecules comprising the barcode sequence of the barcode polynucleotide in the fixed cell. The method can comprise: contacting each of the one or more fixed cells with a plurality of detection probes each comprising a barcode binding sequence. In some embodiments, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore. The method can comprise: detecting the fluorophore, or fluorescence thereof, associated with the detection probe hybridized to the one, at least one, or each barcode molecule in each of the one or more fixed cells using fluorescence imaging. The fluorophore, associated with the detection probe hybridized to the barcode molecule comprising the barcode sequence of the barcode polynucleotide in the fixed cell, detected can indicate the barcode sequence of the barcode polynucleotide in the fixed cell.

In some embodiments, contacting each of the one or more fixed cells with the plurality of detection probes comprises: contacting each of the one or more fixed cells with the plurality of detection probes each comprising the barcode binding sequence and an initiator sequence, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof. Contacting each of the one or more fixed cells with the plurality of detection probes can comprise: contacting each of the one or more fixed cells with pairs of amplifier probes, wherein the amplifier probes of each pair of amplifier probes comprise an identical fluorophore, thereby a first amplifier probe of a pair of amplifier probes hybridizes to (i) the initiator sequence of a detection probe of the plurality of detection probes hybridized to a barcode molecule in the fixed cell and (ii) a second amplifier probe of the pair of amplifier probes.

In some embodiments, the initiator sequence is about 40 nucleotides in length. In some embodiments, two, or different, pairs of amplifier probes comprise different fluorophores, and optionally wherein the two, or different, fluorophores are spectrally distinct. In some embodiments, thereby a first amplifier probe molecule of the first amplifier probe of the pair of amplifier probes hybridize to (i) a detection probe molecule of the detection probe hybridized to the barcode molecule in the fixed cell and (ii) a second amplifier probe molecule of the second amplifier probe of the pairs of amplifier probes, and first amplifier probe molecules of the first amplifier probe of the pair of amplifier probes hybridize to second amplifier probe molecules, comprising the second amplifier probe molecule hybridized to the first amplifier probe molecule, of the second amplifier probe of the pairs of amplifier probes in a chain reaction. At least 10 first amplifier probe molecules can hybridize to at least 10 second amplifier probe molecules in the chain reaction.

In some embodiments, (1) a first amplifier probe of the pair of amplifier probes comprises: (1a) a first amplifier probe subsequence reverse complementary to a first subsequence of the initiator sequence of the detection probe of the plurality of detection probes, (1b) a second amplifier probe subsequence reverse complementary to a second subsequence of the initiator sequence, (1c) a third amplifier probe subsequence, and (1d) a fourth amplifier probe subsequence comprising the second subsequence of the initiator sequence. In some embodiments, (2) a second amplifier probe of the pair of amplifier probes comprises: (2a) a first amplifier probe subsequence comprising a reverse complementary sequence of the third amplifier probe subsequence of the first amplifier probe, (2b) a second amplifier probe subsequence comprising the second amplifier probe subsequence, (2c) a third amplifier probe subsequence comprising the first subsequence of the initiator sequence, and (2d) a fourth amplifier probe subsequence comprising the second subsequence of the initiator sequence. Contacting the plurality of fixed cells with the pairs of amplifier probes can comprise contacting the plurality of fixed cells with the pairs of amplifier probes each comprising the first amplifier probe and the second amplifier probe with hairpin structures formed by the second amplifier probe subsequence hybridizing with fourth amplifier probe subsequence of the first amplifier probe and by the second amplifier probe subsequence hybridizing with the fourth amplifier probe subsequence of the second amplifier probe.

In some embodiments, said detecting comprises detecting the fluorophore of the first amplifier probe hybridized to the initiator sequence of the detection probe hybridized to the barcode molecule in the fixed cell and the fluorophore of the second amplifier probe of the pair of amplifier probes comprising the first amplifier probe.

In some embodiments, contacting each of the one or more fixed cells with the plurality of detection probes comprises: contacting each of the one or more fixed cells with the plurality of detection probes each comprising the barcode binding sequence and an initiator sequence, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof. Contacting each of the one or more fixed cells with the plurality of detection probes can comprise: contacting each of the one or more fixed cells with a plurality of first amplifier probes each comprising a different fluorophore, thereby a first amplifier probe of the plurality of first amplifier probes hybridizes to the initiator sequence of a detection probe of the plurality of detection probes hybridized to a barcode molecule in the fixed cell.

In some embodiments, two, or different, first amplifier probes of the plurality of first amplifier probes comprise different fluorophores. In some embodiments, thereby a first amplifier probe molecule of the first amplifier probe of the plurality of first amplifier probes hybridizes to a detection probe molecule of the detection probe hybridized to the barcode molecule in the fixed cell. In some embodiments, said detecting comprises detecting the fluorophore of the first amplifier probe hybridized to the initiator sequence of the detection probe hybridized to the barcode molecule in the fixed cell.

In some embodiments, contacting each of the one or more fixed cells with the plurality of detection probes comprises: contacting each of the one or more fixed cells with the plurality of detection probes each comprising the barcode binding sequence and a fluorophore, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and the fluorophore. In some embodiments, said detecting comprises detecting the fluorophore of the detection probe hybridized to the barcode molecule in the fixed cell.

In some embodiments, a genome of one, at least one, or each cell of the plurality of cell comprises the barcode polynucleotide with the barcode sequence. In some embodiments, providing the plurality of cells comprises: integrating the barcode polynucleotide into a genome of one, at least one, or each of the plurality of cells. Integrating the barcode polynucleotide can comprise: integrating the barcode polynucleotide into the genome of one, at least one, or each of the plurality of cells at a specific site of the genome. The specific site can be a ROSA26 locus. In some embodiments, said integrating occurs about 12 days prior to said fixing.

In some embodiments, integrating the barcode polynucleotide into the genome of one, at least one, or each of the plurality of cells comprises: transfecting the cell with a donor plasmid comprising the barcode polynucleotide, a sequence thereof, a subsequence thereof, of a reverse complementary sequence of any of the preceding. Transfecting the cell with the donor plasmid can comprise: transfecting the cell with the donor plasmid and a plasmid capable of expressing Cas9 and/or a guide ribonucleic acid (gRNA) for integrating the barcode polynucleotide into the genome of one, at least one, or each of the plurality of cells at the specific site of the genome.

In some embodiments, integrating the barcode polynucleotide comprises: integrating the barcode polynucleotide into the genome of one, at least one, or each of the plurality of cells using a viral vector. The viral vector can comprise a polynucleotide comprising the barcode polynucleotide, a sequence thereof, a subsequence thereof, or a reverse complementary sequence of any of the proceeding. The viral vector can comprise a retrovirus, a lentivirus, an adenovirus, an adeno-associated virus, or a combination thereof. Integrating the barcode polynucleotide can comprise: injecting the viral vector into an organism or a tissue of the organism. The organism can be a mammal.

In some embodiments, the barcode polynucleotide comprises at least one promoter upstream of the barcode sequence. The at least one promoter can comprise three promoters. The at least one promoter can be a phage promoter. The at least one promoter can comprise a bacteriophage T3 promoter, a bacteriophage T7 promoter, a bacteriophage SP6 promoter, or a combination thereof. The at least one promoter can be inactive in one, at least one, or each live cell of the plurality of cells. The at least one promoter can be active in one, at least one, or each of the plurality of fixed cells.

In some embodiments, the barcode polynucleotide of one, at least one, or each of the plurality of cells comprises, for example, about 12 barcode sequences. The barcode sequences can be downstream of at least one promoter. Two of the barcode sequences can be downstream of different promoters, optionally wherein the different promoters comprise an identical promoter sequence. Two or more of the barcode sequences can have an identical length. The 12 barcode sequences can be different. The 12 barcode sequences can each be selected from a different set comprising four, or at least two, possible barcode sequences, and the possible barcode sequences of each set of possible barcode sequences can differ at one position. A combination of the 12 barcode sequences can be selected from about 16 million, or about 500000, possible combinations of 12 barcode sequences. The barcode sequences can be separated from one another by at least about 7 nucleotides.

In some embodiments, the barcode sequence is selected from a set comprising four, or at least two, possible barcode sequences. The possible barcode sequences from the set of possible barcode sequences differ at one position, for example position 7 of the barcode sequence. The possible barcode sequences can comprise adenine (A) nucleobase, guanine (G) nucleobase, or cytosine (C) nucleobase at the one position. The barcode sequence can be 20 nucleotides in length. The barcode polynucleotides of at least two cells of the plurality of cells can comprise an identical barcode sequence. The barcode polynucleotides of at least two cells of the plurality of cells can comprise different barcode sequences. The at least two cells can be cells of a cell type, cells of a cell subtype, and/or cells of an identical lineage. The at least two cells can be cells of different cell types, cells of different cell subtypes, and/or cells of different lineages. A first cell of the at least two cells can be a cell of interest, and/or wherein a second cell of the at least two cells is not a cell of interest. The first cell can be a cancer cell, and/or the second cell is a normal cell.

In some embodiments, the polynucleotide comprises a constitutively active promoter upstream of a marker gene. The at least one promoter and the constitutively active promoter can have divergent orientations. The marker gene can comprise a gene of a fluorescent protein, and optionally wherein the fluorescent protein comprises a green fluorescent protein, a yellow fluorescent protein, a cyan fluorescent protein, or a combination thereof.

In some embodiments, the fixative comprises a non-cross-linking fixative, a precipitating fixative, a denaturing fixative or a combination thereof. The fixative can comprise methanol and acetic acid. The ratio of methanol and acetic acid in the non-cross-linking fixative can be from about 10:1 (v/v) to about 1:10 (v/v). The fixative can comprise from about 5% acetic acid in methanol to about 75% acetic acid in methanol. Fixing the cells can comprise: fixing the cells without using a cross-linking fixative. The plurality of fixed cells can comprise dead cells.

In some embodiments, the method comprises: fixing fixed cells of the plurality of fixed cells using a second fixative to obtain a plurality of second fixed cells. Contacting each of the one or more fixed cells can comprise: contacting each of the one or more second fixed cells with a plurality of detection probes each comprising a barcode binding sequence, thereby (i) one, at least one, or each of the plurality of barcode molecules comprising the barcode sequence of the oligonucleotide in the second fixed cell hybridizes to a detection probe of the plurality of detection probes comprising the barcode binding sequence reverse complementary to the barcode sequence, or a portion thereof, and (ii) the detection probe is associated with a fluorophore. Detecting the fluorophore, or fluorescence thereof can comprise: detecting the fluorophore, or fluorescence thereof, associated with the detection probe hybridized to the one, at least one, or each barcode molecule in each of the one or more second fixed cells using fluorescence imaging, and wherein the fluorophore, associated with the detection probe hybridized to the barcode molecule comprising the barcode sequence of the barcode polynucleotide in the second fixed cell, detected indicates the barcode sequence of the barcode polynucleotide in the second fixed cell. The second fixative can comprise a cross-linking fixative. The second fixative can comprise formaldehyde.

In some embodiments, one, at least one, or each of the plurality of cells comprises no barcode molecule. Generating the plurality of barcode molecules can comprise: transcribing the barcode polynucleotide in each of the plurality of fixed cell to generate the plurality of barcode molecules comprising the barcode sequence of the barcode polynucleotide in the fixed cell. Transcribing the barcode polynucleotide can comprise: transcribing the barcode polynucleotide in each of the plurality of fixed cell to generate the plurality of barcode molecules comprising the barcode sequence of the barcode polynucleotide in the fixed cell using a phage RNA polymerase. The phage RNA polymerase can comprise a bacteriophage T3 RNA polymerase, a bacteriophage T7 RNA polymerase, a bacteriophage SP6 RNA polymerase, or a combination thereof. The plurality of barcode molecules comprises at least 100 barcode molecules comprising the barcode sequence of the barcode polynucleotide in each of the plurality of fixed cells.

In some embodiments, thereby the barcode sequence of each of the plurality of barcode molecules hybridizes to the barcode binding sequence of the detection probe that is reverse complementary to the barcode sequence of the barcode molecule. In some embodiments, contacting the plurality of fixed cells with the plurality of detection probes comprises: contacting each of the one or more fixed cells with detection probe molecules of each of the plurality of detection, thereby (i) one, at least one, or each of the plurality of barcode molecules comprising the barcode sequence of the oligonucleotide in the fixed cell hybridizes to a detection probe molecule of the detection probe of the plurality of detection probes comprising the barcode binding sequence reverse complementary to the barcode sequence, or a portion thereof, and (ii) the detection probe molecule of the detection probe is associated with a fluorophore.

In some embodiments, four, or at least two, detection probes of the plurality of detection probes comprise the barcode binding sequences that differ at one position. In some embodiments, four, or at least two, detection probes of the plurality of detection probes comprise (i) barcode binding sequences that differ at one position and (ii) different initiator sequences. The four, or at least two, detection probes can have an identical concentration. The concentration of one, at least one, or each of the four, or at least two, detection probes can be about 4 nM. One, at least one, or each of the plurality of barcode molecules comprising the barcode sequence of the oligonucleotide in the fixed cell can hybridize to one of the four, or at least two, detection probes comprising the barcode binding sequence reverse complementary to the barcode sequence, or a portion thereof, not the remaining three, or at least one, detection probe(s).

In some embodiments, the plurality of detection probes comprises 12 sets of detection probes, wherein each of the sets of detection probes comprises four, or at least two, detection probes with barcode binding sequences that differ at one position and are reverse complementary to possible barcode sequences of one of the sets of possible barcode sequences. The detection probes of one of the sets of detection probes can comprise different initiator sequences. Said contacting and said detecting comprises: iteratively, contacting each of the one or more fixed cells with a different set of detection probes each comprising a barcode binding sequence, thereby (i) one, at least one, or each of the plurality of barcode molecules comprising the barcode sequence of the oligonucleotide in the fixed cell hybridizes to a detection probe of the set of detection probes comprising the barcode binding sequence reverse complementary to the barcode sequence, or a portion thereof, and (ii) the detection probe is associated with a fluorophore; and detecting the fluorophore associated with the detection probe hybridized to the one, at least one, or each barcode molecule in each of the one or more fixed cells using fluorescence imaging. A combination of the fluorophores associated with detection probes hybridized to the barcode molecule comprising the barcode sequence of the barcode polynucleotide in the fixed cell, detected can indicate the barcode sequence of the barcode polynucleotide in the fixed cell. The method can comprise: removing the detection probe hybridized to the one, at least one, or each barcode molecule in each of the one or more fixed cells. Said removing can comprise: digesting the detection probe hybridized to the one, at least one, or each barcode molecule in each of the one or more fixed cells using DNase.

In some embodiments, the method comprises: determining the barcode sequence in each of the one or more fixed cells using the fluorophore, associated with the detection probe hybridized to the barcode molecule comprising the barcode sequence of the barcode polynucleotide in the fixed cell, detected. In some embodiments, the method comprises: determining lineages of, and/or a clonal relationship between, two or more fixed cells of the plurality of fixed cells using the barcode sequence of the barcode polynucleotide in each of the two or more fixed cells. In some embodiments, the method comprises: determining a spatial relationship of two or more fixed cells of the plurality of fixed cells; and correlating the barcode sequences of the barcode polynucleotide in each of the two or more fixed cells with a spatial relationship of the two or more fixed cells. The two or more cells can be cells of different cell types or cell subtypes. The two or more cells can be cells of an identical cell type or cell subtype.

In some embodiments, the method comprises: staining nuclei of the plurality of fixed cells; and identifying nuclei of the plurality of fixed cells based on the nuclei stained, wherein said detecting comprises: detecting the fluorescence of the fluorophore, associated with the detection probe hybridized to the barcode molecule comprising the barcode sequence of the barcode polynucleotide in the fixed cell, in the nucleus of the cell identified.

In some embodiments, the method comprises: base editing the barcode sequence of the barcode polynucleotide in one, at least one, or each of the plurality of cells. In some embodiments, said base editing comprises: base editing the barcode sequence of the barcode polynucleotide in one, at least one, or each of the plurality of cells at the one position that the possible barcode sequences from the set of possible barcode sequences are different. In some embodiments, said base editing comprises: adenine (A)-to-guanine (G) base editing and/or cytosine (C)-to-thymine (T) base editing.

In some embodiments, said base editing comprises: base editing using a base editor and a guide ribonucleic acid (gRNA) targeting a gRNA targeting sequence of the barcode polynucleotide, and wherein the gRNA targeting sequence comprises the barcode sequence, or a portion thereof, of the barcode polynucleotide. The gRNA targeting sequence is 20 nucleotides in length. The barcode sequence and the gRNA targeting sequence of the barcode polynucleotide can completely overlap. The barcode sequence and the gRNA targeting sequence of the barcode polynucleotide can overlap by 11 nucleotides. The barcode polynucleotide can comprise a Protospacer Adjacent Motif (PAM), and optionally the PAM is downstream of the gRNA targeting sequence. The base editor can comprise an adenine base editor (ABE) and/or a cytosine base editor (CBE). Said base editing can comprise: introducing a plasmid capable of expressing the base editor and the gRNA into one or more of the plurality of cells. Said introducing can comprise: introducing the plasmid capable of expressing the base editor and the gRNA into the one or more cells using transient transfection.

In some embodiments, said base editing comprises base editing the barcode sequence of the barcode polynucleotide in one, at least one, or each of the plurality of cells at one or more predetermined time points. In some embodiments, said base editing comprises base editing the barcode sequence of the barcode polynucleotide in one, at least one, or each of the plurality of cells at an edit rate, optionally wherein the edit rate is predetermined, optionally wherein the edit rate is about 1% to about 100% edit per unit time, and optionally the edit rate is about 1% to 100% edit per cell per cell division cycle.

In some embodiments, the method comprises: determining gene expression in one, at least one, or each of the plurality of cells. In some embodiments, the method comprises: correlating the gene expression of two or more fixed cells of the plurality of fixed cells with the lineages of, the clonal relationship between, and/or the spatial relationship of, the two or more fixed cells.

In some embodiments, the plurality of cells is from a sample comprising a cell culture, a tissue, an organ, an embryo, an organism, a section thereof. In some embodiments, the plurality of cells is from a sample comprising an in vivo sample and/or an in vitro sample. In some embodiments, the plurality of cells comprises one or more tumor cells, one or more immune cells, one or more epithelial cells, one or more nervous cells, one or more blood cells, one or more bone cells, one or more fat cells, one or more muscle cells, and/or one or more sex cells. In some embodiments, the plurality of cells comprises one or more stem cells, one or more progenitor cells, and/or one or more mature cells. In some embodiments, two, at least two, or each of the plurality of cells are cultured under an identical condition. In some embodiments, two, at least two, or each of the plurality of cells are cultured under different conditions. The identical condition or each of the different conditions can comprise a genetic perturbation, an environmental perturbation, or a combination thereof.

Disclosed herein include embodiments of a plurality of compositions for determining barcode sequences in situ. In some embodiments, the plurality of compositions comprises: a plurality of cells each comprising a barcode polynucleotide with a barcode sequence, of any method or embodiment disclosed herein. The plurality of compositions can comprise: (a) a donor plasmid comprising the barcode polynucleotide, a sequence thereof, a subsequence thereof, or a reverse complementary sequence of any of the proceeding, the barcode polynucleotide comprising at least one barcode sequence, (b) a plasmid capable of expressing Cas9 and/or a guide ribonucleic acid (gRNA) for integrating the barcode polynucleotide into the genome, and/or (c) a viral vector for integrating the barcode polynucleotide into each of the plurality of cells, of any method or embodiment disclosed herein. The viral vector can comprise a polynucleotide comprising the barcode polynucleotide, a sequence thereof, a subsequence thereof, or a reverse complementary sequence of any of the proceeding. The plurality of compositions can comprise: a fixative, of any method or embodiment disclosed herein. The plurality of compositions can comprise: a polymerase of any method or embodiment disclosed herein. The plurality of compositions can comprise: a plurality of detection probes of any method or embodiment disclosed herein. The plurality of compositions can comprise: pairs of amplifier probes, or a plurality of first amplifier probes, of any method or embodiment disclosed herein.

Disclosed herein include embodiments of a kit. In some embodiments, the kit comprises: a plurality of compositions disclosed herein. The kit can comprise: instructions for using the plurality of compositions for determining barcode sequences in situ, high throughput screening, analyzing clonal dynamics and heterogeneity in a tumor or tumors, immunology, or developmental biology, and/or lineage or event recording.

Disclosed herein include embodiments of a method comprising using a plurality of compositions or a kit disclosed herein for: high throughput screening, analyzing clonal dynamics and heterogeneity in a tumor or tumors, immunology, or developmental biology, and/or lineage or event recording.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A. Workflow for analysis of Zombie barcodes (left to right). First, barcode constructs containing a phage promoter, such as T7, that is inactive in live cells, are integrated in the genome at 104. Second, and optionally, base editors or other DNA modifying enzymes (brown) can alter barcode sequence to increase barcode diversity at 108. Third, cells are fixed at 112 and phage RNA polymerase (pink) is added at 116. This enables transcription of the barcode to RNA (gray lines) at 120. RNA transcripts can be detected in situ at 124, using for example, fluorescent imaging at 128. RNA transcripts accumulate at the active site (large red dot), and also diffuse away from it (small red dots represent individual transcripts).

FIG. 1B. The Z1 construct was engineered to contain a barcode downstream of T3, T7, and SP6 phage promoters, and to express H2B-Cerulean fluorescent protein (CFP) in living cells from a divergently oriented mammalian promoter. Z1 was stably integrated in mouse ES cells at the ROSA26 locus (single integration per genome). This line was compared to a similar cell line containing the control construct lacking phage promoters. FIG. 1C. Polyclonal control cells and Z1 cells (columns) were imaged with or without the indicated phage polymerases (rows). HCR was used to detect barcode RNA (zBC). Nuclei were visualized by native fluorescence of H2B-CFP (cyan) as well as DAPI staining (blue). Barcode transcripts appear only in Z1 cells with phage polymerase (yellow dots, right column). The experiment was independently repeated twice with similar results. Scale bar is 25 μm.

FIG. 1D. In monoclonal cultures, active sites can be detected in most cells (image). Nuclei (blue) and active sites (yellow) are segmented automatically (green outlines and red dots, respectively). One cell in this field of view does not show any active site (arrowhead). Scale bar is 25 μm. Percentages of cells with detectable active sites for each polymerase are shown on the right. Horizontal lines indicate the mean of replicates (n=3 biologically independent samples). Total of 3916 cells were analyzed, with at least 420 cells for each replicate.

FIG. 1E. The Z3 construct encodes three 900 bp barcodes, each expressed from a distinct set of phage promoters. This construct was integrated at ROSA26, transcribed using T3 RNA polymerase, and imaged in all three color channels. T7 and SP6 promoters are shaded gray because they are not used in FIG. 1F and FIG. 1G. Sizes of elements are not drawn to scale.

FIG. 1F. Schematic: Assuming independence, the conditional probability of detecting barcode i in a cell, given detection of another barcode (j), should equal the overall probability of barcode i detection, with deviations signifying either synergy (green arrow) or interference (red arrow) between barcodes. Bar plot: for Z3, the conditional probability analysis shows independent detection events for all three barcodes. Bars indicate mean of 3 replicates (points).

FIG. 1G. Fraction of Z3 cells with no detectable active sites declines with the number of barcodes analyzed, consistent with independent expression of different phage promoters in the same cell. Thus, detection efficiency can be increased with additional barcode copies. Dots represent the mean for different barcodes or barcode combinations and black vertical lines show the range over three replicates. Blue line indicates the exponential fit. Total of 564 cells were analyzed for plots in F and G.

FIG. 2A. Short probes (colored lines) target 20 bp regions of the larger Z1 barcode sequence and can be detected in distinct fluorescence channels. These probes also contain distinct 40 bp initiator sequences for multi-channel HCR analysis. Local accumulation of transcripts at the active site effectively amplifies signal and enables detection, even with a single probe per target site.

FIG. 2B. Z1 cells were treated with each polymerase (rows) and imaged in three channels (columns) after detection with individual fluorescently labeled probes (colors matching those in FIG. 2A). Final column shows composite images. The barcode in Z1 cells is integrated site-specifically at the ROSA26 locus. The experiment was independently repeated three times with similar results. Scale bar is 25 μm.

FIG. 2C. Signal from each individual probe can be detected in the majority of the cells by single molecule Fluorescence In Situ Hybridization (smFISH) or hybridization chain reaction (HCR). Plot shows the percentage of Z1 cells with active sites detected using a single 20 bp probe. Dots are color-coded based on probe identity. n=3 biologically independent samples. Lines show the average efficiency over three probes and three replicates.

Figure 2A:
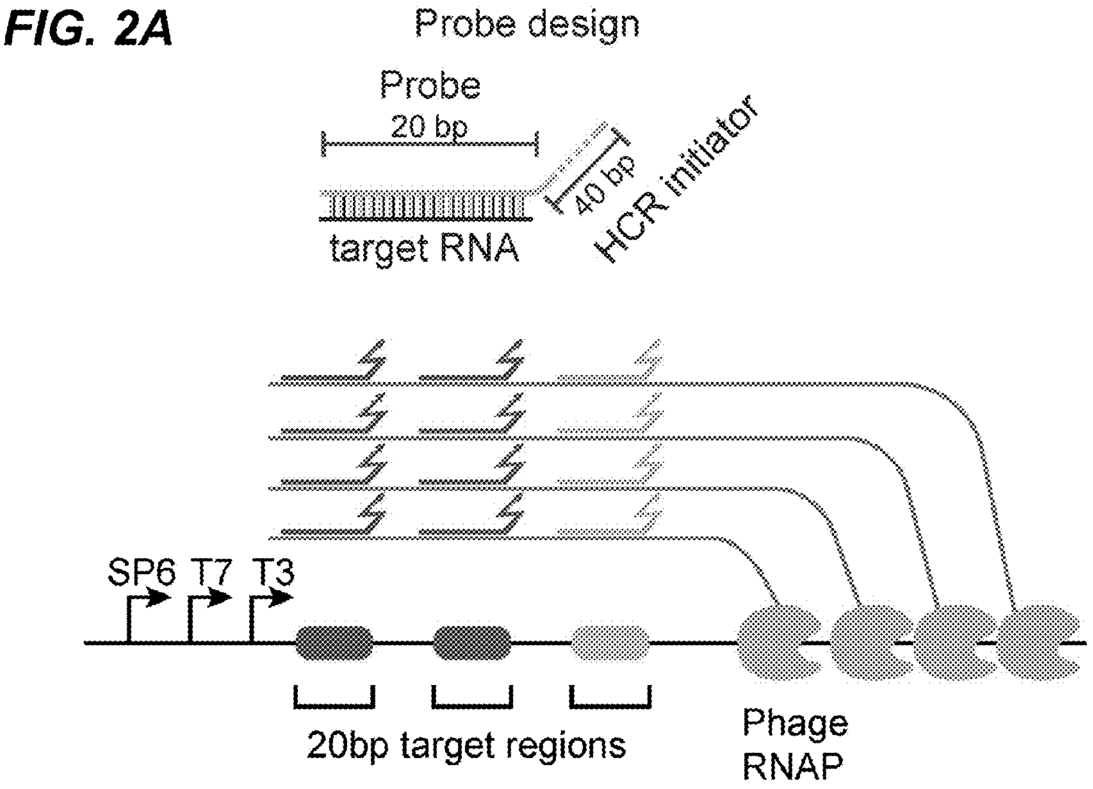
FIGS. 2A-2H. Reliable detection of short barcodes.
Figure 2B:
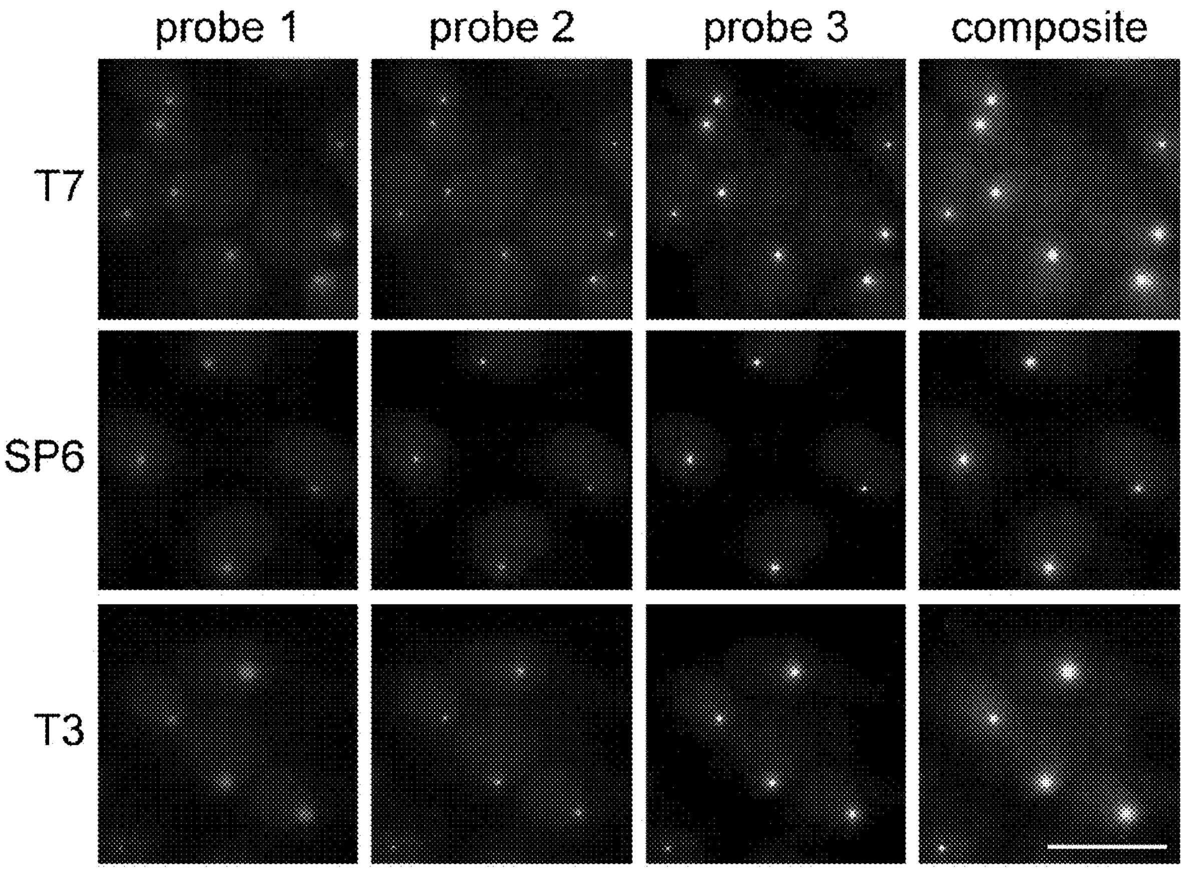
Figure 2C:
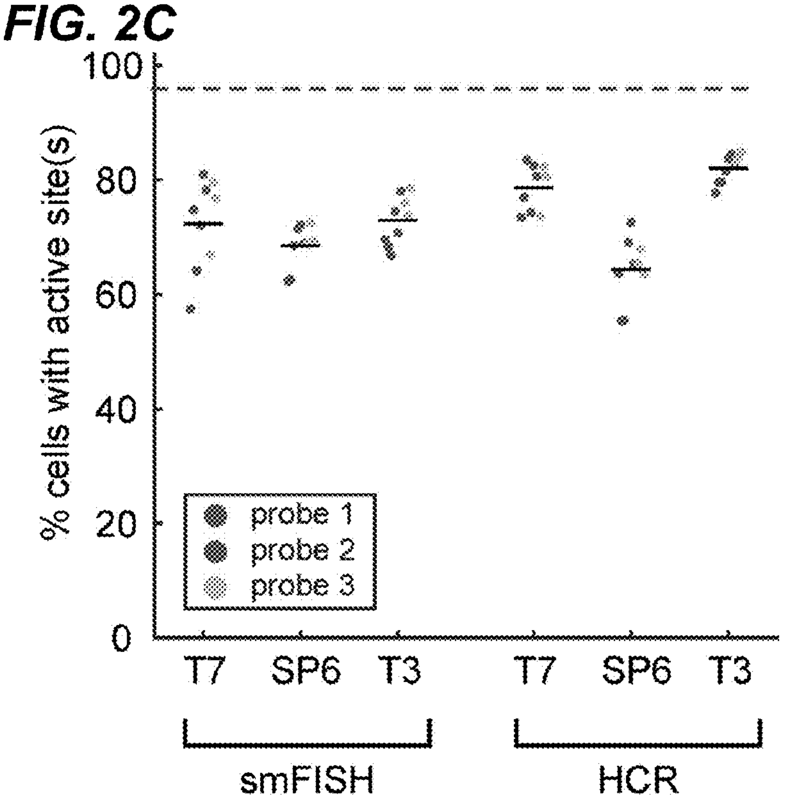
Figure 2D:
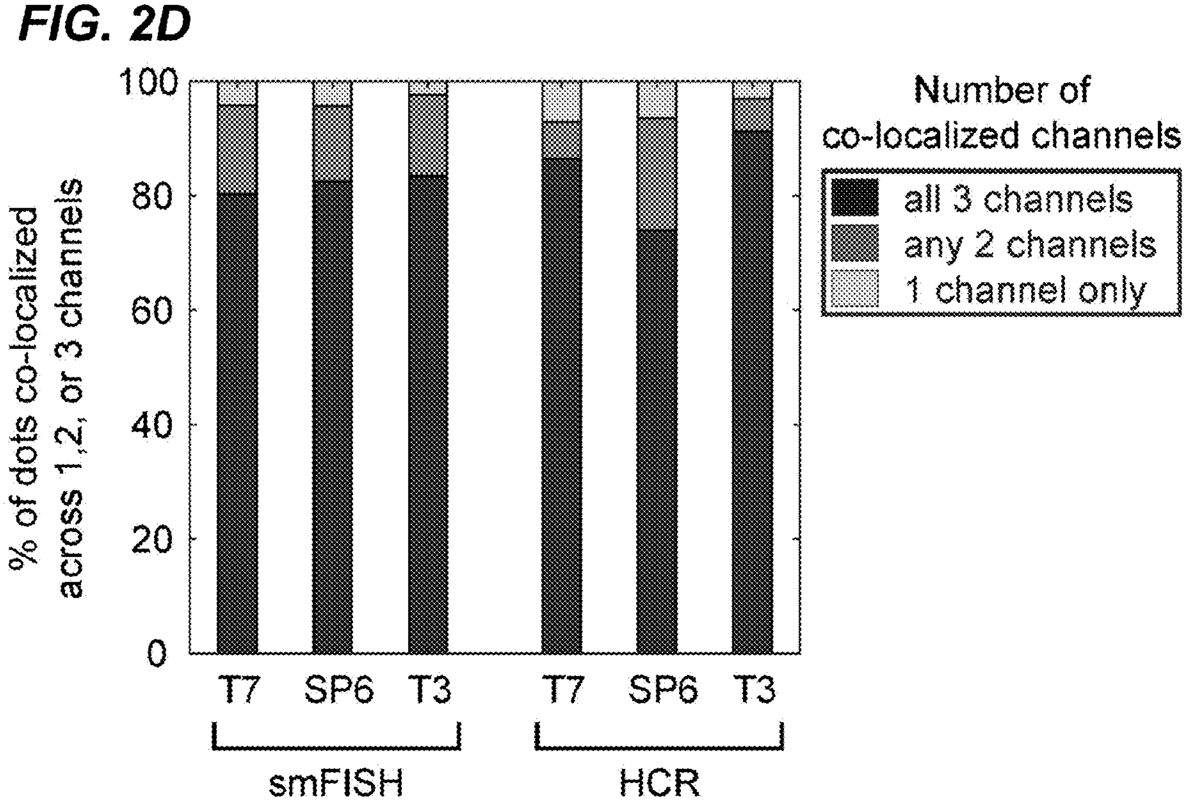

FIG. 2D. Colocalization analysis shows that the majority of dots colocalize in multiple channels, indicating the reliability of single probe detection. For each condition, gray shades indicate fractions of dots that are detected in only 1 channel or co-detected in 2 or 3 channels. Data from three biologically independent samples are combined in each condition. For plots in C and D, total of 5097 cells were analyzed, with at least 669 cells for each condition.

Figure 2F:
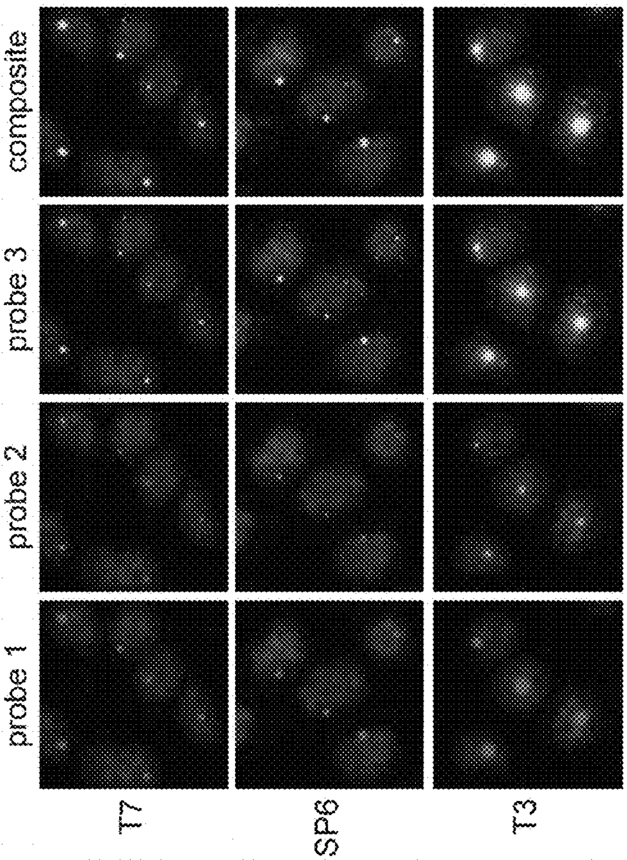
Figure 2E:
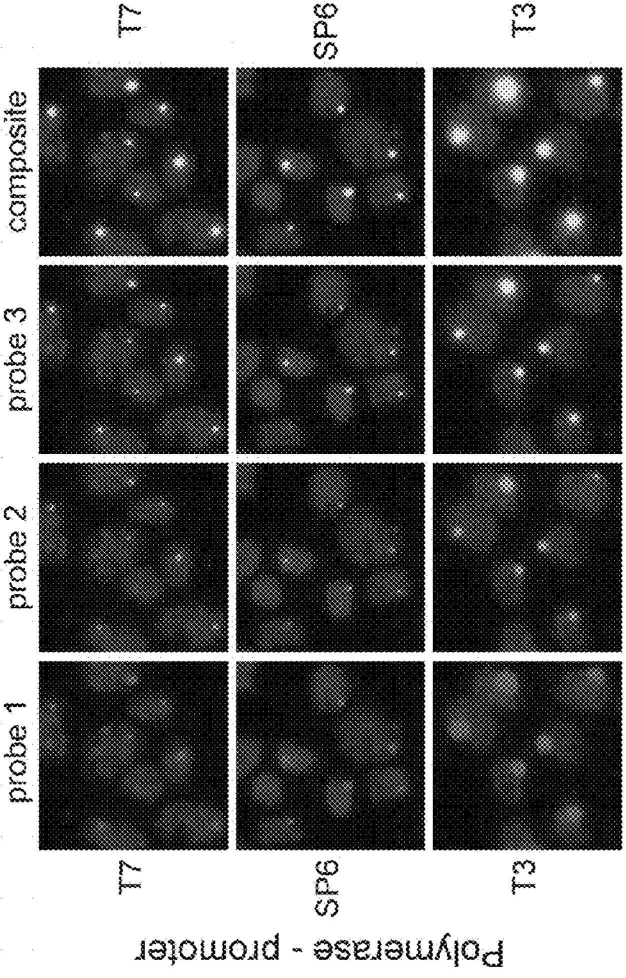

FIG. 2E. Z1 cells were treated with each polymerase (rows), imaged following HCR in three channels (columns).

FIG. 2F. Phage transcripts can be detected without HCR amplification. Images show same treatment as in FIG. 2B, except with only a single HCR hairpin, preventing HCR amplification. Images in FIG. 2B and FIG. 2C are scaled to different intensity ranges.

Figure 2H:
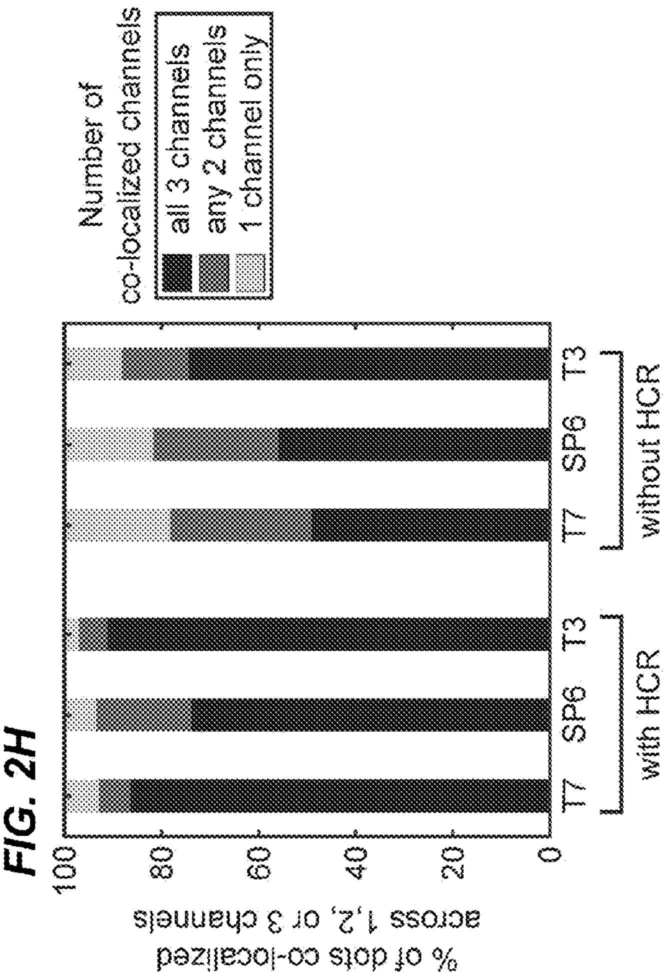
Figure 2G:
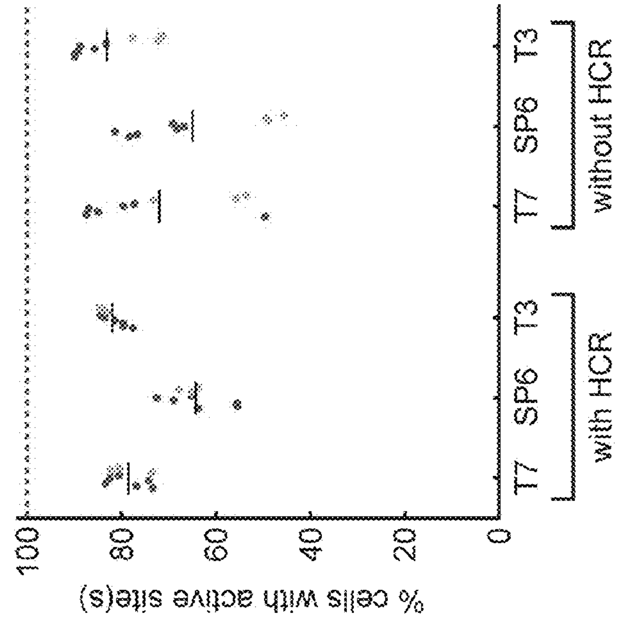

FIG. 2G. Detection efficiency for individual dots is comparable with or without HCR (Wilcoxon rank sum test, $p>0.4$). The percentage of Z1 cells with active sites detected using a single 20 bp probe. Dots are color-coded based on the probe identity. Lines show the average efficiency over three probes and three replicates.

FIG. 2H. Co-localization analysis shows greater overlap between channels with HCR. For each condition, gray shades indicate fractions of dots that are detected in 1, 2, or all 3 channels. In rare cases, two dots from the same channel were detected in one active site, mainly due to the proximity of the active sites. These dots were excluded from the analysis.

FIGS. 3A-3D. Probe competition accurately discriminates single nucleotide variants.

Figures 3A, 3B, 3C, 3D:
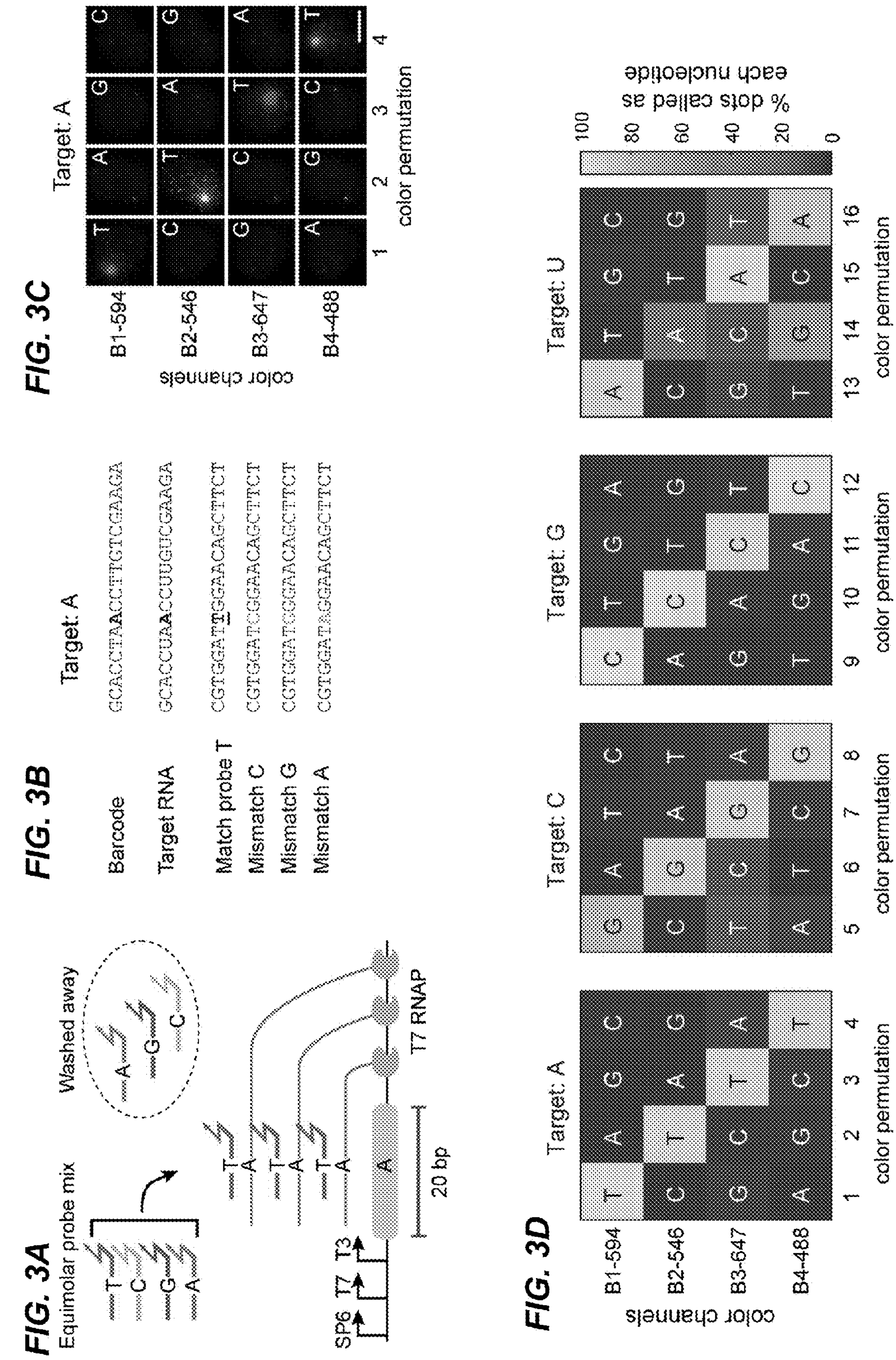

FIG. 3A. Perfect match probes outcompete those with a single mismatch when an equimolar mixture of all 4 probe variants is used. This feature can be used to detect SNVs in situ.

FIG. 3B. Sequences of barcode, target RNA, and probes with SNV position indicated in bold underline (match) and brown (mismatch).

FIG. 3C. Representative images of Z1 cells showing detection of the correct target nucleotide in the barcode (see FIG. 3D for quantification of the results and FIG. 12 for representative images of other target nucleotides). All images were acquired under the same conditions and displayed with identical processing parameters for each channel (row). Each column represents one experiment in which four probes with a SNV and orthogonal HCR initiators (B1-4) were mixed and hybridized to the sample with the indicated color permutation. Letters indicate the probe variant in each image. HCR initiator and the fluorescence channel used for each probe are shown next to the rows. The barcode in Z1 cells is integrated site specifically in ROSA26 locus. Scale bar is 10 μm.

FIG. 3D. Probe competition can detect all four target nucleotides. Each matrix represents SNV analysis with four distinct color permutations, as in FIG. 3C, with the indicated target nucleotide at distinct positions. For targeting U (rightmost matrix), one permutation (14) is ambiguous due to wobble base pairing, but others (e.g. 15) provide accurate discrimination. Color scale represents the percentage of dots in which the indicated color channel has the highest rank of normalized brightness (see Methods). Total of 4009 cells were analyzed, with at least 135 cells for each color permutation.

FIGS. 4A-4F. CRISPR base edits can be read out in situ.

Figure 4A:
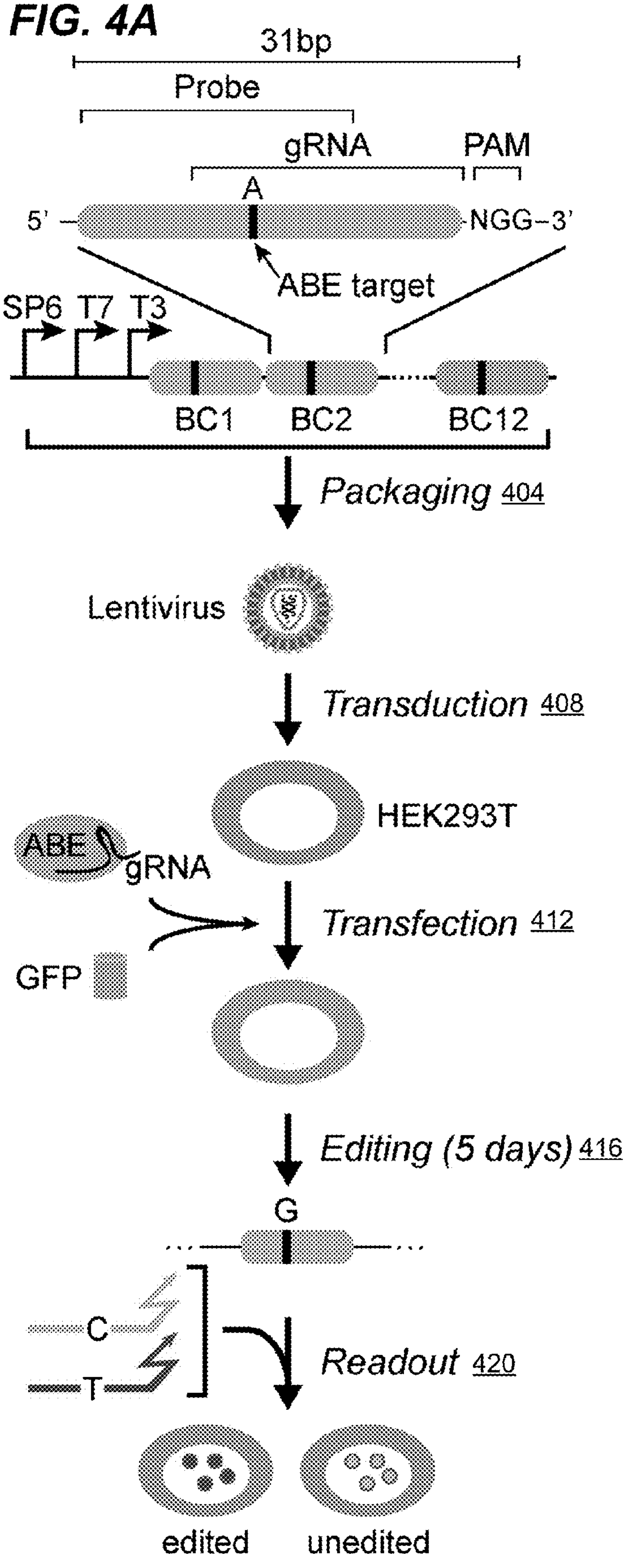

FIG. 4A. Arrays of 12 barcodes were designed so that, in each barcode, a single base pair (black vertical line) can be targeted by the adenine base editor (ABE) and a gRNA. The barcode arrays were packaged in lentivirus at 404 and transduced into HEK293T cells at 408. ABE7.10, gRNA, and a fluorescent co-transfection marker (e.g., GFP), were transiently delivered as DNA into the cells at 412, and editing was allowed to occur for 5 days at 416. Finally, cells were fixed, treated with T3 RNA polymerase and read out by competing probes for original (orange) and edited (red) base variants at 420.

Figures 4B, 4C, 4D:
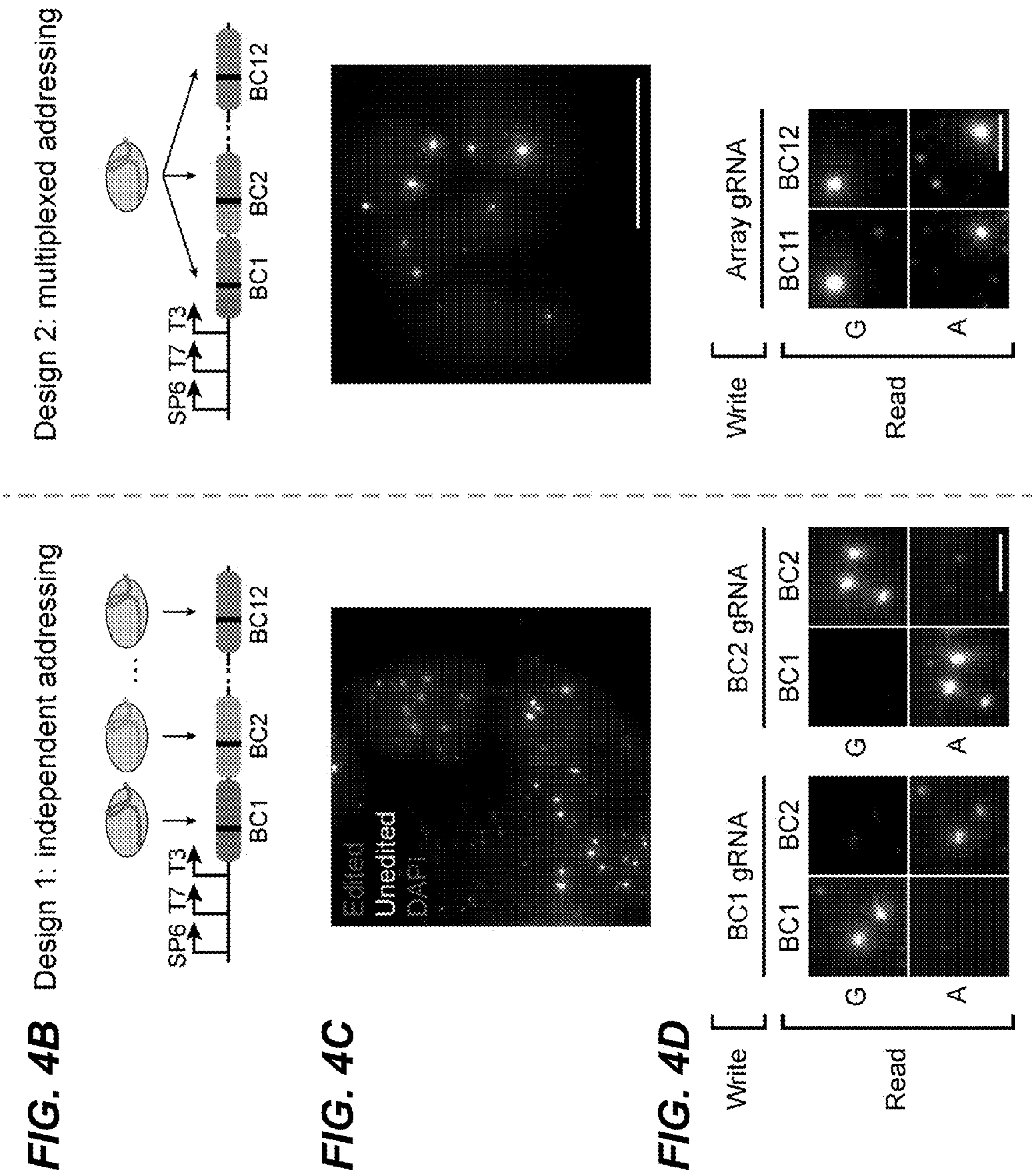

FIG. 4B. Two designs of the memory array. Design 1 allows each barcode to be edited independently by a distinct gRNA, whereas all barcodes in design 2 are targeted by the same gRNA, providing more memory states for an individual gRNA. In both designs, the state of each individual barcode can be readout in situ, using Zombie.

FIG. 4C. Representative images, for design 1 (left) and design 2 (right), showing a mixture of edited (red) and unedited (yellow) active sites. Since barcodes are delivered by lentiviral transduction, cells can carry multiple copies of the barcode in their genome. The experiment was independently repeated twice with similar results. Scale bar is 10 μm.

FIG. 4D. Each barcode in design 1 (left) can be addressed independently using its corresponding gRNA. 2×2 matrices show results of targeting distinct barcodes. Edits are seen at the targeted barcode but not the adjacent non-targeted barcode. In contrast, design 2 gRNA (right) can edit all barcodes. The experiment was independently repeated twice with similar results. Scale bar is 3 μm.

Figure 4E:
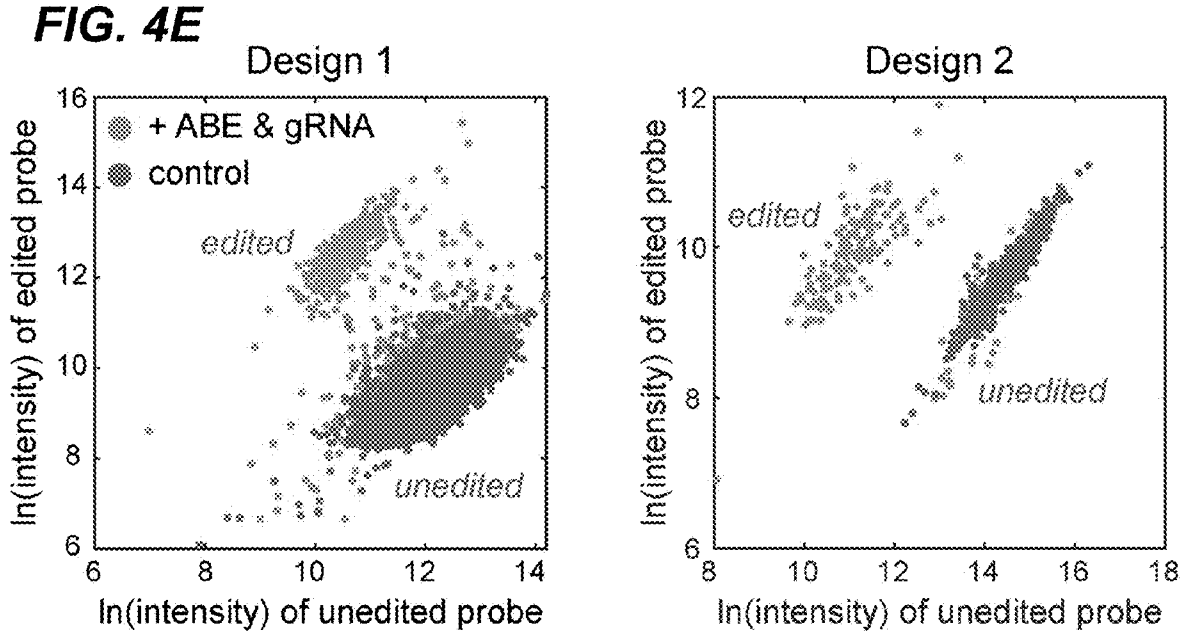

FIG. 4E. Analysis of Barcode 1, Design 1 (left) and Barcode 10, Design 2 (right). Dots can be classified into distinct edited and unedited groups based on the signal intensity in edited and unedited channels. Scatter plots show the natural log of the intensity in edited versus unedited channels. Data from negative control samples (blue) are plotted on top of points from samples which received both ABE7.10 and gRNA plasmids. See FIGS. 16-17 for all barcodes in both designs.

Figure 4F:
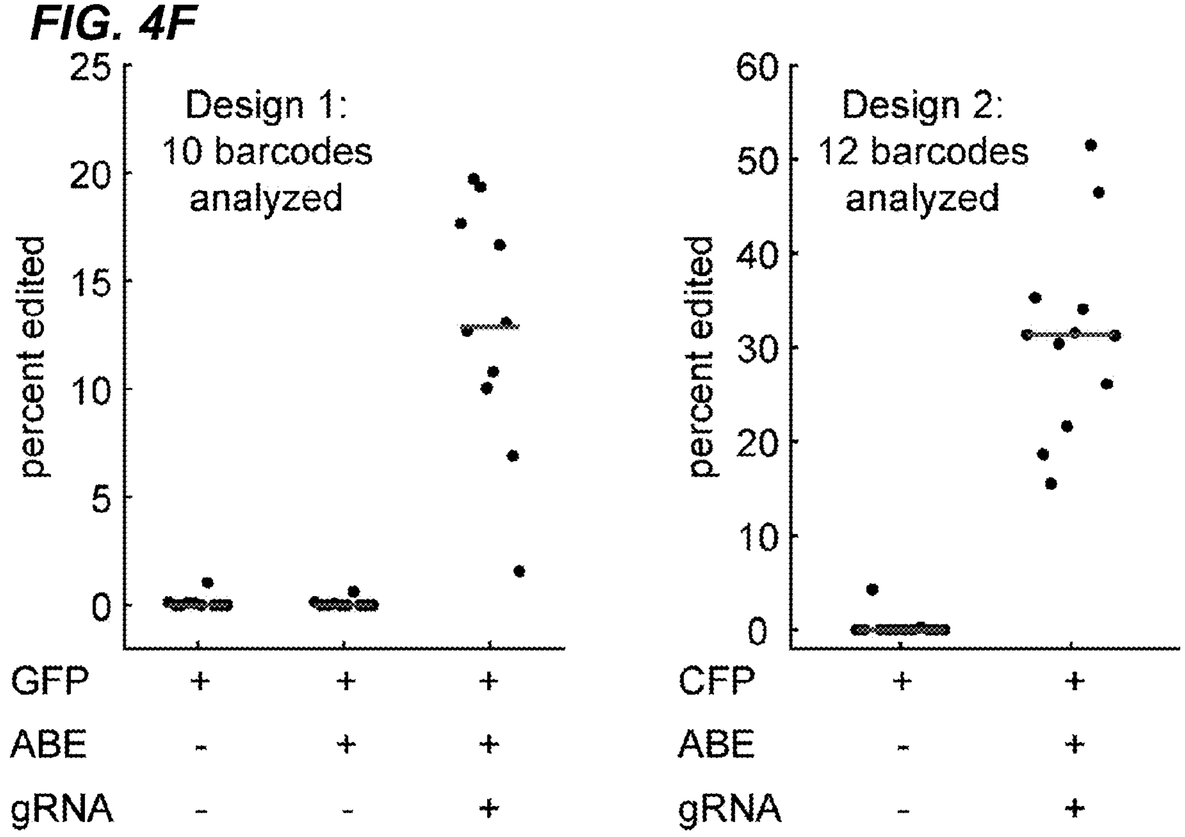

FIG. 4F. Edits are detected when both ABE and gRNA are present. Each point represents one barcode, red lines show the median. Without ABE and barcode-specific gRNA, only a very small fraction of active sites are mis-identified as edited, indicating low false positive rates across barcodes. Note that editing rates differ among barcodes (vertical scatter). On average 1357 and 383 active sites were analyzed for each barcode at each condition, for design 1 and 2, respectively.

FIGS. 5A-5H. Zombie can detect barcodes and discriminate single nucleotide variants in chick embryo and adult mouse brain.

FIG. 5A. The ZL1 construct includes a barcode downstream of phage promoters and a human Ubiquitin C promoter (hUbi) controlling GFP expression to allow identification of transduced cells. ZL1 was packaged in lentivirus at 504 and injected into the olfactory bulb of a 3-month old mouse at 508a or chick neural tube at embryonic stage HH10 at 508b. Chick embryos were incubated for 3 days post-transduction, until stage HH27, at 512a and then frozen and sectioned for analysis of the neural tube at 516a. Mouse brains were frozen and sectioned 3 days post-transduction at 512b to analyze olfactory bulb at 516b. Both samples were then fixed, treated with T7 RNA polymerase, probed, and imaged at 520.

FIG. 5B. In coronal sections through the diencephalon of chick embryos, distinct active sites (arrowheads) were observed with, but not without, transcription by T7 RNA polymerase. Similarly, Zombie active sites could also be detected, in a T7 dependent manner, in the granular cell layer of the olfactory bulb (arrowheads). Although the expression of GFP, detected by HCR, was sparse (arrows), the injection site could still be identified. All experiments were repeated on at least 3 sections with similar results. (C) To test for detection of single base pair mismatches in mouse and chicken tissue sections, samples were hybridized with match and mismatch probes (pink and green, respectively). A reference probe independently identified the active sites.

FIGS. 5D-5E. In both chicken and mouse samples, fluorescent signal at active sites was dominated by the match probe, regardless of channel assignments (columns). Match probes also co-localized with reference channels (bottom rows), indicating competition between match and mismatch probes does not reduce overall detection efficiency. All experiments were repeated on at least 3 sections with similar results. Since barcodes are delivered by lentiviral injection, cells can carry multiple copies of the barcode in their genome. Scale bars are 10 μm.

Figure 5F:
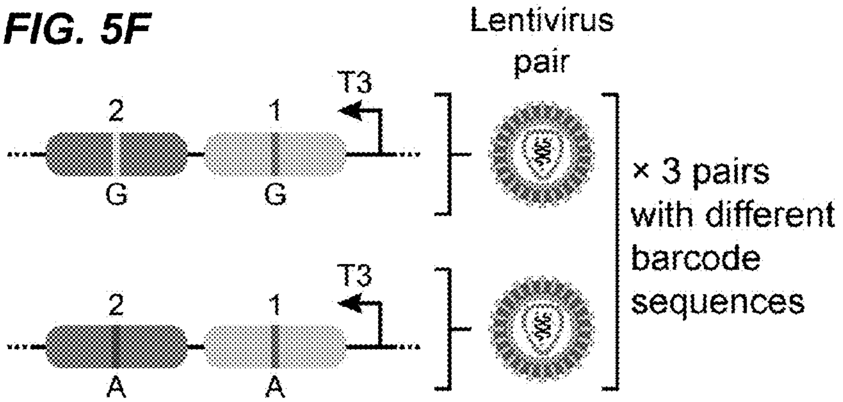

FIG. 5F. Pairs of barcoded lentiviral vectors were used to further assess the SNV detection capability in vivo. Each virus contains two distinct 20 bp barcodes, denoted by 1 and 2. Within a pair, viruses have variants of these barcodes that differ with each other at only one base pair (A or G). A mix of three viral pairs, with different barcode sequences but the same SNV arrangement, was co-injected in the mouse olfactory bulb and read out in three rounds of hybridization and imaging, 12 days post-transduction.

Figure 5G:
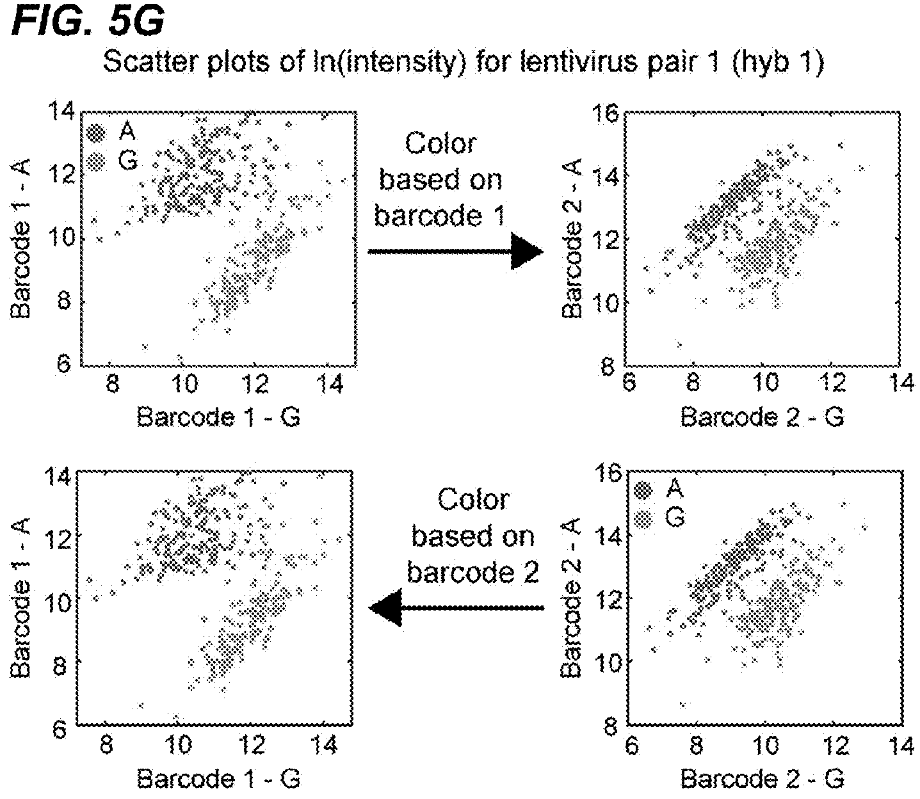

FIG. 5G. Scatter plots showing natural log of signal intensity for two variants (A and G) of two barcodes (1 and 2) for lentivirus pair 1 (see FIG. 19 for the other pairs). Each point represents one active site. The points are color coded based on their barcode 1 state (top) or barcode 2 state (bottom) to show the concordance between the detected state of two barcodes.

Figure 5H:
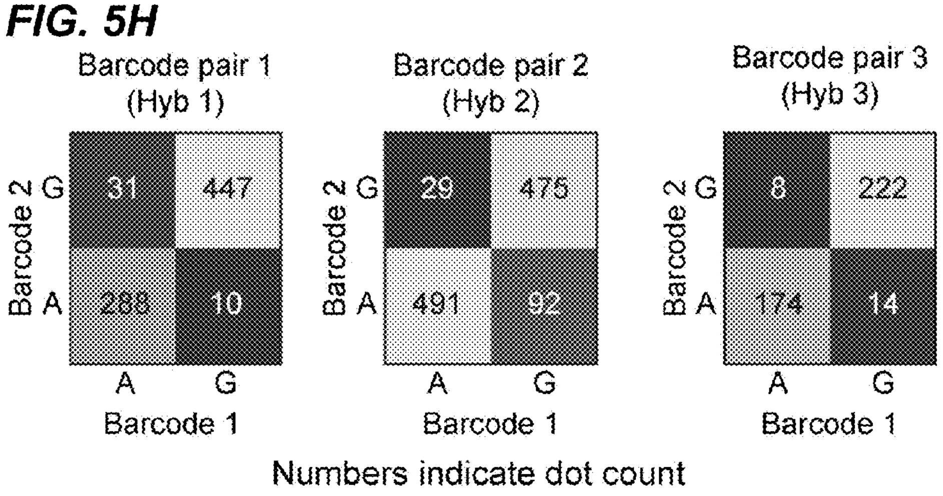

FIG. 5H. In all pairs, the majority of active sites are classified as either A or G for both barcodes. Data are combined from two biological replicates.

FIGS. 6A-6D. In situ readout of a combinatorial barcode library.

Figure 6B:
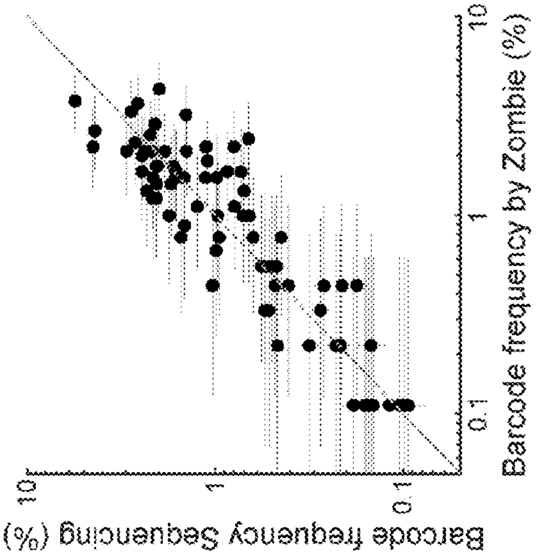
Figure 6A:
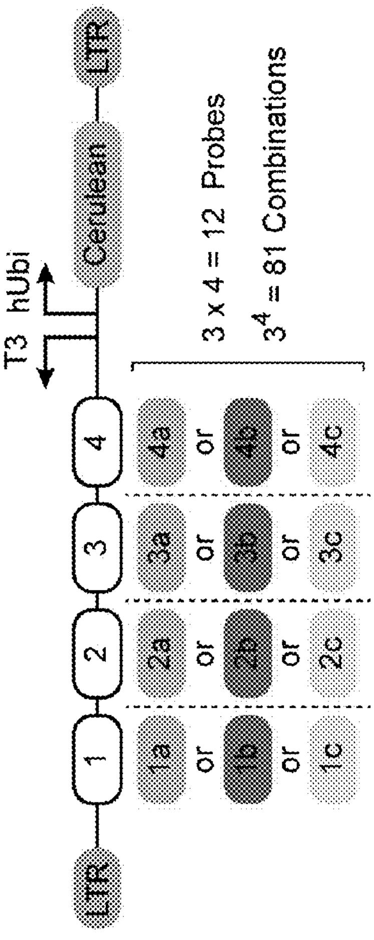

FIG. 6A. A combinatorial lentiviral library in which each of 4 positions can take one of three distinct position-specific 20 bp barcodes to generate 81 possible barcode combinations. The viruses also encode Cerulean downstream of hUbi promoter.

FIG. 6B. The frequency at which barcode combinations are detected in situ, in transduced HEK293T cells, is consistent with the frequency measured by next generation sequencing. Each point represents one barcode combination. 906 active sites were analyzed by Zombie. Error bars are 95% binomial confidence intervals, calculated using Clopper-Pearson method. Since the number of observations by imaging (906 active sites) is lower than the sequencing read count (102056 aligned reads), the horizontal error bars are wider than the vertical ones.

Figure 6C:
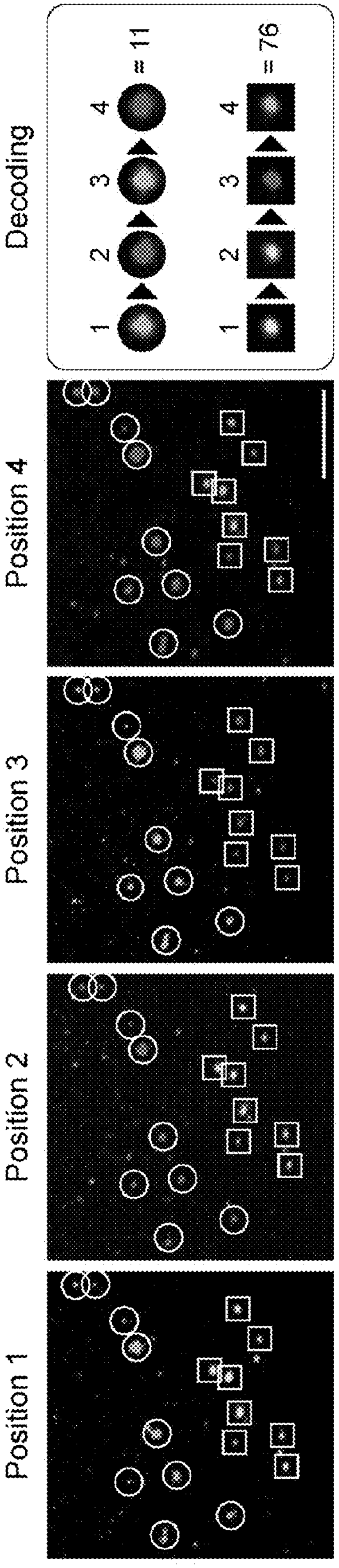

FIG. 6C. Detection of two clones of cells, labeled by two barcode combinations, in a coronal section of chick neural tube. Maximum intensity projected images corresponding to variants in each barcode position are merged in 3 color channels (cyan, magenta, and yellow, corresponding to A). Dots that do not appear consistently in all rounds are excluded from the analysis.

Figure 6D:
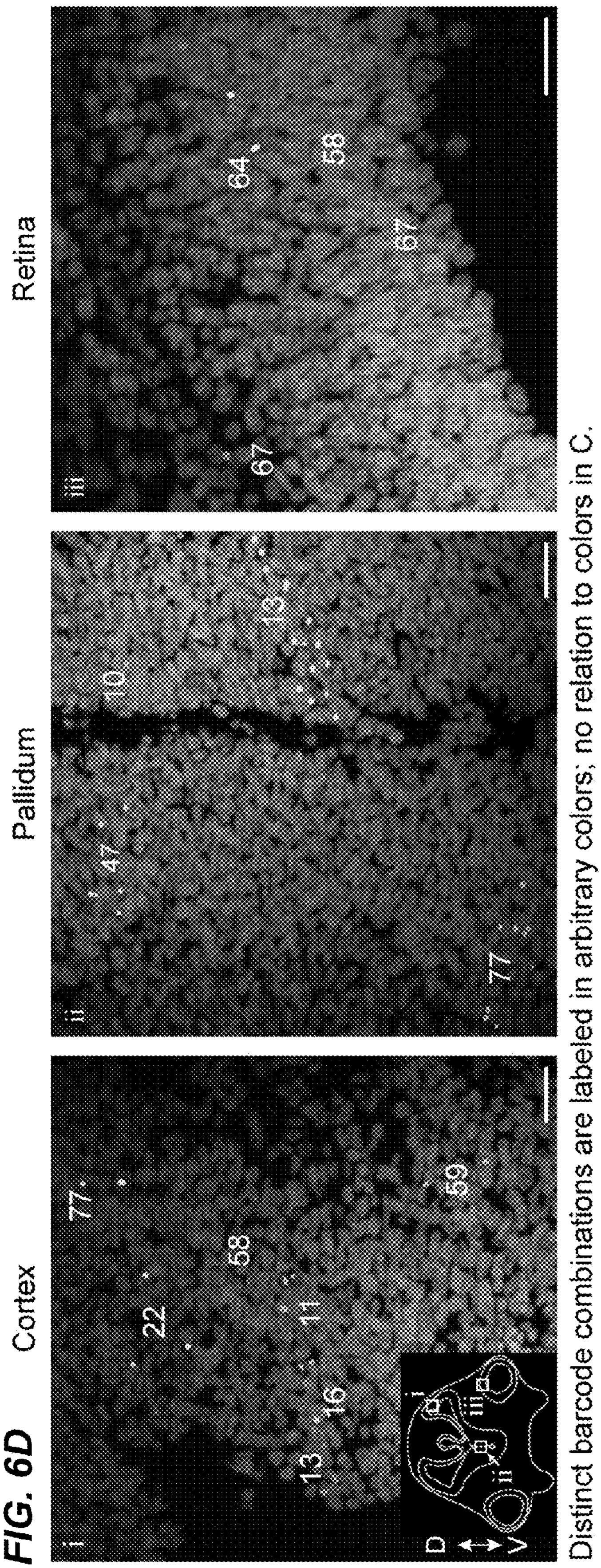

FIG. 6D. Examples of cells in developing chick cortex (i), pallidum (ii), and retina (iii) labeled with various barcode combinations (arbitrary colors). The inset shows the approximate location of the panels on a drawing of a coronal section through chick neural tube and indicates dorsal (D) and ventral (V) directions. For FIGS. 6C and 6D, two embryos were analyzed. 39 out of 81 barcode combinations were identified in one embryo by analyzing 44 images acquired from 10 sections. In the other embryo, 20 distinct barcode combinations were identified in 11 images acquired from 6 consecutive sections. Scale bars are 25 μm.

FIGS. 7A-7D. Zombie active sites are only found in the cells where they are made, whereas the individual transcripts can diffuse away and be detected in cells other than their cell of origin.

Figure 7A:
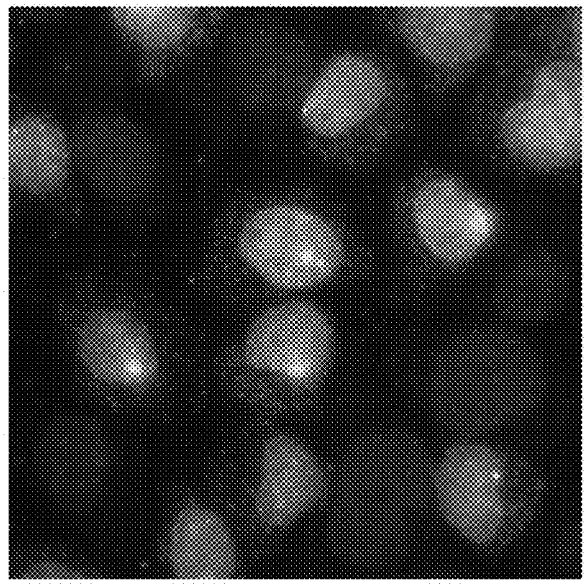

FIG. 7A. Co-culture of mES-Z1 cells with non-transgenic parental cells. Active sites are only found in CFP+ cells. However, small diffraction limited dots are found in all cells including the non-transgenic ones.

Figure 7B:
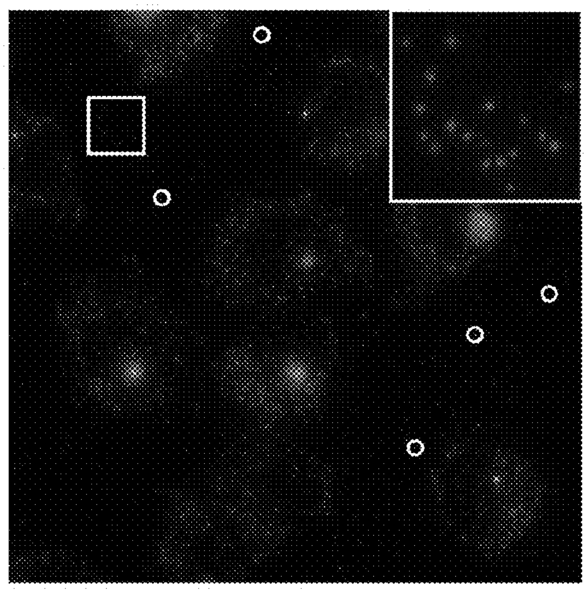

FIG. 7B. Same image as A, but with blue and cyan channels turned off for better visibility of the barcode signal. A few examples of individual barcode transcripts are marked by circles. The inset shows a magnified and contrast adjusted view of a CFP negative cell, marked by the square, which contains some small barcode dots, indicating diffusion of individual RNA molecules from the cells in which they are produced.

Figure 7C:
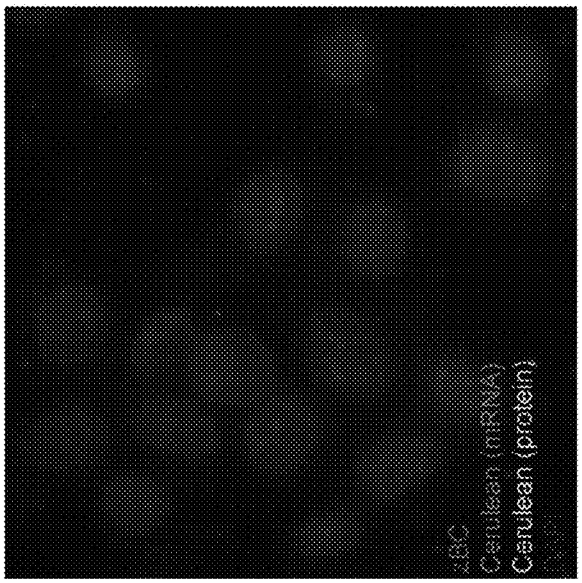

FIG. 7C. In the absence of any transgenic cells, background non-specific signal is low. Indicating that the signal observed in the presence of transgenic cells is not non-specific HCR amplification.

Figure 7D:
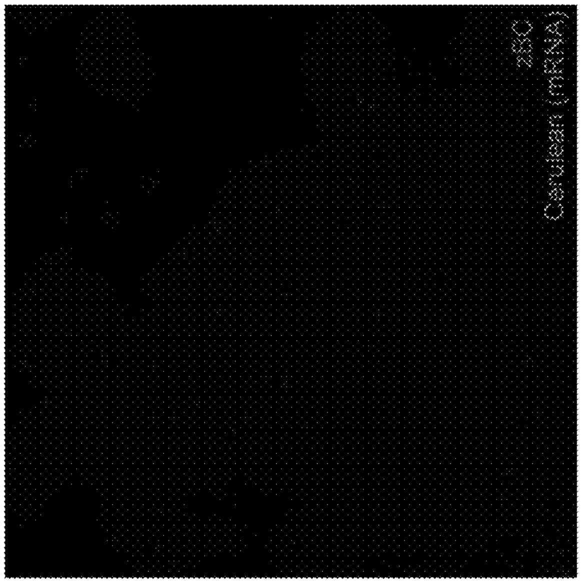

FIG. 7D. Same image as FIG. 7C, but with blue and cyan channels turned off to make the lack of small dots more evident. The experiments were independently repeated three times with similar results. Scale bar is 25 μm.

Figure 8:
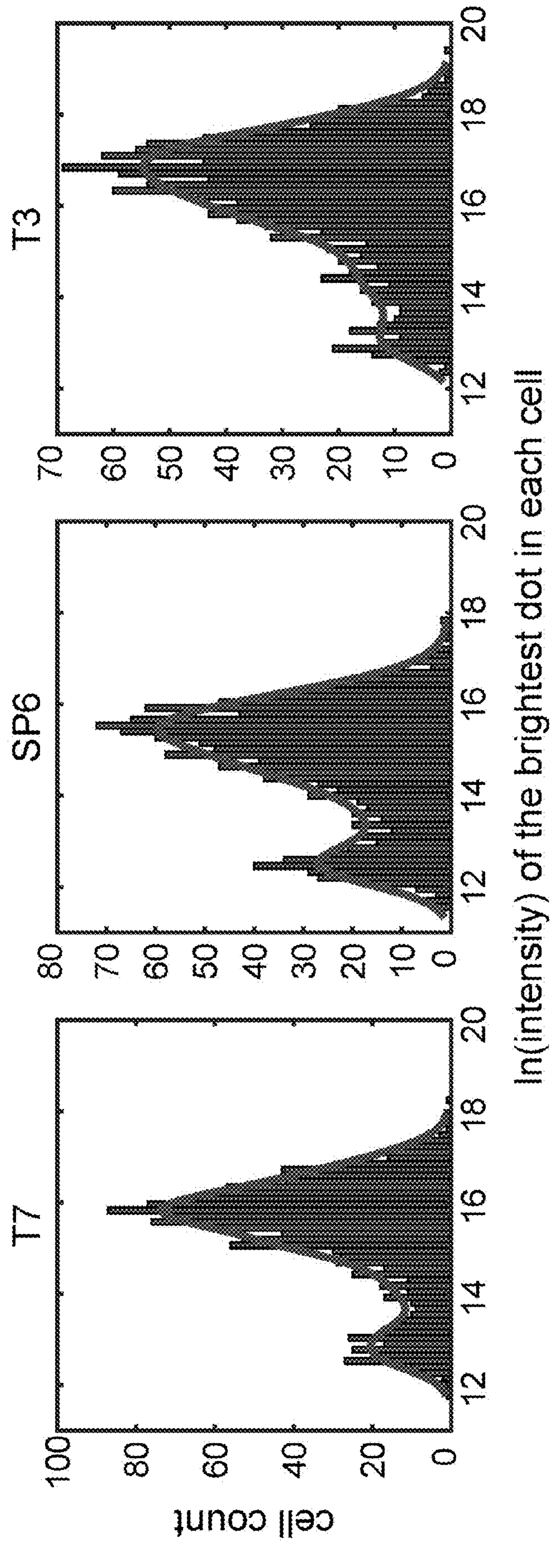

FIG. 8. Histogram of intensity for the brightest dot in each cell shows bimodal distribution, consistent with presence or absence of active sites in the cells.

Figure 9:
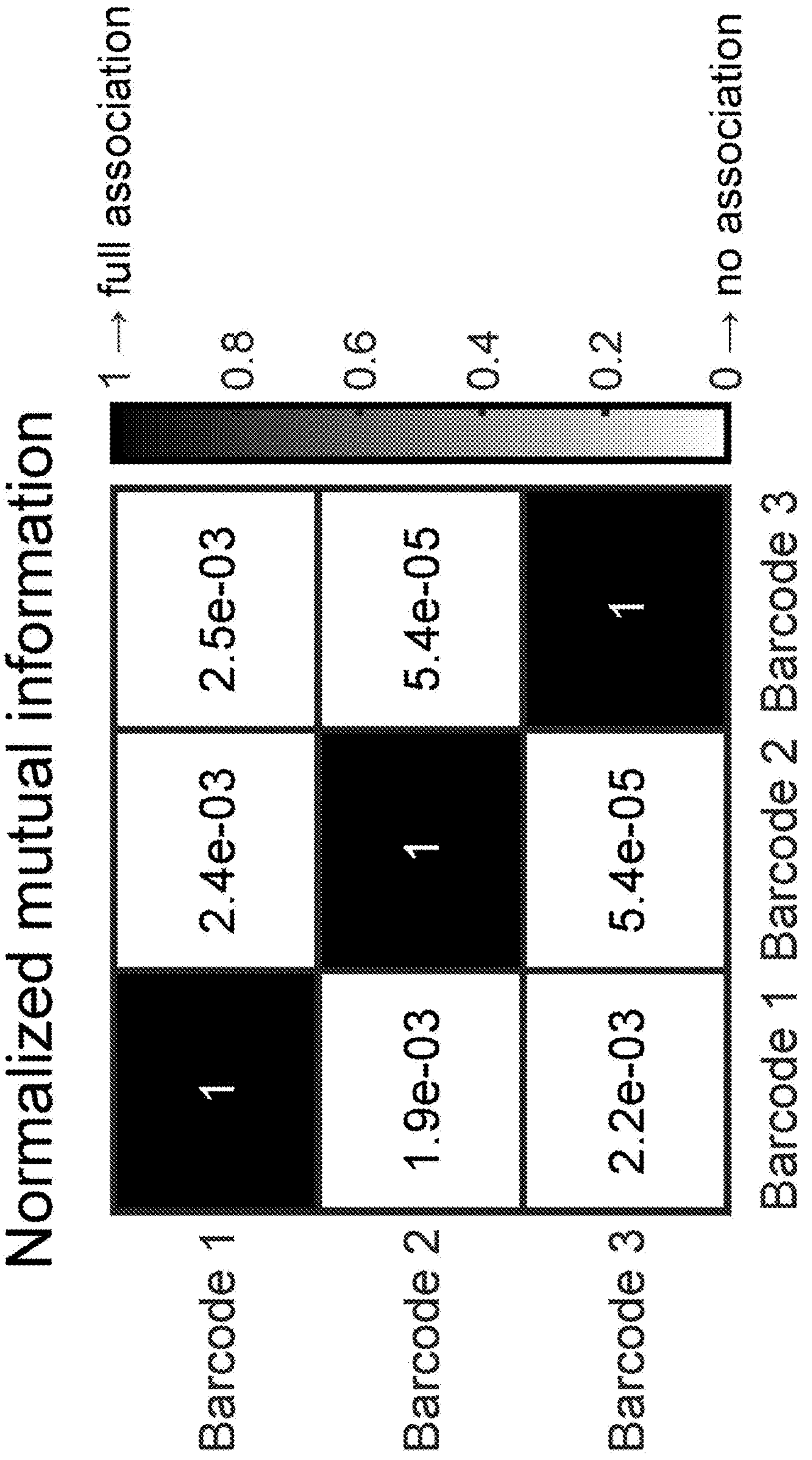

FIG. 9. Mutual information analysis of pairwise correlations between Z3 barcodes. Diagonal elements are set to 1 by definition. Off-diagonal elements represent normalized mutual information (i.e. uncertainty coefficient) between detection of indicated barcode pairs. Low values are consistent with independent detection. For each pair of barcodes, detecting one at a given site does not significantly alter the probability of detection of the other (chi-square test, $p>0.1$). Total of 564 cells were analyzed.

Figure 10:
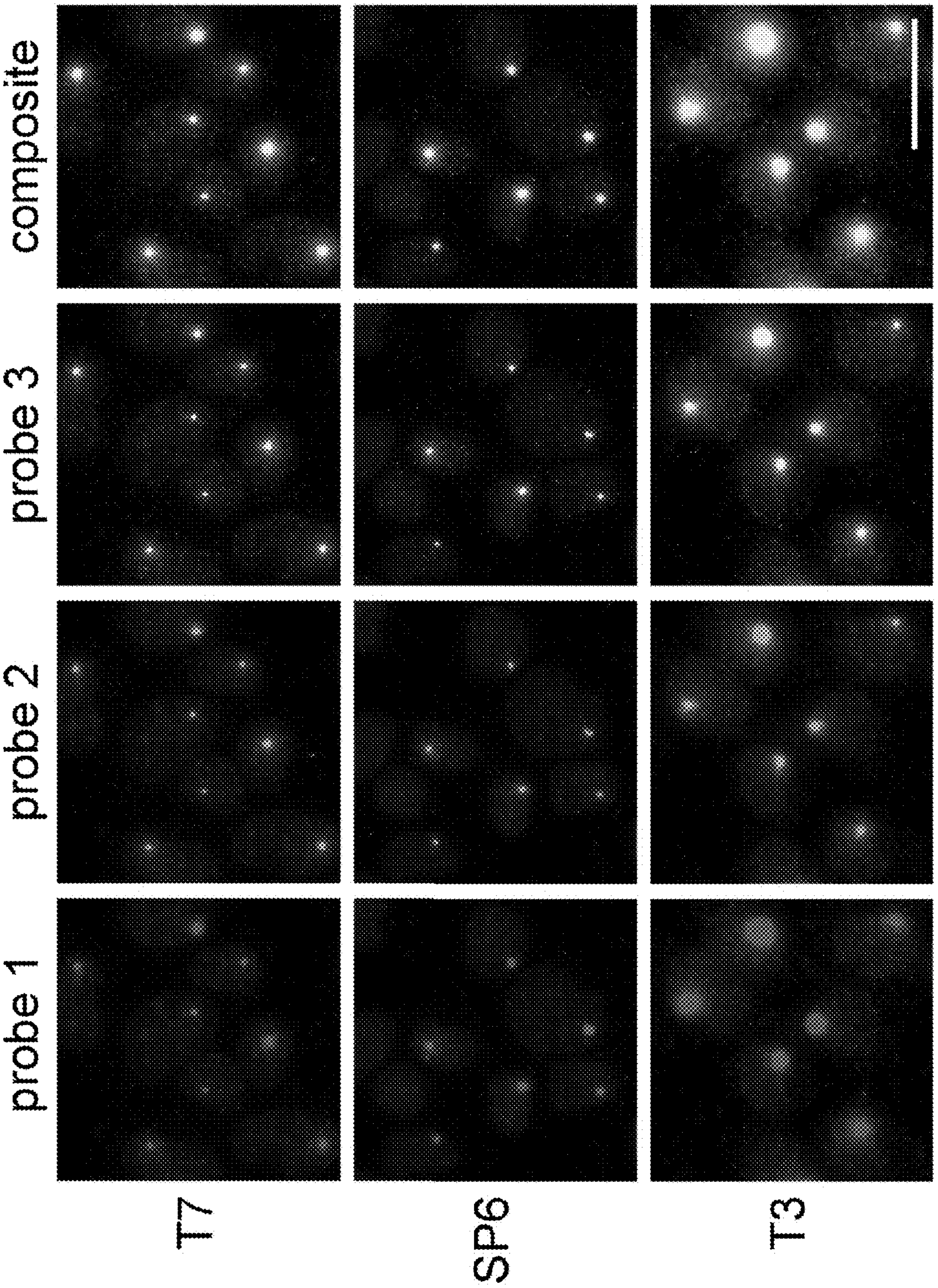

FIG. 10. Reliable detection of 20 bp targets with individual HCR probes. Images show same treatment as in FIG. 2B, except with HCR amplification. Images are scaled to different intensity ranges compared to FIG. 2B. The experiment was independently repeated three times with similar results. Scale bar is 25 μm.

Figure 11:
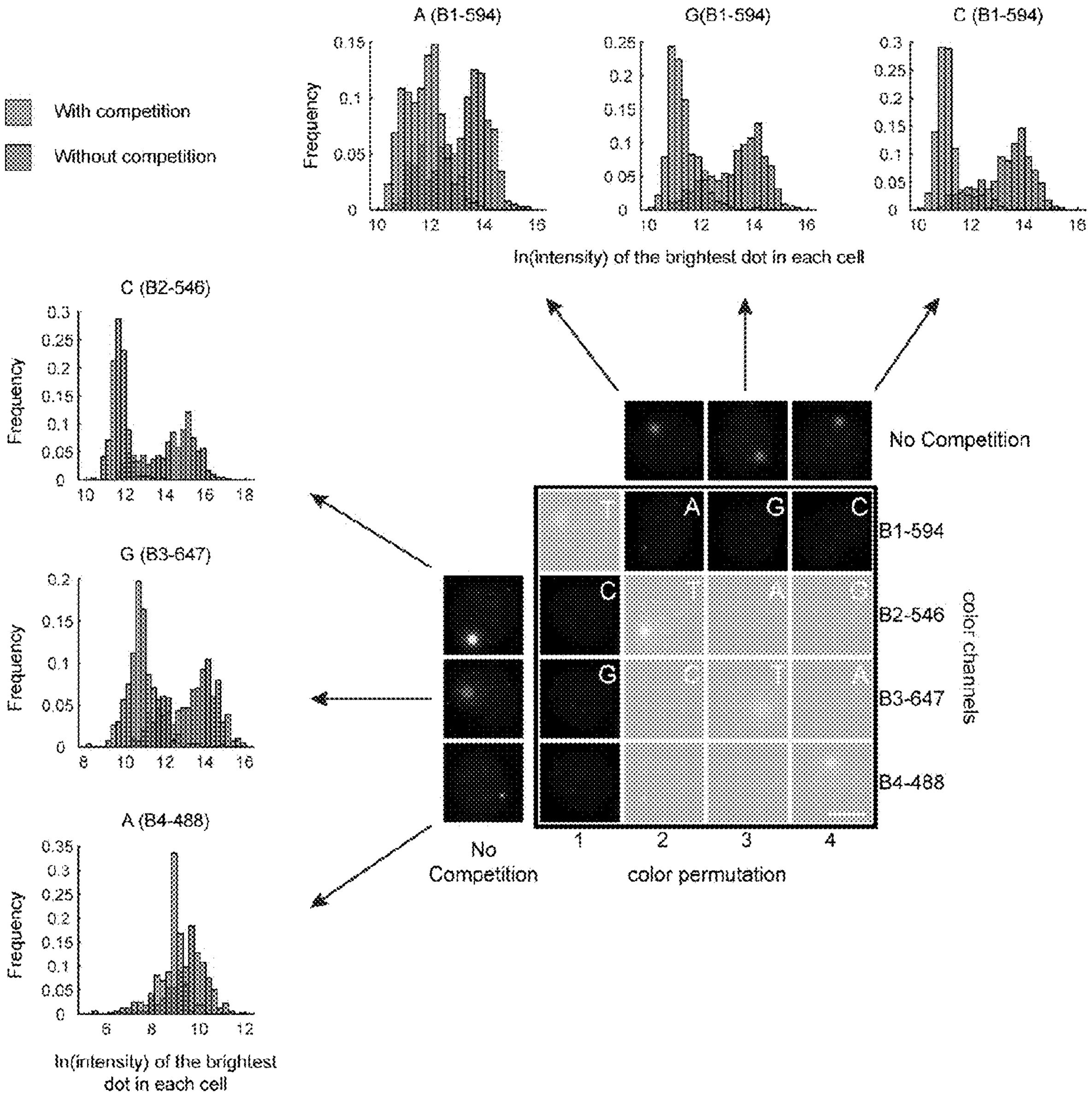

FIG. 11. In the absence of competition, probes with a single mismatch can bind to their targets in the active site and generate significant fluorescent signal. The signal from probes with a single mismatch (A, G, or C) is minimal when they are hybridized together with a match probe (T) in an equimolar mixture (FIG. 3C, reproduced here in the box with the panels not relevant to the current experiment shaded). However, when hybridized individually, without competition, they generate considerable signal in the active sites. Representative images are shown outside the box, next to their corresponding condition. All images were acquired and processed under the same conditions for each channel. Histograms show the distribution of signal intensity (natural log of the intensity of the brightest dot in each cell) for the mismatch probes in the presence and absence of competition. Total of 2374 cells were analyzed for the no competition conditions, with at least 295 cells for each condition.

The bimodal distributions, in the absence of competition, reflect a subset of cells with bright active sites. This background signal is largely reduced in the presence of competition. These results suggest that probe competition is necessary for discrimination of single nucleotide variants.

Figure 12:
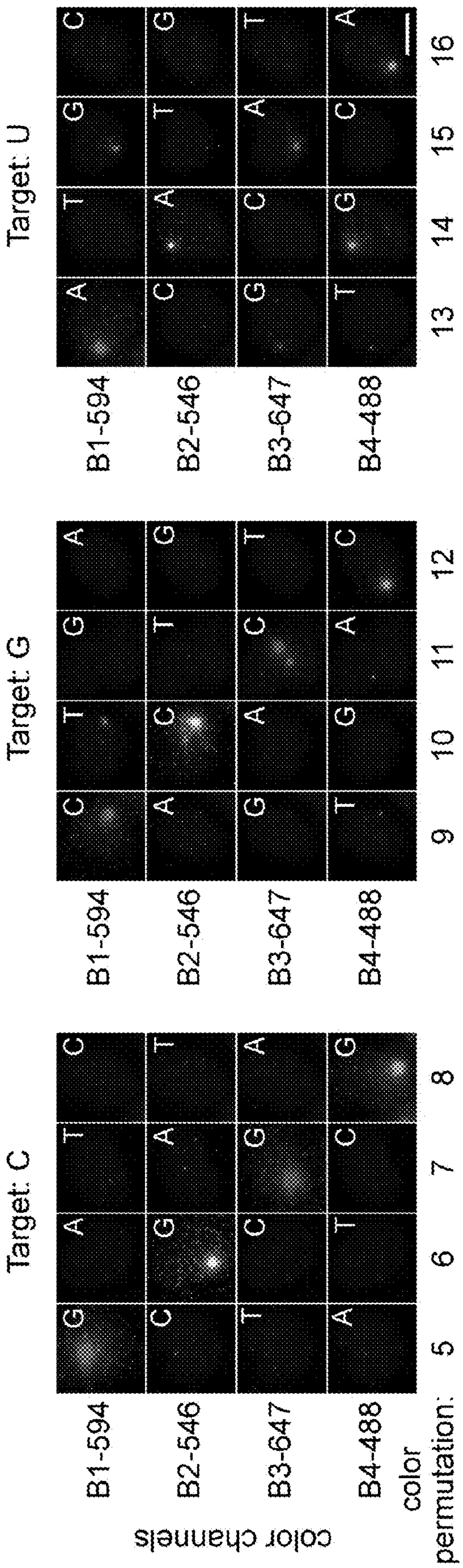

FIG. 12. Representative images showing discrimination based on a single nucleotide mismatch. All images are acquired under the same conditions, and brightness for each channel is adjusted identically across all the images. Each column represents one experiment in which four probes with a single nucleotide variation and orthogonal HCR initiators (B1, B2, B3, and B4) were mixed and hybridized to the sample. The identity of the variable nucleotide is shown by the letter on the panels. HCR initiators and the fluorescent channels used for each probe are shown next to the rows. See FIG. 3D for quantification of the results. Scale bar is 10 μm.

Figure 13:
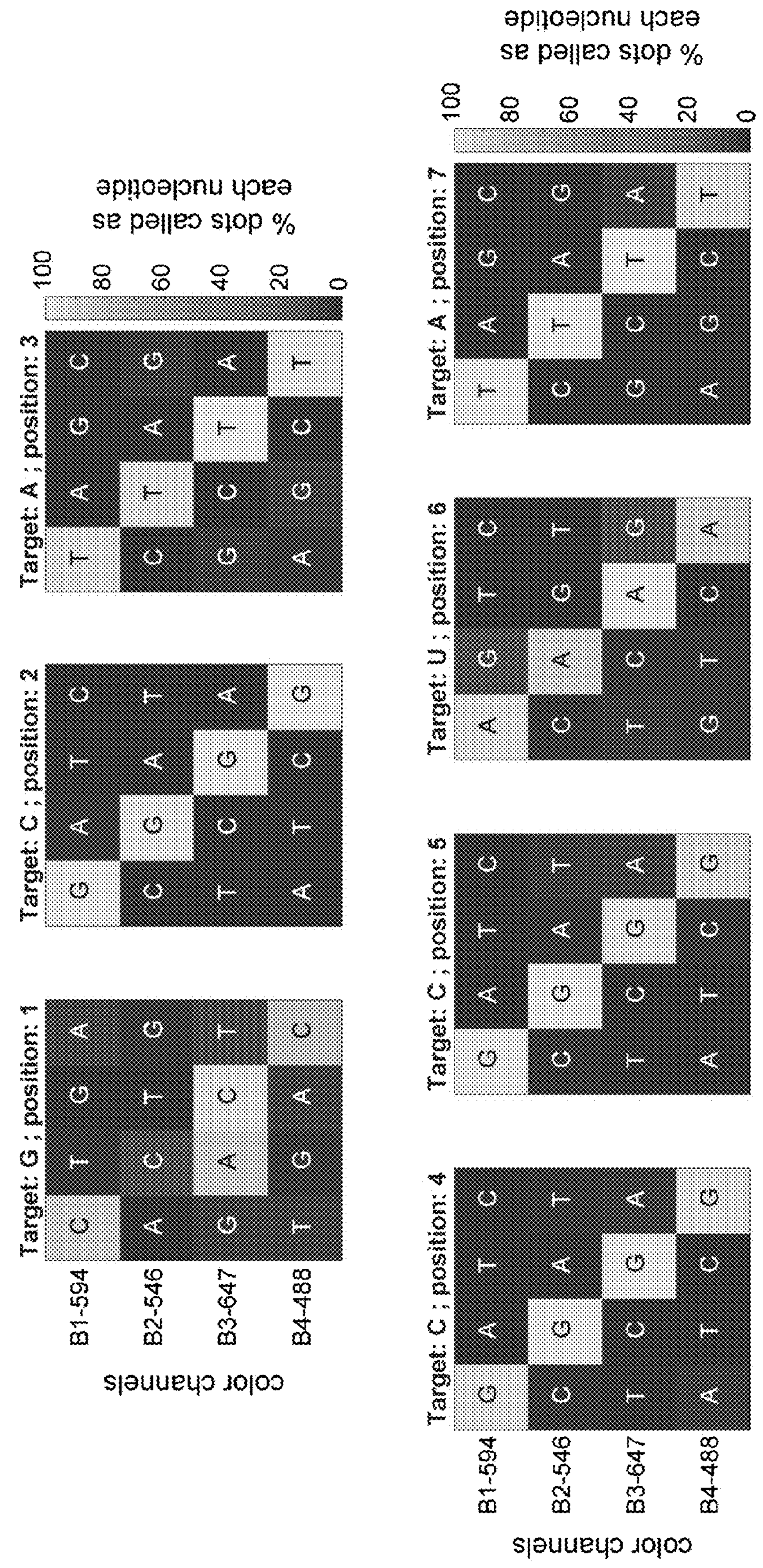

FIG. 13. SNV detection is robust to the position of the variant base pair in the barcode sequence. Matrices represent SNV analysis, as in FIG. 3D, with four distinct color permutations, with the indicated target nucleotide at positions 1 through 7 (starting from the 5' end of the probe). Accurate discrimination can be achieved for positions 2 to 7. Even position 1 provides discrimination ability. Total of 9364 cells were analyzed, with at least 234 cells for each permutation.

Figure 14:
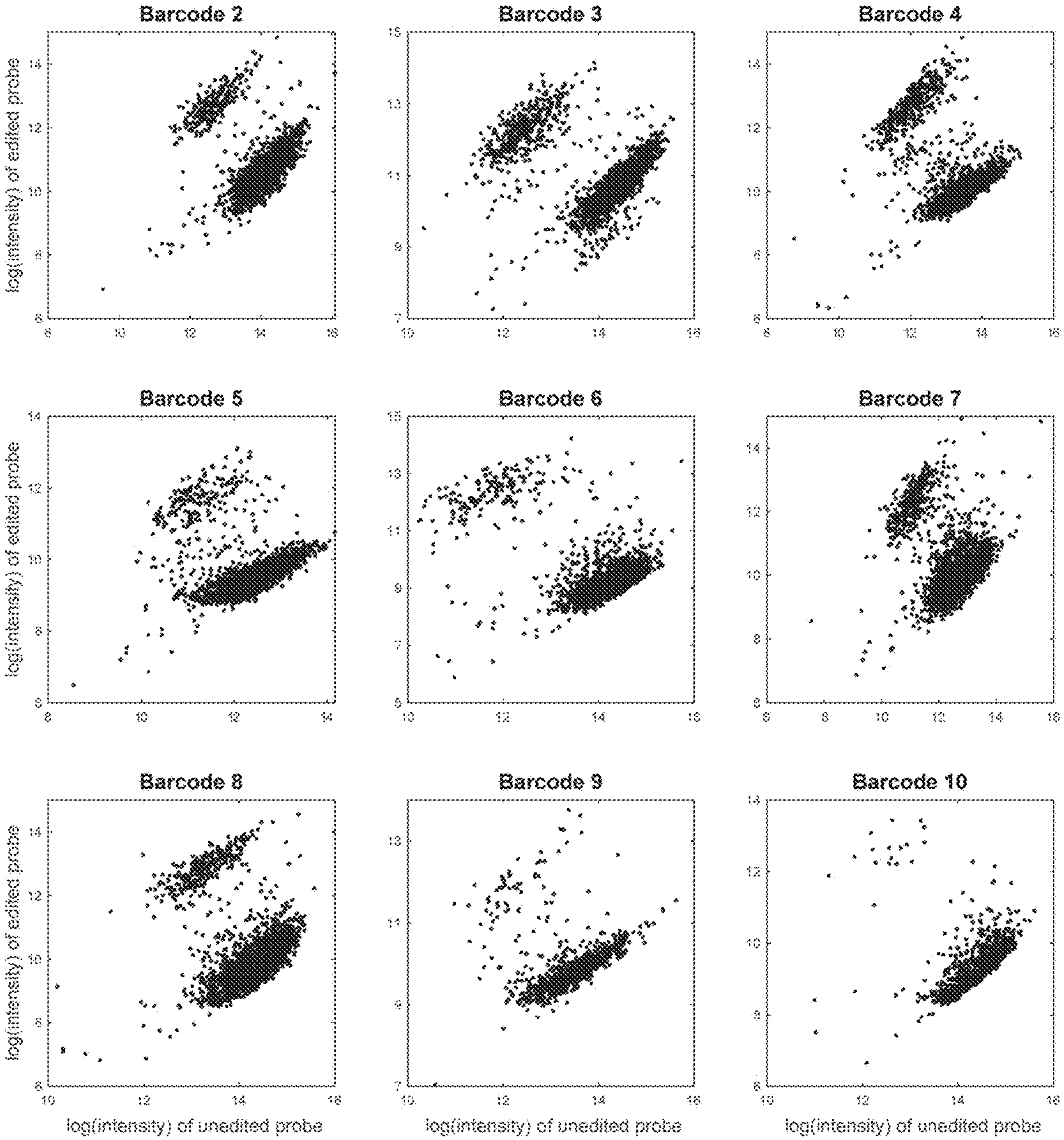

FIG. 14. Edited and unedited barcodes can be distinguished based on the signal intensity of the competing probes. The barcodes in the synthetic memory unit can be edited upon transfection with ABE and their corresponding gRNA. For each active site, signal intensity of probes detecting edited versus unedited state was quantified. The scatter plots show two distinct groups for each barcode, representing the edited and unedited states.

Figure 15:
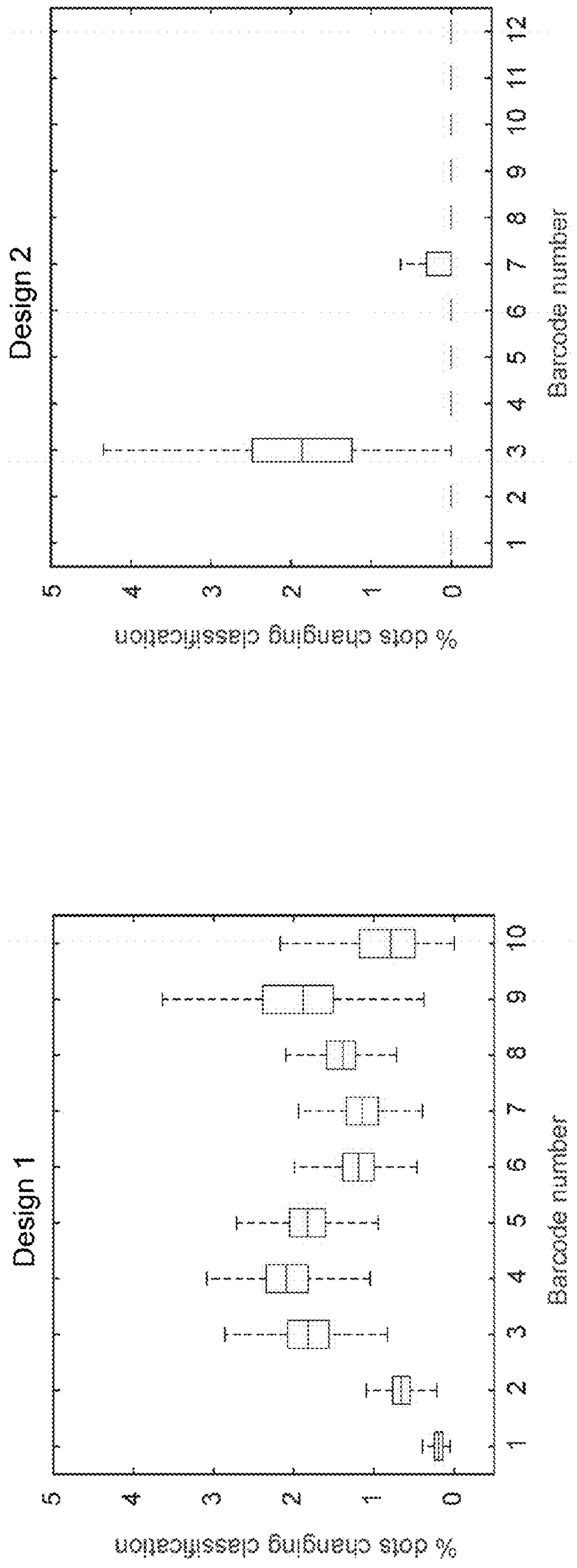

FIG. 15. Bootstrap analysis of active site classification. For each barcode, boxplots show the fraction of active sites that were classified differently when the data were resampled with replacement. The central red line in each box indicates the median, across 5000 bootstrap rounds, and the bottom and top edges of the box indicate the 25th and 75th percentiles, respectively. The whiskers extend to the most extreme data points not considered outliers. Red lines at zero, in design 2, indicate that no dots changed their classification.

Figure 16A:
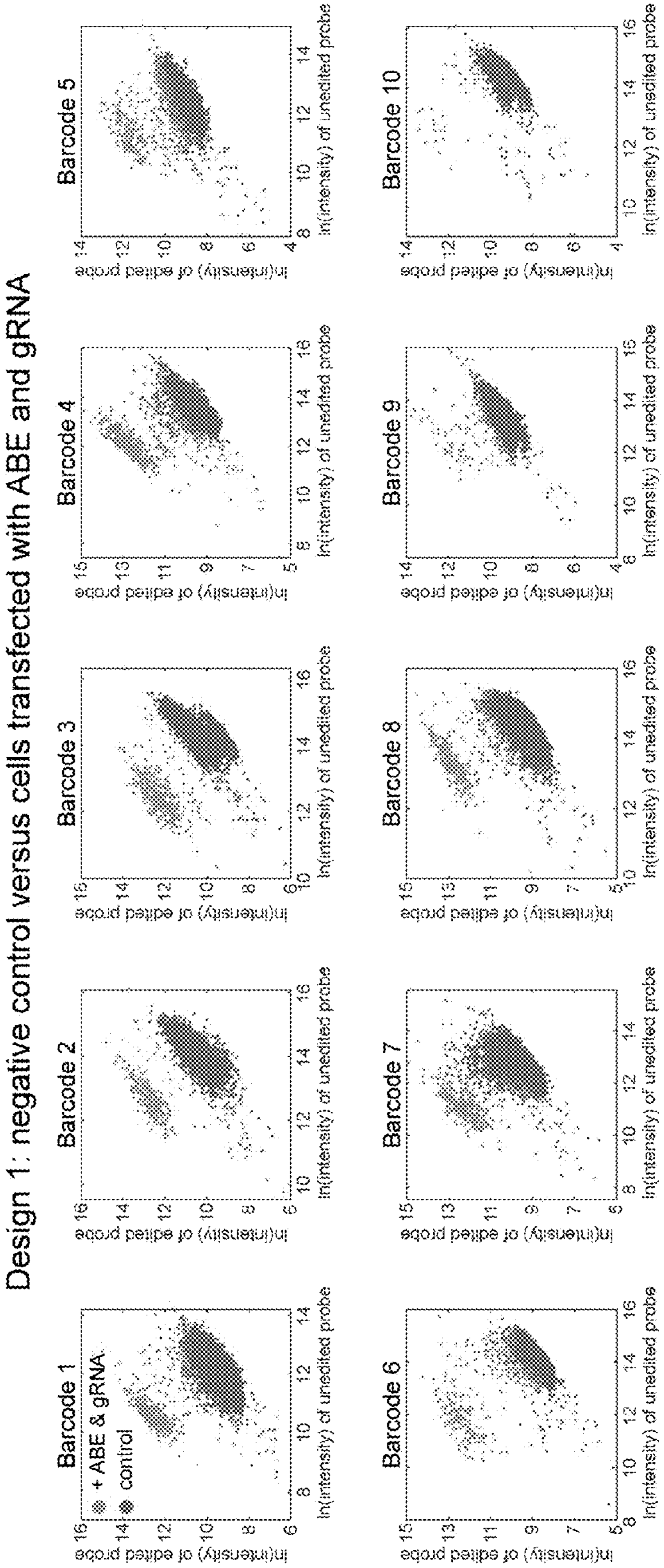
Figure 16B:
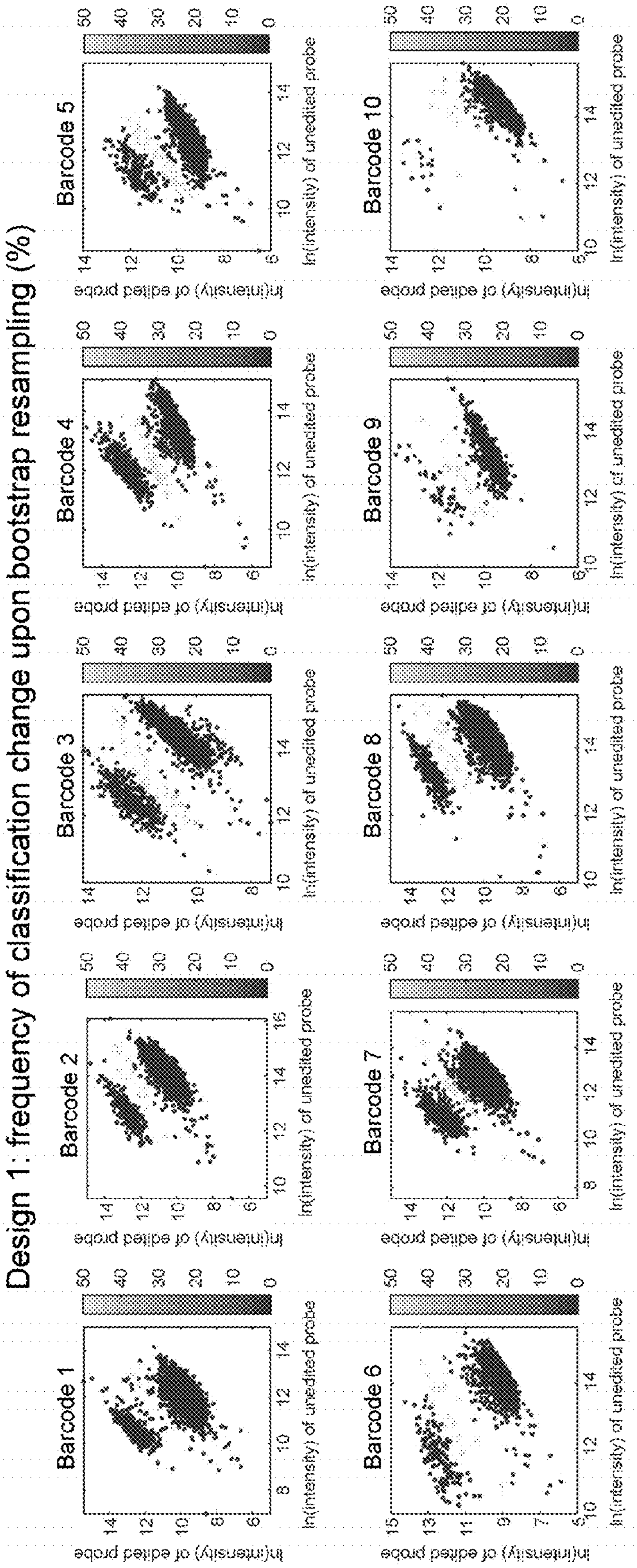

FIGS. 16A-16B. Design 1 barcodes can be classified based on signal intensity in edited and unedited channels.

FIG. 16A. Scatter plots show natural log of signal intensity in the edited (y-axis) versus unedited (x-axis) channels for each barcode. Negative controls lacking ABE and gRNA (blue) are superimposed on samples transfected with all components (orange). Edited (upper orange cloud) and unedited (lower blue cloud) active sites are broadly distinguishable.

FIG. 16B. Natural log of signal intensity in edited versus unedited channels color coded based on the frequency (%) by which classification of each dot, as edited or unedited, is changed across 5000 rounds of bootstrap resampling. All points here are from samples transfected with GFP, ABE, and the gRNA of the specified barcode.

Figure 17A:
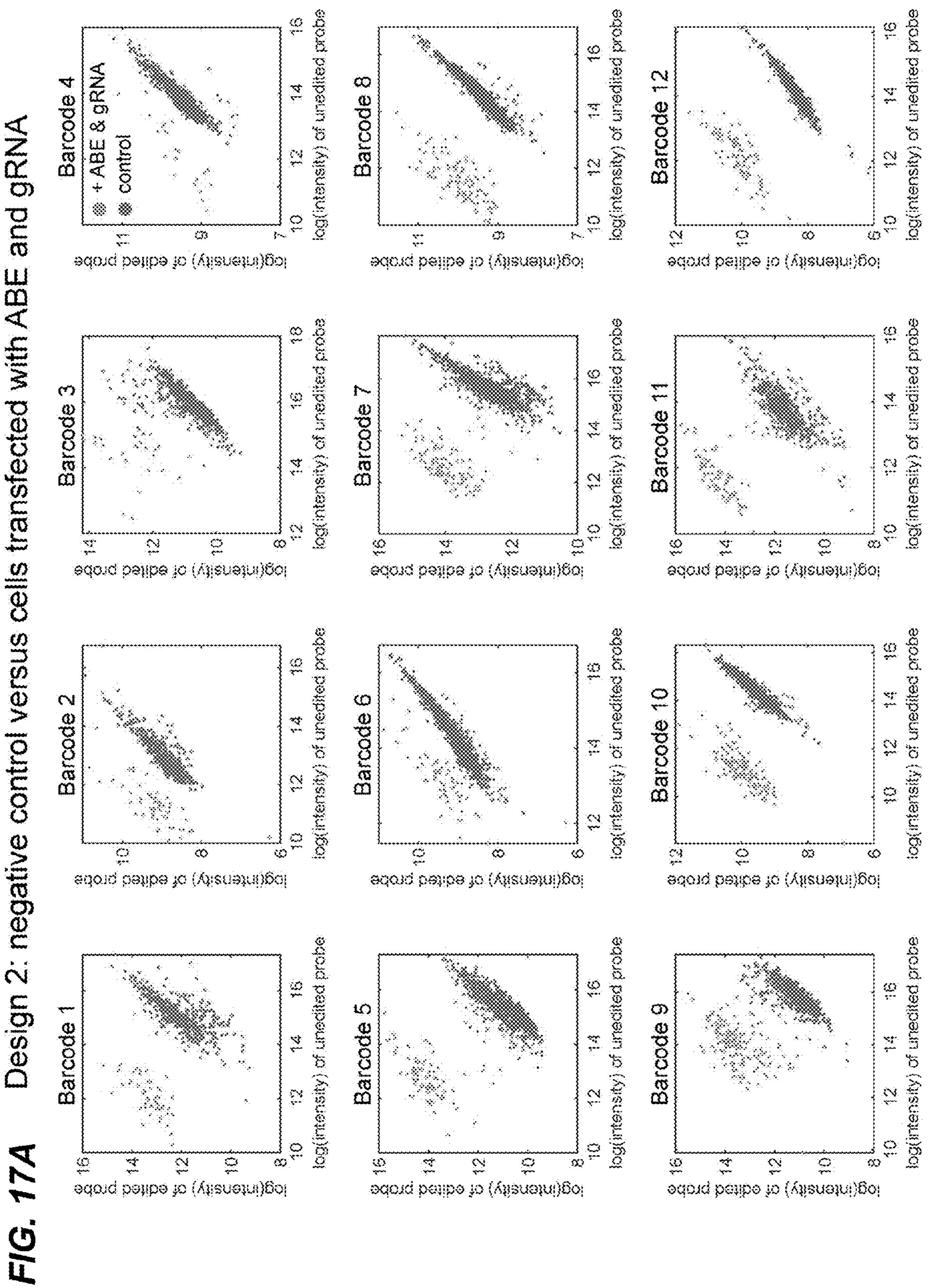
Figure 17B:
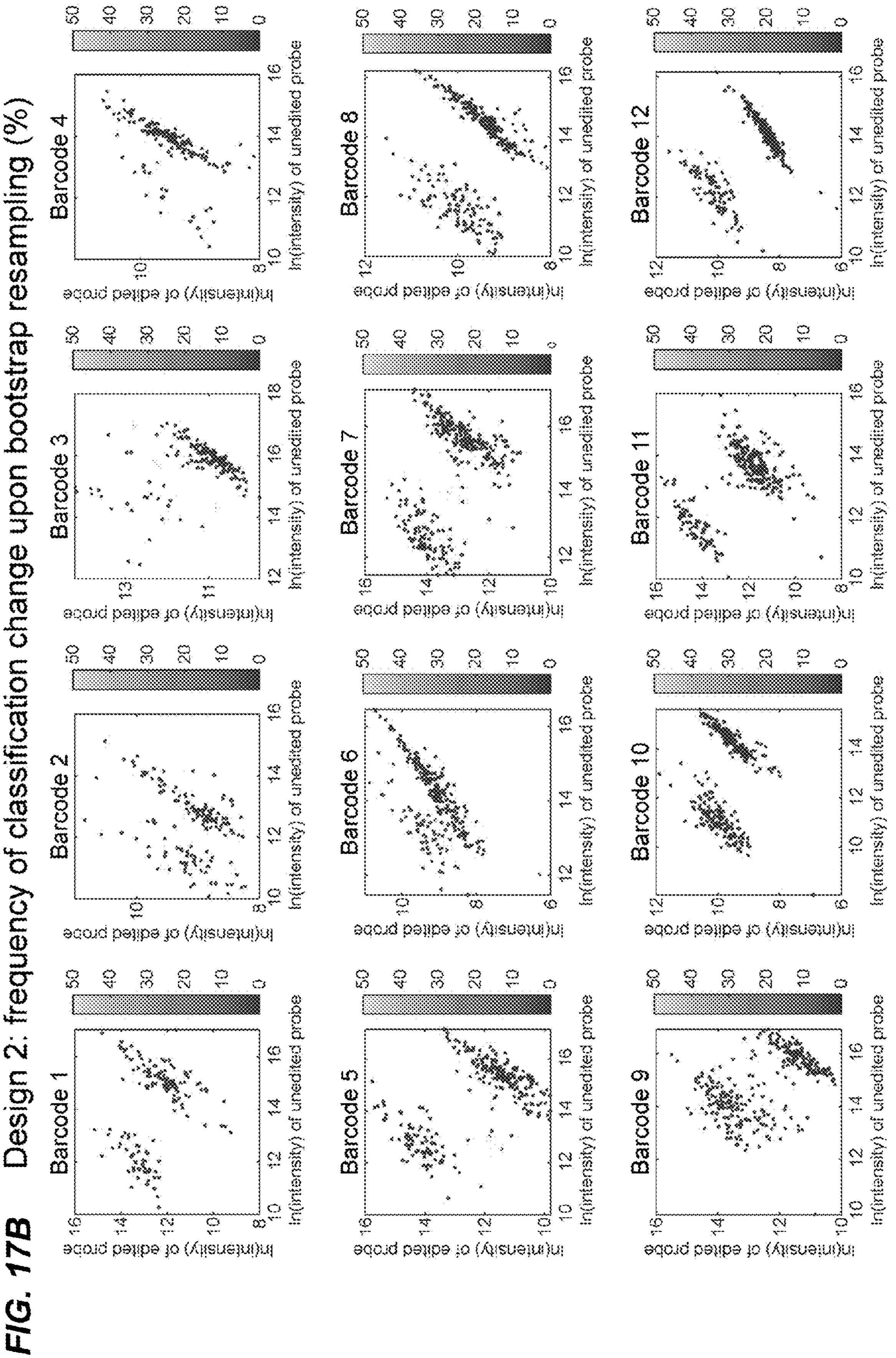

FIGS. 17A-17B. Design 2 barcodes can be classified based on signal intensity in edited and unedited channels.

FIG. 17A. Scatter plots show natural log of signal intensity in the edited (y-axis) versus unedited (x-axis) channels for each barcode. Negative controls lacking ABE and gRNA (blue) are superimposed on samples transfected with all components (orange). Edited (upper orange cloud) and unedited (lower blue cloud) active sites are broadly distinguishable.

FIG. 17B. Natural log of signal intensity in edited versus unedited channels color coded based on the frequency (%) by which classification of each dot, as edited or unedited, is changed across 5000 rounds of bootstrap resampling. All points here are from samples transfected with CFP, ABE, and the gRNA of the specified barcode.

Figure 18:
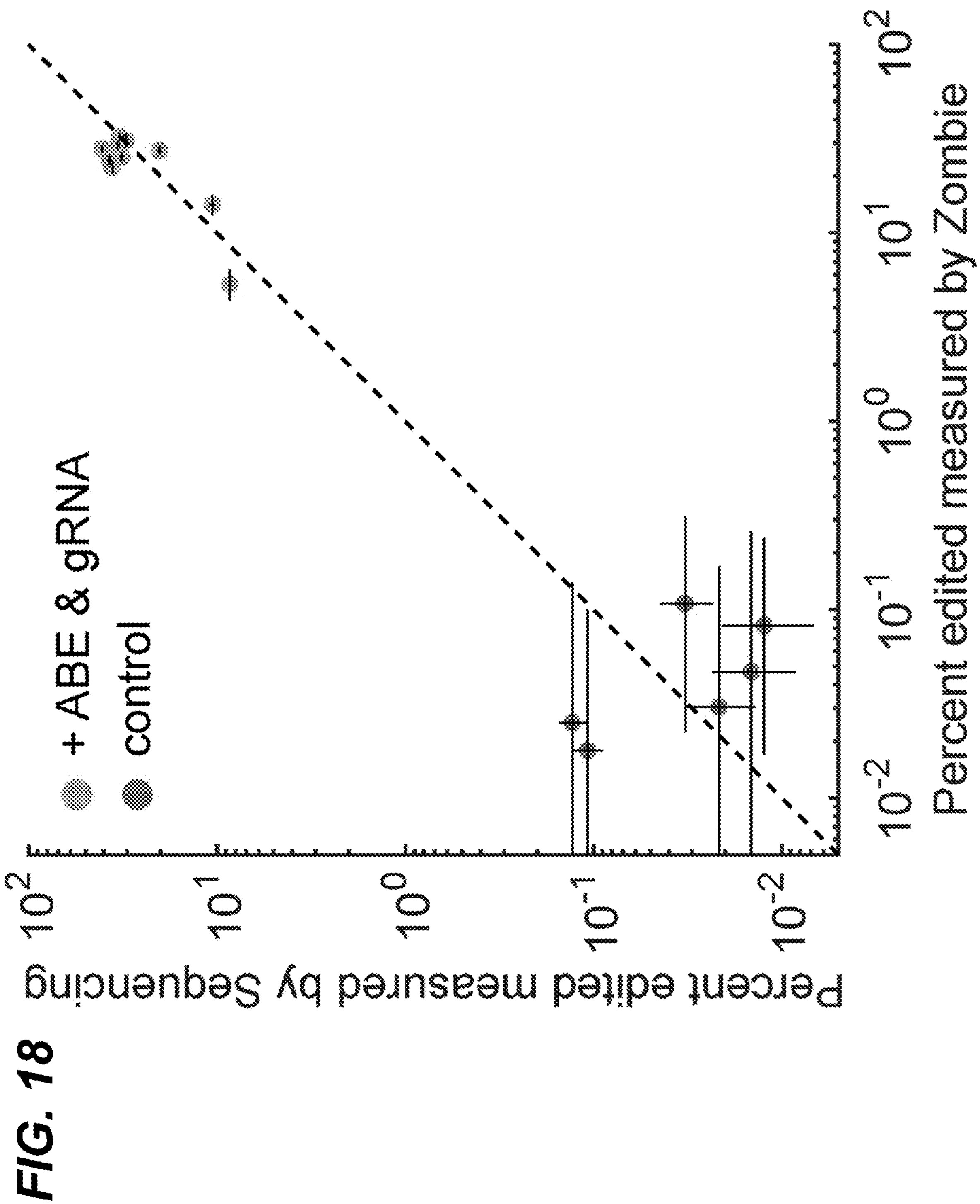

FIG. 18. Edit frequencies measured by Zombie are similar to those measured by next generation sequencing. HEK293T cells containing multiple integrations of lentivirally delivered design 1 memory array were transiently transfected with plasmids for ABE7.10, a barcode specific gRNA, and CFP (orange points). As negative control, a separate group with CFP but not ABE7.10 and gRNA was also transfected (blue points). 5 days after transfection, some cells from each group were analyzed by Zombie, similar to FIGS. 4A-4F, and the rest were analyzed by next generation sequencing (see methods). No edits by Zombie was detected in four negative control samples (not plotted). Error bars are 95% binomial confidence intervals, calculated using Clopper-Pearson method. Number of active sites analyzed by Zombie were 4251, 1237, 2910, 3466, 4883, 3742, 3095, 2465, 1501, and 1991 for barcodes 1 through 10, respectively, in ABE and gRNA positive condition (orange) and 3650, 3293, 4496, 5508, 5347, 3986, 5605, 5020, 2790, and 2142 for barcodes 1 through 10, respectively, in the control condition (blue).

Figure 19:
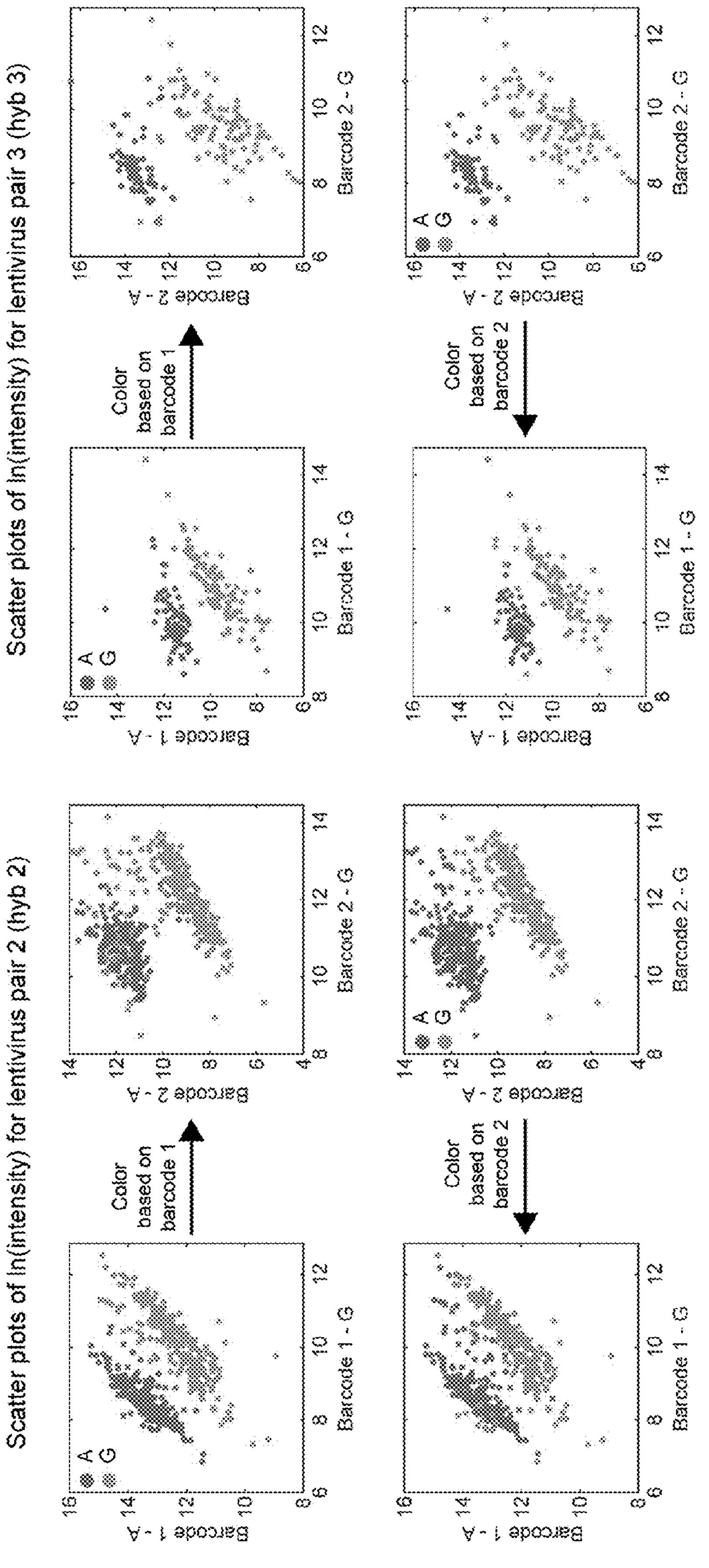

FIG. 19. Zombie accurately discriminates barcodes with single nucleotide variations in mouse brain tissue. Scatter plots showing natural log of signal intensity for two variants (A and G) of two barcodes (1 and 2), as in FIG. 5G, for lentivirus pairs 2 (left) and 3 (right). Each point represents one active site. The experiment was performed on brain sections from two mice. Biological duplicates showed similar results.

FIGS. 20A-20D. Overlapping barcode integration sites can result in underestimation of Zombie SNV detection accuracy in mouse brain sections.

Figure 20A:
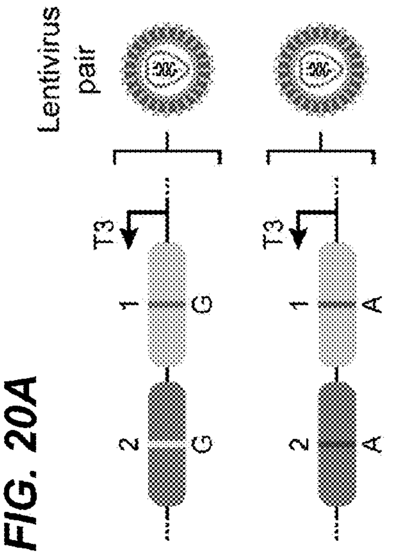

FIG. 20A. Correlation between two SNVs engineered in the same virus can be used to estimate SNV detection accuracy in tissue samples transduced by the viral mix (Schematic reproduced from FIG. 5F). The lentivirus pairs are designed so that each active site incorporates either an A in both barcodes 1 and 2, or a G in both barcodes.

Figure 20B:
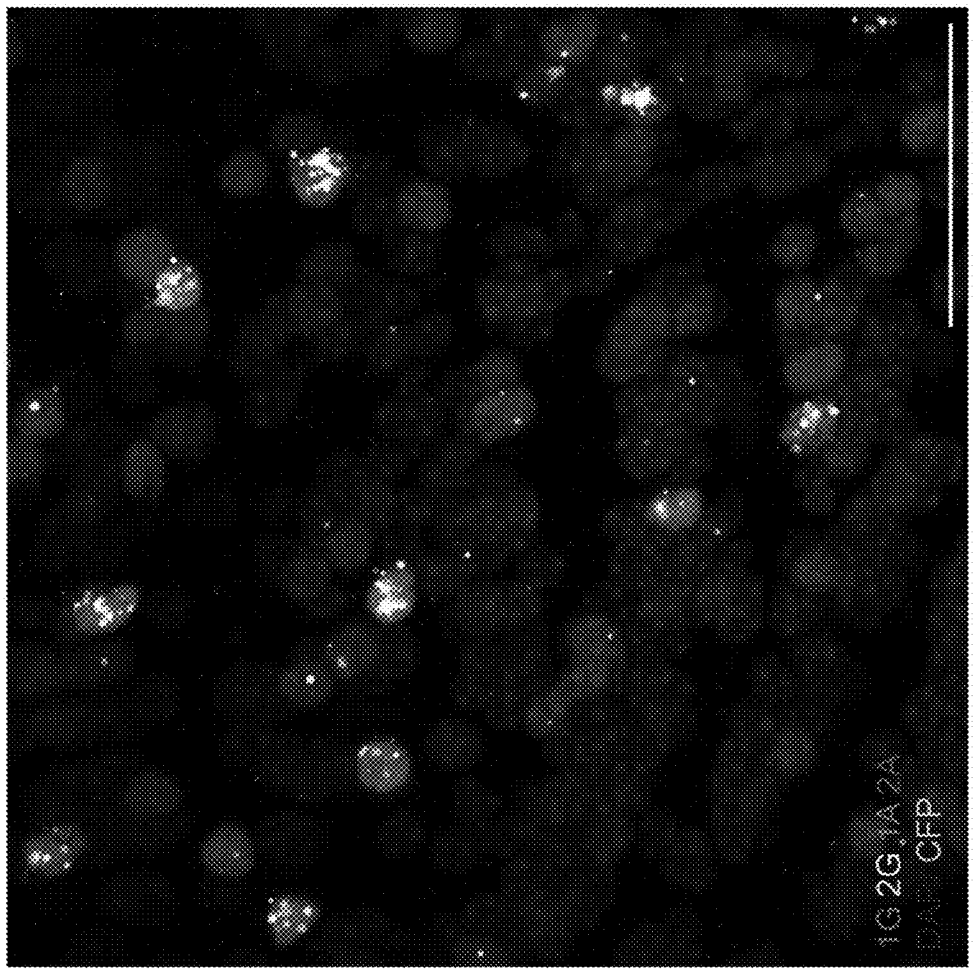

FIG. 20B. Maximum intensity projection of a confocal stack shows transduced cells in a section of mouse olfactory bulb. Scale bar is 50 μm.

Figure 20C:
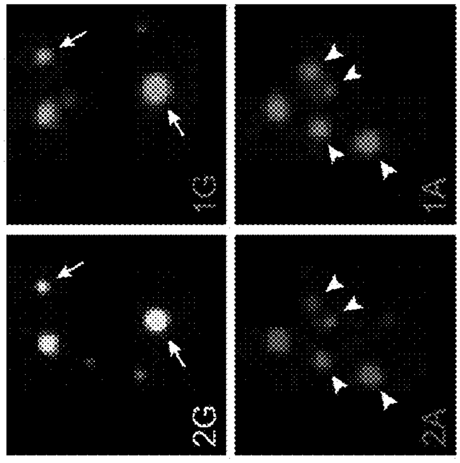

FIG. 20C. Injection of lentivirus mix into the olfactory bulb can result in the integration of multiple viral genomes, containing different barcodes, in the same cell. Imaging reveals multiple “GG” (arrows) and “AA” (arrowheads) integration sites in the same cell, which permit accurate classification.

Figure 20D:
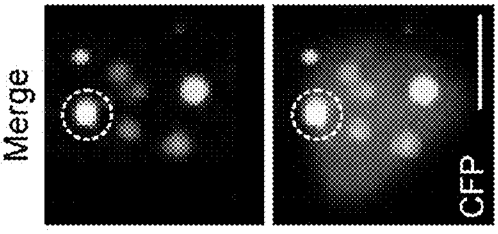

FIG. 20D. In some cases, integration sites for two virus pairs overlap in the nucleus (dashed circle), leading to an erroneous SNV call. Upper and lower images are identical overlays of the four images in FIG. 20C, but the lower image also includes CFP fluorescence in gray. The experiment was repeated on two biologically independent samples with similar results. Scale bar is 5 μm.

Figure 21:
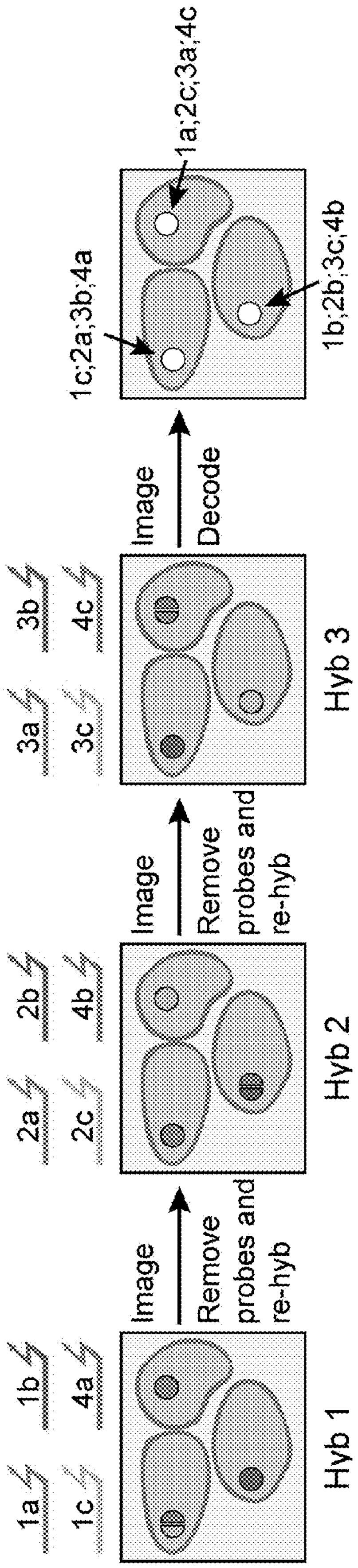

FIG. 21. In situ readout of a viral library with 81 combinations in three rounds of hybridization and imaging. In each round, tissue sections were analyzed using 4 probes, in distinct fluorescence channels, corresponding to three variants in one of the barcode positions 1, 2, or 3 and one variant in position 4 (see FIG. 6A for the design of the library). As a result, in each round, some active sites were visualized in two channels (shown as semi-circles in this illustration).

Information from images of all three rounds was then combined to decode the identity of each active site.

FIGS. 22A-22D. Zombie barcode detection is compatible with in situ detection of endogenous gene expression in tissue sections.

Figures 22A, 22C, 22D:
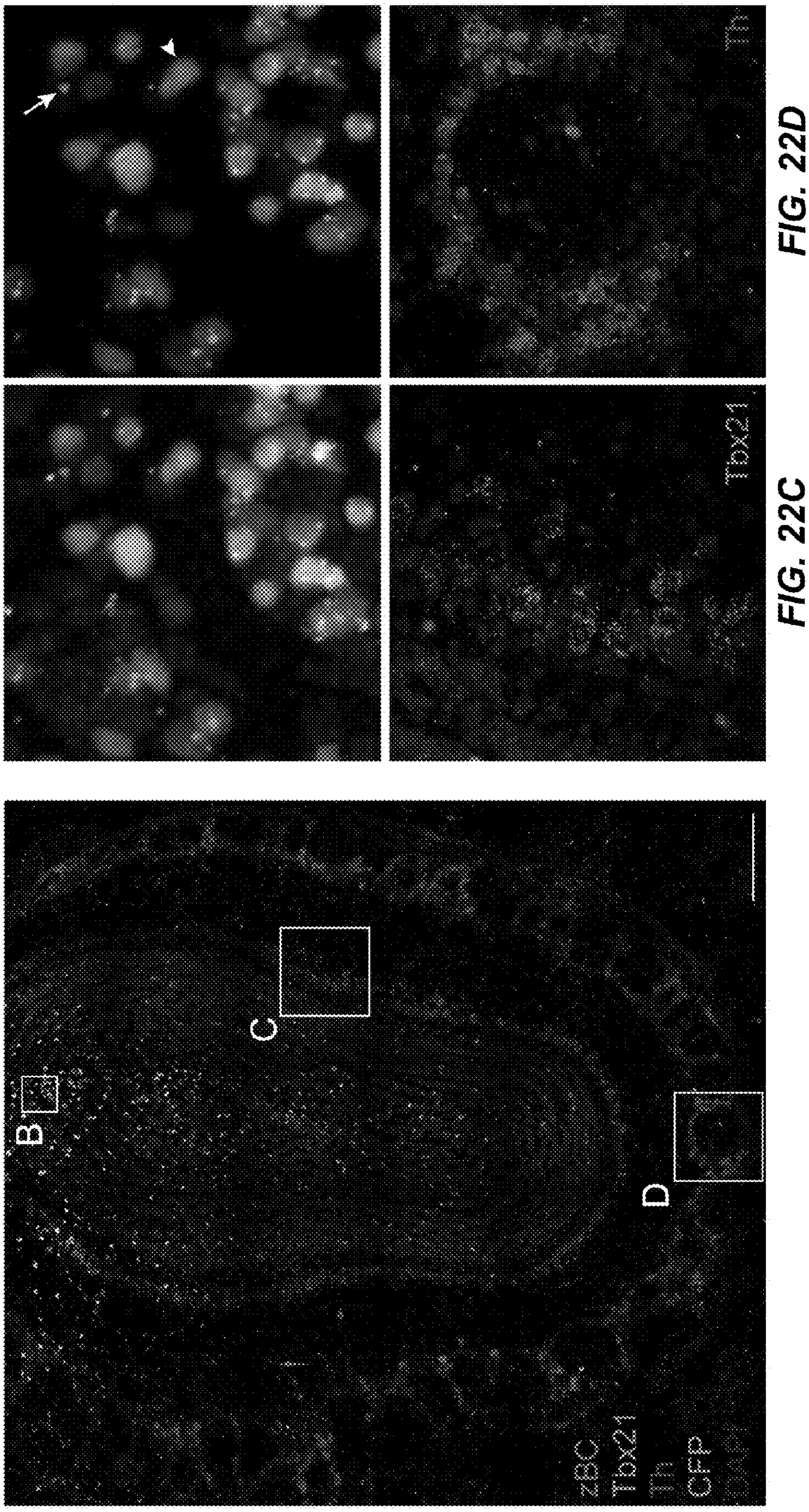

FIG. 22A. Maximum projected confocal images of an olfactory bulb section are tiled to show a larger field of view. The barcode was delivered by injection of a lentivirus that also expresses H2B-Cerulean under human UbiC promoter. Expression of Tbx21 and Tyrosine hydroxylase (Th) was visualized by HCR Fluorescence In Situ Hybridization (FISH). CFP is detected based on its native fluorescence, without any further staining.

FIG. 22B1-22B2. Although there is a correlation between expression of CFP and detection of Zombie active sites, there are instances of cells with low or no CFP that have an active site (arrow), as well as those that show CFP expression but no active site (arrowhead). Without being bound to any particular theory, it is believed that the former is caused by lack of expression of CFP from the integrated viral genome (e.g., due to silencing) and the latter is indicative of imperfect barcode detection efficiency.

FIG. 22C-22D. magnified views showing Tbx21 (green) and Th (red) endogenous mRNA detected by HCR in two orthogonal channels. Four biological replicates showed similar results. scale bar is 200 μm.

Figure 23:
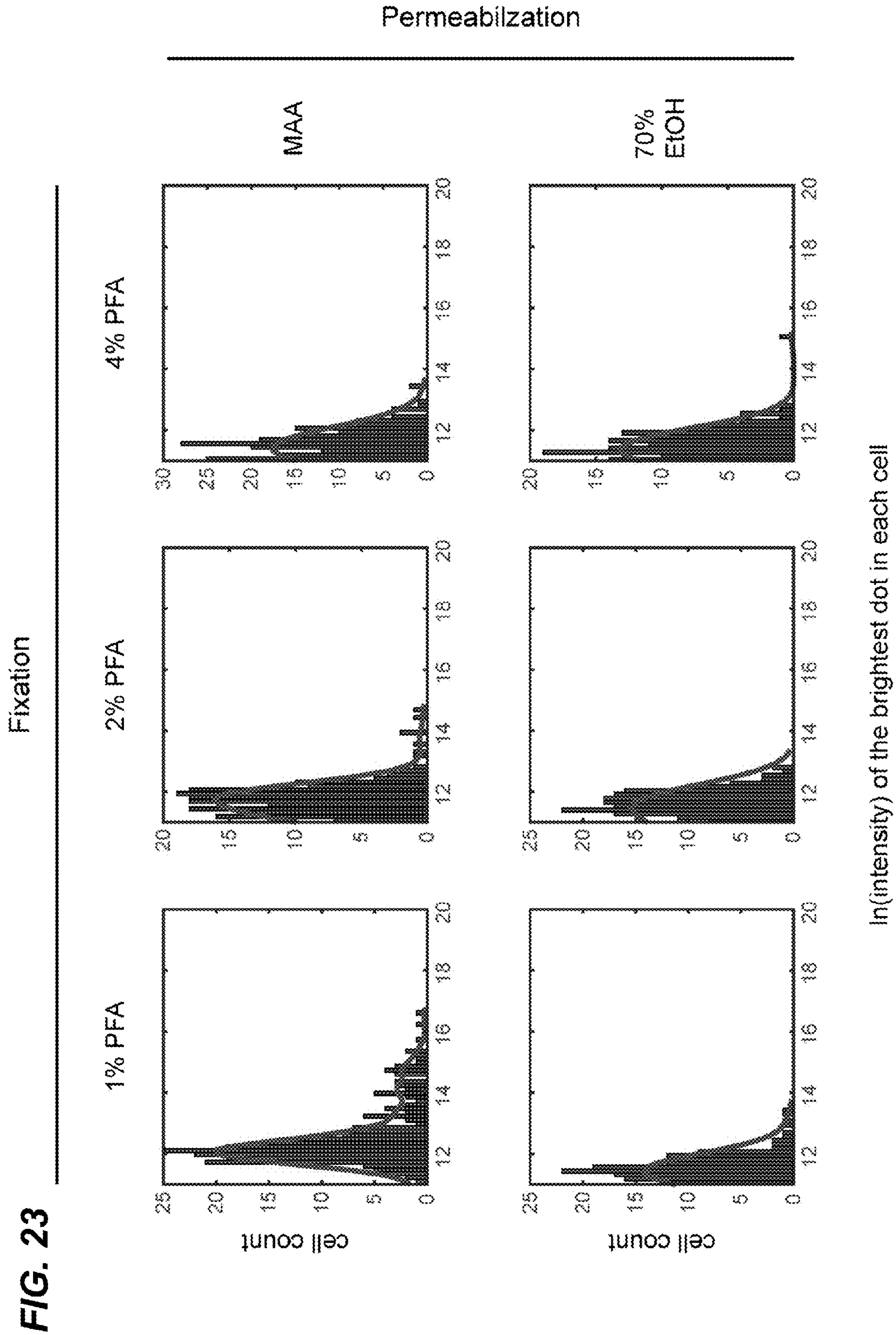

FIG. 23. Formaldehyde (PFA) fixation prior to in situ transcription results in a drastic decrease in detection efficiency. Histogram of intensity of the brightest dot in each cell is shown for different fixation and permeabilization conditions. Fraction of cells with active sites decreases significantly when cells are fixed by 1% PFA and permeabilized by 3:1 mixture of methanol and acetic acid (MAA). Fixation by 2 and 4% PFA leads to almost complete lack of Zombie active site in cells. For this reason, PFA fixation is not used prior to in situ transcription.

Figure 24:
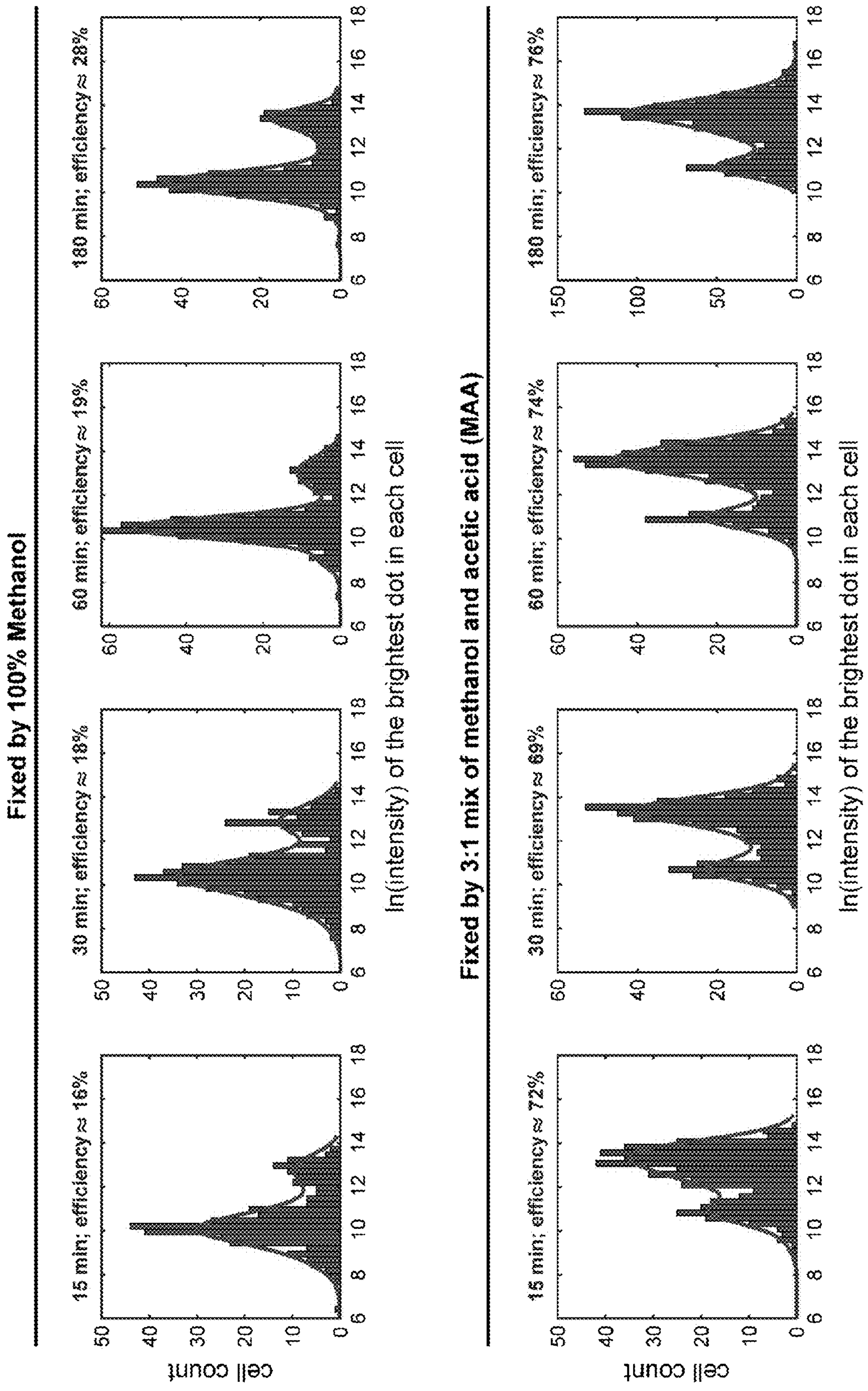

FIG. 24. Effect of transcription time and fixation on detection efficiency. Increasing transcription time from 15 min to 3 hours has a modest effect on transcription efficiency. However, fixing with MAA (3:1 mix of methanol and acetic acid) increases efficiency considerably compared to fixing with 100% methanol.

Figure 25:
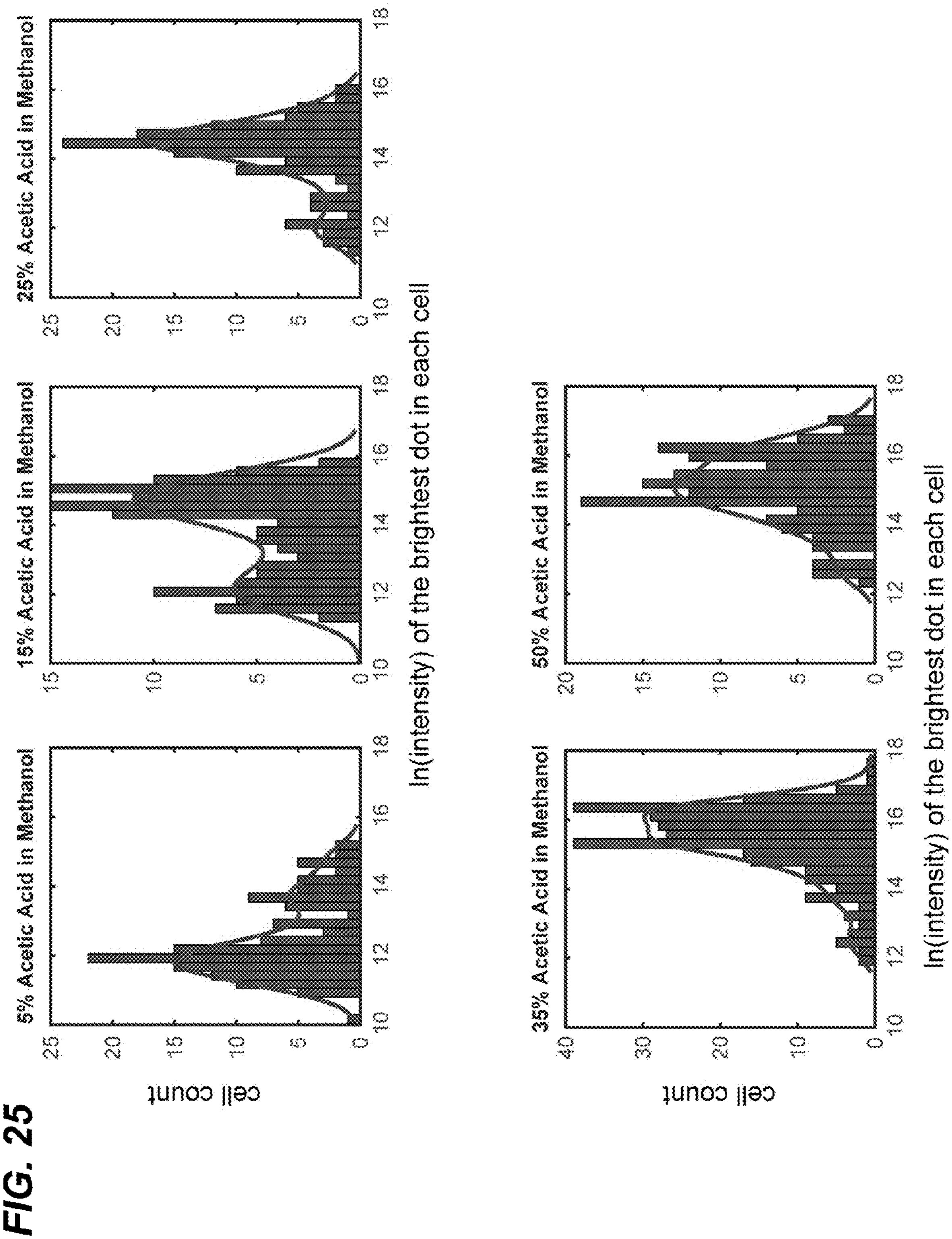

FIG. 25. The ratio of acetic acid to methanol in the fixation step prior to in situ transcription affects detection efficiency. Histogram of intensity of the brightest dot in each cell is shown for different acetic acid to methanol ratios. 25% acetic acid in methanol was used herein for fixation. A modest gain in efficiency can be obtained by increasing acetic acid to 35 or 50 percent.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Molecular barcoding technologies that uniquely identify single cells are hampered by limitations in barcode measurement. Readout by sequencing does not preserve the spatial organization of cells in tissues, whereas imaging methods preserve spatial structure but are less sensitive to barcode sequence. A system for image-based readout of short (20 bp) DNA barcodes is disclosed herein. In this system, referred to herein as Zombie, the spatial location and sequence of DNA barcodes can be detected with high sensitivity in fixed tissues. Phage RNA polymerases can transcribe engineered barcodes in fixed cells. The resulting RNA can be subsequently detected by fluorescent in situ hybridization. Using competing match and mismatch probes, Zombie can accurately discriminate single-nucleotide differences in the barcodes. Zombie can allow in situ readout of dense combinatorial barcode libraries and single-base mutations produced by CRISPR base editors without requiring barcode expression in live cells. Zombie can function across diverse contexts, including cell culture, chick embryos, and adult mouse brain tissue. The ability to sensitively read out compact and diverse DNA barcodes by imaging will facilitate a broad range of barcoding and genomic recording strategies.

Disclosed herein include embodiments of a method of determining barcode sequences in situ. In some embodiments, the method comprises: providing a plurality of cells each comprising a barcode polynucleotide with a barcode sequence. The method can comprise: fixing cells of the plurality of cells using a fixative to obtain a plurality of fixed cells. The method can comprise: generating, for each of one or more fixed cells of the plurality of fixed cells, a plurality of barcode molecules comprising the barcode sequence of the barcode polynucleotide in the fixed cell. The method can comprise: contacting each of the one or more fixed cells with a plurality of detection probes each comprising a barcode binding sequence. In some embodiments, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore. The method can comprise: detecting the fluorophore, or fluorescence thereof, associated with the detection probe hybridized to the one, at least one, or each barcode molecule in each of the one or more fixed cells using fluorescence imaging. The fluorophore, associated with the detection probe hybridized to the barcode molecule comprising the barcode sequence of the barcode polynucleotide in the fixed cell, detected can indicate the barcode sequence of the barcode polynucleotide in the fixed cell.

Disclosed herein include embodiments of a plurality of compositions for determining barcode sequences in situ. In some embodiments, the plurality of compositions comprises: (1) a plurality of cells each comprising a barcode polynucleotide with a barcode sequence, (2a) a donor plasmid comprising the barcode polynucleotide, a sequence thereof, a subsequence thereof, or a reverse complementary sequence of any of the proceeding, the barcode polynucleotide comprising at least one barcode sequence, (2b) a plasmid capable of expressing Cas9 and/or a guide ribonucleic acid (gRNA) for integrating the barcode polynucleotide into the genome, and/or (2c) a viral vector for integrating the barcode polynucleotide into each of the plurality of cells, a polynucleotide comprising the barcode polynucleotide, a sequence thereof, a subsequence thereof, or a reverse complementary sequence of any of the proceeding, (3) a fixative, (4) a plurality of detection probes, and/or (5) pairs of amplifier probes, or a plurality of first amplifier probes, of any method or embodiment disclosed herein. Disclosed herein include embodiments of a kit. In some embodiments, the kit comprises: a plurality of compositions disclosed herein. The kit can comprise: instructions for using the plurality of compositions for determining barcode sequences in situ, high throughput screening, analyzing clonal dynamics and heterogeneity in a tumor or tumors, immunology, or developmental biology, and/or lineage or event recording.

Disclosed herein include embodiments of a method comprising using a plurality of compositions or a kit disclosed herein for: high throughput screening, analyzing clonal dynamics and heterogeneity in a tumor or tumors, immunology, or developmental biology, and/or lineage or event recording.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

In Situ Readout of Barcodes

Molecular recording systems help the study of development and disease by allowing reconstruction of dynamic, single-cell developmental histories from end-point measurements. In these systems, individual cells actively record information within their genome by continuous editing of uniquely identifiable engineered genomic target sites, or 'barcodes'. Multiple methods that use CRISPR/Cas9 or site-specific recombinases to produce barcode diversity have now been developed, including the use of CRISPR base editors, in which catalytically impaired Cas9 is fused to deaminases and other enzymes to target mutations to specific nucleotides without generating double stranded breaks.

In these approaches, readout of barcode edits is most often done by sequencing, which is sensitive to single nucleotide variations and can be performed at high throughput. However, sequencing-based approaches disrupt spatial organization of cells within tissues, and often recover information only from a minority of cells. The ability to accurately and efficiently read out single cell barcode edits in situ would link dynamic developmental history with spatial multicellular organization that is essential for the function of many biological systems.

Nucleic acids can be detected in situ, including using strategies for combinatorially encoding a large diversity of transcripts, techniques for amplifying signal from single mRNA molecules, and approaches for in situ sequencing. Barcodes transcribed in living cells can be detected prior to fixation. However, ensuring detectable barcode expression across a diverse population of living cells can be challenging due to stochastic silencing, bursty expression, and unintended cell-type dependent promoter activity. Eliminating the need for expression in living cells could therefore simplify the design of barcode systems. In addition, some methods only detect large scale differences in target sequence and therefore cannot access single nucleotide variations. For example, recording can be based on detection of large-scale barcode deletions. Thus, there is a need for a simple and effective strategy for discriminating barcode edits in fixed tissues.

Disclosed herein includes an in situ detection method that is sensitive to single nucleotide edits and can be applied in diverse organismal contexts. In some embodiments, it uses well-characterized RNA polymerases from the bacteriophages T3, T7, and SP6 to transcribe genomically integrated barcodes in fixed cells, producing an amplified RNA product that can then be detected using single molecule FISH (smFISH) or Hybridization Chain Reaction (HCR). Phage polymerases are known to be efficient and specific for their target promoters, but have not been applied in fixed cells previously. Because the method is based on 'waking up' otherwise transcriptionally 'dead' (silent) barcodes in fixed cells, it is referred to herein as "Zombie" for 'Zombie is Optical Measurement of Barcodes by In situ Expression'. As disclosed herein, Zombie can efficiently detect short (20 bp) barcodes, accurately discriminates single nucleotide variants (SNVs), and detects edits made by base editors, without requiring endogenous expression in some embodiments. These capabilities allow for compact virally delivered combinatorial barcode libraries, and various recording applications. Furthermore, the simplicity and robustness of this system enables it to function not only in cell culture but also in tissues, organs, and/or organisms, for example chick embryos and adult mouse brain tissues.

As disclosed herein, phage RNA polymerases can enable imaging-based barcode readout in individual fixed cells, producing easily detectable fluorescent dots localized to transcriptional sites (See FIGS. 1A-1G for examples). Transcription can enable detection of 20 bp barcodes (See FIGS. 2A-2D for examples) with discrimination of single nucleotide variants using competing probes (See FIGS. 3A-3D for examples). This capability can further enable recovery of edits made by a CRISPR base editor in live cells (See FIGS. 4A-4F for examples). The system can be versatile, for example, operating not only in cell culture but also in chick embryos and adult mouse brain tissue (See FIGS. 5A-5H for examples) and can therefore be suitable for in vivo barcoding applications (See FIGS. 6A-6D for example). Zombie can allow high density barcoding and recording with in situ readout.

Concatenating multiple 20 bp barcodes, as in FIGS. 6A-6D, can enable combinatorial libraries of distinct barcodes, for example, using a modest library of 81 barcodes. In some embodiments, the same design can be scaled up to produce an exponential increase in coding capacity. For example, an array of 12 barcode positions, with 3 barcode variants per position, is expected to achieve a potential barcode diversity of 531,441 variants, similar to that used in sequencing-based barcoding applications, while requiring only 240 bp of sequence and 9 rounds of imaging for read-out (An error correcting coding scheme would require additional hybridization rounds). Coding capacity can be further expanded by inserting multiple arrays at distinct, spatially resolvable genomic sites.

The kits, compositions, methods and systems disclosed herein can enable viral barcoding with imaging readout. In viral barcoding, cells are labeled at a single time-point or, more recently, at multiple time-points, to enable subsequent identification of their descendants. Viral barcoding methods have been used in the study of hematopoietic development, neurobiology, and cancer. They have also enabled new high-throughput screening approaches. However, the methods so far predominantly relied on sequencing for readout of virally delivered barcodes. Diverse combinatorial libraries of short Zombie-readable barcodes enable simultaneous recovery of lineage, cell fate, and spatial organization in diverse settings, including development, regeneration, and cancer. Similarly, Zombie can facilitate multiplexed high-throughput screening, in which cellular phenotypes are assayed by imaging and connected to genetic or environmental perturbations that are identified by barcodes.

One non-limiting exemplary application of Zombie is to enable improved recording systems with image-based readout. In the previously described MEMOIR recording system, Cas9 stochastically and continuously edited ~1 kb barcoded memory elements over multiple cell cycles. These edits resulted in large scale sequence deletions, providing only a single binary memory state per kilobase of sequence. By contrast, in situ readout of base edits could provide a much higher memory density. Additionally, by circumventing the need for barcode expression in living cells, the method and system disclosed herein can avoid issues with burstiness in expression and stochastic silencing, And thus enable a more powerful imaging-based recording system, while maintaining compatibility with subsequent transcriptome readout, e.g. by sequential Fluorescence In Situ Hybridization (seqFISH), in the same cells.

Currently available methods and systems suffer from a general tradeoff between sequencing-based approaches that provide high throughput single nucleotide level readout but no spatial context and imaging approaches that preserve spatial information but lack the sensitivity of sequencing. Recent work has begun to bridge this gap in both directions. The in situ barcode readout method and system disclosed herein allow imaging-based detection with sensitivity and scalability comparable to sequencing, and thus can facilitate imaging-based barcoding, recording, and other applications currently dominated by sequencing.

Determining Barcode Sequences in Situ

Disclosed herein include embodiments of a method of determining barcode sequences in situ. In some embodiments, the method comprises: providing a plurality of cells each comprising a barcode polynucleotide with a barcode sequence (e.g., at 104 in FIG. 1). The method can comprise: fixing cells of the plurality of cells using a fixative to obtain a plurality of fixed cells (e.g., at 112 in FIG. 1). The method can comprise: generating, for each of one or more fixed cells of the plurality of fixed cells, a plurality of barcode molecules comprising the barcode sequence of the barcode polynucleotide in the fixed cell (e.g., at 120 in FIG. 1 after adding a polymerase, such as a phage polymerase at 116 in FIG. 1). The method can comprise: contacting each of the one or more fixed cells with a plurality of detection probes each comprising a barcode binding sequence (e.g., at 124 in FIG. 1; see FIG. 2A for a non-limiting exemplary schematic illustration of a detection probe design). In some embodiments, thereby (i) one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and (ii) the detection probe is associated with a fluorophore (See FIG. 3A for a non-limiting exemplary schematic illustration). The method can comprise: detecting the fluorophore, or fluorescence thereof, associated with the detection probe hybridized to the one, at least one, or each barcode molecule in each of the one or more fixed cells using fluorescence imaging (e.g., at 128 in FIG. 1; see FIGS. 1D, 1C, 2B, 2E, 2F, and 3C for non-limiting exemplary composite fluorescent images). The fluorophore, associated with the detection probe hybridized to the barcode molecule comprising the barcode sequence of the barcode polynucleotide in the fixed cell, detected can indicate the barcode sequence of the barcode polynucleotide in the fixed cell.

Detecting Barcodes Using Hybridization Chain Reaction

In some embodiments, contacting each of the one or more fixed cells with the plurality of detection probes comprises: contacting each of the one or more fixed cells with the plurality of detection probes each comprising the barcode binding sequence and an initiator sequence (See FIG. 2A for an example). In some embodiments, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof (See FIG. 3A for an example). Contacting each of the one or more fixed cells with the plurality of detection probes can comprise: contacting each of the one or more fixed cells with pairs of amplifier probes (e.g., pairs of chain reaction probes). The amplifier probes of each pair of amplifier probes can comprise an identical fluorophore. In some embodiments, thereby a first amplifier probe of a pair of amplifier probes hybridizes to (i) the initiator sequence of a detection probe of the plurality of detection probes hybridized to a barcode molecule in the fixed cell and (ii) a second amplifier probe of the pair of amplifier probes.

Amplification. In some embodiments, the initiator sequence is about 40 nucleotides in length. The length of the initiator sequence can be different in different implementations. In some embodiments, the initiator sequence can be, can be about, can be at least, or can be at most, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length.

In some embodiments, two, or different, pairs of amplifier probes comprise different fluorophores. The two, or different, fluorophores can be spectrally distinct. In some embodiments, thereby a first amplifier probe molecule of the first amplifier probe of the pair of amplifier probes hybridize to (i) a detection probe molecule of the detection probe hybridized to the barcode molecule in the fixed cell and (ii) a second amplifier probe molecule of the second amplifier probe of the pairs of amplifier probes, and first amplifier probe molecules of the first amplifier probe of the pair of amplifier probes hybridize to second amplifier probe molecules, comprising the second amplifier probe molecule hybridized to the first amplifier probe molecule, of the second amplifier probe of the pairs of amplifier probes in a chain reaction. First amplifier probe molecules and second amplifier probe molecules not in the chain reaction (e.g., first amplifier probe molecules not hybridized to second amplifier probe molecules, or second amplifier probe molecules not hybridized to first amplifier probe molecules) can be removed (e.g., washed away).

The number of first amplifier probe molecules and the number of second amplifier probe molecules in the chain reaction can be different in different implementations. For example, at least 10 first amplifier probe molecules can hybridize to at least 10 second amplifier probe molecules in the chain reaction. In some embodiments, the number of first amplifier probe molecules hybridized to the second amplifier probe molecules, the number of second amplifier probe molecules hybridized to the first amplifier probe molecules, or the total number of first and second amplifier probe molecules in the chain reaction, can be, can be about, can be at least, or can be at most, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 2000, 3000, 4000, 5000, 6000, 7000, 8000, 9000, 10000, or a number or a range between any two of these values.

In some embodiments, (1) a first amplifier probe of the pair of amplifier probes comprises (1a) a first amplifier probe subsequence that is reverse complementary to a first subsequence of the initiator sequence of the detection probe of the plurality of detection probes. The first amplifier probe can comprise (1b) a second amplifier probe subsequence that is reverse complementary to a second subsequence of the initiator sequence. The first amplifier probe can comprise (1c) a third amplifier probe subsequence. The first amplifier probe can comprise (1d) a fourth amplifier probe subsequence comprising the second subsequence of the initiator sequence. In some embodiments, (2) a second amplifier probe of the pair of amplifier probes comprises (2a) a first amplifier probe subsequence comprising a reverse complementary sequence of the third amplifier probe subsequence of the first amplifier probe. The second amplifier probe can comprise (2b) a second amplifier probe subsequence comprising the second amplifier probe subsequence. The second amplifier probe can comprise (2c) a third amplifier probe subsequence comprising the first subsequence of the initiator sequence. The second amplifier probe can comprise (2d) a fourth amplifier probe subsequence comprising the second subsequence of the initiator sequence. Contacting the plurality of fixed cells with the pairs of amplifier probes can comprise contacting the plurality of fixed cells with the pairs of amplifier probes each comprising the first amplifier probe and the second amplifier probe with hairpin structures formed by the second amplifier probe subsequence hybridizing with fourth amplifier probe subsequence of the first amplifier probe and by the second amplifier probe subsequence hybridizing with the fourth amplifier probe subsequence of the second amplifier probe.

Barcode Readout. In some embodiments, said detecting comprises detecting the fluorophore of the first amplifier probe hybridized to the initiator sequence of the detection probe hybridized to the barcode molecule in the fixed cell and the fluorophore of the second amplifier probe of the pair of amplifier probes comprising the first amplifier probe (See FIGS. 2B and 2E for a non-limiting exemplary composite fluorescent image).

Detecting Barcodes without Hybridization Chain Reaction

In some embodiments, contacting each of the one or more fixed cells with the plurality of detection probes comprises: contacting each of the one or more fixed cells with the plurality of detection probes each comprising the barcode binding sequence and an initiator sequence. In some embodiments, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof. Contacting each of the one or more fixed cells with the plurality of detection probes can comprise: contacting each of the one or more fixed cells with a plurality of first amplifier probes each comprising a different fluorophore. In some embodiments, thereby a first amplifier probe of the plurality of first amplifier probes hybridizes to the initiator sequence of a detection probe of the plurality of detection probes hybridized to a barcode molecule in the fixed cell.

In some embodiments, two, or different, first amplifier probes of the plurality of first amplifier probes comprise different fluorophores. In some embodiments, thereby a first amplifier probe molecule of the first amplifier probe of the plurality of first amplifier probes hybridizes to a detection probe molecule of the detection probe hybridized to the barcode molecule in the fixed cell. In some embodiments, said detecting comprises detecting the fluorophore of the first amplifier probe hybridized to the initiator sequence of the detection probe hybridized to the barcode molecule in the fixed cell (See FIG. 2F for a non-limiting exemplary composite fluorescent image).

Detecting Barcodes Using Single Molecule FISH

In some embodiments, contacting each of the one or more fixed cells with the plurality of detection probes comprises: contacting each of the one or more fixed cells with the plurality of detection probes each comprising the barcode binding sequence and a fluorophore, thereby one, at least one, or each of the plurality of barcode molecules comprising the barcode sequence of the oligonucleotide in the fixed cell hybridizes to a detection probe of the plurality of detection probes comprising the barcode binding sequence reverse complementary to the barcode sequence, or a portion thereof, and the fluorophore. In some embodiments, said detecting comprises detecting the fluorophore of the detection probe hybridized to the barcode molecule in the fixed cell.

Barcode Construct and Integration

Barcode Genomic Integration

In some embodiments, a genome of one, at least one, or each cell of the plurality of cell comprises the barcode polynucleotide with the barcode sequence. In some embodiments, providing the plurality of cells comprises: integrating the barcode polynucleotide into a genome of one, at least one, or each of the plurality of cells. Integrating the barcode polynucleotide can comprise: integrating the barcode polynucleotide into the genome of one, at least one, or each of the plurality of cells at a specific site of the genome. The specific site can be a ROSA26 locus, for example.

In some embodiments, said integrating occurs, occurs about, occurs at least, or occurs at most, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, 110 days, 120 days, 130 days, 140 day, 150 days, 160 days, 170 days, 180 days, 190 days, 200 days, 210 days, 220 days, 230 days, 240 days, 250 days, 260 days, 270 days, 280 days, 290 days, 300 days, 310 days, 320 days, 330 days, 340 days, 350 days, 1 year, 2 years, 3 years, 4 years, 5 years, 6 years, 7 years, 8 years, 9 years, 10 years, 20 years, 30 years, 40 years, 50 years, 60 years, 70 years, 80 years, 90 years, 100 years, or a number or a range between any two of these values, prior to said fixing.

In some embodiments, integrating the barcode polynucleotide into the genome of one, at least one, or each of the plurality of cells comprises: transfecting the cell with a donor plasmid comprising the barcode polynucleotide, a sequence thereof, a subsequence thereof, of a reverse complementary sequence of any of the preceding. Transfecting the cell with the donor plasmid can comprise: transfecting the cell with the donor plasmid and a plasmid capable of expressing Cas9 and/or a guide ribonucleic acid (gRNA) for integrating the barcode polynucleotide into the genome of one, at least one, or each of the plurality of cells at the specific site of the genome.

In some embodiments, integrating the barcode polynucleotide comprises: integrating the barcode polynucleotide into the genome of one, at least one, or each of the plurality of cells using a viral vector (See FIGS. 4A and 5A for non-limiting exemplary schematic illustrations). The viral vector can comprise a polynucleotide comprising the barcode polynucleotide, a sequence thereof, a subsequence thereof, or a reverse complementary sequence of any of the proceeding. The viral vector can comprise a retrovirus, a lentivirus, an adenovirus, an adeno-associated virus, or a combination thereof. Integrating the barcode polynucleotide can comprise: injecting the viral vector into an organism or a tissue of the organism. The organism can be a mammal.

Promoter

In some embodiments, the barcode polynucleotide comprises at least one promoter upstream (e.g., immediate upstream) of the barcode sequence. The at least one promoter can comprise three promoters. The at least one promoter can be a phage promoter. The at least one promoter can comprise a bacteriophage T3 promoter, a bacteriophage T7 promoter, a bacteriophage SP6 promoter, or a combination thereof. The at least one promoter can be inactive in one, at least one, or each live cell of the plurality of cells. The at least one promoter can be active in one, at least one, or each of the plurality of fixed cells.

Figures 1A, 1B, 1D:
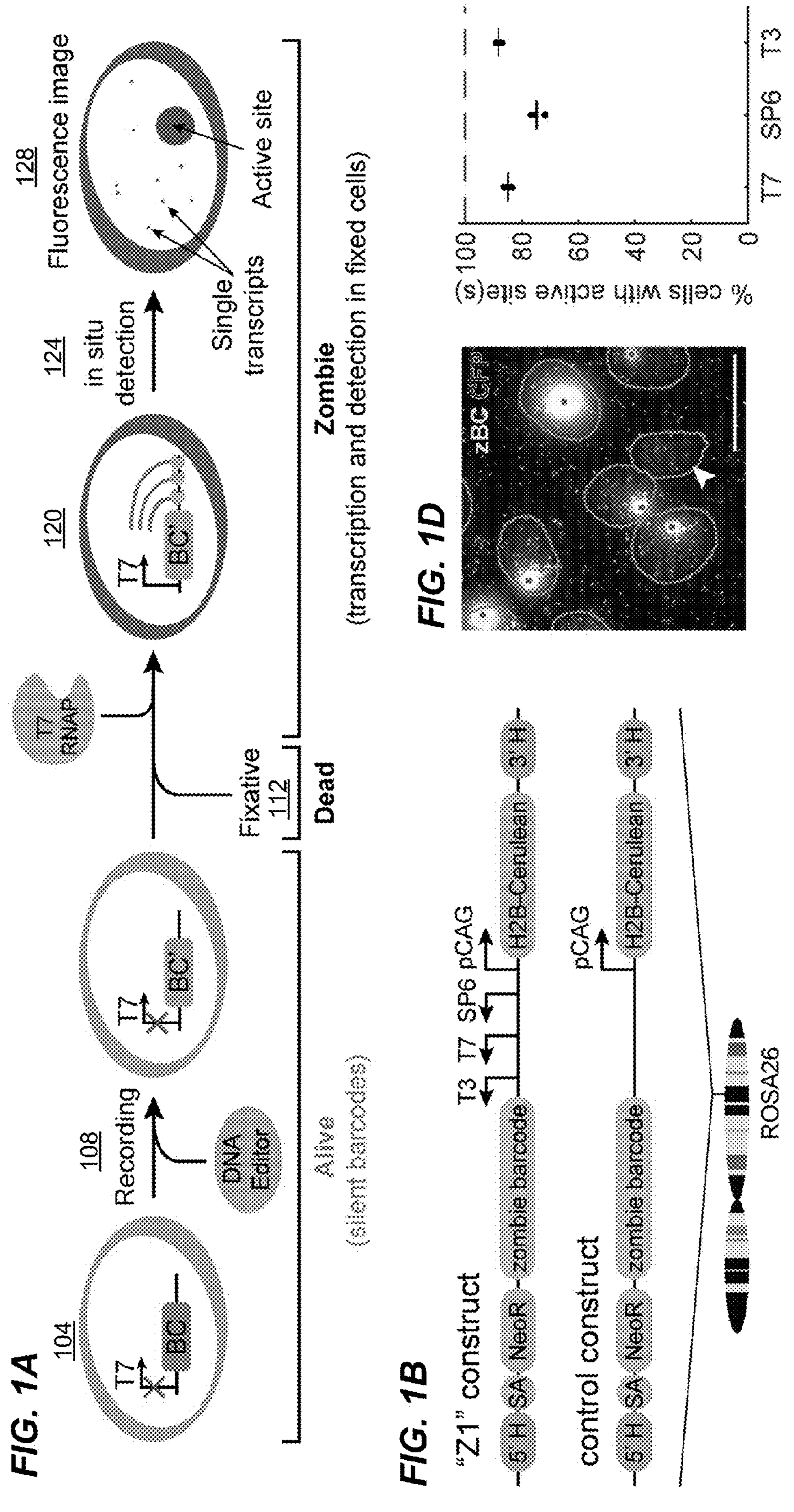
FIGS. 1A-1G. Phage RNA polymerases enable in situ readout of DNA barcodes without in vivo expression.

The number of promoter(s) upstream (e.g., immediate upstream) of a barcode sequence can be different in different implementations (See FIGS. 1B, 2A, and 3A for examples). In some embodiments, the number of promoter(s) upstream (e.g., immediate upstream) of a barcode sequence can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of barcode sequences under the control of a promoter can be different in different implementations. In some embodiments, the number of barcode sequences under the control of a promoter can be, be about, be at least, or at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The total number of promoter(s) can be different in different implementations. In some embodiments, the total number of promoter(s) can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

Barcode Sequences

The length of a barcode sequence can be different in different implementations. In some embodiments, the barcode sequence can be, can be about, can be at least, or can be at most, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, nucleotides in length.

In some embodiments, the barcode sequence is selected from a set of possible barcode sequences. A set of possible barcode sequences can comprise, comprise about, comprise at least, or comprise at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, possible barcode sequences. The possible barcode sequences of each set of possible barcode sequences can differ at one position. The one position can be, for example, position 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, of the barcode sequence. The possible barcode sequences can comprise adenine (A) nucleobase, guanine (G) nucleobase, or cytosine (C) nucleobase at the one position. The possible barcode sequences can comprise adenine (A) nucleobase, thymine (T) nucleobase, guanine (G) nucleobase, or cytosine (C) nucleobase at the one position. The possible barcode sequences of each set of possible barcode sequences can differ at more than one positions (e.g., 2, 3, 4, 5, 6, 7, 8, 9, or 10, positions).

The barcode sequence of the barcode polynucleotide in a cell can be unique. No cell can comprise a barcode polynucleotide with an identical barcode sequence. At least two cells of the plurality of cells can comprise an identical barcode sequence. In some embodiments, the number of cells comprising barcode polynucleotides with an identical barcode sequence can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

The barcode polynucleotides of at least two cells of the plurality of cells can comprise different barcode sequences. The at least two cells can be cells of a cell type, cells of a cell subtype, and/or cells of an identical lineage. The at least two cells can be cells of different cell types, cells of different cell subtypes, and/or cells of different lineages. A first cell of the at least two cells can be a cell of interest, and/or a second cell of the at least two cells is not a cell of interest. The first cell can be a cancer cell, and/or the second cell is a normal cell. In some embodiments, the number of cells comprising barcode polynucleotides with different barcode sequences can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

Marker Gene

In some embodiments, the polynucleotide comprises a constitutively active promoter upstream of a marker gene. The at least one promoter and the constitutively active promoter can have divergent orientations (See FIGS. 1B, 5A, and 6A for examples). The marker gene, the protein encoded by the marker gene, or the expression of any of the proceeding, can be used to identify cells comprising the barcode polynucleotide and/or the barcode sequence. The marker gene can comprise a gene of a fluorescent protein, such as the fluorescent protein comprises a green fluorescent protein (GFP), a yellow fluorescent protein (YFP), a cyan fluorescent protein (CFP), or a combination thereof.

Fixation

In some embodiments, the fixative comprises a non-cross-linking fixative, such as a precipitating fixative (e.g., an alcohol, such as methanol), a denaturing fixative (e.g., a weak acid, such as acetic acid), or a combination thereof. In some embodiments, fixing the cells can comprise: fixing the cells without using a cross-linking fixative. The plurality of fixed cells can comprise dead cells. The plurality of cells can comprise live cells and/or dead cells.

The fixative can comprise methanol (or another alcohol, or another precipitating fixative) and acetic acid (or another weak acid). The ratio of methanol and acetic acid in fixative can be, for example, from about 10:1 (e.g., v/v, w/w, v/w, or w/v) to about 1:10 (e.g. v/v, w/w, v/w, or w/v). In some embodiments, the ratio (e.g., v/v, w/w, v/w, and w/v) of methanol and acetic acid (or any two components in the fixative, such as a precipitating fixative and a denaturing fixative) can be, can be about, can be at least, or can be at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, or a number or a range between any two of these values. In some embodiments, the ratio (e.g., v/v, w/w, v/w, and w/v) of methanol and acetic acid (or any two components in the fixative, such as a precipitating fixative and a denaturing fixative) can be, can be about, can be at least, or can be at most, 1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these values.

The fixative can comprise, for example, from about 5% acetic acid in methanol to about 75% acetic acid in methanol (e.g., v/v, w/w, v/w, and w/v). The fixative can comprise, comprise about, comprise at least, or comprise at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values acetic acid in methanol (e.g., v/v, w/w, v/w, and w/v). The fixative can comprise, comprise about, comprise at least, or comprise at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values, methanol (e.g., v/v, w/w, v/w, and w/v).

In some embodiments, the method comprises: fixing fixed cells of the plurality of fixed cells using a second fixative to obtain a plurality of second fixed cells. Contacting each of the one or more fixed cells can comprise: contacting each of the one or more second fixed cells with a plurality of detection probes each comprising a barcode binding sequence. In some embodiments, thereby (i) one, at least one, or each of the plurality of barcode molecules comprising the barcode sequence of the oligonucleotide in the second fixed cell hybridizes to a detection probe of the plurality of detection probes comprising the barcode binding sequence reverse complementary to the barcode sequence, or a portion thereof, and (ii) the detection probe is associated with a fluorophore. Detecting the fluorophore, or fluorescence thereof can comprise: detecting the fluorophore, or fluorescence thereof, associated with the detection probe hybridized to the one, at least one, or each barcode molecule in each of the one or more second fixed cells using fluorescence imaging. The fluorophore, associated with the detection probe hybridized to the barcode molecule comprising the barcode sequence of the barcode polynucleotide in the second fixed cell, detected can indicate the barcode sequence of the barcode polynucleotide in the second fixed cell. The second fixative can comprise a cross-linking fixative. The second fixative can comprise an aldehyde, such as formaldehyde (e.g., such as 3%-4% formaldehyde in phosphate-buffered saline) and glutaraldehyde.

Barcode Expression

In some embodiments, one, at least one, or each of the plurality of cells (e.g., cells before being fixed with a non-cross-linking fixative) comprises no barcode molecule. Generating the plurality of barcode molecules can comprise: transcribing the barcode polynucleotide in each of the plurality of fixed cell to generate the plurality of barcode molecules comprising the barcode sequence of the barcode polynucleotide in the fixed cell (e.g., at 116 in FIG. 1). Transcribing the barcode polynucleotide can comprise: transcribing the barcode polynucleotide in each of the plurality of fixed cell to generate the plurality of barcode molecules comprising the barcode sequence of the barcode polynucleotide in the fixed cell using a phage RNA polymerase. The phage RNA polymerase can comprise a bacteriophage T3 RNA polymerase, a bacteriophage T7 RNA polymerase, a bacteriophage SP6 RNA polymerase, or a combination thereof.

The plurality of barcode molecules comprises at least 100 barcode molecules comprising the barcode sequence of the barcode polynucleotide in each of the plurality of fixed cells. The number of barcode molecules generated in each cell can be different in different implementations. The number of barcode molecules generated in each cell can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

Barcode Detection

In some embodiments, thereby the barcode sequence of each of the plurality of barcode molecules hybridizes to the barcode binding sequence of the detection probe that is reverse complementary to the barcode sequence of the barcode molecule (See FIG. 3A for an example). In some embodiments, contacting the plurality of fixed cells with the plurality of detection probes comprises: contacting each of the one or more fixed cells with detection probe molecules of each of the plurality of detection. In some embodiments, thereby (i) one, at least one, or each of the plurality of barcode molecules comprising the barcode sequence of the oligonucleotide in the fixed cell hybridizes to a detection probe molecule of the detection probe of the plurality of detection probes comprising the barcode binding sequence reverse complementary to the barcode sequence, or a portion thereof, and (ii) the detection probe molecule of the detection probe is associated with a fluorophore.

In some embodiments, two, three, or four (or about two, three, or four) detection probes of the plurality of detection probes comprise the barcode binding sequences that differ at one position. In some embodiments, two, three, or four (or about two, three, or four), detection probes of the plurality of detection probes comprise (i) barcode binding sequences that differ at one position and (ii) different initiator sequences. The (about) two, three, or four detection probes can have an identical concentration. One, at least one, or each of the plurality of barcode molecules comprising the barcode sequence of the oligonucleotide in the fixed cell can hybridize to one of the (about) two, three, or four detection probes comprising the barcode binding sequence reverse complementary to the barcode sequence, or a portion thereof, not the remaining (about) one, two, or three, detection probe(s).

The concentration of one, at least one, or each of the (about) two, three, or four detection probes can be different in different implementations, such as about 4 nM. In some embodiments, the concentration of a detection probe can be, can be about, can be at least, or can be at most, 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 86 nM, 87 nM, 88 nM, 89 nM, 90 nM, 91 nM, 92 nM, 93 nM, 94 nM, 95 nM, 96 nM, 97 nM, 98 nM, 99 nM, 100 nM, or a range between any two of these values.

The plurality of detection probes can comprise a set of detection probes. The set of detection probe can comprise, or comprise about, 2, 3, or 4 detection probes with barcode binding sequences that differ at one position (or more positions) and are reverse complementary to possible barcode sequences of one of the sets of possible barcode sequences. For example, a set of detection probes can comprise 4 detection probes that differ at one position. A barcode sequence can be selected from a set of 4 possible barcode sequences that differ at one position. Each detection probes in the set of detection probes can be reverse complementary to one barcode sequence of the set of possible barcode sequences.

Combinatorial Barcoding

The barcode polynucleotide can comprise different numbers of barcode sequence(s) in different implementations (See FIGS. 4A and 6A for examples). In some embodiments, the barcode polynucleotide of one, at least one, or each of the plurality of cells comprises, comprises about, comprises at least, or comprises at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, barcode sequences.

One or more barcode sequences can be downstream (e.g., immediately downstream) of at least one promoter (e.g., such as 1, 2, 3, 4, 5, 6, 7, 8, 9, or 10 promoters). Two (or more) of the barcode sequences can be downstream of different promoter. The number of barcode sequences downstream of different promoters can be different in different implementations. In some embodiments, the number of barcode sequences downstream of different promoters can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The different promoters can comprise an identical promoter sequence or different promoter sequences. The number of different promoters comprising an identical promoter sequence can be different in different implementations. In some embodiments, the number of different promoters comprising an identical promoter sequence can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of different promoters comprising different promoter sequences can be different in different implementations. In some embodiments, the number of different promoters comprising different promoter sequences can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The number of barcode sequences having an identical length can be different in different implementations. In some embodiments, the number of barcode sequences having an identical length can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of barcode sequences having different lengths can be different in different implementations. In some embodiments, the number of barcode sequences having different lengths can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The number of barcode sequences having different sequences can be different in different implementations. In some embodiments, the number of barcode sequences having different sequences can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. The number of barcode sequences having an identical sequence can be different in different implementations. In some embodiments, the number of barcode sequences having an identical sequence can be, can be about, can be at least, or can be at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The barcode sequences of a barcode polynucleotide can each be selected from a different set of possible barcode sequences. A set of possible barcode sequences can comprise, comprise about, comprise at least, or comprise at most, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, possible barcode sequences. The possible barcode sequences of each set of possible barcode sequences can differ at one position. The possible barcode sequences of each set of possible barcode sequences can differ at more than one positions (e.g., 2, 3, 4, 5, 6, 7, 8, 9, or 10, positions).

A combination of the barcode sequences (e.g., 12 barcode sequences) on a barcode polynucleotide can be selected from about 16 million, or about 500000, possible combinations of barcode sequences (e.g., 12 barcode sequences). In some embodiments, a combination of barcode sequences on a barcode polynucleotide can be selected from, from about, from at least, or from at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2 million, 3 million, 4 million, 5 million, 6 million, 7 million, 8 million, 9 million, 10 million, 20 million, 30 million, 40 million, 50 million, 60 million, 70 million, 80 million, 90 million, 100 million, or a number or a range between any two of these values, possible combinations of barcode sequences.

Adjacent barcode sequences can be separated from one another by different numbers of nucleotides in different implementations. In some embodiments, adjacent barcode sequences can be separated from one another by, by about, by at least, or by at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values, nucleotides.

The plurality of detection probes comprises different sets of detection probes (e.g., 12 sets of detection probes). In some embodiments, the number of set(s) of detection probes in the plurality of detection probes can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The detection probes of one of the sets of detection probes can comprise different initiator sequences. Said contacting and said detecting comprises: iteratively, contacting each of the one or more fixed cells with a different set of detection probes each comprising a barcode binding sequence, thereby (i) one, at least one, or each of the plurality of barcode molecules comprising the barcode sequence of the oligonucleotide in the fixed cell hybridizes to a detection probe of the set of detection probes comprising the barcode binding sequence reverse complementary to the barcode sequence, or a portion thereof, and (ii) the detection probe is associated with a fluorophore; and detecting the fluorophore associated with the detection probe hybridized to the one, at least one, or each barcode molecule in each of the one or more fixed cells using fluorescence imaging. A combination of the fluorophores associated with detection probes hybridized to the barcode molecule comprising the barcode sequence of the barcode polynucleotide in the fixed cell, detected can indicate the barcode sequence of the barcode polynucleotide in the fixed cell.

The method can comprise: removing the detection probe hybridized to the one, at least one, or each barcode molecule in each of the one or more fixed cells (e.g., after a round of detection). Said removing can comprise: digesting the detection probe hybridized to the one, at least one, or each barcode molecule in each of the one or more fixed cells using DNase. The number of rounds of detection for detecting the barcode sequences can be different in different implementation. In some embodiments, the number of rounds of detection can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

Barcode Readout

In some embodiments, the method comprises: determining the barcode sequence in each of the one or more fixed cells using the fluorophore, associated with the detection probe hybridized to the barcode molecule comprising the barcode sequence of the barcode polynucleotide in the fixed cell, detected. In some embodiments, the method comprises: determining lineages of, and/or a clonal relationship between, two or more fixed cells of the plurality of fixed cells (or corresponding cells of the plurality of cells) using the barcode sequence of the barcode polynucleotide in each of the two or more fixed cells (or corresponding cells). In some embodiments, the method comprises: determining a spatial relationship (e.g., in close proximity) of two or more fixed cells of the plurality of fixed cells; and correlating the barcode sequences of the barcode polynucleotide in each of the two or more fixed cells with a spatial relationship (e.g., intermixed spatial relationship) of the two or more fixed cells. The two or more cells can be cells of different cell types or cell subtypes. The two or more cells can be cells of an identical cell type or cell subtype.

Staining

In some embodiments, the method comprises: staining nuclei of the plurality of fixed cells. The method can comprise: identifying nuclei of the plurality of fixed cells based on the nuclei stained. Said detecting can comprise: detecting the fluorescence of the fluorophore, associated with the detection probe hybridized to the barcode molecule comprising the barcode sequence of the barcode polynucleotide in the fixed cell, in the nucleus of the cell identified.

Barcode Editing

In some embodiments, the method comprises: base editing the barcode sequence of the barcode polynucleotide in one, at least one, or each of the plurality of cells (e.g., at 108 in FIG. 1). In some embodiments, said base editing comprises: base editing the barcode sequence of the barcode polynucleotide in one, at least one, or each of the plurality of cells at the one position that the possible barcode sequences from the set of possible barcode sequences are different. In some embodiments, said base editing comprises: adenine (A)-to-guanine (G) base editing and/or cytosine (C)-to-thymine (T) base editing.

In some embodiments, said base editing comprises: base editing using a base editor and a guide ribonucleic acid (gRNA) targeting a gRNA targeting sequence of the barcode polynucleotide. The barcode polynucleotide can comprise a Protospacer Adjacent Motif (PAM). The PAM can be downstream of the gRNA targeting sequence. The base editor can comprise an adenine base editor (ABE) and/or a cytosine base editor (CBE). Said base editing can comprise: introducing a plasmid capable of expressing the base editor and the gRNA into one or more of the plurality of cells (See FIG. 4A for an example). Said introducing can comprise: introducing the plasmid capable of expressing the base editor and the gRNA into the one or more cells using transient transfection.

The gRNA targeting sequence can comprise the barcode sequence, or a portion thereof, of the barcode polynucleotide (See FIG. 4A for an example). Two or more barcode sequences of a barcode polynucleotide can be edited by independently addressing (e.g., the two or more barcode sequences can be edited using two or more gRNA) or by multiplexed addressing (e.g., the two or more barcode sequences can be edited using one gRNA) (See FIG. 4B for an example). The number of barcode sequences of a barcode polynucleotide with an identical gRNA targeting sequence, or different gRNA targeting sequences, can be different in different implementations. In some embodiments, the number of barcode sequences of a barcode polynucleotide with an identical gRNA targeting sequence can be, can be about, can be at least, or can be at most, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values. In some embodiments, the number of barcode sequences of a barcode polynucleotide with different gRNA targeting sequences can be, can be about, can be at least, or can be at most, 2, 3, 4, 5, 6, 7, 8, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or a number or a range between any two of these values.

The gRNA targeting sequence can have different lengths in different implementations, such as 20 nucleotides in length. In some embodiments, the gRNA targeting sequence can be, can be about, can be at least, or can be at most, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, nucleotides in length.

A memory unit referred to herein can include the barcode sequence and the gRNA targeting sequence of the barcode polynucleotide. The number of memory units on a barcode polynucleotide can be different in different implementations, such as 12. The number of memory unit(s) on a barcode polynucleotide can be, can be about, can be at least, or can be at most, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values.

The barcode sequence and the gRNA targeting sequence of the barcode polynucleotide can completely overlap. The barcode sequence and the gRNA targeting sequence of the barcode polynucleotide can overlap by different numbers of nucleotides in different implementations, such as 11 nucleotides. In some embodiments, the barcode sequence and the gRNA targeting sequence of the barcode polynucleotide can overlap by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a range between any two of these values, nucleotide(s).

In some embodiments, said base editing comprises base editing the barcode sequence of the barcode polynucleotide in one, at least one, or each of the plurality of cells at one or more predetermined time points. The time points can be different in different implementations. In some embodiments, the time point is, is about, is at least, or is at most, 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, 21 hrs, 22 hrs, 23 hrs, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, 100 days, or a number or a range between any two of these values, days after an event. The event can be, for example, introducing a plasmid capable of expressing the base editor and the gRNA into one or more of the plurality of cells.

In some embodiments, said base editing comprises base editing the barcode sequence of the barcode polynucleotide in one, at least one, or each of the plurality of cells at an edit rate. The edit rate can be predetermined. The edit rate can be different in different implementations, for example, from about 1% to about 100% edit per unit time. In some embodiments, the edit rate is, is about, is at least, or is at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, edit per unit time. The edit rate can be, for example, about 1% to 100% edit per cell per cell division cycle. In some embodiments, the edit rate is, is about, is at least, or is at most, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, edit per cell per cell division cycle.

Gene Expression

In some embodiments, the method comprises: determining gene expression (or other-omics data, such as proteomics data, and epigenomics data) in one, at least one, or each of the plurality of cells. Determining the gene expression can comprise: determining the gene expression in one, at least one, or each of the plurality of cells using seqFISH. In some embodiments, the method comprises: correlating the gene expression of two or more fixed cells of the plurality of fixed cells with the lineages of, the clonal relationship between, and/or the spatial relationship of, the two or more fixed cells. The lineages of, the clonal relationship between, and/or the spatial relationship of, the two or more fixed cells can be determined using the barcode sequences (or combinations of barcode sequences) of the barcodes in the fixed cells. For example, the method can include determining whether cells with similar expression of one or more genes correlate with the lineages of the cells. As another example, the method can include determining whether cells in close proximity have similar expression.

Sample

The plurality of cells can comprise, comprise about, comprise at least, or comprise at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values, cells. All cells can be cells of a cell type, of a cell subtype, and/or of an identical lineage. At least two cells can be cells of a cell type, cells of a cell subtype, and/or cells of an identical lineage. In some embodiments, the number of cells of a cell type, of a cell subtype, and/or of an identical lineage can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

No two cells can be cells of a cell type, of a cell subtype, and/or of an identical lineage. At least two cells can be cells of different cell types, cells of different cell subtypes, and/or cells of different lineages. In some embodiments, the number of cells of different cell types, of different cell subtypes, and/or of different lineages can be, can be about, can be at least, or can be at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

The plurality of cells can comprise a cell of interest (e.g., a cancer cell) and/or a cell not of interest (e.g., a normal cell). The number of cell(s) of the plurality of cells being cell(s) of interest can be different in different implementations. In some embodiments, the number of cell(s) of the plurality of cells being cell(s) of interest can be, can be about, can be at least, or can be at most, 1, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values. The number of cell(s) of the plurality of cells being cell(s) not of interest can be different in different implementations. In some embodiments, the number of cell(s) of the plurality of cells being cell(s) not of interest can be, can be about, can be at least, or can be at most, 1, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, or a number or a range between any two of these values.

In some embodiments, the plurality of cells is from a sample comprising a cell culture, a tissue, an organ (e.g., the brain), an embryo, an organism (e.g., a mammal), a section thereof. In some embodiments, the plurality of cells is from a sample comprising an in vivo sample and/or an in vitro sample. In some embodiments, the plurality of cells comprises one or more tumor cells, one or more immune cells, one or more epithelial cells, one or more nervous cells, one or more blood cells, one or more bone cells, one or more fat cells, one or more muscle cells, and/or one or more sex cells. In some embodiments, the plurality of cells comprises one or more stem cells, one or more progenitor cells, and/or one or more mature cells. In some embodiments, two, at least two, or each of the plurality of cells are cultured under an identical condition. In some embodiments, two, at least two, or each of the plurality of cells are cultured under different conditions. The number of different conditions can be different in different implementations. In some embodiments, the number of different implementations is, is about, is at last, or is at most, 2, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, or a number or a range between any two of these values. The identical condition or each of the different conditions can comprise a genetic perturbation, an environmental perturbation, or a combination thereof.

Composition & Kit

Disclosed herein include embodiments of a plurality of compositions for determining barcode sequences in situ. In some embodiments, the plurality of compositions comprises: a plurality of cells each comprising a barcode polynucleotide with a barcode sequence disclosed herein. The plurality of compositions can comprise: (a) a donor plasmid comprising the barcode polynucleotide, a sequence thereof, a subsequence thereof, or a reverse complementary sequence of any of the proceeding, the barcode polynucleotide comprising at least one barcode sequence disclosed herein, (b) a plasmid capable of expressing Cas9 and/or a guide ribonucleic acid (gRNA) for integrating the barcode polynucleotide into the genome disclosed herein, and/or (c) a viral vector for integrating the barcode polynucleotide into each of the plurality of cells disclosed herein. The viral vector can comprise a polynucleotide comprising the barcode polynucleotide, a sequence thereof, a subsequence thereof, or a reverse complementary sequence disclosed herein. The plurality of compositions can comprise: a fixative (e.g., a non-cross-linking fixative) disclosed herein. The plurality of compositions can comprise: a polymerase (e.g., a phage polymerase). The plurality of compositions can comprise: a plurality of detection probes (e.g., detection probes conjugated with fluorophores, or detection probes not conjugated with fluorophores) disclosed herein. The plurality of compositions can comprise: pairs of amplifier probes (e.g., pairs of amplifier probes with amplifier probes of a pair conjugated with an identical fluorophore), or a plurality of first amplifier probes disclosed herein.

Disclosed herein include embodiments of a kit. In some embodiments, the kit comprises: a plurality of compositions disclosed herein. The kit can comprise: instructions for using the plurality of compositions for determining barcode sequences in situ, high throughput screening, analyzing clonal dynamics and heterogeneity in a tumor or tumors, immunology, or developmental biology, and/or lineage or event recording.

Applications

Disclosed herein include embodiments of a method comprising using a plurality of compositions or a kit disclosed herein for applications including, but are not limited to, high throughput screening, analyzing clonal dynamics and heterogeneity in a tumor or tumors, immunology, or developmental biology, and/or lineage or event recording.

Genetic barcodes are unique DNA sequences that identify individual cells and their descendants. Barcoding are used in diverse biological fields, including immunology, neurobiology, and cancer biology. It has also enabled high throughput screening methods leading to discovery of novel genetic regulators and pharmaceutical perturbations. Dynamic barcoding, in which targeted genomic sequences are continuously modified to generate sequence diversity, has opened up the ability to reconstruct history of cellular events based on information recorded through genomic edits.

Analysis of barcodes has previously been limited to sequencing-based methods. Sequencing approaches provide accurate readout but disrupt the spatial context of cells and, in the case of single cell sequencing methods, typically recover information from a low percentage of cells in a given sample. The ability to read out barcode features and discriminate barcodes using imaging methods would enable identification and analysis of clones, lineages, and recorded genetic information by in situ imaging, without requiring sequencing. It would also be advantageously to enable efficient and straightforward readout of compact barcodes and detection of small changes in the barcode sequence, and be compatible with in situ transcriptional profiling techniques.

Disclosed herein includes compositions, kits, methods and systems based on phage RNA polymerases for imaging-based barcode readout in single cells. Phage polymerases efficiently transcribe barcodes in fixed cells, producing easily detectable fluorescent dots localized to transcriptional sites. Transcription enables detection of, for example, short 20 bp barcodes with discrimination of single nucleotide variants using competing probes. This capability enables recovery of edits made by a CRISPR base editors in living cells. This system, termed Zombie (for "Optical Measurement of Barcodes by In-situ Expression"), is versatile, operating in diverse contexts including cultured cells from various sources, for example human and mouse, and various animal tissues, including chick and mouse tissues. Thus, the method and system disclosed herein can allow high density barcoding and recording with imaging-based readout.

Applications in which the in-situ barcode readout method and system disclosed herein can be used include, but are not limited to:

High throughput screening applications. Cellular phenotypes can be assayed, for example, by imaging and connected to genetic or environmental perturbations that can be identified by barcode sequences. In such applications, large numbers of conditions or perturbations can be analyzed in parallel by in situ imaging rather than sequencing. Also, dynamic phenotypes can be recovered this way by using time-lapse imaging to analyze the temporal dynamics of cellular behaviors, with end-point analysis of barcodes in the same cell.

Analysis of clonal dynamics and heterogeneity in tumors, immunology, and developmental biology. A major question in cancer is the lineage structure of tumors and metastases and its relationship to the spatial organization of the tumor. Sequencing-based barcoding methods have been applied to this problem, but do not preserve spatial organization. The method and system disclosed herein will allow in situ analysis of lineage structure within animal or human tumor contexts for biomedical research and clinical applications. Similar approaches can provide insights into immune system development and tissue development.

Lineage and event recording. Recent work has provided methods for active recording of lineage and event history information in cellular genomes by continuous editing or modification of barcodes over multiple cell division cycles. In particular, "base editors' can be used to modify barcodes by changing single nucleotides. The method and system disclosed herein can enable read out of such single base edits in situ by imaging.

EXAMPLES

Some aspects of the embodiments discussed above are disclosed in further detail in the following examples, which are not in any way intended to limit the scope of the present disclosure.

Experimental Materials and Methods

The following experimental materials and methods were used for Examples 1-5 described below.

Cell Culture

E14 mouse embryonic stem (mES) cells (ATCC cat no. CRL-1821) were cultured in media containing Glasgow's Modified Eagle Medium (GMEM) (Sigma, St. Louis, MO), 15% embryonic stem (ES) cell (fetal bovine serum) FBS qualified (Atlanta Biologicals, Norcross, GA), 1×Modified Eagle Medium (MEM) Non-Essential Amino Acids (Thermo Fisher Scientific, Canoga Park, CA), 1 mM Sodium Pyruvate (Thermo Fisher Scientific, Canoga Park, CA), 100 μM β-mercaptoethanol (Thermo Fisher Scientific, Canoga Park, CA), 1× Penicillin-Streptomycin-L-Glutamine (Thermo Fisher Scientific, Canoga Park, CA), and 1000 U/ml Leukaemia Inhibitory Factor (Millipore). Cells were maintained on polystyrene (Falcon) coated with 0.1% gelatin (Sigma, St. Louis, MO) at 37° C. and 5% $CO_2$.

HEK293T cells were cultured in 1× Dulbecco's Modified Eagle Medium (DMEM) (Corning, Compton, CA), 10% FBS (Corning, Compton, CA), 1× Penicillin-Streptomycin-L-Glutamine (Corning, Compton, CA), 1 mM Sodium Pyruvate (Corning, Compton, CA), and 1×MEM Nonessential Amino Acids (Corning, Compton, CA) on polystyrene (Falcon) plates at 37° C. and 5% $CO_2$.

For transient transfections, HEK293T cells were plated in 48-well plates at the density of 125000 cells per well. The next day, cells were transfected with 1.5 μl Lipofectamine 2000 (Thermo Fisher Scientific, Canoga Park, CA) according to the manufacturer's instruction. 350 ng of ABE7.10 plasmid, 150 ng of gRNA expression plasmid, and 100 ng of GFP plasmid was used per well. In control wells, ABE7.10 and gRNA plasmids were replaced by pUC19 plasmid (NEB) to maintain the total amount of plasmids transfected at a constant level. Cells were then passaged to 24-well plates the day after transfection.

For in situ detection of barcodes, cells were plated on glass bottom 96-well plates (Cellvis) that were coated with 20 μg/ml laminin-511 (Biolamina) for at least 3 hours at 37° C.

Cell Line Engineering

Sequences of constructs, barcodes, and probes used in the examples below are shown in Tables 1A-1B, 2, 3A-3B, 4A-4D, 5A-5D, and 6A-6B. To create stable polyclonal cell lines, mES cells were cultured in 24-well plates to approximately 70% confluency and co-transfected with 600 ng of donor plasmid (Z1, control, or Z3) and 200 ng of modified pX330 plasmid (Addgene #42230) expressing Cas9 and a gRNA targeting ROSA26 locus (CAGGACAACGCC-CACACACC (SEQ ID NO. 1)). Transfection was performed using Lipofectamine LTX with Plus reagent (Thermo Fisher Scientific, Canoga Park, CA) based on the manufacturer's protocol. The cells were then passaged to a 6-well plate the next day and selected with 500 ug/ml Geneticin starting at 2 days after transfection.

TABLE 1A

Sequences of the constructs, barcodes, and/or probes used in Example 1. See FIGS. 1C, 1D, 1F, 1G, and related figures for results.

Figures 1C, 1E, 1F, 1G:
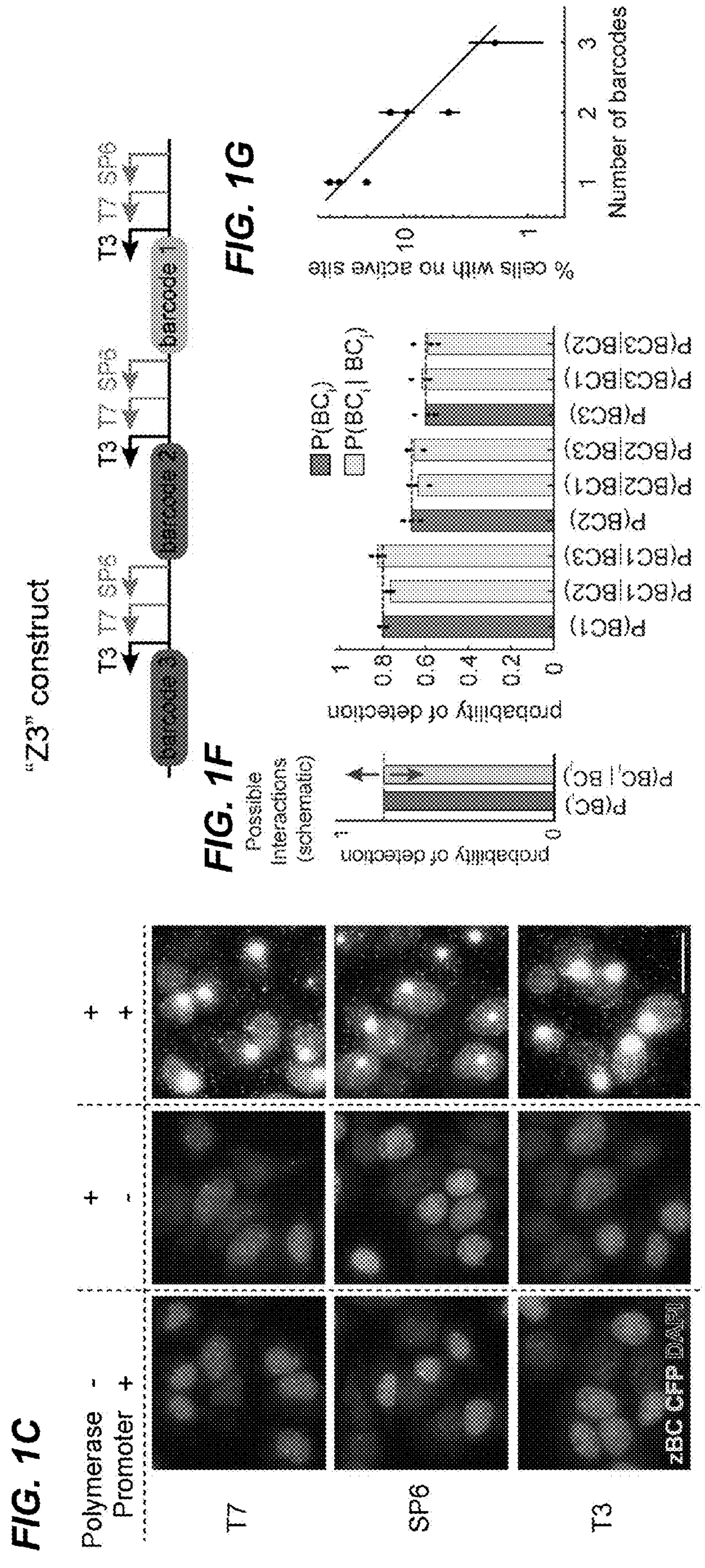

| Probe target | HCR initiator | Fluorophore | Related figure(s) |
|---|---|---|---|
| Z1-barcode | B1 | Alexa 546 | FIGS. 1C, 1D, and 8 |
| Cerulean | B3 | Alexa 488 | |

TABLE 1A-continued

Sequences of the constructs, barcodes, and/or probes used in Example 1. See FIGS. 1C, 1D, 1F, 1G, and related figures for results.

| Probe target | HCR initiator | Fluorophore | Related figure(s) |
|---|---|---|---|
| Cerulean-3'UTR | B2 | Alexa 647 | |
| Z3-barcode1 | B1 | Alexa 488 | FIGS. 1F, 1G, and 9 |
| Z3-barcode2 | B2 | Alexa 647 | |
| Z3-barcode3 | B4 | Alexa 546 | |
| Cerulean | B3 | Alexa 594 | |
| Z1-barcode | B1 | Alexa 647 | FIG. 7 |
| Cerulean | B3 | Alexa 488 | |
| Cerulean-3'UTR | B2 | Alexa 594 | |

Pooled split initiator (v3.0) probes were purchased from Molecular Instruments and used according to their protocol.

TABLE IB

Sequences of the constructs, barcodes, and/or probes used in Example 1. See FIGS. 1C, 1D, 1F, 1G, and related figures for results.

| Name | Sequence | SEQ ID NO. |
|---|---|---|
| Z1-barcode | taacaggaaacagctatgacgggcccccctaggtaagcagtatcttcgacagcttgtctctccagatg<br>ctcttgggccatcttccacatcgtccgtagcagccttggcaatttgccatcactggcaaatacacat<br>aaatccaatgaatacggttaccaccatcacattaccatgcaggtacacagcaagaattgacgttggc<br>atatcacatggtgtaataaccccacttgtgaaacaacccagaataaggtacaaggcggaaatgtcgt<br>cattctaaaataaaaggcatggccaggaatttgtctaataccgggaacttaaattcagcttgaacac<br>cagtcgcaaaaaattcaaagaaagtgattcaggttcgggttcgtggattggaacagcttcttttgtt<br>tcagtgatgagagaatcctcctgtcactcgagaaagaatcaaagaggccaacaacgcagaacaggaa<br>acagctatgacgggcccccctaggtaagcagtatcttcgacagcttgtctctccagatgctcttgggc<br>catcttccacatcgtccgtagcagccttggcaatttgccatcactggcaaatacacataaatccaat<br>gaatacggttaccaccatcacattaccatgcaggtacacagcaagaattgacgttggcatatcacat<br>ggtgtaataaccccacttgtgaaacaacccagaataaggtacaaggcggaaatgtcgtcattctaaa<br>ataaaaggcatggccaggaatttgtctaataccgggaacttaaattcagcttgaacaccagtcgcaa<br>aaaattcaaagaaagtgattcaggttcgggttcgtggattggaacagcttcttttgtttcagtgatg<br>agagaatcctcctgtcactcgagaaagaatcaaagaggccaacaa | 2 |
| Z3-barcode1 | taacaggaaacagctatgacgggcccccctaggtaagcagtatcttcgacagcttgtctctccagatg<br>ctcttgggccatcttccacatcgtccgtagcagccttggcaatttgccatcactggcaaatacacat<br>aaatccaatgaatacggttaccaccatcacattaccatgcaggtacacagcaagaattgacgttggc<br>atatcacatggtgtaataaccccacttgtgaaacaacccagaataaggtacaaggcggaaatgtcgt<br>cattctaaaataaaaggcatggccaggaatttgtctaataccgggaacttaaattcagcttgaacac<br>cagtcgcaaaaaattcaaagaaagtgattcaggttcgggttcgtggattggaacagcttcttttgtt<br>tcagtgatgagagaatcctcctgtcactcgagaaagaatcaaagaggccaacaacgcagaacaggaa<br>acagctatgacgggcccccctaggtaagcagtatcttcgacagcttgtctctccagatgctcttgggc<br>catcttccacatcgtccgtagcagccttggcaatttgccatcactggcaaatacacataaatccaat<br>gaatacggttaccaccatcacattaccatgcaggtacacagcaagaattgacgttggcatatcacat<br>ggtgtaataaccccacttgtgaaacaacccagaataaggtacaaggcggaaatgtcgtcattctaaa<br>ataaaaggcatggccaggaatttgtctaataccgggaacttaaattcagcttgaacaccagtcgcaa<br>aaaattcaaagaaagtgattcaggttcgggttcgtggattggaacagcttcttttgtttcagtgatg<br>agagaatcctcctgtcactcgagaaagaatcaaagaggccaacaa | 3 |
| Z3-barcode2 | taacaggaaacagctatgacgggcccccctagggggttctgacttcttacgaaaatgtggctagcatt<br>ccattctctgacgttcaaagaatcggaataagtcatggtaatggtgggaaatctaatagaagcgact<br>cccataacctccatatttcttggcaaataattctgtctgggttaccgttcacgagccttcagagatc<br>tacgacgtgtagtgggtgggcttgccctccagggtgtagtttgtaattagaatgggatttcctgttt<br>taagtacccaaatacgaaaattgctcttgatgtttaacggctcacttttaagtaaagtttgtgccaa<br>taccgtgcatgggagtaagttattgccaatcttcgagaatttaggcaattttggtatactcaactgg<br>gtctaatatggtggacggaatgatttctcgagaaagaatcaaagaggccaacaacgcagaacaggaa<br>acagctatgacgggcccccctagggggttctgacttcttacgaaaatgtggctagcattccattctct<br>gacgttcaaagaatcggaataagtcatggtaatggtgggaaatctaatagaagcgactcccataacc<br>tccatatttcttggcaaataattctgtctgggttaccgttcacgagccttcagagatctacgacgtg<br>tagtgggtgggcttgccctccagggtgtagtttgtaattagaatgggatttcctgttttaagtaccc<br>aaatacgaaaattgctcttgatgtttaacggctcacttttaagtaaagtttgtgccaataccgtgca<br>tgggagtaagttattgccaatcttcgagaatttaggcaattttggtatactcaactgggtctaatat<br>ggtggacggaatgatttctcgagaaagaatcaaagaggccaacaa | 4 |
| Z3 barcode3 | taacaggaaacagctatgacgggcccccctaggcacattgcgtctttataaacttactaaaggttttg<br>gatagttttgaacccattgtttgacgaatattccatattaaaaactctaaaataaaccccagccacc<br>aacatttgaaccagcgttcccccccatctccgctgtgatcattctagatctgtattatggcatcgact<br>atgggaatacagggttattctcccattttattgaggtatatggccagttgcgcaacttctttgatga<br>aattttatttgtccgttgcatgattgaaatcctaccagtagttatatatatgtctttttcattgttg | 5 |

TABLE IB-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | tactttggataaagctgcttcttcagaacgctccctactatgctttaaacgcttattttcggaagaa<br>atcatgtgggtcatattttttttgcttctcgagaaagaatcaaagaggccaacaacgcagaacaggaa<br>acagctatgacgggccccctaggcacattgcgtctttataaacttactaaaggttttggatagtttt<br>gaacccattgtttgacgaatattccatattaaaaactctaaaataaaccccagccaccaacatttga<br>accagcgttcccccccatctccgctgtgatcattctagatctgtattatggcatcgactatgggaata<br>cagggttattctcccattttattgaggtatatggccagttgcgcaacttctttgatgaaattttatt<br>tgtccgttgcatgattgaaatcctaccagtagttatatatatgtctttttcattgttgtactttgga<br>taaagctgcttcttcagaacgctccctactatgctttaaacgcttattttcggaagaaatcatgtgg<br>gtcatattttttttgcttctcgagaaagaatcaaagaggccaacaa | |
| Z1 construct | agacacctcgagacccaataaaagatctttattttcattagatctgtgtgttggtttttttgtgtgtc<br>tagagtgtgggtgtgggcgttgtcctgcaggggaattgaacaggtgtaaaattggagggacaagact<br>tcccacagattttcggttttgtcgggaagtttttttaataggggcaaataaggaaaatgggaggatag<br>gtagtcatctggggttttatgcagcaaaactacaggttattattgcttgtgatccgcctcggagtat<br>tttccatcgaggtagattaaagacatgctcacccgagttttatactctcctgcttgagatccttact<br>acagtatgaaattacagtgtcgcgagttagactatgtaagcagaattttaatcatttttaaagagcc<br>cagtacttcatatccatttctcccgctccttctgcagccttatcaaaaggtattttagaacactcat<br>tttagccccattttcatttattatactggcttatccaacccctagacagagcattggcattttccct<br>ttcctgatcttagaagtctgatgactcatgaaaccagacagattaccctgttatccctagaattcag<br>cttgggataaaaagctatggcataggcggtaatacggttatccacagaatcaggggataacgcagga<br>aagaacatgtgagcaaaaggccagcaaaaggccaggaaccgtaaaaaggccgcgttgctggcgtttt<br>tccataggctccgcccccctgacgagcatcacaaaaatcgacgctcaagtcagaggtggcgaaaccc<br>gacaggactataaagataccaggcgtttccccctggaagctccctcgtgcgctctcctgttccgacc<br>ctgccgcttaccggatacctgtccgcctttctcccttcgggaagcgtggcgctttctcatagctcac<br>gctgtaggtatctcagttcggtgtaggtcgttcgctccaagctgggctgtgtgcacgaaccccccgt<br>tcagcccgaccgctgcgccttatccggtaactatcgtcttgagtccaacccggtaagacacgactta<br>tcgccactggcagcagccactggtaacaggattagcagagcgaggtatgtaggcggtgctacagagt<br>tcttgaagtggtggcctaactacggctacactagaagaacagtatttggtatctgcgctctgctgaa<br>gccagttaccttcggaaaaagagttggtagctcttgatccggcaaacaaaccaccgctggtagcggt<br>ggtttttttgtttgcaagcagcagattacgcgcagaaaaaaaggatctcaagaagatcctttgatct<br>tttctacggggtctgacgctcagtggaacgaaaactcacgttaagggattttggtcatgagattatc<br>aaaaaggatcttcacctagatccttttaaattaaaaatgaagttttaaatcaatctaaagtatatat<br>gagtaaacttggtctgacagttaccaatgcttaatcagtgaggcacctatctcagcgatctgtctat<br>ttcgttcatccatagttgcctgactccccgtcgtgtagataactacgatacgggagggcttaccatc<br>tggccccagtgctgcaatgataccgcgagatccacgctcaccggctccagatttatcagcaataaac<br>cagccagccggaagggccgagcgcagaagtggtcctgcaactttatccgcctccatccagtctatta<br>attgttgccgggaagctagagtaagtagttcgccagttaatagtttgcgcaacgttgttgccattgc<br>tacaggcatcgtggtgtcacgctcgtcgtttggtatggcttcattcagctccggttcccaacgatca<br>aggcgagttacatgatcccccatgttgtgcaaaaaagcggttagctccttcggtcctccgatcgttg<br>tcagaagtaagttggccgcagtgttatcactcatggttatggcagcactgcataattctcttactgt<br>catgccatccgtaagatgcttttctgtgactggtgagtactcaaccaagtcattctgagaatagtgt<br>atgcggcgaccgagttgctcttgcccggcgtcaatacgggataataccgcgccacatagcagaactt<br>taaaagtgctcatcattggaaaacgttcttcggggcgaaaactctcaaggatcttaccgctgttgag<br>atccagttcgatgtaacccactcgtgcacccaactgatcttcagcatcttttactttcaccagcgtt<br>tctgggtgagcaaaaacaggaaggcaaaatgccgcaaaaaagggaataagggcgacacggaaatgtt<br>gaatactcatactcttcctttttcaatattattgaagcatttatcagggttattgtctcatgagcgg<br>atacatatttgaatgtatttagaaaaataaacaaataggggtgatttaatctgtatcaggggcgtat<br>agtggagcaaagcgaattctaactataacggtcctaaggtagcgaaggccctcccctcggccccgcg<br>ccgcagagtctggccgcgcgcccctgcgcaacgtggcaggaagcgcgcgctgggggcggggacgggc<br>agtagggctgagcggctgcggggcgggtgcaagcacgtttccgacttgagttgcctcaagaggggcg<br>tgctgagccagacctccatcgcgcactccggggagtggagggaaggagcgagggctcagttgggctg<br>ttttggaggcaggaagcacttgctctcccaaagtcgctctgagttgttatcagtaagggagctgcag<br>tggagtaggcggggagaaggccgcacccttctccggaggggggaggggagtgttgcaatacctttct<br>gggagttctctgctgcctcctggcttctgaggaccgccctgggcctgggagaatcccttcccccctct<br>tccctcgtgatctgcaactccagtctttctagaagatgggcgggagtcttttgggcaggcttaaagg<br>ctaacctggttagggcgcagtagtccagggtttccttgatgatgtcatacttatcctgtcccttttt<br>tttccacagctcgcggttgaggacaaactcttcgcggtctttccagtgttgacaattaatcatcggc<br>atagtatatcggcatagtataatacgacaaggtgaggaacgccaccatgattgaacaagatggattg<br>cacgcaggttctccggccgcttgggtggagaggctattcggctatgactgggcacaacagacaatcg<br>gctgctctgatgccgccgtgttccggctgtcagcgcaggggcgcccggttctttttgtcaagaccga<br>cctgtccggtgccctgaatgaactgcaagacgaggcagcgcggctatcgtggctggccacgacgggc<br>gttccttgcgcagctgtgctcgacgttgtcactgaagcgggaagggactggctgctattgggcgaag<br>tgccggggcaggatctcctgtcatctcaccttgctcctgccgagaaagtatccatcatggctgatgc<br>aatgcggcggctgcatacgcttgatccggctacctgcccattcgaccaccaagcgaaacatcgcatc<br>gagcgagcacgtactcggatggaagccggtcttgtcgatcaggatgatctggacgaagagcatcagg<br>ggctcgcgccagccgaactgttcgccaggctcaaggcgagcatgcccgacggcgaggatctcgtcgt<br>gacccatggcgatgcctgcttgccgaatatcatggtggaaaatggccgcttttctggattcatcgac<br>tgtggccggctgggtgtggcggaccgctatcaggacatagcgttggctacccgtgatattgctgaag<br>agcttggcggcgaatgggctgaccgcttcctcgtgctttacggtatcgccgctcccgattcgcagcg<br>catcgccttctatcgccttcttgacgagttcttctgatgtacaagtaaagcggccgcgactctagat<br>cataatcagccataccacatttgtagaggttttacttgctttaaaaaacctcccacacctccccctg<br>aacctgaaacataaaatgaatgcaattgttgttgttaacttgtttattgcagcttataatggttaca<br>aataaagcaatagcatcacaaatttcacaaataaagcatttttttcactgcattctagttgtggttt | 6 |

TABLE IB-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | gtccaaactcatcaatgtatcttaggtctcgcgtactgtaggtcctttcagcaaaaaacccctcaag | |
| | acccgtttagaggccccaaggggttatgctagttattgctcagcggtggcagcagccaactcagctt | |
| | cctttcgggctttgttagcagccggatctcagtggtggtggtggtggtgctcccatctgacttgcaa | |
| | gaaaacagatggcaagcatgacaatcatttcgagtgcggccgcagcgacaaacaacagataaaacga | |
| | aaggcccagtctttcgactgagcctttcgttttatttgaagcttctttcagcaaaaaaccccgcagg | |
| | acccccgaagaggccccgcggggttatgctaggtcgactacgcagacgtaacaggaaacagctatga | |
| | cgggccccctaggtaagcagtatcttcgacagcttgtctctccagatgctcttgggccatcttccac | |
| | atcgtccgtagcagccttggcaatttgccatcactggcaaatacacataaatccaatgaatacggtt | |
| | accaccatcacattaccatgcaggtacacagcaagaattgacgttggcatatcacatggtgtaataa | |
| | ccccacttgtgaaacaacccagaataaggtacaaggcggaaatgtcgtcattctaaaataaaaggca | |
| | tggccaggaatttgtctaataccgggaacttaaattcagcttgaacaccagtcgcaaaaaattcaaa | |
| | gaaagtgattcaggttcgggttcgtggattggaacagcttcttttgtttcagtgatgagagaatcct | |
| | cctgtcactcgagaaagaatcaaagaggccaacaacgcagaacaggaaacagctatgacgggccccc | |
| | taggtaagcagtatcttcgacagcttgtctctccagatgctcttgggccatcttccacatcgtccgt | |
| | agcagccttggcaatttgccatcactggcaaatacacataaatccaatgaatacggttaccaccatc | |
| | acattaccatgcaggtacacagcaagaattgacgttggcatatcacatggtgtaataaccccacttg | |
| | tgaaacaacccagaataaggtacaaggcggaaatgtcgtcattctaaaataaaaggcatggccagga | |
| | atttgtctaataccgggaacttaaattcagcttgaacaccagtcgcaaaaaattcaaagaaagtgat | |
| | tcaggttcgggttcgtggattggaacagcttcttttgtttcagtgatgagagaatcctcctgtcact | |
| | cgagaaagaatcaaagaggccaacaacgacctgtagaggtcctccctttagtgagggttaattctcg | |
| | agtctccctatagtgagtcgtattaattccgtgtattctatagtgtcacctaaatcgttacgggttc | |
| | gtaaattctgcaggacttctagttattaatagtaatcaattacggggtcattagttcatagcccata | |
| | tatggagttccgcgttacataacttacggtaaatggcccgcctggctgaccgcccaacgacccccgc | |
| | ccattgacgtcaataatgacgtatgttcccatagtaacgccaatagggactttccattgacgtcaat | |
| | gggtggagtatttacggtaaactgcccacttggcagtacatcaagtgtatcatatgccaagtacgcc | |
| | ccctattgacgtcaatgacggtaaatggcccgcctggcattatgcccagtacatgaccttatgggac | |
| | tttcctacttggcagtacatctacgtattagtcatcgctattaccatggtcgaggtgagccccacgt | |
| | tctgcttcactctccccatctcccccccctccccacccccaattttgtatttatttattttttaatt | |
| | attttgtgcagcgatgggggcgggggggggggggggcgcgcgccaggcggggcggggcggggcgag | |
| | gggcggggcggggcgaggcggagaggtgcggcggcagccaatcagagcggcgcgctccgaaagtttc | |
| | cttttatggcgaggcggcggcggcggcggccctataaaaagcgaagcgcgcggcgggcgggagtcgc | |
| | tgcgcgctgccttcgccccgtgccccgctccgccgccgcctcgcgccgcccgccccggctctgactg | |
| | accgcgttactcccacaggtgagcgggcgggacggcccttctcctccgggctgtaattagcgcttgg | |
| | tttaatgacggcttgtttcttttctgtggctgcgtgaaagccttgaggggctccgggagggcccttt | |
| | gtgcggggggagcggctcgggggggtgcgtgcgtgtgtgtgtgcgtggggagcgccgcgtgcggctcc | |
| | gcgctgcccggcggctgtgagcgctgcgggcgcggcgcggggctttgtgcgctccgcagtgtgcgcg | |
| | aggggagcgcggccgggggcggtgccccgcggtgcggggggggctgcgaggggaacaaaggctgcgtg | |
| | cggggtgtgtgcgtgggggggtgagcagggggtgtgggcgcgtcggtcgggctgcaaccccccctg | |
| | cacccccctccccgagttgctgagcacggcccggcttcgggtgcggggctccgtacggggcgtggcg | |
| | cggggctcgccgtgccgggcggggggtggcggcaggtgggggtgccgggcggggcggggccgcctcg | |
| | ggccggggagggctcgggggagggggcgcggcggcccccggagcgccggcggctgtcgaggcgcggcg | |
| | agccgcagccattgccttttatggtaatcgtgcgagagggcgcagggacttcctttgtcccaaatct | |
| | gtgcggagccgaaatctgggaggcgccgccgcaccccctctagcgggcgcggggcgaagcggtgcgg | |
| | cgccggcaggaaggaaatgggcggggagggccttcgtgcgtcgccgcgccgccgtccccttctccct | |
| | ctccagcctcggggctgtccgcgggggggacggctgccttcgggggggacggggcagggcggggttcg | |
| | gcttctggcgtgtgaccggcggctctagagcctctgctaaccatgttcatgccttcttctttttcct | |
| | acagctcctgggcaacgtgctggttattgtgctgtctcatcattttggcaaagaattgatttgatac | |
| | cgcgggcccgggatcccctcgagggaattacctttggcgtagccgccaccatgccagagccagcgaa | |
| | gtctgctcccgccccgaaaaagggctccaagaaggcggtgactaaggcgcagaagaaaggcggcaag | |
| | aagcgcaagcgcagccgcaaggagagctattccatctatgtgtacaaggttctgaagcaggtccacc | |
| | ctgacaccggcatttcgtccaaggccatgggcatcatgaattcgtttgtgaacgacattttcgagcg | |
| | catcgctggtgaggcttcccgcctggcgcattacaacaagcgctcgaccatcacctccagggagatc | |
| | cagacggccgtgcgcctgctgctgcctggggagttggccaagcacgccgtgtccgagggtactaagg | |
| | ccatcaccaagtacaccagcgctaaggatccccgggtaccggtcgccaccatggtgagcaagggcga | |
| | ggagctgttcaccggggtggtgcccatcctggtcgagctggacggcgacgtaaacggccacaagttc | |
| | agcgtgtccggcgagggcgagggcgatgccacctacggcaagctgaccctgaagttcatctgcacca | |
| | ccggcaagctgcccgtgccctggcccaccctcgtgaccaccctgacctggggcgtgcagtgcttcgc | |
| | ccgctaccccgaccacatgaagcagcacgacttcttcaagtccgccatgcccgaaggctacgtccag | |
| | gagcgcaccatcttcttcaaggacgacggcaactacaagacccgcgccgaggtgaagttcgagggcg | |
| | acaccctggtgaaccgcatcgagctgaagggcatcgacttcaaggaggacggcaacatcctggggca | |
| | caagctggagtacaacgccatcagcgacaacgtctatatcaccgccgacaagcagaagaacggcatc | |
| | aaggccaacttcaagatccgccacaacatcgaggacggcagcgtgcagctcgccgaccactaccagc | |
| | agaacacccccatcggcgacggccccgtgctgctgcccgacaaccactacctgagcacccagtccaa | |
| | gctgagcaaagaccccaacgagaagcgcgatcacatggtcctgctggagttcgtgaccgccgccggg | |
| | atcactctcggcatggacgagctgtacaagtgaacctgagtcgtaacaggaaacagctatgacgggc | |
| | cccctaggacgttcccatagctccttttgatgtcttaatgtaggttcaacagatatgcggcttcttc | |
| | gcattctgatggcgtcagctacgataggcgagagctgaatagttgaaaatttttagcagatgcctga | |
| | gaaaattaaacttgatttgattccagtaatttaccaaaatacgcacagttgccttcttcgatgtaat | |
| | cttttcaatcgtactatgtcgtatgcagttagcaaatgaaagtagcaacaccaatttgcgccagaat | |
| | ttcacgtcgaaaatatccttaaaccttgcaagccaagttacggagttgaaatttccgtaagctacgg | |
| | ttatcttccaatggcccatacttggctaaatcagagttccctttcgtggaaactgcaatagccaaat | |
| | tcctcgagaaagaatcaaagaggccaacaacgcagaacaggaaacagctatgacgggcccccctagga | |
| | cgttcccatagctccttttgatgtcttaatgtaggttcaacagatatgcggcttcttcgcattctga | |

TABLE IB-continued

Sequences of the constructs, barcodes, and/or probes used in Example 1. See FIGS. 1C, 1D, 1F, 1G, and related figures for results.

| Name | Sequence | SEQ ID NO. |
| --- | --- | --- |
| | tggcgtcagctacgataggcgagagctgaatagttgaaaatttttagcagatgcctgagaaaattaa<br>acttgatttgattccagtaatttaccaaaatacgcacagttgccttcttcgatgtaatcttttcaat<br>cgtactatgtcgtatgcagttagcaaatgaaagtagcaacaccaatttgcgccagaatttcacgtcg<br>aaaatatccttaaaccttgcaagccaagttacggagttgaaatttccgtaagctacggttatcttcc<br>aatggcccatacttggctaaatcagagttccctttcgtggaaactgcaatagccaaattcctcgaga<br>aagaatcaaagaggccaacaacgacctgctaaggtctgtgccttctagttgccagccatctgttgtt<br>tgcccctcccccgtgccttccttgaccctggaaggtgccactcccactgtcctttcctaataaaatg<br>aggaaattgcatcgcattgtctgagtaggtgtcattctattctggggggtggggtggggcaggacag<br>caagggggaggattgggaagagaatagcaggcatgctggggatgcggtgggctctatggtacg | |
| Control construct | agacacctcgagacccaataaaagatctttattttcattagatctgtgtgttggttttttgtgtgtc<br>tagagtgtgggtgtgggcgttgtcctgcaggggaattgaacaggtgtaaaattggagggacaagact<br>tcccacagattttcggttttgtcgggaagtttttaataggggcaaataaggaaaatgggaggatag<br>gtagtcatctggggttttatgcagcaaaactacaggttattattgcttgtgatccgcctcggagtat<br>tttccatcgaggtagattaaagacatgctcacccgagttttatactctcctgcttgagatccttact<br>acagtatgaaattacagtgtcgcgagttagactatgtaagcagaattttaatcatttttaaagagcc<br>cagtacttcatatccatttctcccgctccttctgcagccttatcaaaaggtattttagaacactcat<br>tttagccccattttcatttattatactggcttatccaacccctagacagagcattggcattttccct<br>ttcctgatcttagaagtctgatgactcatgaaaccagacagattaccctgttatccctagaattcag<br>cttgggataaaaagctatggcataggcggtaatacggttatccacagaatcaggggataacgcagga<br>aagaacatgtgagcaaaaggccagcaaaaggccaggaaccgtaaaaaggccgcgttgctggcgtttt<br>tccataggctccgcccccctgacgagcatcacaaaaatcgacgctcaagtcagaggtggcgaaaccc<br>gacaggactataaagataccaggcgtttccccctggaagctccctcgtgcgctctcctgttccgacc<br>ctgccgcttaccggatacctgtccgcctttctcccttcgggaagcgtggcgctttctcatagctcac<br>gctgtaggtatctcagttcggtgtaggtcgttcgctccaagctgggctgtgtgcacgaaccccccgt<br>tcagcccgaccgctgcgccttatccggtaactatcgtcttgagtccaacccggtaagacacgactta<br>tcgccactggcagcagccactggtaacaggattagcagagcgaggtatgtaggcggtgctacagagt<br>tcttgaagtggtggcctaactacggctacactagaagaacagtatttggtatctgcgctctgctgaa<br>gccagttaccttcggaaaaagagttggtagctcttgatccggcaaacaaaccaccgctggtagcggt<br>ggtttttttgtttgcaagcagcagattacgcgcagaaaaaaaggatctcaagaagatcctttgatct<br>tttctacggggtctgacgctcagtggaacgaaaactcacgttaagggattttggtcatgagattatc<br>aaaaaggatcttcacctagatccttttaaattaaaaatgaagttttaaatcaatctaaagtatatat<br>gagtaaacttggtctgacagttaccaatgcttaatcagtgaggcacctatctcagcgatctgtctat<br>ttcgttcatccatagttgcctgactccccgtcgtgtagataactacgatacgggagggcttaccatc<br>tggccccagtgctgcaatgataccgcgagatccacgctcaccggctccagatttatcagcaataaac<br>cagccagccggaagggccgagcgcagaagtggtcctgcaactttatccgcctccatccagtctatta<br>attgttgccgggaagctagagtaagtagttcgccagttaatagtttgcgcaacgttgttgccattgc<br>tacaggcatcgtggtgtcacgctcgtcgtttggtatggcttcattcagctccggttcccaacgatca<br>aggcgagttacatgatcccccatgttgtgcaaaaaagcggttagctccttcggtcctccgatcgttg<br>tcagaagtaagttggccgcagtgttatcactcatggttatggcagcactgcataattctcttactgt<br>catgccatccgtaagatgcttttctgtgactggtgagtactcaaccaagtcattctgagaatagtgt<br>atgcggcgaccgagttgctcttgcccggcgtcaatacgggataataccgcgccacatagcagaactt<br>taaaagtgctcatcattggaaaacgttcttcggggcgaaaactctcaaggatcttaccgctgttgag<br>atccagttcgatgtaacccactcgtgcacccaactgatcttcagcatcttttactttcaccagcgtt<br>tctgggtgagcaaaaacaggaaggcaaaatgccgcaaaaaagggaataagggcgacacggaaatgtt<br>gaatactcatactcttcctttttcaatattattgaagcatttatcagggttattgtctcatgagcgg<br>atacatatttgaatgtatttagaaaaataaacaaataggggtgatttaatctgtatcaggggcgtat<br>agtggagcaaagcgaattctaactataacggtcctaaggtagcgaaggccctcccctcggccccgcg<br>ccgcagagtctggccgcgcgcccctgcgcaacgtggcaggaagcgcgcgctgggggcggggacgggc<br>agtagggctgagcggctgcggggcgggtgcaagcacgtttccgacttgagttgcctcaagaggggcg<br>tgctgagccagacctccatcgcgcactccggggagtggagggaaggagcgagggctcagttgggctg<br>ttttggaggcaggaagcacttgctctcccaaagtcgctctgagttgttatcagtaagggagctgcag<br>tggagtaggcggggagaaggccgcacccttctccggagggggaggggagtgttgcaatacctttct<br>gggagttctctgctgcctcctggcttctgaggaccgccctgggcctgggagaatcccttccccctct<br>tccctcgtgatctgcaactccagtctttctagaagatgggcgggagtcttttgggcaggcttaaagg<br>ctaacctggttagggcgcagtagtccagggtttccttgatgatgtcatacttatcctgtcccttttt<br>tttccacagctcgcggttgaggacaaactcttcgcggtctttccagtgttgacaattaatcatcggc<br>atagtatatcggcatagtataatacgacaaggtgaggaacgccaccatgattgaacaagatggattg<br>cacgcaggttctccggccgcttgggtggagaggctattcggctatgactgggcacaacagacaatcg<br>gctgctctgatgccgccgtgttccggctgtcagcgcaggggcgcccggttctttttgtcaagaccga<br>cctgtccggtgccctgaatgaactgcaagacgaggcagcgcggctatcgtggctggccacgacgggc<br>gttccttgcgcagctgtgctcgacgttgtcactgaagcgggaagggactggctgctattgggcgaag<br>tgccggggcaggatctcctgtcatctcaccttgctcctgccgagaaagtatccatcatggctgatgc<br>aatgcggcggctgcatacgcttgatccggctacctgcccattcgaccaccaagcgaaacatcgcatc<br>gagcgagcacgtactcggatggaagccggtcttgtcgatcaggatgatctggacgaagagcatcagg<br>ggctcgcgccagccgaactgttcgccaggctcaaggcgagcatgcccgacggcgaggatctcgtcgt<br>gacccatggcgatgcctgcttgccgaatatcatggtggaaaatggccgcttttctggattcatcgac<br>tgtggccggctgggtgtggcggaccgctatcaggacatagcgttggctacccgtgatattgctgaag<br>agcttggcggcgaatgggctgaccgcttcctcgtgctttacggtatcgccgctcccgattcgcagcg<br>catcgccttctatcgccttcttgacgagttcttctgatgtacaagtaaagcggccgcgactctagat<br>cataatcagccataccacatttgtagaggttttacttgctttaaaaaacctcccacacctccccctg<br>aacctgaaacataaaatgaatgcaattgttgttgttaacttgtttattgcagcttataatggttaca<br>aataaagcaatagcatcacaaatttcacaaataaagcatttttttcactgcattctagttgtggttt | 7 |

TABLE IB-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | gtccaaactcatcaatgtatcttaggtctcgcgtactgtaggtcctttcagcaaaaaacccctcaag | |
| | acccgtttagaggccccaaggggttatgctagttattgctcagcggtggcagcagccaactcagctt | |
| | cctttcgggctttgttagcagccggatctcagtggtggtggtggtggtgctcccatctgacttgcaa | |
| | gaaaacagatggcaagcatgacaatcatttcgagtgcggccgcagcgacaaacaacagataaaacga | |
| | aaggcccagtctttcgactgagcctttcgttttatttgaagcttctttcagcaaaaaaccccgcagg | |
| | acccccgaagaggccccgcggggttatgctaggtcgactacgcagacgtaacaggaaacagctatga | |
| | cgggccccctaggtaagcagtatcttcgacagcttgtctctccagatgctcttgggccatcttccac | |
| | atcgtccgtagcagccttggcaatttgccatcactggcaaatacacataaatccaatgaatacggtt | |
| | accaccatcacattaccatgcaggtacacagcaagaattgacgttggcatatcacatggtgtaataa | |
| | ccccacttgtgaaacaacccagaataaggtacaaggcggaaatgtcgtcattctaaaataaaaggca | |
| | tggccaggaatttgtctaataccgggaacttaaattcagcttgaacaccagtcgcaaaaaattcaaa | |
| | gaaagtgattcaggttcgggttcgtggattggaacagcttcttttgtttcagtgatgagagaatcct | |
| | cctgtcactcgagaaagaatcaaagaggccaacaacgcagaacaggaaacagctatgacgggccccc | |
| | taggtaagcagtatcttcgacagcttgtctctccagatgctcttgggccatcttccacatcgtccgt | |
| | agcagccttggcaatttgccatcactggcaaatacacataaatccaatgaatacggttaccaccatc | |
| | acattaccatgcaggtacacagcaagaattgacgttggcatatcacatggtgtaataaccccacttg | |
| | tgaaacaacccagaataaggtacaaggcggaaatgtcgtcattctaaaataaaaggcatggccagga | |
| | atttgtctaataccgggaacttaaattcagcttgaacaccagtcgcaaaaaattcaaagaaagtgat | |
| | tcaggttcgggttcgtggattggaacagcttcttttgtttcagtgatgagagaatcctcctgtcact | |
| | cgagaaagaatcaaagaggccaacaacgacctgtagcgtaaattctgcaggacttctagttattaat | |
| | agtaatcaattacggggtcattagttcatagcccatatatggagttccgcgttacataacttacggt | |
| | aaatggcccgcctggctgaccgcccaacgacccccgcccattgacgtcaataatgacgtatgttccc | |
| | atagtaacgccaatagggactttccattgacgtcaatgggtggagtatttacggtaaactgcccact | |
| | tggcagtacatcaagtgtatcatatgccaagtacgccccctattgacgtcaatgacggtaaatggcc | |
| | cgcctggcattatgcccagtacatgaccttatgggactttcctacttggcagtacatctacgtatta | |
| | gtcatcgctattaccatggtcgaggtgagccccacgttctgcttcactctccccatctcccccccct | |
| | ccccacccccaattttgtatttatttattttttaattattttgtgcagcgatgggggcgggggggg | |
| | gggggggcgcgcgccaggcggggcggggcggggcgaggggcggggcggggcgaggcggagaggtgcg | |
| | gcggcagccaatcagagcggcgcgctccgaaagtttccttttatggcgaggcggcggcggcggcggc | |
| | cctataaaaagcgaagcgcgcggcgggcgggagtcgctgcgcgctgccttcgccccgtgccccgctc | |
| | cgccgccgcctcgcgccgcccgccccggctctgactgaccgcgttactcccacaggtgagcgggcgg | |
| | gacggcccttctcctccgggctgtaattagcgcttggtttaatgacggcttgtttcttttctgtggc | |
| | tgcgtgaaagccttgaggggctccgggagggccctttgtgcggggggagcggctcggggggtgcgtg | |
| | cgtgtgtgtgtgcgtggggagcgccgcgtgcggctccgcgctgcccggcggctgtgagcgctgcggg | |
| | cgcggcgcggggctttgtgcgctccgcagtgtgcgcgaggggagcgcggccgggggcggtgccccgc | |
| | ggtgcggggggggctgcgaggggaacaaaggctgcgtgcggggtgtgtgcgtgggggggtgagcaggg | |
| | ggtgtgggcgcgtcggtcgggctgcaaccccccctgcacccccctccccgagttgctgagcacggc | |
| | ccggcttcgggtgcggggctccgtacggggcgtggcgcggggctcgccgtgccgggcggggggtggc | |
| | ggcaggtgggggtgccgggcggggcggggccgcctcgggccggggagggctcgggggaggggcgcgg | |
| | cggcccccggagcgccggcggctgtcgaggcgcggcgagccgcagccattgccttttatggtaatcg | |
| | tgcgagagggcgcagggacttcctttgtcccaaatctgtgcggagccgaaatctgggaggcgccgcc | |
| | gcaccccctctagcgggcgcggggcgaagcggtgcggcgccggcaggaaggaaatgggcggggaggg | |
| | ccttcgtgcgtcgccgcgccgccgtccccttctccctctccagcctcggggctgtccgcggggggac | |
| | ggctgccttcgggggggacggggcagggcggggttcggcttctggcgtgtgaccggcggctctagag | |
| | cctctgctaaccatgttcatgccttcttctttttcctacagctcctgggcaacgtgctggttattgt | |
| | gctgtctcatcattttggcaaagaattgatttgataccgcgggcccgggatcccctcgagggaatta | |
| | cctggttcgtagccgccaccatgccagagccagcgaagtctgctcccgccccgaaaaagggctccaa | |
| | gaaggcggtgactaaggcgcagaagaaaggcggcaagaagcgcaagcgcagccgcaaggagagctat | |
| | tccatctatgtgtacaaggttctgaagcaggtccaccctgacaccggcatttcgtccaaggccatgg | |
| | gcatcatgaattcgtttgtgaacgacattttcgagcgcatcgctggtgaggcttcccgcctggcgca | |
| | ttacaacaagcgctcgaccatcacctccagggagatccagacggccgtgcgcctgctgctgcctggg | |
| | gagttggccaagcacgccgtgtccgagggtactaaggccatcaccaagtacaccagcgctaaggatc | |
| | cccgggtaccggtcgccaccatggtgagcaagggcgaggagctgttcaccggggtggtgcccatcct | |
| | ggtcgagctggacggcgacgtaaacggccacaagttcagcgtgtccggcgagggcgagggcgatgcc | |
| | acctacggcaagctgaccctgaagttcatctgcaccaccggcaagctgcccgtgccctggcccaccc | |
| | tcgtgaccaccctgacctggggcgtgcagtgcttcgcccgctaccccgaccacatgaagcagcacga | |
| | cttcttcaagtccgccatgcccgaaggctacgtccaggagcgcaccatcttcttcaaggacgacggc | |
| | aactacaagacccgcgccgaggtgaagttcgagggcgacaccctggtgaaccgcatcgagctgaagg | |
| | gcatcgacttcaaggaggacggcaacatcctggggcacaagctggagtacaacgccatcagcgacaa | |
| | cgtctatatcaccgccgacaagcagaagaacggcatcaaggccaacttcaagatccgccacaacatc | |
| | gaggacggcagcgtgcagctcgccgaccactaccagcagaacacccccatcggcgacggccccgtgc | |
| | tgctgcccgacaaccactacctgagcacccagtccaagctgagcaaagaccccaacgagaagcgcga | |
| | tcacatggtcctgctggagttcgtgaccgccgccgggatcactctcggcatggacgagctgtacaag | |
| | tgaacctttggcgtaacaggaaacagctatgacgggcccccctaggacgttcccatagctcctttttga | |
| | tgtcttaatgtaggttcaacagatatgcggcttcttcgcattctgatggcgtcagctacgataggcg | |
| | agagctgaatagttgaaaatttttagcagatgcctgagaaaattaaacttgatttgattccagtaat | |
| | ttaccaaaatacgcacagttgccttcttcgatgtaatcttttcaatcgtactatgtcgtatgcagtt | |
| | agcaaatgaaagtagcaacaccaatttgcgccagaatttcacgtcgaaaatatccttaaaccttgca | |
| | agccaagttacggagttgaaatttccgtaagctacggttatcttccaatggcccatacttggctaaa | |
| | tcagagttccctttcgtggaaactgcaatagccaaattcctcgagaaagaatcaaagaggccaacaa | |
| | cgcagaacaggaaacagctatgacgggcccccctaggacgttcccatagctcctttttgatgtcttaat | |
| | gtaggttcaacagatatgcggcttcttcgcattctgatggcgtcagctacgataggcgagagctgaa | |
| | tagttgaaaatttttagcagatgcctgagaaaattaaacttgatttgattccagtaatttaccaaaa | |

TABLE IB-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | tacgcacagttgccttcttcgatgtaatcttttcaatcgtactatgtcgtatgcagttagcaaatga<br>aagtagcaacaccaatttgcgccagaatttcacgtcgaaaatatccttaaaccttgcaagccaagtt<br>acggagttgaaatttccgtaagctacggttatcttccaatggcccatacttggctaaatcagagttc<br>cctttcgtggaaactgcaatagccaaattcctcgagaaagaatcaaagaggccaacaacgacctgag<br>taggtctgtgccttctagttgccagccatctgttgtttgcccctcccccgtgccttccttgaccctg<br>gaaggtgccactcccactgtcctttcctaataaaatgaggaaattgcatcgcattgtctgagtaggt<br>gtcattctattctggggggtggggtggggcaggacagcaagggggaggattgggaagagaatagcag<br>gcatgctggggatgcggtgggctctatggtacg | |
| Z3 construct | agacacctcgagacccaataaaagatctttattttcattagatctgtgtgttggtttttttgtgtgtc<br>tagagtgtgggtgtgggcgttgtcctgcaggggaattgaacaggtgtaaaattggagggacaagact<br>tcccacagattttcggttttgtcgggaagtttttttaataggggcaaataaggaaaatgggaggatag<br>gtagtcatctggggttttatgcagcaaaactacaggttattattgcttgtgatccgcctcggagtat<br>tttccatcgaggtagattaaagacatgctcacccgagttttatactctcctgcttgagatccttact<br>acagtatgaaattacagtgtcgcgagttagactatgtaagcagaattttaatcatttttaaagagcc<br>cagtacttcatatccatttctcccgctccttctgcagccttatcaaaaggtattttagaacactcat<br>tttagccccattttcatttattatactggcttatccaacccctagacagagcattggcattttccct<br>ttcctgatcttagaagtctgatgactcatgaaaccagacagattaccctgttatccctagaattcag<br>cttgggataaaaagctatggcataggcggtaatacggttatccacagaatcaggggataacgcagga<br>aagaacatgtgagcaaaaggccagcaaaaggccaggaaccgtaaaaaggccgcgttgctggcgtttt<br>tccataggctccgcccccctgacgagcatcacaaaaatcgacgctcaagtcagaggtggcgaaaccc<br>gacaggactataaagataccaggcgtttccccctggaagctccctcgtgcgctctcctgttccgacc<br>ctgccgcttaccggatacctgtccgcctttctcccttcgggaagcgtggcgctttctcatagctcac<br>gctgtaggtatctcagttcggtgtaggtcgttcgctccaagctgggctgtgtgcacgaaccccccgt<br>tcagcccgaccgctgcgccttatccggtaactatcgtcttgagtccaacccggtaagacacgactta<br>tcgccactggcagcagccactggtaacaggattagcagagcgaggtatgtaggcggtgctacagagt<br>tcttgaagtggtggcctaactacggctacactagaagaacagtatttggtatctgcgctctgctgaa<br>gccagttaccttcggaaaaagagttggtagctcttgatccggcaaacaaaccaccgctggtagcggt<br>ggtttttttgtttgcaagcagcagattacgcgcagaaaaaaaggatctcaagaagatcctttgatct<br>tttctacggggtctgacgctcagtggaacgaaaactcacgttaagggattttggtcatgagattatc<br>aaaaaggatcttcacctagatccttttaaattaaaaatgaagttttaaatcaatctaaagtatatat<br>gagtaaacttggtctgacagttaccaatgcttaatcagtgaggcacctatctcagcgatctgtctat<br>ttcgttcatccatagttgcctgactccccgtcgtgtagataactacgatacgggagggcttaccatc<br>tggccccagtgctgcaatgataccgcgagatccacgctcaccggctccagatttatcagcaataaac<br>cagccagccggaagggccgagcgcagaagtggtcctgcaactttatccgcctccatccagtctatta<br>attgttgccgggaagctagagtaagtagttcgccagttaatagtttgcgcaacgttgttgccattgc<br>tacaggcatcgtggtgtcacgctcgtcgtttggtatggcttcattcagctccggttcccaacgatca<br>aggcgagttacatgatcccccatgttgtgcaaaaaagcggttagctccttcggtcctccgatcgttg<br>tcagaagtaagttggccgcagtgttatcactcatggttatggcagcactgcataattctcttactgt<br>catgccatccgtaagatgcttttctgtgactggtgagtactcaaccaagtcattctgagaatagtgt<br>atgcggcgaccgagttgctcttgcccggcgtcaatacgggataataccgcgccacatagcagaactt<br>taaaagtgctcatcattggaaaacgttcttcggggcgaaaactctcaaggatcttaccgctgttgag<br>atccagttcgatgtaacccactcgtgcacccaactgatcttcagcatcttttactttcaccagcgtt<br>tctgggtgagcaaaaacaggaaggcaaaatgccgcaaaaaagggaataagggcgacacggaaatgtt<br>gaatactcatactcttcctttttcaatattattgaagcatttatcagggttattgtctcatgagcgg<br>atacatatttgaatgtatttagaaaaataaacaaataggggtgatttaatctgtatcaggggcgtat<br>agtggagcaaagcgaattctaactataacggtcctaaggtagcgaaggccctcccctcggccccgcg<br>ccgcagagtctggccgcgcgcccctgcgcaacgtggcaggaagcgcgcgctgggggcggggacgggc<br>agtagggctgagcggctgcggggcgggtgcaagcacgtttccgacttgagttgcctcaagaggggcg<br>tgctgagccagacctccatcgcgcactccggggagtggagggaaggagcgagggctcagttgggctg<br>ttttggaggcaggaagcacttgctctcccaaagtcgctctgagttgttatcagtaagggagctgcag<br>tggagtaggcggggagaaggccgcacccttctccggaggggggaggggagtgttgcaataccttttct<br>gggagttctctgctgcctcctggcttctgaggaccgccctgggcctgggagaatcccttcccccctct<br>tccctcgtgatctgcaactccagtctttctagaagatgggcgggagtcttttgggcaggcttaaagg<br>ctaacctggttagggcgcagtagtccagggtttccttgatgatgtcatacttatcctgtcccttttt<br>tttccacagctcgcggttgaggacaaactcttcgcggtctttccagtgttgacaattaatcatcggc<br>atagtatatcggcatagtataatacgacaaggtgaggaacgccaccatgattgaacaagatggattg<br>cacgcaggttctccggccgcttgggtggagaggctattcggctatgactgggcacaacagacaatcg<br>gctgctctgatgccgccgtgttccggctgtcagcgcaggggcgcccggttctttttgtcaagaccga<br>cctgtccggtgccctgaatgaactgcaagacgaggcagcgcggctatcgtggctggccacgacgggc<br>gttccttgcgcagctgtgctcgacgttgtcactgaagcgggaagggactggctgctattgggcgaag<br>tgccggggcaggatctcctgtcatctcaccttgctcctgccgagaaagtatccatcatggctgatgc<br>aatgcggcggctgcatacgcttgatccggctacctgcccattcgaccaccaagcgaaacatcgcatc<br>gagcgagcacgtactcggatggaagccggtcttgtcgatcaggatgatctggacgaagagcatcagg<br>ggctcgcgccagccgaactgttcgccaggctcaaggcgagcatgcccgacggcgaggatctcgtcgt<br>gacccatggcgatgcctgcttgccgaatatcatggtggaaaatggccgcttttctggattcatcgac<br>tgtggccggctgggtgtggcggaccgctatcaggacatagcgttggctacccgtgatattgctgaag<br>agcttggcggcgaatgggctgaccgcttcctcgtgctttacggtatcgccgctcccgattcgcagcg<br>catcgccttctatcgccttcttgacgagttcttctgatgtacaagtaaagcggccgcgactctagat<br>cataatcagccataccacatttgtagaggttttacttgctttaaaaaacctcccacacctccccctg<br>aacctgaaacataaaatgaatgcaattgttgttgttaacttgtttattgcagcttataatggttaca<br>aataaagcaatagcatcacaaatttcacaaataaagcatttttttcactgcattctagttgtggttt<br>gtccaaactcatcaatgtatcttaggtctcgcgtactgtcgtactgtcgtaggtttgtctggtcaac | 8 |

TABLE IB-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | caccgcgttctcagtggtgtacggtacaaaccacctcagaaggtggtttgtaccgtacaccactgag | |
| | aacgcggtggttgaccagacaaacctacggtagcgtaacaggaaacagctatgacgggccccctagg | |
| | cacattgcgtctttataaacttactaaaggttttggatagttttgaacccattgtttgacgaatatt | |
| | ccatattaaaaactctaaaataaaccccagccaccaacatttgaaccagcgttcccccatctccgc | |
| | tgtgatcattctagatctgtattatggcatcgactatgggaatacagggttattctcccattttatt | |
| | gaggtatatggccagttgcgcaacttctttgatgaaattttatttgtccgttgcatgattgaaatcc | |
| | taccagtagttatatatatgtctttttcattgttgtactttggataaagctgcttcttcagaacgct | |
| | ccctactatgctttaaacgcttattttcggaagaaatcatgtgggtcatatttttttgcttctcgag | |
| | aaagaatcaaagaggccaacaacgcagaacaggaaacagctatgacgggccccctaggcacattgcg | |
| | tctttataaacttactaaaggttttggatagttttgaacccattgtttgacgaatattccatattaa | |
| | aaactctaaaataaaccccagccaccaacatttgaaccagcgttcccccatctccgctgtgatcat | |
| | tctagatctgtattatggcatcgactatgggaatacagggttattctcccattttattgaggtatat | |
| | ggccagttgcgcaacttctttgatgaaattttatttgtccgttgcatgattgaaatcctaccagtag | |
| | ttatatatatgtctttttcattgttgtactttggataaagctgcttcttcagaacgctccctactat | |
| | gctttaaacgcttattttcggaagaaatcatgtgggtcatatttttttgcttctcgagaaagaatca | |
| | aagaggccaacaacgacctggttcgtaggcttgtcgacgacggcgttctccgtcgtcaggatcatac | |
| | ctagacacctcagaaggtcctccctttagtgagggttaattctcgagtctccctatagtgagtcgta | |
| | ttaattccgtgtattctatagtgtcacctaaatcgttacggtagcgtactgtcgtaggtttgtctgg | |
| | tcaaccaccgcgctctcagtggtgtacggtacaaaccacctcagaaggtggtttgtaccgtacacca | |
| | ctgagagcgcggtggttgaccagacaaacctacggtagcgtaacaggaaacagctatgacgggcccc | |
| | ctagggggttctgacttcttacgaaaatgtggctagcattccattctctgacgttcaaagaatcgga | |
| | ataagtcatggtaatggtgggaaatctaatagaagcgactcccataacctccatatttcttggcaaa | |
| | taattctgtctgggttaccgttcacgagccttcagagatctacgacgtgtagtgggtgggcttgccc | |
| | tccagggtgtagtttgtaattagaatgggatttcctgttttaagtacccaaatacgaaaattgctct | |
| | tgatgtttaacggctcacttttaagtaaagtttgtgccaataccgtgcatgggagtaagttattgcc | |
| | aatcttcgagaatttaggcaattttggtatactcaactgggtctaatatggtggacggaatgatttc | |
| | tcgagaaagaatcaaagaggccaacaacgcagaacaggaaacagctatgacgggccccctagggggt | |
| | tctgacttcttacgaaaatgtggctagcattccattctctgacgttcaaagaatcggaataagtcat | |
| | ggtaatggtgggaaatctaatagaagcgactcccataacctccatatttcttggcaaataattctgt | |
| | ctgggttaccgttcacgagccttcagagatctacgacgtgtagtgggtgggcttgccctccagggtg | |
| | tagtttgtaattagaatgggatttcctgttttaagtacccaaatacgaaaattgctcttgatgttta | |
| | acggctcacttttaagtaaagtttgtgccaataccgtgcatgggagtaagttattgccaatcttcga | |
| | gaatttaggcaattttggtatactcaactgggtctaatatggtggacggaatgatttctcgagaaag | |
| | aatcaaagaggccaacaacgacctggttcgtaggcttgtcgacgacggcgctctccgtcgtcaggat | |
| | catacctagacacctggttaggtcctccctttagtgagggttaattctcgagtctccctatagtgag | |
| | tcgtattaattccgtgtattctatagtgtcacctaaatcgttacgttggcgtactgtcgtaggtttg | |
| | tctggtcaaccaccgcgcactcagtggtgtacggtacaaaccacctcagaaggtggtttgtaccgta | |
| | caccactgagtgcgcggtggttgaccagacaaacctacggtagcgtaacaggaaacagctatgacgg | |
| | gccccctaggtaagcagtatcttcgacagcttgtctctccagatgctcttgggccatcttccacatc | |
| | gtccgtagcagccttggcaatttgccatcactggcaaatacacataaatccaatgaatacggttacc | |
| | accatcacattaccatgcaggtacacagcaagaattgacgttggcatatcacatggtgtaataaccc | |
| | cacttgtgaaacaacccagaataaggtacaaggcggaaatgtcgtcattctaaaataaaaggcatgg | |
| | ccaggaatttgtctaataccgggaacttaaattcagcttgaacaccagtcgcaaaaaattcaaagaa | |
| | agtgattcaggttcgggttcgtggattggaacagcttcttttgtttcagtgatgagagaatcctcct | |
| | gtcactcgagaaagaatcaaagaggccaacaacgcagaacaggaaacagctatgacgggccccctag | |
| | gtaagcagtatcttcgacagcttgtctctccagatgctcttgggccatcttccacatcgtccgtagc | |
| | agccttggcaatttgccatcactggcaaatacacataaatccaatgaatacggttaccaccatcaca | |
| | ttaccatgcaggtacacagcaagaattgacgttggcatatcacatggtgtaataaccccacttgtga | |
| | aacaacccagaataaggtacaaggcggaaatgtcgtcattctaaaataaaaggcatggccaggaatt | |
| | tgtctaataccgggaacttaaattcagcttgaacaccagtcgcaaaaaattcaaagaaagtgattca | |
| | ggttcgggttcgtggattggaacagcttcttttgtttcagtgatgagagaatcctcctgtcactcga | |
| | gaaagaatcaaagaggccaacaacgacctggttcgtaggcttgtcgacgacggcgcactccgtcgtc | |
| | aggatcatacctagacacctgagtaggtcctccctttagtgagggttaattctcgagtctccctata | |
| | gtgagtcgtattaattccgtgtattctatagtgtcacctaaatcgttacggctacgtaaattctgca | |
| | ggacttctagttattaatagtaatcaattacggggtcattagttcatagcccatatatggagttccg | |
| | cgttacataacttacggtaaatggcccgcctggctgaccgcccaacgacccccgcccattgacgtca | |
| | ataatgacgtatgttcccatagtaacgccaatagggactttccattgacgtcaatgggtggagtatt | |
| | tacggtaaactgcccacttggcagtacatcaagtgtatcatatgccaagtacgccccctattgacgt | |
| | caatgacggtaaatggcccgcctggcattatgcccagtacatgaccttatgggactttcctacttgg | |
| | cagtacatctacgtattagtcatcgctattaccatggtcgaggtgagccccacgttctgcttcactc | |
| | tccccatctcccccccctccccacccccaattttgtatttatttattttttaattattttgtgcagc | |
| | gatgggggcggggggggggggggggcgcgcgccaggcggggcggggcggggcgaggggcggggcggg | |
| | gcgaggcggagaggtgcggcggcagccaatcagagcggcgcgctccgaaagtttccttttatggcga | |
| | ggcggcggcggcggcggccctataaaaagcgaagcgcgcggcgggcgggagtcgctgcgcgctgcct | |
| | tcgccccgtgccccgctccgccgccgcctcgcgccgcccgccccggctctgactgaccgcgttactc | |
| | ccacaggtgagcgggcgggacggcccttctcctccgggctgtaattagcgcttggtttaatgacggc | |
| | ttgtttcttttctgtggctgcgtgaaagccttgaggggctccgggagggccctttgtgcggggggag | |
| | cggctcggggggtgcgtgcgtgtgtgtgtgcgtggggagcgccgcgtgcggctccgcgctgcccggc | |
| | ggctgtgagcgctgcgggcgcggcgcggggctttgtgcgctccgcagtgtgcgcgaggggagcgcgg | |
| | ccgggggcggtgccccgcggtgcggggggggctgcgaggggaacaaaggctgcgtgcggggtgtgtgc | |
| | gtgggggggtgagcagggggtgtgggcgcgtcggtcgggctgcaaccccccctgcacccccctccc | |
| | cgagttgctgagcacggcccggcttcgggtgcggggctccgtacggggcgtggcgcggggctcgccg | |
| | tgccgggcggggggtggcggcaggtgggggtgccgggcggggcggggccgcctcgggccggggaggg | |

TABLE IB-continued

Sequences of the constructs, barcodes, and/or probes used in Example 1. See FIGS. 1C, 1D, 1F, 1G, and related figures for results.

| Name | Sequence | SEQ ID NO. |
|---|---|---|
| | ctcgggggaggggcgcggcggcccccggagcgccggcggctgtcgaggcgcggcgagccgcagccat<br>tgccttttatggtaatcgtgcgagagggcgcagggacttcctttgtcccaaatctgtgcggagccga<br>aatctgggaggcgccgccgcacccccctctagcgggcgcggggcgaagcggtgcggcgccggcaggaa<br>ggaaatgggcggggagggccttcgtgcgtcgccgcgccgccgtccccttctccctctccagcctcgg<br>ggctgtccgcgggggggacggctgccttcgggggggacggggcagggcggggttcggcttctggcgtg<br>tgaccggcggctctagagcctctgctaaccatgttcatgccttcttctttttcctacagctcctggg<br>caacgtgctggttattgtgctgtctcatcattttggcaaagaattgatttgataccgcgggcccggg<br>atcccctcgagggaattacctgaaccgtagccgccaccatgccagagccagcgaagtctgctcccgc<br>cccgaaaaagggctccaagaaggcggtgactaaggcgcagaagaaaggcggcaagaagcgcaagcgc<br>agccgcaaggagagctattccatctatgtgtacaaggttctgaagcaggtccaccctgacaccggca<br>tttcgtccaaggccatgggcatcatgaattcgtttgtgaacgacattttcgagcgcatcgctggtga<br>ggcttcccgcctggcgcattacaacaagcgctcgaccatcacctccagggagatccagacggccgtg<br>cgcctgctgctgcctggggagttggccaagcacgccgtgtccgagggtactaaggccatcaccaagt<br>acaccagcgctaaggatccccgggtaccggtcgccaccatggtgagcaagggcgaggagctgttcac<br>cggggtggtgcccatcctggtcgagctggacggcgacgtaaacggccacaagttcagcgtgtccggc<br>gagggcgagggcgatgccacctacggcaagctgaccctgaagttcatctgcaccaccggcaagctgc<br>ccgtgccctggcccaccctcgtgaccaccctgacctggggcgtgcagtgcttcgcccgctaccccga<br>ccacatgaagcagcacgacttcttcaagtccgccatgcccgaaggctacgtccaggagcgcaccatc<br>ttcttcaaggacgacggcaactacaagacccgcgccgaggtgaagttcgagggcgacaccctggtga<br>accgcatcgagctgaagggcatcgacttcaaggaggacggcaacatcctggggcacaagctggagta<br>caacgccatcagcgacaacgtctatatcaccgccgacaagcagaagaacggcatcaaggccaacttc<br>aagatccgccacaacatcgaggacggcagcgtgcagctcgccgaccactaccagcagaacacccccca<br>tcggcgacggccccgtgctgctgcccgacaaccactacctgagcacccagtccaagctgagcaaaga<br>ccccaacgagaagcgcgatcacatggtcctgctggagttcgtgaccgccgccgggatcactctcggc<br>atggacgagctgtacaagtgaacctccttcgtaacaggaaacagctatgacgggcccccctaggacgt<br>tcccatagctcctttttgatgtcttaatgtaggttcaacagatatgcggcttcttcgcattctgatgg<br>cgtcagctacgataggcgagagctgaatagttgaaaatttttagcagatgcctgagaaaattaaact<br>tgatttgattccagtaatttaccaaaatacgcacagttgccttcttcgatgtaatcttttcaatcgt<br>actatgtcgtatgcagttagcaaatgaaagtagcaacaccaatttgcgccagaatttcacgtcgaaa<br>atatccttaaaccttgcaagccaagttacggagttgaaatttccgtaagctacggttatcttccaat<br>ggcccatacttggctaaatcagagttccctttcgtggaaactgcaatagccaaattcctcgagaaag<br>aatcaaagaggccaacaacgcagaacaggaaacagctatgacgggcccccctaggacgttcccatagc<br>tcctttttgatgtcttaatgtaggttcaacagatatgcggcttcttcgcattctgatggcgtcagcta<br>cgataggcgagagctgaatagttgaaaatttttagcagatgcctgagaaaattaaacttgatttgat<br>tccagtaatttaccaaaatacgcacagttgccttcttcgatgtaatcttttcaatcgtactatgtcg<br>tatgcagttagcaaatgaaagtagcaacaccaatttgcgccagaatttcacgtcgaaaatatcctta<br>aaccttgcaagccaagttacggagttgaaatttccgtaagctacggttatcttccaatggcccatac<br>ttggctaaatcagagttccctttcgtggaaactgcaatagccaaattcctcgagaaagaatcaaaga<br>ggccaacaacgacctcttgaggtctgtgccttctagttgccagccatctgttgtttgcccctccccc<br>gtgccttccttgaccctggaaggtgccactcccactgtcctttcctaataaaatgaggaaattgcat<br>cgcattgtctgagtaggtgtcattctattctggggggtggggtggggcaggacagcaagggggagga<br>ttgggaagagaatagcaggcatgctggggatgcggtgggctctatggtacg | |

TABLE 2

Sequences the constructs, barcodes, and/or probes used in Example 2. See FIGS. 2B-2H and related figures for results.

| Probe name | Probe sequence (probe-LINKER-INITIATOR) | HCR initiator | Fluorophore | SEQ ID NO. |
|---|---|---|---|---|
| smFISH Probe 1 | cgtggattggaacagcttct | N/A | Alexa 647 | 9 |
| smFISH Probe 2 | agcttgaacaccagtcgcaa | N/A | Alexa 488 | 10 |
| smFISH Probe 3 | gcatggccaggaatttgtct | N/A | Alexa 546 | 11 |
| HCR Probe 1 | cgtggattggaacagcttct-TATA-GCATTCTTTCTTGAGGAGGGCAGCAAACGGGAAGAG | B1 | Alexa 647 | 12 |
| HCR Probe 2 | agcttgaacaccagtcgcaa-TATA-AGGTCAGTCCATCCTCGTAAATCCTCATCAATCATC | B2 | Alexa 488 | 13 |
| HCR Probe 3 | gcatggccaggaatttgtct-TATA-AAAGTCTAATCCGTCCCTGCCTCTATATCTCCACTC | B3 | Alexa 546 | 14 |

TABLE 3A

Sequences the constructs, barcodes, and/or probes used in Example 3. See FIGS. 3C-3D and related figures for results.

| Color permutation | Probe name | Probe sequence (probe-LINKER-INITIATOR) | HCR initiator | Fluorophore | SEQ ID NO. |
|---|---|---|---|---|---|
| 1 | B1P2 | cgtggattggaacagcttct-TATA-GCATTCTTTCTTGAGGAGGGCAGCAAACGGGAAGAG | B1 | Alexa 594 | 15 |
| 1 | B2P2-TtoC | cgtggatcggaacagcttct-TATA-AGCTCAGTCCATCCTCGTAAATCCTCATCAATCATC | B2 | Alexa 546 | 16 |
| 1 | B3P2-TtoG | cgtggatgggaacagcttct-TATA-AAAGTCTAATCCGTCCCTGCCTCTATATCTCCACTC | B3 | Alexa 647 | 17 |
| 1 | B4P2-TtoA | cgtggataggaacagcttct-TATA-CACATTTACAGACCTCAACCTACCTCCAACTCTCAC | B4 | Alexa 488 | 18 |
| 2 | B2P2 | cgtggattggaacagcttct-TATA-AGCTCAGTCCATCCTCGTAAATCCTCATCAATCATC | B2 | Alexa 546 | 19 |
| 2 | B3P2-TtoC | cgtggatcggaacagcttct-TATA-AAAGTCTAATCCGTCCCTGCCTCTATATCTCCACTC | B3 | Alexa 647 | 20 |
| 2 | B4P2-TtoG | cgtggatgggaacagcttct-TATA-CACATTTACAGACCTCAACCTACCTCCAACTCTCAC | B4 | Alexa 488 | 21 |
| 2 | B1P2-TtoA | cgtggataggaacagcttct-TATA-GCATTCTTTCTTGAGGAGGGCAGCAAACGGGAAGAG | B1 | Alexa 594 | 22 |
| 3 | B3P2 | cgtggattggaacagcttct-TATA-AAAGTCTAATCCGTCCCTGCCTCTATATCTCCACTC | B3 | Alexa 647 | 23 |
| 3 | B4P2-TtoC | cgtggatcggaacagcttct-TATA-CACATTTACAGACCTCAACCTACCTCCAACTCTCAC | B4 | Alexa 488 | 24 |
| 3 | B1P2-TtoG | cgtggatgggaacagcttct-TATA-GCATTCTTTCTTGAGGAGGGCAGCAAACGGGAAGAG | B1 | Alexa 594 | 25 |
| 3 | B2P2-TtoA | cgtggataggaacagcttct-TATA-AGCTCAGTCCATCCTCGTAAATCCTCATCAATCATC | B2 | Alexa 546 | 26 |
| 4 | B4P2 | cgtggattggaacagcttct-TATA-CACATTTACAGACCTCAACCTACCTCCAACTCTCAC | B4 | Alexa 488 | 27 |
| 4 | B1P2-TtoC | cgtggatcggaacagcttct-TATA-GCATTCTTTCTTGAGGAGGGCAGCAAACGGGAAGAG | B1 | Alexa 594 | 28 |
| 4 | B2P2-TtoG | cgtggatgggaacagcttct-TATA-AGCTCAGTCCATCCTCGTAAATCCTCATCAATCATC | B2 | Alexa 546 | 29 |
| 4 | B3P2-TtoA | cgtggataggaacagcttct-TATA-AAAGTCTAATCCGTCCCTGCCTCTATATCTCCACTC | B3 | Alexa 647 | 30 |
| 5 | B1P2 | cgtggattggaacagcttct-TATA-GCATTCTTTCTTGAGGAGGGCAGCAAACGGGAAGAG | B1 | Alexa 594 | 31 |
| 5 | B2P2-GtoC | cgtggattgcaacagcttct-TATA-AGCTCAGTCCATCCTCGTAAATCCTCATCAATCATC | B2 | Alexa 546 | 32 |
| 5 | B3P2-GtoT | cgtggattgtaacagcttct-TATA-AAAGTCTAATCCGTCCCTGCCTCTATATCTCCACTC | B3 | Alexa 647 | 33 |
| 5 | B4P2-GtoA | cgtggattgaaacagcttct-TATA-CACATTTACAGACCTCAACCTACCTCCAACTCTCAC | B4 | Alexa 488 | 34 |
| 6 | B2P2 | cgtggattggaacagcttct-TATA-AGCTCAGTCCATCCTCGTAAATCCTCATCAATCATC | B2 | Alexa 546 | 35 |
| 6 | B3P2-GtoC | cgtggattgcaacagcttct-TATA-AAAGTCTAATCCGTCCCTGCCTCTATATCTCCACTC | B3 | Alexa 647 | 36 |
| 6 | B4P2-GtoT | cgtggattgtaacagcttct-TATA-CACATTTACAGACCTCAACCTACCTCCAACTCTCAC | B4 | Alexa 488 | 37 |
| 6 | B1P2-GtoA | cgtggattgaaacagcttct-TATA-GCATTCTTTCTTGAGGAGGGCAGCAAACGGGAAGAG | B1 | Alexa 594 | 38 |
| 7 | B3P2 | cgtggattggaacagcttct-TATA-AAAGTCTAATCCGTCCCTGCCTCTATATCTCCACTC | B3 | Alexa 647 | 39 |

TABLE 3A-continued

Sequences the constructs, barcodes, and/or probes used in Example 3. See FIGS. 3C-3D and related figures for results.

| Color permutation | Probe name | Probe sequence (probe-LINKER-INITIATOR) | HCR initiator | Fluorophore | SEQ ID NO. |
|---|---|---|---|---|---|
| 7 | B4P2-GtoC | cgtggattgcaacagcttct-TATA-CACATTTACAGACCTCAACCTACCTCCAACTCTCAC | B4 | Alexa 488 | 40 |
| 7 | B1P2-GtoT | cgtggattgtaacagcttct-TATA-GCATTCTTTCTTGAGGAGGGCAGCAAACGGGAAGAG | B1 | Alexa 594 | 41 |
| 7 | B2P2-GtoA | cgtggattgaaacagcttct-TATA-AGCTCAGTCCATCCTCGTAAATCCTCATCAATCATC | B2 | Alexa 546 | 42 |
| 8 | B4P2 | cgtggattggaacagcttct-TATA-CACATTTACAGACCTCAACCTACCTCCAACTCTCAC | B4 | Alexa 488 | 43 |
| 8 | B1P2-GtoC | cgtggattgcaacagcttct-TATA-GCATTCTTTCTTGAGGAGGGCAGCAAACGGGAAGAG | B1 | Alexa 594 | 44 |
| 8 | B2P2-GtoT | cgtggattgtaacagcttct-TATA-AGCTCAGTCCATCCTCGTAAATCCTCATCAATCATC | B2 | Alexa 546 | 45 |
| 8 | B3P2-GtoA | cgtggattgaaacagcttct-TATA-AAAGTCTAATCCGTCCCTGCCTCTATATCTCCACTC | B3 | Alexa 647 | 46 |
| 9 | B1P2 | cgtggattggaacagcttct-TATA-GCATTCTTTCTTGAGGAGGGCAGCAAACGGGAAGAG | B1 | Alexa 594 | 47 |
| 9 | B2P2-CtoA | cgtggattggaaaagcttct-TATA-AGCTCAGTCCATCCTCGTAAATCCTCATCAATCATC | B2 | Alexa 546 | 48 |
| 9 | B3P2-CtoG | cgtggattggaagagcttct-TATA-AAAGTCTAATCCGTCCCTGCCTCTATATCTCCACTC | B3 | Alexa 647 | 49 |
| 9 | B4P2-CtoT | cgtggattggaatagcttct-TATA-CACATTTACAGACCTCAACCTACCTCCAACTCTCAC | B4 | Alexa 488 | 50 |
| 10 | B2P2 | cgtggattggaacagcttct-TATA-AGCTCAGTCCATCCTCGTAAATCCTCATCAATCATC | B2 | Alexa 546 | 51 |
| 10 | B3P2-CloA | cgtggattggaaaagcttct-TATA-AAAGTCTAATCCGTCCCTGCCTCTATATCTCCACTC | B3 | Alexa 647 | 52 |
| 10 | B4P2-CtoG | cgtggattggaagagcttct-TATA-CACATTTACAGACCTCAACCTACCTCCAACTCTCAC | B4 | Alexa 488 | 53 |
| 10 | B1P2-CtoT | cgtggattggaatagcttct-TATA-GCATTCTTTCTTGAGGAGGGCAGCAAACGGGAAGAG | B1 | Alexa 594 | 54 |
| 11 | B3P2 | cgtggattggaacagcttct-TATA-AAAGTCTAATCCGTCCCTGCCTCTATATCTCCACTC | B3 | Alexa 647 | 55 |
| 11 | B4P2-CtoA | cgtggattggaaaagcttct-TATA-CACATTTACAGACCTCAACCTACCTCCAACTCTCAC | B4 | Alexa 488 | 56 |
| 11 | B1P2-CtoG | cgtggattggaagagcttct-TATA-GCATTCTTTCTTGAGGAGGGCAGCAAACGGGAAGAG | B1 | Alexa 594 | 57 |
| 11 | B2P2-CtoT | cgtggattggaatagcttct-TATA-AGCTCAGTCCATCCTCGTAAATCCTCATCAATCATC | B2 | Alexa 546 | 58 |
| 12 | B4P2 | cgtggattggaacagcttct-TATA-CACATTTACAGACCTCAACCTACCTCCAACTCTCAC | B4 | Alexa 488 | 59 |
| 12 | B1P2-CtoA | cgtggattggaaaagcttct-TATA-GCATTCTTTCTTGAGGAGGGCAGCAAACGGGAAGAG | B1 | Alexa 594 | 60 |
| 12 | B2P2-CtoG | cgtggattggaagagcttct-TATA-AGCTCAGTCCATCCTCGTAAATCCTCATCAATCATC | B2 | Alexa 546 | 61 |
| 12 | B3P2-CtoT | cgtggattggaatagcttct-TATA-AAAGTCTAATCCGTCCCTGCCTCTATATCTCCACTC | B3 | Alexa 647 | 62 |
| 13 | B1P2 | cgtggattggaacagcttct-TATA-GCATTCTTTCTTGAGGAGGGCAGCAAACGGGAAGAG | B1 | Alexa 594 | 63 |

TABLE 3A-continued

Sequences the constructs, barcodes, and/or probes used in Example 3. See FIGS. 3C-3D and related figures for results.

| Color permutation | Probe name | Probe sequence (probe-LINKER-INITIATOR) | HCR initiator | Fluorophore | SEQ ID NO. |
|---|---|---|---|---|---|
| 13 | B2P2-AtoC | cgtggattggcacagcttct-TATA-AGCTCAGTCCATCCTCGTAAATCCTCATCAATCATC | B2 | Alexa 546 | 64 |
| 13 | B3P2-AtoG | cgtggattgggacagcttct-TATA-AAAGTCTAATCCGTCCCTGCCTCTATATCTCCACTC | B3 | Alexa 647 | 65 |
| 13 | B4P2-AtoT | cgtggattggtacagcttct-TATA-CACATTTACAGACCTCAACCTACCTCCAACTCTCAC | B4 | Alexa 488 | 66 |
| 14 | B2P2 | cgtggattggaacagcttct-TATA-AGCTCAGTCCATCCTCGTAAATCCTCATCAATCATC | B2 | Alexa 546 | 67 |
| 14 | B3P2-AtoC | cgtggattggcacagcttct-TATA-AAAGTCTAATCCGTCCCTGCCTCTATATCTCCACTC | B3 | Alexa 647 | 68 |
| 14 | B4P2-AtoG | cgtggattgggacagcttct-TATA-CACATTTACAGACCTCAACCTACCTCCAACTCTCAC | B4 | Alexa 488 | 69 |
| 14 | B1P2-AtoT | cgtggattggtacagcttct-TATA-GCATTCTTTCTTGAGGAGGGCAGCAAACGGGAAGAG | B1 | Alexa 594 | 70 |
| 15 | B3P2 | cgtggattggaacagcttct-TATA-AAAGTCTAATCCGTCCCTGCCTCTATATCTCCACTC | B3 | Alexa 647 | 71 |
| 15 | B4P2-AtoC | cgtggattggcacagcttct-TATA-CACATTTACAGACCTCAACCTACCTCCAACTCTCAC | B4 | Alexa 488 | 72 |
| 15 | B1P2-AtoG | cgtggattgggacagcttct-TATA-GCATTCTTTCTTGAGGAGGGCAGCAAACGGGAAGAG | B1 | Alexa 594 | 73 |
| 15 | B2P2-AtoT | cgtggattggtacagcttct-TATA-AGCTCAGTCCATCCTCGTAAATCCTCATCAATCATC | B2 | Alexa 546 | 74 |
| 16 | B4P2 | cgtggattggaacagcttct-TATA-CACATTTACAGACCTCAACCTACCTCCAACTCTCAC | B4 | Alexa 488 | 75 |
| 16 | B1P2-AtoC | cgtggattggcacagcttct-TATA-GCATTCTTTCTTGAGGAGGGCAGCAAACGGGAAGAG | B1 | Alexa 594 | 76 |
| 16 | B2P2-AtoG | cgtggattgggacagcttct-TATA-AGCTCAGTCCATCCTCGTAAATCCTCATCAATCATC | B2 | Alexa 546 | 77 |
| 16 | B3P2-AtoT | cgtggattggtacagcttct-TATA-AAAGTCTAATCCGTCCCTGCCTCTATATCTCCACTC | B3 | Alexa 647 | 78 |

TABLE 3B

Sequences the constructs, barcodes, and/or probes used in Example 3. See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B2P2-C1toA | Agtggattggaacagcttct-TATA-AGCTCAGTCCATCCTCGTAAATCCTCATCAATCATC | B2 | 546 | 1 | A | 79 |
| B2P2-G2toC | cCtggattggaacagcttct-TATA-AGCTCAGTCCATCCTCGTAAATCCTCATCAATCATC | B2 | 546 | 2 | C | 80 |
| B2P2-T3toC | cgCggattggaacagcttct-TATA-AGCTCAGTCCATCCTCGTAAATCCTCATCAATCATC | B2 | 546 | 3 | C | 81 |
| B2P2-G4toC | cgtCgattggaacagcttct-TATA-AGCTCAGTCCATCCTCGTAAATCCTCATCAATCATC | B2 | 546 | 4 | C | 82 |
| B2P2-G5toC | cgtgCattggaacagcttct-TATA-AGCTCAGTCCATCCTCGTAAATCCTCATCAATCATC | B2 | 546 | 5 | C | 83 |

TABLE 3B-continued

Sequences the constructs, barcodes, and/or probes used in Example 3. See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B2P2-A6toC | cgtggCttggaacagcttct-TATA-AGCTCAGTCCATCCTCGTAAATCCTCATCAATCATC | B2 | 546 | 6 | C | 84 |
| B2P2-T7toC | cgtggaCtggaacagcttct-TATA-AGCTCAGTCCATCCTCGTAAATCCTCATCAATCATC | B2 | 546 | 7 | C | 85 |
| B3P2-C1toG | Ggtggattggaacagcttct-TATA-AAAGTCTAATCCGTCCCTGCCTCTATATCTCCACTC | B3 | 647 | 1 | G | 86 |
| B3P2-G2toT | cTtggattggaacagcttct-TATA-AAAGTCTAATCCGTCCCTGCCTCTATATCTCCACTC | B3 | 647 | 2 | T | 87 |
| B3P2-T3toG | cgGggattggaacagcttct-TATA-AAAGTCTAATCCGTCCCTGCCTCTATATCTCCACTC | B3 | 647 | 3 | G | 88 |
| B3P2-G4toT | cgtTgattggaacagcttct-TATA-AAAGTCTAATCCGTCCCTGCCTCTATATCTCCACTC | B3 | 647 | 4 | T | 89 |
| B3P2-G5toT | cgtgTattggaacagcttct-TATA-AAAGTCTAATCCGTCCCTGCCTCTATATCTCCACTC | B3 | 647 | 5 | T | 90 |
| B3P2-A6toT | cgtggTttggaacagcttct-TATA-AAAGTCTAATCCGTCCCTGCCTCTATATCTCCACTC | B3 | 647 | 6 | T | 91 |
| B3P2-T7toG | cgtggaGtggaacagcttct-TATA-AAAGTCTAATCCGTCCCTGCCTCTATATCTCCACTC | B3 | 647 | 7 | G | 92 |
| B4P2-C1toT | Tgtggattggaacagcttct-TATA-CACATTTACAGACCTCAACCTACCTCCAACTCTCAC | B4 | 488 | 1 | T | 93 |
| B4P2-G2toA | cAtggattggaacagcttct-TATA-CACATTTACAGACCTCAACCTACCTCCAACTCTCAC | B4 | 488 | 2 | A | 94 |
| B4P2-T3toA | cgAggattggaacagcttct-TATA-CACATTTACAGACCTCAACCTACCTCCAACTCTCAC | B4 | 488 | 3 | A | 95 |
| B4P2-G4toA | cgtAgattggaacagcttct-TATA-CACATTTACAGACCTCAACCTACCTCCAACTCTCAC | B4 | 488 | 4 | A | 96 |
| B4P2-G5toA | cgtgAattggaacagcttct-TATA-CACATTTACAGACCTCAACCTACCTCCAACTCTCAC | B4 | 488 | 5 | A | 97 |
| B4P2-A6toG | cgtggGttggaacagcttct-TATA-CACATTTACAGACCTCAACCTACCTCCAACTCTCAC | B4 | 488 | 6 | G | 98 |
| B4P2-T7toA | cgtggaAtggaacagcttct-TATA-CACATTTACAGACCTCAACCTACCTCCAACTCTCAC | B4 | 488 | 7 | A | 99 |
| B1P2-C1toT | Tgtggattggaacagcttct-TATA-GCATTCTTTCTTGAGGAGGGCAGCAAACGGGAAGAG | B1 | 594 | 1 | T | 100 |
| B1P2-G2toA | cAtggattggaacagcttct-TATA-GCATTCTTTCTTGAGGAGGGCAGCAAACGGGAAGAG | B1 | 594 | 2 | A | 101 |
| B1P2-T3toA | cgAggattggaacagcttct-TATA-GCATTCTTTCTTGAGGAGGGCAGCAAACGGGAAGAG | B1 | 594 | 3 | A | 102 |
| B1P2-G4toA | cgtAgattggaacagcttct-TATA-GCATTCTTTCTTGAGGAGGGCAGCAAACGGGAAGAG | B1 | 594 | 4 | A | 103 |
| B1P2-G5toA | cgtgAattggaacagcttct-TATA-GCATTCTTTCTTGAGGAGGGCAGCAAACGGGAAGAG | B1 | 594 | 5 | A | 104 |
| B1P2-A6toG | cgtggGttggaacagcttct-TATA-GCATTCTTTCTTGAGGAGGGCAGCAAACGGGAAGAG | B1 | 594 | 6 | G | 105 |
| B1P2-T7toA | cgtggaAtggaacagcttct-TATA-GCATTCTTTCTTGAGGAGGGCAGCAAACGGGAAGAG | B1 | 594 | 7 | A | 106 |
| B3P2-C1toA | Agtggattggaacagcttct-TATA-AAAGTCTAATCCGTCCCTGCCTCTATATCTCCACTC | B3 | 647 | 1 | A | 107 |

TABLE 3B-continued

Sequences the constructs, barcodes, and/or probes used in Example 3. See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B3P2-G2toC | cCtggattggaacagcttct-TATA-AAAGTCTAATCCGTCCCTGCCTCTATATCTCCACTC | B3 | 647 | 2 | C | 108 |
| B3P2-T3toC | cgCggattggaacagcttct-TATA-AAAGTCTAATCCGTCCCTGCCTCTATATCTCCACTC | B3 | 647 | 3 | C | 109 |
| B3P2-G4toC | cgtCgattggaacagcttct-TATA-AAAGTCTAATCCGTCCCTGCCTCTATATCTCCACTC | B3 | 647 | 4 | C | 110 |
| B3P2-G5toC | cgtgCattggaacagcttct-TATA-AAAGTCTAATCCGTCCCTGCCTCTATATCTCCACTC | B3 | 647 | 5 | C | 111 |
| B3P2-A6toC | cgtggCttggaacagcttct-TATA-AAAGTCTAATCCGTCCCTGCCTCTATATCTCCACTC | B3 | 647 | 6 | C | 112 |
| B3P2-T7toC | cgtggaCtggaacagcttct-TATA-AAAGTCTAATCCGTCCCTGCCTCTATATCTCCACTC | B3 | 647 | 7 | C | 113 |
| B4P2-C1toG | Ggtggattggaacagcttct-TATA-CACATTTACAGACCTCAACCTACCTCCAACTCTCAC | B4 | 488 | 1 | G | 114 |
| B4P2-G2toT | cTtggattggaacagcttct-TATA-CACATTTACAGACCTCAACCTACCTCCAACTCTCAC | B4 | 488 | 2 | T | 115 |
| B4P2-T3toG | cgGggattggaacagcttct-TATA-CACATTTACAGACCTCAACCTACCTCCAACTCTCAC | B4 | 488 | 3 | G | 116 |
| B4P2-G4toT | cgtTgattggaacagcttct-TATA-CACATTTACAGACCTCAACCTACCTCCAACTCTCAC | B4 | 488 | 4 | T | 117 |
| B4P2-G5toT | cgtgTattggaacagcttct-TATA-CACATTTACAGACCTCAACCTACCTCCAACTCTCAC | B4 | 488 | 5 | T | 118 |
| B4P2-A6toT | cgtggTttggaacagcttct-TATA-CACATTTACAGACCTCAACCTACCTCCAACTCTCAC | B4 | 488 | 6 | T | 119 |
| B4P2-T7toG | cgtggaGtggaacagcttct-TATA-CACATTTACAGACCTCAACCTACCTCCAACTCTCAC | B4 | 488 | 7 | G | 120 |
| B1P2-C1toG | Ggtggattggaacagcttct-TATA-GCATTCTTTCTTGAGGAGGGCAGCAAACGGGAAGAG | B1 | 594 | 1 | G | 121 |
| B1P2-G2toT | cTtggattggaacagcttct-TATA-GCATTCTTTCTTGAGGAGGGCAGCAAACGGGAAGAG | B1 | 594 | 2 | T | 122 |
| B1P2-T3toG | cgGggattggaacagcttct-TATA-GCATTCTTTCTTGAGGAGGGCAGCAAACGGGAAGAG | B1 | 594 | 3 | G | 123 |
| B1P2-G4toT | cgtTgattggaacagcttct-TATA-GCATTCTTTCTTGAGGAGGGCAGCAAACGGGAAGAG | B1 | 594 | 4 | T | 124 |
| B1P2-G5toT | cgtgTattggaacagcttct-TATA-GCATTCTTTCTTGAGGAGGGCAGCAAACGGGAAGAG | B1 | 594 | 5 | T | 125 |
| B1P2-A6toT | cgtggTttggaacagcttct-TATA-GCATTCTTTCTTGAGGAGGGCAGCAAACGGGAAGAG | B1 | 594 | 6 | T | 126 |
| B1P2-T7toG | cgtggaGtggaacagcttct-TATA-GCATTCTTTCTTGAGGAGGGCAGCAAACGGGAAGAG | B1 | 594 | 7 | G | 127 |
| B2P2-C1toT | Tgtggattggaacagcttct-TATA-AGCTCAGTCCATCCTCGTAAATCCTCATCAATCATC | B2 | 546 | 1 | T | 128 |
| B2P2-G2toA | cAtggattggaacagcttct-TATA-AGCTCAGTCCATCCTCGTAAATCCTCATCAATCATC | B2 | 546 | 2 | A | 129 |
| B2P2-T3toA | cgAggattggaacagcttct-TATA-AGCTCAGTCCATCCTCGTAAATCCTCATCAATCATC | B2 | 546 | 3 | A | 130 |
| B2P2-G4toA | cgtAgattggaacagcttct-TATA-AGCTCAGTCCATCCTCGTAAATCCTCATCAATCATC | B2 | 546 | 4 | A | 131 |

TABLE 3B-continued

Sequences the constructs, barcodes, and/or probes used in Example 3. See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B2P2-G5toA | cgtgAattggaacagcttct-TATA-AGCTCAGTCCATCCTCGTAAATCCTCATCAATCATC | B2 | 546 | 5 | A | 132 |
| B2P2-A6toG | cgtggGttggaacagcttct-TATA-AGCTCAGTCCATCCTCGTAAATCCTCATCAATCATC | B2 | 546 | 6 | G | 133 |
| B2P2-T7toA | cgtggaAtggaacagcttct-TATA-AGCTCAGTCCATCCTCGTAAATCCTCATCAATCATC | B2 | 546 | 7 | A | 134 |
| B4P2-C1toA | Agtggattggaacagcttct-TATA-CACATTTACAGACCTCAACCTACCTCCAACTCTCAC | B4 | 488 | 1 | A | 135 |
| B4P2-G2toC | cCtggattggaacagcttct-TATA-CACATTTACAGACCTCAACCTACCTCCAACTCTCAC | B4 | 488 | 2 | C | 136 |
| B4P2-T3toC | cgCggattggaacagcttct-TATA-CACATTTACAGACCTCAACCTACCTCCAACTCTCAC | B4 | 488 | 3 | C | 137 |
| B4P2-G4toC | cgtCgattggaacagcttct-TATA-CACATTTACAGACCTCAACCTACCTCCAACTCTCAC | B4 | 488 | 4 | C | 138 |
| B4P2-G5toC | cgtgCattggaacagcttct-TATA-CACATTTACAGACCTCAACCTACCTCCAACTCTCAC | B4 | 488 | 5 | C | 139 |
| B4P2-A6toC | cgtggCttggaacagcttct-TATA-CACATTTACAGACCTCAACCTACCTCCAACTCTCAC | B4 | 488 | 6 | C | 140 |
| B4P2-T7toC | cgtggaCtggaacagcttct-TATA-CACATTTACAGACCTCAACCTACCTCCAACTCTCAC | B4 | 488 | 7 | C | 141 |
| B1P2-C1toA | Agtggattggaacagcttct-TATA-GCATTCTTTCTTGAGGAGGGCAGCAAACGGGAAGAG | B1 | 594 | 1 | A | 142 |
| B1P2-G2toC | cCtggattggaacagcttct-TATA-GCATTCTTTCTTGAGGAGGGCAGCAAACGGGAAGAG | B1 | 594 | 2 | C | 143 |
| B1P2-T3toC | cgCggattggaacagcttct-TATA-GCATTCTTTCTTGAGGAGGGCAGCAAACGGGAAGAG | B1 | 594 | 3 | C | 144 |
| B1P2-G4toC | cgtCgattggaacagcttct-TATA-GCATTCTTTCTTGAGGAGGGCAGCAAACGGGAAGAG | B1 | 594 | 4 | C | 145 |
| B1P2-G5toC | cgtgCattggaacagcttct-TATA-GCATTCTTTCTTGAGGAGGGCAGCAAACGGGAAGAG | B1 | 594 | 5 | C | 146 |
| B1P2-A6toC | cgtggCttggaacagcttct-TATA-GCATTCTTTCTTGAGGAGGGCAGCAAACGGGAAGAG | B1 | 594 | 6 | C | 147 |
| B1P2-T7toC | cgtggaCtggaacagcttct-TATA-GCATTCTTTCTTGAGGAGGGCAGCAAACGGGAAGAG | B1 | 594 | 7 | C | 148 |
| B2P2-C1toG | Ggtggattggaacagcttct-TATA-AGCTCAGTCCATCCTCGTAAATCCTCATCAATCATC | B2 | 546 | 1 | G | 149 |
| B2P2-G2toT | cTtggattggaacagcttct-TATA-AGCTCAGTCCATCCTCGTAAATCCTCATCAATCATC | B2 | 546 | 2 | T | 150 |
| B2P2-T3toG | cgGggattggaacagcttct-TATA-AGCTCAGTCCATCCTCGTAAATCCTCATCAATCATC | B2 | 546 | 3 | G | 151 |
| B2P2-G4toT | cgtTgattggaacagcttct-TATA-AGCTCAGTCCATCCTCGTAAATCCTCATCAATCATC | B2 | 546 | 4 | T | 152 |
| B2P2-G5toT | cgtgTattggaacagcttct-TATA-AGCTCAGTCCATCCTCGTAAATCCTCATCAATCATC | B2 | 546 | 5 | T | 153 |
| B2P2-A6toT | cgtggTttggaacagcttct-TATA-AGCTCAGTCCATCCTCGTAAATCCTCATCAATCATC | B2 | 546 | 6 | T | 154 |
| B2P2-T7toG | cgtggaGtggaacagcttct-TATA-AGCTCAGTCCATCCTCGTAAATCCTCATCAATCATC | B2 | 546 | 7 | G | 155 |

TABLE 3B-continued

Sequences the constructs, barcodes, and/or probes used in Example 3. See FIG. 13 for results.

| Probe name | Probe sequence (probe-LINKER-INITIATOR) | HCR initiator | Fluorophore | Position | SNV | SEQ ID NO. |
|---|---|---|---|---|---|---|
| B3P2-C1toT | Tgtggattggaacagcttct-TATA-AAAGTCTAATCCGTCCCTGCCTCTATATCTCCACTC | B3 | 647 | 1 | T | 156 |
| B3P2-G2toA | cAtggattggaacagcttct-TATA-AAAGTCTAATCCGTCCCTGCCTCTATATCTCCACTC | B3 | 647 | 2 | A | 157 |
| B3P2-T3toA | cgAggattggaacagcttct-TATA-AAAGTCTAATCCGTCCCTGCCTCTATATCTCCACTC | B3 | 647 | 3 | A | 158 |
| B3P2-G4toA | cgtAgattggaacagcttct-TATA-AAAGTCTAATCCGTCCCTGCCTCTATATCTCCACTC | B3 | 647 | 4 | A | 159 |
| B3P2-G5toA | cgtgAattggaacagcttct-TATA-AAAGTCTAATCCGTCCCTGCCTCTATATCTCCACTC | B3 | 647 | 5 | A | 160 |
| B3P2-A6toG | cgtggGttggaacagcttct-TATA-AAAGTCTAATCCGTCCCTGCCTCTATATCTCCACTC | B3 | 647 | 6 | G | 161 |
| B3P2-T7toA | cgtggaAtggaacagcttct-TATA-AAAGTCTAATCCGTCCCTGCCTCTATATCTCCACTC | B3 | 647 | 7 | A | 162 |
| B1P2 | cgtggattggaacagcttct-TATA-GCATTCTTTCTTGAGGAGGGCAGCAAACGGGAAGAG | B1 | 594 | All | Match | 163 |
| B2P2 | cgtggattggaacagcttct-TATA-AGCTCAGTCCATCCTCGTAAATCCTCATCAATCATC | B2 | 546 | All | Match | 164 |
| B3P2 | cgtggattggaacagcttct-TATA-AAAGTCTAATCCGTCCCTGCCTCTATATCTCCACTC | B3 | 647 | All | Match | 165 |
| B4P2 | Cgtggattggaacagcttct-TATA-CACATTTACAGACCTCAACCTACCTCCAACTCTCAC | B4 | 488 | All | Match | 166 |

TABLE 4A

Sequences the constructs, barcodes, and/or probes used in Example 4. See FIGS. 4C-4F and related figures for results.

Design 1

| Target barcode | Control barcode | Probe name | Probe sequence (probe-LINKER-INITIATOR) | HCR initiator | Fluoro-phore | SEQ ID NO. |
|---|---|---|---|---|---|---|
| 1 | 2 | design1_probe1T-B1 | taaagaatgcgttggggcga-TATA-GCATTCTTTCTTGAGGAGGGCAGCAAACGGGAAGAG | B1 | Alexa 546 | 167 |
| | | design1_probe2T-B2 | ttccacatccctctgcgatt-TATA-AGCTCAGTCCATCCTCGTAAATCCTCATCAATCATC | B2 | Alexa 594 | 168 |
| | | design1_probe1C-B3 | taaagaacgcgttggggcga-TATA-AAAGTCTAATCCGTCCCTGCCTCTATATCTCCACTC | B3 | Alexa 647 | 169 |
| | | design1_probe2C-B4 | ttccacacccctctgcgatt-TATA-CACATTTACAGACCTCAACCTACCTCCAACTCTCAC | B4 | Alexa 488 | 170 |
| 2 | 1 | design1_probe1T-B1 | taaagaatgcgttggggcga-TATA-GCATTCTTTCTTGAGGAGGGCAGCAAACGGGAAGAG | B1 | Alexa 594 | 171 |
| | | design1_probe2T-B2 | ttccacatccctctgcgatt-TATA-AGCTCAGTCCATCCTCGTAAATCCTCATCAATCATC | B2 | Alexa 546 | 172 |
| | | design1_probe1C-B3 | taaagaacgcgttggggcga-TATA-AAAGTCTAATCCGTCCCTGCCTCTATATCTCCACTC | B3 | Alexa 488 | 173 |
| | | design1_probe2C-B4 | ttccacacccctctgcgatt-TATA-CACATTTACAGACCTCAACCTACCTCCAACTCTCAC | B4 | Alexa 647 | 174 |
| 3 | 4 | design1_probe3T-B3 | ataccaatcccttcggcgat-TATA-AAAGTCTAATCCGTCCCTGCCTCTATATCTCCACTC | B3 | Alexa 546 | 175 |
| | | design1_probe4T-B1 | ttagcgatacatccgaccca-TATA-GCATTCTTTCTTGAGGAGGGCAGCAAACGGGAAGAG | B1 | Alexa 594 | 176 |
| | | design1_probe3C-B2 | ataccaacccccttcggcgat-TATA-AGCTCAGTCCATCCTCGTAAATCCTCATCAATCATC | B2 | Alexa 647 | 177 |
| | | design1_probe4C-B4 | ttagcgacacatccgaccca-TATA-CACATTTACAGACCTCAACCTACCTCCAACTCTCAC | B4 | Alexa 488 | 178 |

TABLE 4A-continued

Sequences the constructs, barcodes, and/or probes used in Example 4. See FIGS. 4C-4F and related figures for results.
Design 1

| Target barcode | Control barcode | Probe name | Probe sequence (probe-LINKER-INITIATOR) | HCR initiator | Fluoro-phore | SEQ ID NO. |
|---|---|---|---|---|---|---|
| 4 | 3 | design1_probe3T-B3 | ataccaatcccttcggcgat-TATA-AAAGTCTAATCCGTCCCTGCCTCTATATCTCCACTC | B3 | Alexa 594 | 179 |
| | | design1_probe4T-B1 | ttagcgatacatccgaccca-TATA-GCATTCTTTCTTGAGGAGGGCAGCAAACGGGAAGAG | B1 | Alexa 546 | 180 |
| | | design1_probe3C-B2 | ataccaaccccttcggcgat-TATA-AGCTCAGTCCATCCTCGTAAATCCTCATCAATCATC | B2 | Alexa 488 | 181 |
| | | design1_probe4C-B4 | ttagcgacacatccgaccca-TATA-CACATTTACAGACCTCAACCTACCTCCAACTCTCAC | B4 | Alexa 647 | 182 |
| 5 | 6 | design1_probe5T-B2 | ctccaactgaatgaaggcga-TATA-AGCTCAGTCCATCCTCGTAAATCCTCATCAATCATC | B2 | Alexa 546 | 183 |
| | | design1_probe6T-B3 | ttcaacatacgccaatgcgg-TATA-AAAGTCTAATCCGTCCCTGCCTCTATATCTCCACTC | B3 | Alexa 594 | 184 |
| | | design1_probe5C-B1 | ctccaaccgaatgaaggcga-TATA-GCATTCTTTCTTGAGGAGGGCAGCAAACGGGAAGAG | B1 | Alexa 647 | 185 |
| | | design1_probe6C-B4 | ttcaacacacgccaatgcgg-TATA-CACATTTACAGACCTCAACCTACCTCCAACTCTCAC | B4 | Alexa 488 | 186 |
| 6 | 5 | design1_probe5T-B2 | ctccaactgaatgaaggcga-TATA-AGCTCAGTCCATCCTCGTAAATCCTCATCAATCATC | B2 | Alexa 594 | 187 |
| | | design1_probe6T-B3 | ttcaacatacgccaatgcgg-TATA-AAAGTCTAATCCGTCCCTGCCTCTATATCTCCACTC | B3 | Alexa 546 | 188 |
| | | design1_probe5C-B1 | ctccaaccgaatgaaggcga-TATA-GCATTCTTTCTTGAGGAGGGCAGCAAACGGGAAGAG | B1 | Alexa 488 | 189 |
| | | design1_probe6C-B4 | ttcaacacacgccaatgcgg-TATA-CACATTTACAGACCTCAACCTACCTCCAACTCTCAC | B4 | Alexa 647 | 190 |
| 7 | 8 | design1_probe7T-B1 | atcgcaatccaccaaagcag-TATA-GCATTCTTTCTTGAGGAGGGCAGCAAACGGGAAGAG | B1 | Alexa 546 | 191 |
| | | design1_probe8T-B2 | gtcaacatacacgccctgat-TATA-AGCTCAGTCCATCCTCGTAAATCCTCATCAATCATC | B2 | Alexa 594 | 192 |
| | | design1_probe7C-B3 | atcgcaacccaccaaagcag-TATA-AAAGTCTAATCCGTCCCTGCCTCTATATCTCCACTC | B3 | Alexa 647 | 193 |
| | | design1_probe8C-B4 | gtcaacacacacgccctgat-TATA-CACATTTACAGACCTCAACCTACCTCCAACTCTCAC | B4 | Alexa 488 | 194 |
| 8 | 7 | design1_probe7T-B1 | atcgcaatccaccaaagcag-TATA-GCATTCTTTCTTGAGGAGGGCAGCAAACGGGAAGAG | B1 | Alexa 594 | 195 |
| | | design1_probe8T-B2 | gtcaacatacacgccctgat-TATA-AGCTCAGTCCATCCTCGTAAATCCTCATCAATCATC | B2 | Alexa 546 | 196 |
| | | design1_probe7C-B3 | atcgcaacccaccaaagcag-TATA-AAAGTCTAATCCGTCCCTGCCTCTATATCTCCACTC | B3 | Alexa 488 | 197 |
| | | design1_probe8C-B4 | gtcaacacacacgccctgat-TATA-CACATTTACAGACCTCAACCTACCTCCAACTCTCAC | B4 | Alexa 647 | 198 |
| 9 | 10 | design1_probe9T-B3 | ttagagatgaacgccaacgc-TATA-AAAGTCTAATCCGTCCCTGCCTCTATATCTCCACTC | B3 | Alexa 546 | 199 |
| | | design1_probe10T-B1 | acacgactcaactccgaaga-TATA-GCATTCTTTCTTGAGGAGGGCAGCAAACGGGAAGAG | B1 | Alexa 594 | 200 |
| | | design1_probe9C-B2 | ttagagacgaacgccaacgc-TATA-AGCTCAGTCCATCCTCGTAAATCCTCATCAATCATC | B2 | Alexa 647 | 201 |
| | | design1_probe10C-B4 | acacgacccaactccgaaga-TATA-CACATTTACAGACCTCAACCTACCTCCAACTCTCAC | B4 | Alexa 488 | 202 |
| 10 | 9 | design1_probe9T-B3 | ttagagatgaacgccaacgc-TATA-AAAGTCTAATCCGTCCCTGCCTCTATATCTCCACTC | B3 | Alexa 594 | 203 |
| | | design1_probe10T-B1 | acacgactcaactccgaaga-TATA-GCATTCTTTCTTGAGGAGGGCAGCAAACGGGAAGAG | B1 | Alexa 546 | 204 |
| | | design1_probe9C-B2 | ttagagacgaacgccaacgc-TATA-AGCTCAGTCCATCCTCGTAAATCCTCATCAATCATC | B2 | Alexa 488 | 205 |
| | | design1_probe10C-B4 | acacgacccaactccgaaga-TATA-CACATTTACAGACCTCAACCTACCTCCAACTCTCAC | B4 | Alexa 647 | 206 |
| 11 | 12 | design1_probe11T-B2 | atccgcatcaacggtagcaa-TATA-AGCTCAGTCCATCCTCGTAAATCCTCATCAATCATC | B2 | Alexa 546 | 207 |
| | | design1_probe12T-B3 | atcagcgtgacaactgtgct-TATA-AAAGTCTAATCCGTCCCTGCCTCTATATCTCCACTC | B3 | Alexa 594 | 208 |
| | | design1_probe11C-B1 | atccgcaccaacggtagcaa-TATA-GCATTCTTTCTTGAGGAGGGCAGCAAACGGGAAGAG | B1 | Alexa 647 | 209 |
| | | design1_probe12C-B4 | atcagcgcgacaactgtgct-TATA-CACATTTACAGACCTCAACCTACCTCCAACTCTCAC | B4 | Alexa 488 | 210 |

TABLE 4A-continued

Sequences the constructs, barcodes, and/or probes used in Example 4. See FIGS. 4C-4F and related figures for results.
Design 1

| Target barcode | Control barcode | Probe name | Probe sequence (probe-LINKER-INITIATOR) | HCR initiator | Fluoro-phore | SEQ ID NO. |
|---|---|---|---|---|---|---|
| 12 | 11 | design1_ probe11T-B2 | atccgcatcaacggtagcaa-TATA-AGCTCAGTCCATCCTCGTAAATCCTCATCAATCATC | B2 | Alexa 594 | 211 |
| | | design1_ probe12T-B3 | atcagcgtgacaactgtgct-TATA-AAAGTCTAATCCGTCCCTGCCTCTATATCTCCACTC | B3 | Alexa 546 | 212 |
| | | design1_ probe11C-B1 | atccgcaccaacggtagcaa-TATA-GCATTCTTTCTTGAGGAGGGCAGCAAACGGGAAGAG | B1 | Alexa 488 | 213 |
| | | design1_ probe12C-B4 | atcagcgcgacaactgtgct-TATA-CACATTTACAGACCTCAACCTACCTCCAACTCTCAC | B4 | Alexa 647 | 214 |

TABLE 4B

Sequences the constructs, barcodes, and/or probes used in Example 4. See FIGS. 4C-4F and related figures for results.
Design 2*

| Target barcodes | Probe name | Probe sequence (probe-LINKER-INITIATOR) | HCR initiator | Fluorophore | SEQ ID NO. |
|---|---|---|---|---|---|
| 1 and 2 | design2_ probe1T-B1 | ttacaactgactctccgtcc-TATA-GCATTCTTTCTTGAGGAGGGCAGCAAACGGGAAGAG | B1 | Alexa 546 | 215 |
| | design2_ probe2T-B2 | ttacaactgactcctcctcg-TATA-AGCTCAGTCCATCCTCGTAAATCCTCATCAATCATC | B2 | Alexa 594 | 216 |
| | design2_ probe1C-B3 | ttacaaccgactctccgtcc-TATA-AAAGTCTAATCCGTCCCTGCCTCTATATCTCCACTC | B3 | Alexa 647 | 217 |
| | design2_ probe2C-B4 | ttacaaccgactcctcctcg-TATA-CACATTTACAGACCTCAACCTACCTCCAACTCTCAC | B4 | Alexa 488 | 218 |
| 3 and 4 | design2_ probe3T-B3 | ttacaactgactcgtgcggt-TATA-AAAGTCTAATCCGTCCCTGCCTCTATATCTCCACTC | B3 | Alexa 546 | 219 |
| | design2_ probe4T-B1 | ttacaactgactctggggtg-TATA-GCATTCTTTCTTGAGGAGGGCAGCAAACGGGAAGAg | B1 | Alexa 594 | 220 |
| | design2_ probe3C-B2 | ttacaaccgactcgtgcggt-TATA-AGCTCAGTCCATCCTCGTAAATCCTCATCAATCATC | B2 | Alexa 647 | 221 |
| | design2_ probe4C-B4 | ttacaaccgactctggggtg-TATA-CACATTTACAGACCTCAACCTACCTCCAACTCTCAC | B4 | Alexa 488 | 222 |
| 5 and 6 | design2_ probe5T-B2 | ttacaactgacttgggcgtc-TATA-AGCTCAGTCCATCCTCGTAAATCCTCATCAATCATC | B2 | Alexa 546 | 223 |
| | design2_ probe6T-B3 | ttacaactgactgcgtcctg-TATA-AAAGTCTAATCCGTCCCTGCCTCTATATCTCCACTC | B3 | Alexa 594 | 224 |
| | design2_ probe5C-B1 | ttacaaccgacttgggcgtc-TATA-GCATTCTTTCTTGAGGAGGGCAGCAAACGGGAAGAg | B1 | Alexa 647 | 225 |
| | design2_ probe6C-B4 | ttacaaccgactgcgtcctg-TATA-CACATTTACAGACCTCAACCTACCTCCAACTCTCAC | B4 | Alexa 488 | 226 |
| 7 and 8 | design2_ probe7T-B1 | ttacaactgactgtcgccct-TATA-GCATTCTTTCTTGAGGAGGGCAGCAAACGGGAAGAg | B1 | Alexa 546 | 227 |
| | design2_ probe8T-B2 | ttacaactgactgtgcctgc-TATA-AGCTCAGTCCATCCTCGTAAATCCTCATCAATCATC | B2 | Alexa 594 | 228 |
| | design2_ probe7C-B3 | ttacaaccgactgtcgccct-TATA-AAAGTCTAATCCGTCCCTGCCTCTATATCTCCACTC | B3 | Alexa 647 | 229 |
| | design2_ probe8C-B4 | ttacaaccgactgtgcctgc-TATA-CACATTTACAGACCTCAACCTACCTCCAACTCTCAC | B4 | Alexa 488 | 230 |
| 9 and 10 | design2_ probe9T-B3 | ttacaactgactggtcgctc-TATA-AAAGTCTAATCCGTCCCTGCCTCTATATCTCCACTC | B3 | Alexa 546 | 231 |
| | design2_ probe10T-B1 | ttacaactgactgctgtccg-TATA-GCATTCTTTCTTGAGGAGGGCAGCAAACGGGAAGAg | B1 | Alexa 594 | 232 |
| | design2_ probe9C-B2 | ttacaaccgactggtcgctc-TATA-AGCTCAGTCCATCCTCGTAAATCCTCATCAATCATC | B2 | Alexa 647 | 233 |
| | design2_ probe10C-B4 | ttacaaccgactgctgtccg-TATA-CACATTTACAGACCTCAACCTACCTCCAACTCTCAC | B4 | Alexa 488 | 234 |
| 11 and 12 | design2_ probe11T-B2 | ttacaactgactggctgtgg-TATA-AGCTCAGTCCATCCTCGTAAATCCTCATCAATCATC | B2 | Alexa 546 | 235 |
| | design2_ probe12T-B3 | ttacaactgacttccctggc-TATA-AAAGTCTAATCCGTCCCTGCCTCTATATCTCCACTC | B3 | Alexa 594 | 236 |

TABLE 4B-continued

Sequences the constructs, barcodes, and/or probes used in Example 4. See FIGS. 4C-4F and related figures for results.
Design 2*

| Target barcodes | Probe name | Probe sequence (probe-LINKER-INITIATOR) | HCR initiator | Fluorophore | SEQ ID NO. |
|---|---|---|---|---|---|
| | design2_ probe11C-B1 | ttacaaccgactggctgtgg-TATA-GCATTCTTTCTTGAGGAGGGCAGCAAACGGGAAGAg | B1 | Alexa 647 | 237 |
| | design2_ probe12C-B4 | ttacaaccgacttccctggc-TATA-CACATTTACAGACCTCAACCTACCTCCAACTCTCAC | B4 | Alexa 488 | 238 |

*For design 2 experiments, in addition to the probes for barcodes being analyzed, all other probes targeting other barcodes of the array are also added, but in an orthogonal channel (i.e. B5 initiator), to reduce background.

TABLE 4C

Sequences the constructs, barcodes, and/or probes used in Example 4. See FIGS. 4C-4F and 15-18 for results.

| Target barcode | gRNA name | gRNA sequence | SEQ ID NO. |
|---|---|---|---|
| 1 | design1_gRNA1 | ACGCATTCTTTATGACACGG | 239 |
| 2 | design1_gRNA2 | AGGGATGTGGAAACAGAACA | 240 |
| 3 | design1_gRNA3 | AGGGATTGGTATCTGAACAG | 241 |
| 4 | design1_gRNA4 | ATGTATCGCTAACAACCCAG | 242 |
| 5 | design1_gRNA5 | ATTCAGTTGGAGGATAACGG | 243 |
| 6 | design1_gRNA6 | GCGTATGTTGAATCACAGGG | 244 |
| 7 | design1_gRNA7 | GTGGATTGCGATACATACCG | 245 |
| 8 | design1_gRNA8 | GTGTATGTTGACGAATCACA | 246 |
| 9 | design1_gRNA9 | GTTCATCTCTAATAGCCGAG | 247 |
| 10 | design1_gRNA10 | GTTGAGTCGTGTAAGCAGAG | 248 |
| 11 | design1_gRNA11 | GTTGATGCGGATACAATGTG | 249 |
| 12 | design1_gRNA12 | TGTCACGCTGATGAATCTGG | 250 |
| 1 through 12 | design2_gRNA | AGTCAGTTGTAATCACAGGG | 251 |

TABLE 4D

Sequences the constructs, barcodes, and/or probes used in Example 4. See FIGS. 4C-4F and related igures for results.

| Name | Sequence | SEQ ID NO. |
|---|---|---|
| Design 1 array | GCCTCCAGATTCATCAGCGTGACAACTGTGCTGTAGGACCCCACATTGTATCCGCATCAACGGTAGC AAGCAATCCCACTCTGCTTACACGACTCAACTCCGAAGAGTCGAACCGCTCGGCTATTAGAGATGAA CGCCAACGCGTCGGCCCCTGTGATTCGTCAACATACACGCCCTGATAAATATCCTCGGTATGTATCG CAATCCACCAAAGCAGAGCGACCCACCCTGTGATTCAACATACGCCAATGCGGACGCGGCCGCCGTT ATCCTCCAACTGAATGAAGGCGACAACCACCCCTGGGTTGTTAGCGATACATCCGACCCAATCATAC CGCTGTTCAGATACCAATCCCTTCGGCGATTTCCCGCCGTGTTCTGTTTCCACATCCCTCTGCGATT CGTGGCCCGCCGTGTCATAAAGAATGCGTTGGGGCGA | 252 |
| Design 1 lentiviral transfer plasmid | GTCGACGGATCGGGAGATCTCCCGATCCCCTATGGTGCACTCTCAGTACAATCTGCTCTGATGCCGC ATAGTTAAGCCAGTATCTGCTCCCTGCTTGTGTGTTGGAGGTCGCTGAGTAGTGCGCGAGCAAAATT TAAGCTACAACAAGGCAAGGCTTGACCGACAATTGCATGAAGAATCTGCTTAGGGTTAGGCGTTTTG CGCTGCTTCGCGATGTACGGGCCAGATATACGCGTTGACATTGATTATTGACTAGTTATTAATAGTA ATCAATTACGGGGTCATTAGTTCATAGCCCATATATGGAGTTCCGCGTTACATAACTTACGGTAAAT GGCCCGCCTGGCTGACCGCCCAACGACCCCCGCCCATTGACGTCAATAATGACGTATGTTCCCATAG TAACGCCAATAGGGACTTTCCATTGACGTCAATGGGTGGAGTATTTACGGTAAACTGCCCACTTGGC AGTACATCAAGTGTATCATATGCCAAGTACGCCCCCTATTGACGTCAATGACGGTAAATGGCCCGCC TGGCATTATGCCCAGTACATGACCTTATGGGACTTTCCTACTTGGCAGTACATCTACGTATTAGTCA TCGCTATTACCATGGTGATGCGGTTTTGGCAGTACATCAATGGGCGTGGATAGCGGTTTGACTCACG GGGATTTCCAAGTCTCCACCCCATTGACGTCAATGGGAGTTTGTTTTGGCACCAAAATCAACGGGAC TTTCCAAAATGTCGTAACAACTCCGCCCCATTGACGCAAATGGGCGGTAGGCGTGTACGGTGGGAGG TCTATATAAGCAGCGCGTTTTGCCTGTACTGGGTCTCTCTGGTTAGACCAGATCTGAGCCTGGGAGC | 253 |

TABLE 4D-continued

Sequences the constructs, barcodes, and/or probes used in Example 4. See FIGS. 4C-4F and related igures for results.

| Name | Sequence | SEQ ID NO. |
|---|---|---|
| | TCTCTGGCTAACTAGGGAACCCACTGCTTAAGCCTCAATAAAGCTTGCCTTGAGTGCTTCAAGTAGT | |
| | GTGTGCCCGTCTGTTGTGTGACTCTGGTAACTAGAGATCCCTCAGACCCTTTTAGTCAGTGTGGAAA | |
| | ATCTCTAGCAGTGGCGCCCGAACAGGGACTTGAAAGCGAAAGGGAAACCAGAGGAGCTCTCTCGACG | |
| | CAGGACTCGGCTTGCTGAAGCGCGCACGGCAAGAGGCGAGGGGCGGCGACTGGTGAGTACGCCAAAA | |
| | ATTTTGACTAGCGGAGGCTAGAAGGAGAGAGATGGGTGCGAGAGCGTCAGTATTAAGCGGGGGAGAA | |
| | TTAGATCGCGATGGGAAAAAATTCGGTTAAGGCCAGGGGGAAAGAAAAAATATAAATTAAAACATAT | |
| | AGTATGGGCAAGCAGGGAGCTAGAACGATTCGCAGTTAATCCTGGCCTGTTAGAAACATCAGAAGGC | |
| | TGTAGACAAATACTGGGACAGCTACAACCATCCCTTCAGACAGGATCAGAAGAACTTAGATCATTAT | |
| | ATAATACAGTAGCAACCCTCTATTGTGTGCATCAAAGGATAGAGATAAAAGACACCAAGGAAGCTTT | |
| | AGACAAGATAGAGGAAGAGCAAAACAAAAGTAAGACCACCGCACAGCAAGCGGCCGCTGATCTTCAG | |
| | ACCTGGAGGAGGAGATATGAGGGACAATTGGAGAAGTGAATTATATAAATATAAAGTAGTAAAAATT | |
| | GAACCATTAGGAGTAGCACCCACCAAGGCAAAGAGAAGAGTGGTGCAGAGAGAAAAAAGAGCAGTGG | |
| | GAATAGGAGCTTTGTTCCTTGGGTTCTTGGGAGCAGCAGGAAGCACTATGGGCGCAGCGTCAATGAC | |
| | GCTGACGGTACAGGCCAGACAATTATTGTCTGGTATAGTGCAGCAGCAGAACAATTTGCTGAGGGCT | |
| | ATTGAGGCGCAACAGCATCTGTTGCAACTCACAGTCTGGGGCATCAAGCAGCTCCAGGCAAGAATCC | |
| | TGGCTGTGGAAAGATACCTAAAGGATCAACAGCTCCTGGGGATTTGGGGTTGCTCTGGAAAACTCAT | |
| | TTGCACCACTGCTGTGCCTTGGAATGCTAGTTGGAGTAATAAATCTCTGGAACAGATTTGGAATCAC | |
| | ACGACCTGGATGGAGTGGGACAGAGAAATTAACAATTACACAAGCTTAATACACTCCTTAATTGAAG | |
| | AATCGCAAAACCAGCAAGAAAAGAATGAACAAGAATTATTGGAATTAGATAAATGGGCAAGTTTGTG | |
| | GAATTGGTTTAACATAACAAATTGGCTGTGGTATATAAAATTATTCATAATGATAGTAGGAGGCTTG | |
| | GTAGGTTTAAGAATAGTTTTTGCTGTACTTTCTATAGTGAATAGAGTTAGGCAGGGATATTCACCAT | |
| | TATCGTTTCAGACCCACCTCCCAACCCCGAGGGGACCCGACAGGCCCGAAGGAATAGAAGAAGAAGG | |
| | TGGAGAGAGAGACAGAGACAGATCCATTCGATTAGTGAACGGATCGGCACTGCGTGCGCCAATTCTG | |
| | CAGACAAATGGCAGTATTCATCCACAATTTTAAAAGAAAAGGGGGGATTGGGGGGTACAGTGCAGGG | |
| | GAAAGAATAGTAGACATAATAGCAACAGACATACAAACTAAAGAATTACAAAAACAAATTACAAAAA | |
| | TTCAAAATTTTCGGGTTTATTACAGGGACAGCAGAGATCCAGTTTGGTTAATTTATAGCCTCCAGAT | |
| | TCATCAGCGTGACAACTGTGCTGTAGGACCCCACATTGTATCCGCATCAACGGTAGCAAGCAATCCC | |
| | ACTCTGCTTACACGACTCAACTCCGAAGAGTCGAACCGCTCGGCTATTAGAGATGAACGCCAACGCG | |
| | TCGGCCCCTGTGATTCGTCAACATACACGCCCTGATAAATATCCTCGGTATGTATCGCAATCCACCA | |
| | AAGCAGAGCGACCCACCCTGTGATTCAACATACGCCAATGCGGACGCGGCCGCCGTTATCCTCCAAC | |
| | TGAATGAAGGCGACAACCACCCCTGGGTTGTTAGCGATACATCCGACCCAATCATACCGCTGTTCAG | |
| | ATACCAATCCCTTCGGCGATTTCCCGCCGTGTTCTGTTTCCACATCCCTCTGCGATTCGTGGCCCGC | |
| | CGTGTCATAAAGAATGCGTTGGGGCGAccctttagtgagggttaattctcgagtctccctatagtga | |
| | gtcgtattaattccgtgtattctatagtgtcacctaaatcgttacgggATTAACCCGTGTCGGCTCC | |
| | AGATCTggcctccgcgccgggttttggcgcctcccgcgggcgcccccctcctcacggcgagcgctgc | |
| | cacgtcagacgaagggcgcagCgagcgtcctgatccttccgcccggacgctcaggacagcggcccgc | |
| | tgctcataagactcggccttagaaccccagtatcagcagaaggacattttaggacgggacttgggtg | |
| | actctagggcactggttttctttccagagagcggaacaggcgaggaaaagtagtcccttctcggcga | |
| | ttctgcggagggatctccgtggggcggtgaacgccgatgattatataaggacgcgccgggtgtggca | |
| | cagctagttccgtcgcagccgggatttgggtcgcggttcttgtttgtggatcgctgtgatcgtcact | |
| | tggtgagtAgcgggctgctgggctggccggggctttcgtggccgccgggccgctcggtgggacggaa | |
| | gcgtgtggagagaccgccaagggctgtagtctgggtccgcgagcaaggttgccctgaactgggggtt | |
| | ggggggagcgcaGcaaaatggcggctgttcccgagtcttgaatggaagacgcttgtGaggcgggctg | |
| | tgaggtcgttgaaacaaggtgggggggcatggtgggcggcaagaacccaaggtcttgaggccttcgct | |
| | aatgcgggaaagctcttattcgggtgagatgggctggggcaccatctggggaccctgacgtgaagtt | |
| | tgtcactgactggagaactcggtttgtcgtctgttgcgggggcggcagttatgGcggtgccgttggg | |
| | cagtgcacccgtacctttgggagcgcgcgccCtcgtcgtgtcgtgacgtcacccgttctgttggctt | |
| | ataatgcagggtggggccacctgccggtaggtgtgcggtaggcttttctccgtcgcaggacgcaggg | |
| | ttcgggcctagggtaggctctcctgaatcgacaggcgccggacctctggtgaggggagggataagtg | |
| | aggcgtcagtttctttggtcggttttatgtacctatcttcttaagtagctgaagctccggttttgaa | |
| | ctatgcgctcggggttggcgagtgtgttttgtgaagtttttttaggcaccttttgaaatgtaatcatt | |
| | tgggtcaatatgtaattttcagtgttagactagtaaattgtccgctaaattctggccgtttttggct | |
| | tttttgttagacGAAGCTTGGGCTGCAGGTCGACTCTAGaGGATCCCCGGGTAaggatccccgggta | |
| | ccggtcgccaccatggtgagcaagggcgaggagctgttcaccggggtggtgcccatcctggtcgagc | |
| | tggacggcgacgtaaacggccacaagttcagcgtgtccggcgagggcgagggcgatgccacctacgg | |
| | caagctgaccctgaagttcatctgcaccaccggcaagctgcccgtgccctggcccaccctcgtgacc | |
| | accctgacctggggcgtgcagtgcttcgcccgctaccccgaccacatgaagcagcacgacttcttca | |
| | gacccgcgccgaggtgaagttcgagggcgacaccctggtgaaccgcatcgagctgaagggcatcgac | |
| | ttcaaggaggacggcaacatcctggggcacaagctggagtacaacgccatcagcgacaacgtctata | |
| | tcaccgccgacaagcagaagaacggcatcaaggccaacttcaagatccgccacaacatcgaggacgg | |
| | cagcgtgcagctcgccgaccactaccagcagaacacccccatcggcgacggccccgtgctgctgccc | |
| | gacaaccactacctgagcacccagtccaagctgagcaaagaccccaacgagaagcgcgatcacatgg | |
| | tcctgctggagttcgtgaccgccgccgggatcactctcggcatggacgagctgtacaagtgaacctG | |
| | AATTCGATATCAAGCTTATCGATAATCAACCTCTGGATTACAAAATTTGTGAAAGATTGACTGGTAT | |
| | TCTTAACTATGTTGCTCCTTTTACGCTATGTGGATACGCTGCTTTAATGCCTTTGTATCATGCTATT | |
| | GCTTCCCGTATGGCTTTCATTTTCTCCTCCTTGTATAAATCCTGGTTGCTGTCTCTTTATGAGGAGT | |
| | TGTGGCCCGTTGTCAGGCAACGTGGCGTGGTGTGCACTGTGTTTGCTGACGCAACCCCCACTGGTTG | |
| | GGGCATTGCCACCACCTGTCAGCTCCTTTCCGGGACTTTCGCTTTCCCCCTCCCTATTGCCACGGCG | |
| | GAACTCATCGCCGCCTGCCTTGCCCGCTGCTGGACAGGGGCTCGGCTGTTGGGCACTGACAATTCCG | |
| | TGGTGTTGTCGGGGAAATCATCGTCCTTTCCTTGGCTGCTCGCCTGTGTTGCCACCTGGATTCTGCG | |
| | CGGGACGTCCTTCTGCTACGTCCCTTCGGCCCTCAATCCAGCGGACCTTCCTTCCCGCGGCCTGCTG | |
| | CCGGCTCTGCGGCCTCTTCCGCGTCTTCGCCTTCGCCCTCAGACGAGTCGGATCTCCCTTTGGGCCG | |
| | CCTCCCCGCATCGATACCGTCGACCTCGAGACCTAGAAAAACATGGAGCAATCACAAGTAGCAATAC | |
| | AGCAGCTACCAATGCTGATTGTGCCTGGCTAGAAGCACAAGAGGAGGAGGAGGTGGGTTTTCCAGTC | |

TABLE 4D-continued

Sequences the constructs, barcodes, and/or probes used in Example 4. See FIGS. 4C-4F and related igures for results.

| Name | Sequence | SEQ ID NO. |
|---|---|---|
| | ACACCTCAGGTACCTTTAAGACCAATGACTTACAAGGCAGCTGTAGATCTTAGCCACTTTTTAAAAG | |
| | AAAAGGGGGGACTGGAAGGGCTAATTCACTCCCAACGAAGACAAGATATCCTTGATCTGTGGATCTA | |
| | CCACACACAAGGCTACTTCCCTGATTGGCAGAACTACACACCAGGGCCAGGGATCAGATATCCACTG | |
| | ACCTTTGGATGGTGCTACAAGCTAGTACCAGTTGAGCAAGAGAAGGTAGAAGAAGCCAATGAAGGAG | |
| | AGAACACCCGCTTGTTACACCCTGTGAGCCTGCATGGGATGGATGACCCGGAGAGAGAAGTATTAGA | |
| | GTGGAGGTTTGACAGCCGCCTAGCATTTCATCACATGGCCCGAGAGCTGCATCCGGACTGTACTGGG | |
| | TCTCTCTGGTTAGACCAGATCTGAGCCTGGGAGCTCTCTGGCTAACTAGGGAACCCACTGCTTAAGC | |
| | CTCAATAAAGCTTGCCTTGAGTGCTTCAAGTAGTGTGTGCCCGTCTGTTGTGTGACTCTGGTAACTA | |
| | GAGATCCCTCAGACCCTTTTAGTCAGTGTGGAAAATCTCTAGCAGGGCCCGTTTAAACCCGCTGATC | |
| | AGCCTCGACTGTGCCTTCTAGTTGCCAGCCATCTGTTGTTTGCCCCTCCCCCGTGCCTTCCTTGACC | |
| | CTGGAAGGTGCCACTCCCACTGTCCTTTCCTAATAAAATGAGGAAATTGCATCGCATTGTCTGAGTA | |
| | GGTGTCATTCTATTCTGGGGGGTGGGGTGGGGCAGGACAGCAAGGGGGAGGATTGGGAAGACAATAG | |
| | CAGGCATGCTGGGGATGCGGTGGGCTCTATGGCTTCTGAGGCGGAAAGAACCAGCTGGGGCTCTAGG | |
| | GGGTATCCCCACGCGCCCTGTAGCGGCGCATTAAGCGCGGCGGGTGTGGTGGTTACGCGCAGCGTGA | |
| | CCGCTACACTTGCCAGCGCCCTAGCGCCCGCTCCTTTCGCTTTCTTCCCTTCCTTTCTCGCCACGTT | |
| | CGCCGGCTTTCCCCGTCAAGCTCTAAATCGGGGGCTCCCTTTAGGGTTCCGATTTAGTGCTTTACGG | |
| | CACCTCGACCCCAAAAAACTTGATTAGGGTGATGGTTCACGTAGTGGGCCATCGCCCTGATAGACGG | |
| | TTTTTCGCCCTTTGACGTTGGAGTCCACGTTCTTTAATAGTGGACTCTTGTTCCAAACTGGAACAAC | |
| | ACTCAACCCTATCTCGGTCTATTCTTTTGATTTATAAGGGATTTTGCCGATTTCGGCCTATTGGTTA | |
| | AAAAATGAGCTGATTTAACAAAAATTTAACGCGAATTAATTCTGTGGAATGTGTGTCAGTTAGGGTG | |
| | TGGAAAGTCCCCAGGCTCCCCAGCAGGCAGAAGTATGCAAAGCATGCATCTCAATTAGTCAGCAACC | |
| | AGGTGTGGAAAGTCCCCAGGCTCCCCAGCAGGCAGAAGTATGCAAAGCATGCATCTCAATTAGTCAG | |
| | CAACCATAGTCCCGCCCCTAACTCCGCCCATCCCGCCCCTAACTCCGCCCAGTTCCGCCCATTCTCC | |
| | GCCCCATGGCTGACTAATTTTTTTTATTTATGCAGAGGCCGAGGCCGCCTCTGCCTCTGAGCTATTC | |
| | CAGAAGTAGTGAGGAGGCTTTTTTGGAGGCCTAGGCTTTTGCAAAAAGCTCCCGGGAGCTTGTATAT | |
| | CCATTTTCGGATCTGATCAGCACGTGTTGACAATTAATCATCGGCATAGTATATCGGCATAGTATAA | |
| | TACGACAAGGTGAGGAACTAAACCATGGCCAAGTTGACCAGTGCCGTTCCGGTGCTCACCGCGCGCG | |
| | ACGTCGCCGGAGCGGTCGAGTTCTGGACCGACCGGCTCGGGTTCTCCCGGGACTTCGTGGAGGACGA | |
| | CTTCGCCGGTGTGGTCCGGGACGACGTGACCCTGTTCATCAGCGCGGTCCAGGACCAGGTGGTGCCG | |
| | GACAACACCCTGGCCTGGGTGTGGGTGCGCGGCCTGGACGAGCTGTACGCCGAGTGGTCGGAGGTCG | |
| | TGTCCACGAACTTCCGGGACGCCTCCGGGCCGGCCATGACCGAGATCGGCGAGCAGCCGTGGGGGCG | |
| | GGAGTTCGCCCTGCGCGACCCGGCCGGCAACTGCGTGCACTTCGTGGCCGAGGAGCAGGACTGACAC | |
| | GTGCTACGAGATTTCGATTCCACCGCCGCCTTCTATGAAAGGTTGGGCTTCGGAATCGTTTTCCGGG | |
| | ACGCCGGCTGGATGATCCTCCAGCGCGGGGATCTCATGCTGGAGTTCTTCGCCCACCCCAACTTGTT | |
| | TATTGCAGCTTATAATGGTTACAAATAAAGCAATAGCATCACAAATTTCACAAATAAAGCATTTTTT | |
| | TCACTGCATTCTAGTTGTGGTTTGTCCAAACTCATCAATGTATCTTATCATGTCTGTATACCGTCGA | |
| | CCTCTAGCTAGAGCTTGGCGTAATCATGGTCATAGCTGTTTCCTGTGTGAAATTGTTATCCGCTCAC | |
| | AATTCCACACAACATACGAGCCGGAAGCATAAAGTGTAAAGCCTGGGGTGCCTAATGAGTGAGCTAA | |
| | CTCACATTAATTGCGTTGCGCTCACTGCCCGCTTTCCAGTCGGGAAACCTGTCGTGCCAGCTGCATT | |
| | AATGAATCGGCCAACGCGCGGGGAGAGGCGGTTTGCGTATTGGGCGCTCTTCCGCTTCCTCGCTCAC | |
| | TGACTCGCTGCGCTCGGTCGTTCGGCTGCGGCGAGCGGTATCAGCTCACTCAAAGGCGGTAATACGG | |
| | TTATCCACAGAATCAGGGGATAACGCAGGAAAGAACATGTGAGCAAAAGGCCAGCAAAAGGCCAGGA | |
| | ACCGTAAAAAGGCCGCGTTGCTGGCGTTTTTCCATAGGCTCCGCCCCCCTGACGAGCATCACAAAAA | |
| | TCGACGCTCAAGTCAGAGGTGGCGAAACCCGACAGGACTATAAAGATACCAGGCGTTTCCCCCTGGA | |
| | AGCTCCCTCGTGCGCTCTCCTGTTCCGACCCTGCCGCTTACCGGATACCTGTCCGCCTTTCTCCCTT | |
| | CGGGAAGCGTGGCGCTTTCTCATAGCTCACGCTGTAGGTATCTCAGTTCGGTGTAGGTCGTTCGCTC | |
| | CAAGCTGGGCTGTGTGCACGAACCCCCCGTTCAGCCCGACCGCTGCGCCTTATCCGGTAACTATCGT | |
| | CTTGAGTCCAACCCGGTAAGACACGACTTATCGCCACTGGCAGCAGCCACTGGTAACAGGATTAGCA | |
| | GAGCGAGGTATGTAGGCGGTGCTACAGAGTTCTTGAAGTGGTGGCCTAACTACGGCTACACTAGAAG | |
| | AACAGTATTTGGTATCTGCGCTCTGCTGAAGCCAGTTACCTTCGGAAAAAGAGTTGGTAGCTCTTGA | |
| | TCCGGCAAACAAACCACCGCTGGTAGCGGTGGTTTTTTTGTTTGCAAGCAGCAGATTACGCGCAGAA | |
| | AAAAAGGATCTCAAGAAGATCCTTTGATCTTTTCTACGGGGTCTGACGCTCAGTGGAACGAAAACTC | |
| | ACGTTAAGGGATTTTGGTCATGAGATTATCAAAAAGGATCTTCACCTAGATCCTTTTAAATTAAAAA | |
| | TGAAGTTTTAAATCAATCTAAAGTATATATGAGTAAACTTGGTCTGACAGTTACCAATGCTTAATCA | |
| | GTGAGGCACCTATCTCAGCGATCTGTCTATTTCGTTCATCCATAGTTGCCTGACTCCCCGTCGTGTA | |
| | GATAACTACGATACGGGAGGGCTTACCATCTGGCCCCAGTGCTGCAATGATACCGCGAGACCCACGC | |
| | TCACCGGCTCCAGATTTATCAGCAATAAACCAGCCAGCCGGAAGGGCCGAGCGCAGAAGTGGTCCTG | |
| | CAACTTTATCCGCCTCCATCCAGTCTATTAATTGTTGCCGGGAAGCTAGAGTAAGTAGTTCGCCAGT | |
| | TAATAGTTTGCGCAACGTTGTTGCCATTGCTACAGGCATCGTGGTGTCACGCTCGTCGTTTGGTATG | |
| | GCTTCATTCAGCTCCGGTTCCCAACGATCAAGGCGAGTTACATGATCCCCCATGTTGTGCAAAAAAG | |
| | CGGTTAGCTCCTTCGGTCCTCCGATCGTTGTCAGAAGTAAGTTGGCCGCAGTGTTATCACTCATGGT | |
| | TATGGCAGCACTGCATAATTCTCTTACTGTCATGCCATCCGTAAGATGCTTTTCTGTGACTGGTGAG | |
| | TACTCAACCAAGTCATTCTGAGAATAGTGTATGCGGCGACCGAGTTGCTCTTGCCCGGCGTCAATAC | |
| | GGGATAATACCGCGCCACATAGCAGAACTTTAAAAGTGCTCATCATTGGAAAACGTTCTTCGGGGCG | |
| | AAAACTCTCAAGGATCTTACCGCTGTTGAGATCCAGTTCGATGTAACCCACTCGTGCACCCAACTGA | |
| | TCTTCAGCATCTTTTACTTTCACCAGCGTTTCTGGGTGAGCAAAAACAGGAAGGCAAAATGCCGCAA | |
| | AAAAGGGAATAAGGGCGACACGGAAATGTTGAATACTCATACTCTTCCTTTTTCAATATTATTGAAG | |
| | CATTTATCAGGGTTATTGTCTCATGAGCGGATACATATTTGAATGTATTTAGAAAAATAAACAAATA | |
| | GGGGTTCCGCGCACATTTCCCCGAAAAGTGCCACCTGAC | |
| Design 2 array | ctgtaggtTAGCAACCACCCTGTGATTACAACTGACTCCTCCTCGCGCAAGCCACCCTGTGATTACA | 254 |
| | ACTGACTCTCCGTCCtacgcagaaggtCCTCTTCCACCCTGTGATTACAACTGACTCTGGGGTGGGT | |
| | GCTCCACCCTGTGATTACAACTGACTCGTGCGGTtacggtagaggtTTGACCCCACCCTGTGATTAC | |
| | AACTGACTGCGTCCTGTTGTATCCACCCTGTGATTACAACTGACTTGGGCGTCtacgggttaggtCT | |

TABLE 4D-continued

Sequences the constructs, barcodes, and/or probes used in Example 4. See FIGS. 4C-4F and related igures for results.

| Name | Sequence | SEQ ID NO. |
|---|---|---|
| | GGGGCCACCCTGTGATTACAACTGACTGTGCCTGCCACTATCCACCCTGTGATTACAACTGACTGTC<br>GCCCTtacgttggaggtCCATGCCCACCCTGTGATTACAACTGACTGCTGTCCGTCCCTCCCACCCT<br>GTGATTACAACTGACTGGTCGCTCtacggagtaggtGTCTCACCACCCTGTGATTACAACTGACTTC<br>CCTGGCCACTATCCACCCTGTGATTACAACTGACTGGCTGTGGtacggctaaggt | |
| Design 2 lentiviral transfer plasmid | GTCGACGGATCGGGAGATCTCCCGATCCCCTATGGTGCACTCTCAGTACAATCTGCTCTGATGCCGC<br>ATAGTTAAGCCAGTATCTGCTCCCTGCTTGTGTGTTGGAGGTCGCTGAGTAGTGCGCGAGCAAAATT<br>TAAGCTACAACAAGGCAAGGCTTGACCGACAATTGCATGAAGAATCTGCTTAGGGTTAGGCGTTTTG<br>CGCTGCTTCGCGATGTACGGGCCAGATATACGCGTTGACATTGATTATTGACTAGTTATTAATAGTA<br>ATCAATTACGGGGTCATTAGTTCATAGCCCATATATGGAGTTCCGCGTTACATAACTTACGGTAAAT<br>GGCCCGCCTGGCTGACCGCCCAACGACCCCCGCCCATTGACGTCAATAATGACGTATGTTCCCATAG<br>TAACGCCAATAGGGACTTTCCATTGACGTCAATGGGTGGAGTATTTACGGTAAACTGCCCACTTGGC<br>AGTACATCAAGTGTATCATATGCCAAGTACGCCCCCTATTGACGTCAATGACGGTAAATGGCCCGCC<br>TGGCATTATGCCCAGTACATGACCTTATGGGACTTTCCTACTTGGCAGTACATCTACGTATTAGTCA<br>TCGCTATTACCATGGTGATGCGGTTTTGGCAGTACATCAATGGGCGTGGATAGCGGTTTGACTCACG<br>GGGATTTCCAAGTCTCCACCCCATTGACGTCAATGGGAGTTTGTTTTGGCACCAAAATCAACGGGAC<br>TTTCCAAAATGTCGTAACAACTCCGCCCCATTGACGCAAATGGGCGGTAGGCGTGTACGGTGGGAGG<br>TCTATATAAGCAGCGCGTTTTGCCTGTACTGGGTCTCTCTGGTTAGACCAGATCTGAGCCTGGGAGC<br>TCTCTGGCTAACTAGGGAACCCACTGCTTAAGCCTCAATAAAGCTTGCCTTGAGTGCTTCAAGTAGT<br>GTGTGCCCGTCTGTTGTGTGACTCTGGTAACTAGAGATCCCTCAGACCCTTTTAGTCAGTGTGGAAA<br>ATCTCTAGCAGTGGCGCCCGAACAGGGACTTGAAAGCGAAAGGGAAACCAGAGGAGCTCTCTCGACG<br>CAGGACTCGGCTTGCTGAAGCGCGCACGGCAAGAGGCGAGGGGCGGCGACTGGTGAGTACGCCAAAA<br>ATTTTGACTAGCGGAGGCTAGAAGGAGAGAGATGGGTGCGAGAGCGTCAGTATTAAGCGGGGGAGAA<br>TTAGATCGCGATGGGAAAAAATTCGGTTAAGGCCAGGGGGAAAGAAAAAATATAAATTAAAACATAT<br>AGTATGGGCAAGCAGGGAGCTAGAACGATTCGCAGTTAATCCTGGCCTGTTAGAAACATCAGAAGGC<br>TGTAGACAAATACTGGGACAGCTACAACCATCCCTTCAGACAGGATCAGAAGAACTTAGATCATTAT<br>ATAATACAGTAGCAACCCTCTATTGTGTGCATCAAAGGATAGAGATAAAAGACACCAAGGAAGCTTT<br>AGACAAGATAGAGGAAGAGCAAAACAAAAGTAAGACCACCGCACAGCAAGCGGCCGCTGATCTTCAG<br>ACCTGGAGGAGGAGATATGAGGGACAATTGGAGAAGTGAATTATATAAATATAAAGTAGTAAAAATT<br>GAACCATTAGGAGTAGCACCCACCAAGGCAAAGAGAAGAGTGGTGCAGAGAGAAAAAAGAGCAGTGG<br>GAATAGGAGCTTTGTTCCTTGGGTTCTTGGGAGCAGCAGGAAGCACTATGGGCGCAGCGTCAATGAC<br>GCTGACGGTACAGGCCAGACAATTATTGTCTGGTATAGTGCAGCAGCAGAACAATTTGCTGAGGGCT<br>ATTGAGGCGCAACAGCATCTGTTGCAACTCACAGTCTGGGGCATCAAGCAGCTCCAGGCAAGAATCC<br>TGGCTGTGGAAAGATACCTAAAGGATCAACAGCTCCTGGGGATTTGGGGTTGCTCTGGAAAACTCAT<br>TTGCACCACTGCTGTGCCTTGGAATGCTAGTTGGAGTAATAAATCTCTGGAACAGATTTGGAATCAC<br>ACGACCTGGATGGAGTGGGACAGAGAAATTAACAATTACACAAGCTTAATACACTCCTTAATTGAAG<br>AATCGCAAAACCAGCAAGAAAAGAATGAACAAGAATTATTGGAATTAGATAAATGGGCAAGTTTGTG<br>GAATTGGTTTAACATAACAAATTGGCTGTGGTATATAAAATTATTCATAATGATAGTAGGAGGCTTG<br>GTAGGTTTAAGAATAGTTTTTGCTGTACTTTCTATAGTGAATAGAGTTAGGCAGGGATATTCACCAT<br>TATCGTTTCAGACCCACCTCCCAACCCCGAGGGGACCCGACAGGCCCGAAGGAATAGAAGAAGAAGG<br>TGGAGAGAGAGACAGAGACAGATCCATTCGATTAGTGAACGGATCGGCACTGCGTGCGCCAATTCTG<br>CAGACAAATGGCAGTATTCATCCACAATTTTAAAAGAAAAGGGGGGATTGGGGGGTACAGTGCAGGG<br>GAAAGAATAGTAGACATAATAGCAACAGACATACAAACTAAAGAATTACAAAAACAAATTACAAAAA<br>TTCAAAATTTTCGGGTTTATTACAGGGACAGCAGAGATCCAGTTTGGTTAATctgtaggtTAGCAAC<br>CACCCTGTGATTACAACTGACTCCTCCTCGCGCAAGCCACCCTGTGATTACAACTGACTCTCCGTCC<br>tacgcagaaggtCCTCTTCCACCCTGTGATTACAACTGACTCTGGGGTGGGTGCTCCACCCTGTGAT<br>TACAACTGACTCGTGCGGTtacggtagaggtTTGACCCCACCCTGTGATTACAACTGACTGCGTCCT<br>GTTGTATCCACCCTGTGATTACAACTGACTTGGGCGTCtacgggttaggtCTGGGGCCACCCTGTGA<br>TTACAACTGACTGTGCCTGCCACTATCCACCCTGTGATTACAACTGACTGTCGCCCTtacgttggag<br>gtCCATGCCCACCCTGTGATTACAACTGACTGCTGTCCGTCCCTCCCACCCTGTGATTACAACTGAC<br>TGGTCGCTCtacggagtaggtGTCTCACCACCCTGTGATTACAACTGACTTCCCTGGCCACTATCCA<br>CCCTGTGATTACAACTGACTGGCTGTGGtacggctaaggtcctccctttagtgagggttaattctcg<br>agtctccctatagtgagtcgtattaattccgtgtattctatagtgtcacctaaatcgttacgagaca<br>cctATTAACCCGTGTCGGCTCCAGATCTggcctccgcgccgggttttggcgcctcccgcgggcgccc<br>ccctcctcacggcgagcgctgccacgtcagacgaagggcgcagCgagcgtcctgatccttccgcccg<br>gacgctcaggacagcggcccgctgctcataagactcggccttagaaccccagtatcagcagaaggac<br>attttaggacgggacttgggtgactctagggcactggttttctttccagagagcggaacaggcgagg<br>aaaagtagtcccttctcggcgattctgcggagggatctccgtggggcggtgaacgccgatgattata<br>taaggacgcgccgggtgtggcacagctagttccgtcgcagccgggatttgggtcgcggttcttgttt<br>gtggatcgctgtgatcgtcacttggtgagtAgcgggctgctgggctggccggggctttcgtggccgc<br>cgggccgctcggtgggacggaagcgtgtggagagaccgccaagggctgtagtctgggtccgcgagca<br>aggttgccctgaactgggggttggggggagcgcaGcaaaatggcggctgttcccgagtcttgaatgg<br>aagacgcttgtGaggcgggctgtgaggtcgttgaaacaaggtgggggcatggtgggcggcaagaac<br>ccaaggtcttgaggccttcgctaatgcgggaaagctcttattcgggtgagatgggctggggcaccat<br>ctggggaccctgacgtgaagtttgtcactgactggagaactcggtttgtcgtctgttgcgggggcgg<br>cagttatgGcggtgccgttgggcagtgcacccgtacctttgggagcgcgcgccCtcgtcgtgtcgtg<br>acgtcacccgttctgttggcttataatgcagggtggggccacctgccggtaggtgtgcggtaggctt<br>ttctccgtcgcaggacgcagggttcgggcctagggtaggctctcctgaatcgacaggcgccggacct<br>ctggtgaggggagggataagtgaggcgtcagtttctttggtcggttttatgtacctatcttcttaag<br>tagctgaagctccggttttgaactatgcgctcggggttggcgagtgtgttttgtgaagtttttttagg<br>caccttttgaaatgtaatcatttgggtcaatatgtaattttcagtgttagactagtaaattgtccgc<br>taaattctggccgtttttggctttttttgttagacGAAGCTTGGGCTGCAGGTCGACTCTAGaGGATC<br>CCCGGGTAaggatccccgggtaccggtcgccaccatggtgagcaagggcgaggagctgttcaccggg<br>gtggtgcccatcctggtcgagctggacggcgacgtaaacggccacaagttcagcgtgtccggcgagg | 255 |

TABLE 4D-continued

Sequences the constructs, barcodes, and/or probes used in Example 4. See FIGS. 4C-4F and related igures for results.

| Name | Sequence | SEQ ID NO. |
|---|---|---|
| | gcgagggcgatgccacctacggcaagctgaccctgaagttcatctgcaccaccggcaagctgcccgt | |
| | gccctggcccaccctcgtgaccaccctgacctggggcgtgcagtgcttcgcccgctaccccgaccac | |
| | atgaagcagcacgacttcttcaagtccgccatgcccgaaggctacgtccaggagcgcaccatcttct | |
| | tcaaggacgacggcaactacaagacccgcgccgaggtgaagttcgagggcgacaccctggtgaaccg | |
| | catcgagctgaagggcatcgacttcaaggaggacggcaacatcctggggcacaagctggagtacaac | |
| | gccatcagcgacaacgtctatatcaccgccgacaagcagaagaacggcatcaaggccaacttcaaga | |
| | tccgccacaacatcgaggacggcagcgtgcagctcgccgaccactaccagcagaacacccccatcgg | |
| | cgacggccccgtgctgctgcccgacaaccactacctgagcacccagtccaagctgagcaaagacccc | |
| | aacgagaagcgcgatcacatggtcctgctggagttcgtgaccgccgccgggatcactctcggcatgg | |
| | acgagctgtacaagtgaacctGAATTCGATATCAAGCTTATCGATAATCAACCTCTGGATTACAAAA | |
| | TTTGTGAAAGATTGACTGGTATTCTTAACTATGTTGCTCCTTTTACGCTATGTGGATACGCTGCTTT | |
| | AATGCCTTTGTATCATGCTATTGCTTCCCGTATGGCTTTCATTTTCTCCTCCTTGTATAAATCCTGG | |
| | TTGCTGTCTCTTTATGAGGAGTTGTGGCCCGTTGTCAGGCAACGTGGCGTGGTGTGCACTGTGTTTG | |
| | CTGACGCAACCCCCACTGGTTGGGGCATTGCCACCACCTGTCAGCTCCTTTCCGGGACTTTCGCTTT | |
| | CCCCCTCCCTATTGCCACGGCGGAACTCATCGCCGCCTGCCTTGCCCGCTGCTGGACAGGGGCTCGG | |
| | CTGTTGGGCACTGACAATTCCGTGGTGTTGTCGGGGAAATCATCGTCCTTTCCTTGGCTGCTCGCCT | |
| | GTGTTGCCACCTGGATTCTGCGCGGGACGTCCTTCTGCTACGTCCCTTCGGCCCTCAATCCAGCGGA | |
| | CCTTCCTTCCCGCGGCCTGCTGCCGGCTCTGCGGCCTCTTCCGCGTCTTCGCCTTCGCCCTCAGACG | |
| | AGTCGGATCTCCCTTTGGGCCGCCTCCCCGCATCGATACCGTCGACCTCGAGACCTAGAAAAACATG | |
| | GAGCAATCACAAGTAGCAATACAGCAGCTACCAATGCTGATTGTGCCTGGCTAGAAGCACAAGAGGA | |
| | GGAGGAGGTGGGTTTTCCAGTCACACCTCAGGTACCTTTAAGACCAATGACTTACAAGGCAGCTGTA | |
| | GATCTTAGCCACTTTTTAAAAGAAAAGGGGGGACTGGAAGGGCTAATTCACTCCCAACGAAGACAAG | |
| | ATATCCTTGATCTGTGGATCTACCACACACAAGGCTACTTCCCTGATTGGCAGAACTACACACCAGG | |
| | GCCAGGGATCAGATATCCACTGACCTTTGGATGGTGCTACAAGCTAGTACCAGTTGAGCAAGAGAAG | |
| | GTAGAAGAAGCCAATGAAGGAGAGAACACCCGCTTGTTACACCCTGTGAGCCTGCATGGGATGGATG | |
| | ACCCGGAGAGAGAAGTATTAGAGTGGAGGTTTGACAGCCGCCTAGCATTTCATCACATGGCCCGAGA | |
| | GCTGCATCCGGACTGTACTGGGTCTCTCTGGTTAGACCAGATCTGAGCCTGGGAGCTCTCTGGCTAA | |
| | CTAGGGAACCCACTGCTTAAGCCTCAATAAAGCTTGCCTTGAGTGCTTCAAGTAGTGTGTGCCCGTC | |
| | TGTTGTGTGACTCTGGTAACTAGAGATCCCTCAGACCCTTTTAGTCAGTGTGGAAAATCTCTAGCAG | |
| | GGCCCGTTTAAACCCGCTGATCAGCCTCGACTGTGCCTTCTAGTTGCCAGCCATCTGTTGTTTGCCC | |
| | CTCCCCCGTGCCTTCCTTGACCCTGGAAGGTGCCACTCCCACTGTCCTTTCCTAATAAAATGAGGAA | |
| | ATTGCATCGCATTGTCTGAGTAGGTGTCATTCTATTCTGGGGGGTGGGGTGGGGCAGGACAGCAAGG | |
| | GGGAGGATTGGGAAGACAATAGCAGGCATGCTGGGGATGCGGTGGGCTCTATGGCTTCTGAGGCGGA | |
| | AAGAACCAGCTGGGGCTCTAGGGGGTATCCCCACGCGCCCTGTAGCGGCGCATTAAGCGCGGCGGGT | |
| | GTGGTGGTTACGCGCAGCGTGACCGCTACACTTGCCAGCGCCCTAGCGCCCGCTCCTTTCGCTTTCT | |
| | TCCCTTCCTTTCTCGCCACGTTCGCCGGCTTTCCCCGTCAAGCTCTAAATCGGGGGCTCCCTTTAGG | |
| | GTTCCGATTTAGTGCTTTACGGCACCTCGACCCCAAAAAACTTGATTAGGGTGATGGTTCACGTAGT | |
| | GGGCCATCGCCCTGATAGACGGTTTTTCGCCCTTTGACGTTGGAGTCCACGTTCTTTAATAGTGGAC | |
| | TCTTGTTCCAAACTGGAACAACACTCAACCCTATCTCGGTCTATTCTTTTGATTTATAAGGGATTTT | |
| | GCCGATTTCGGCCTATTGGTTAAAAAATGAGCTGATTTAACAAAAATTTAACGCGAATTAATTCTGT | |
| | GGAATGTGTGTCAGTTAGGGTGTGGAAAGTCCCCAGGCTCCCCAGCAGGCAGAAGTATGCAAAGCAT | |
| | GCATCTCAATTAGTCAGCAACCAGGTGTGGAAAGTCCCCAGGCTCCCCAGCAGGCAGAAGTATGCAA | |
| | AGCATGCATCTCAATTAGTCAGCAACCATAGTCCCGCCCCTAACTCCGCCCATCCCGCCCCTAACTC | |
| | CGCCCAGTTCCGCCCATTCTCCGCCCCATGGCTGACTAATTTTTTTTATTTATGCAGAGGCCGAGGC | |
| | CGCCTCTGCCTCTGAGCTATTCCAGAAGTAGTGAGGAGGCTTTTTTGGAGGCCTAGGCTTTTGCAAA | |
| | AAGCTCCCGGGAGCTTGTATATCCATTTTCGGATCTGATCAGCACGTGTTGACAATTAATCATCGGC | |
| | ATAGTATATCGGCATAGTATAATACGACAAGGTGAGGAACTAAACCATGGCCAAGTTGACCAGTGCC | |
| | GTTCCGGTGCTCACCGCGCGCGACGTCGCCGGAGCGGTCGAGTTCTGGACCGACCGGCTCGGGTTCT | |
| | CCCGGGACTTCGTGGAGGACGACTTCGCCGGTGTGGTCCGGGACGACGTGACCCTGTTCATCAGCGC | |
| | GGTCCAGGACCAGGTGGTGCCGGACAACACCCTGGCCTGGGTGTGGGTGCGCGGCCTGGACGAGCTG | |
| | TACGCCGAGTGGTCGGAGGTCGTGTCCACGAACTTCCGGGACGCCTCCGGGCCGGCCATGACCGAGA | |
| | TCGGCGAGCAGCCGTGGGGGCGGGAGTTCGCCCTGCGCGACCCGGCCGGCAACTGCGTGCACTTCGT | |
| | GGCCGAGGAGCAGGACTGACACGTGCTACGAGATTTCGATTCCACCGCCGCCTTCTATGAAAGGTTG | |
| | GGCTTCGGAATCGTTTTCCGGGACGCCGGCTGGATGATCCTCCAGCGCGGGGATCTCATGCTGGAGT | |
| | TCTTCGCCCACCCCAACTTGTTTATTGCAGCTTATAATGGTTACAAATAAAGCAATAGCATCACAAA | |
| | TTTCACAAATAAAGCATTTTTTTCACTGCATTCTAGTTGTGGTTTGTCCAAACTCATCAATGTATCT | |
| | TATCATGTCTGTATACCGTCGACCTCTAGCTAGAGCTTGGCGTAATCATGGTCATAGCTGTTTCCTG | |
| | TGTGAAATTGTTATCCGCTCACAATTCCACACAACATACGAGCCGGAAGCATAAAGTGTAAAGCCTG | |
| | GGGTGCCTAATGAGTGAGCTAACTCACATTAATTGCGTTGCGCTCACTGCCCGCTTTCCAGTCGGGA | |
| | AACCTGTCGTGCCAGCTGCATTAATGAATCGGCCAACGCGCGGGGAGAGGCGGTTTGCGTATTGGGC | |
| | GCTCTTCCGCTTCCTCGCTCACTGACTCGCTGCGCTCGGTCGTTCGGCTGCGGCGAGCGGTATCAGC | |
| | TCACTCAAAGGCGGTAATACGGTTATCCACAGAATCAGGGGATAACGCAGGAAAGAACATGTGAGCA | |
| | AAAGGCCAGCAAAAGGCCAGGAACCGTAAAAAGGCCGCGTTGCTGGCGTTTTTCCATAGGCTCCGCC | |
| | CCCCTGACGAGCATCACAAAAATCGACGCTCAAGTCAGAGGTGGCGAAACCCGACAGGACTATAAAG | |
| | ATACCAGGCGTTTCCCCCTGGAAGCTCCCTCGTGCGCTCTCCTGTTCCGACCCTGCCGCTTACCGGA | |
| | TACCTGTCCGCCTTTCTCCCTTCGGGAAGCGTGGCGCTTTCTCATAGCTCACGCTGTAGGTATCTCA | |
| | GTTCGGTGTAGGTCGTTCGCTCCAAGCTGGGCTGTGTGCACGAACCCCCCGTTCAGCCCGACCGCTG | |
| | CGCCTTATCCGGTAACTATCGTCTTGAGTCCAACCCGGTAAGACACGACTTATCGCCACTGGCAGCA | |
| | GCCACTGGTAACAGGATTAGCAGAGCGAGGTATGTAGGCGGTGCTACAGAGTTCTTGAAGTGGTGGC | |
| | CTAACTACGGCTACACTAGAAGAACAGTATTTGGTATCTGCGCTCTGCTGAAGCCAGTTACCTTCGG | |
| | AAAAAGAGTTGGTAGCTCTTGATCCGGCAAACAAACCACCGCTGGTAGCGGTGGTTTTTTTGTTTGC | |
| | AAGCAGCAGATTACGCGCAGAAAAAAAGGATCTCAAGAAGATCCTTTGATCTTTTCTACGGGGTCTG | |
| | ACGCTCAGTGGAACGAAAACTCACGTTAAGGGATTTTGGTCATGAGATTATCAAAAAGGATCTTCAC | |
| | CTAGATCCTTTTAAATTAAAAATGAAGTTTTAAATCAATCTAAAGTATATATGAGTAAACTTGGTCT | |

TABLE 4D-continued

Sequences the constructs, barcodes, and/or probes used in Example 4. See FIGS. 4C-4F and related igures for results.

| Name | Sequence | SEQ ID NO. |
|---|---|---|
| | GACAGTTACCAATGCTTAATCAGTGAGGCACCTATCTCAGCGATCTGTCTATTTCGTTCATCCATAG<br>TTGCCTGACTCCCCGTCGTGTAGATAACTACGATACGGGAGGGCTTACCATCTGGCCCCAGTGCTGC<br>AATGATACCGCGAGACCCACGCTCACCGGCTCCAGATTTATCAGCAATAAACCAGCCAGCCGGAAGG<br>GCCGAGCGCAGAAGTGGTCCTGCAACTTTATCCGCCTCCATCCAGTCTATTAATTGTTGCCGGGAAG<br>CTAGAGTAAGTAGTTCGCCAGTTAATAGTTTGCGCAACGTTGTTGCCATTGCTACAGGCATCGTGGT<br>GTCACGCTCGTCGTTTGGTATGGCTTCATTCAGCTCCGGTTCCCAACGATCAAGGCGAGTTACATGA<br>TCCCCCATGTTGTGCAAAAAAGCGGTTAGCTCCTTCGGTCCTCCGATCGTTGTCAGAAGTAAGTTGG<br>CCGCAGTGTTATCACTCATGGTTATGGCAGCACTGCATAATTCTCTTACTGTCATGCCATCCGTAAG<br>ATGCTTTTCTGTGACTGGTGAGTACTCAACCAAGTCATTCTGAGAATAGTGTATGCGGCGACCGAGT<br>TGCTCTTGCCCGGCGTCAATACGGGATAATACCGCGCCACATAGCAGAACTTTAAAAGTGCTCATCA<br>TTGGAAAACGTTCTTCGGGGCGAAAACTCTCAAGGATCTTACCGCTGTTGAGATCCAGTTCGATGTA<br>ACCCACTCGTGCACCCAACTGATCTTCAGCATCTTTTACTTTCACCAGCGTTTCTGGGTGAGCAAAA<br>ACAGGAAGGCAAAATGCCGCAAAAAAGGGAATAAGGGCGACACGGAAATGTTGAATACTCATACTCT<br>TCCTTTTTCAATATTATTGAAGCATTTATCAGGGTTATTGTCTCATGAGCGGATACATATTTGAATG<br>TATTTAGAAAAATAAACAAATAGGGGTTCCGCGCACATTTCCCCGAAAAGTGCCACCTGAC | |

TABLE 5A

Sequences the constructs, barcodes, and/or probes used in Example 5. See FIGS. 5B, 5D-5E, 5G-5H, and related figures for results.

| Probe target | HCR initiator | Fluorophore | Related figure(s) |
|---|---|---|---|
| ZL1-barcode | B1 | Alexa 594 | FIG. 5B (chick) |
| GFP | B3 | Alexa 647 | |
| ZL1-barcode | B1 | Alexa 594 | FIG. 5E (mouse) |
| GFP | B3 | Alexa 488 | |

TABLE 5A-continued

Sequences the constructs, barcodes, and/or probes used in Example 5. See FIGS. 5B, 5D-5E, 5G-5H, and related figures for results.

| Probe target | HCR initiator | Fluorophore | Related figure(s) |
|---|---|---|---|
| Tbx21 | B1 | Alexa 488 | FIGS. 22A-22 D(mouse) |
| Th | B4 | Alexa 647 | |

Pooled split initiator (v3.0) probes were purchased from Molecular Instruments and used according to their protocol.

TABLE 5B

Sequences the constructs, barcodes, and/or probes used in Example 5. See FIGS 5B, 5D-5E, 5G-5H, and related figures for results.

| Probe name | HCR initiator | Fluoro-phore | Related figure(s) | Probe sequence (probe-LINKER-INITIATOR) | SEQ ID NO. |
|---|---|---|---|---|---|
| P2B1 | B1 | Aelexa 594 | FIGS. 5D and 5E, left panels | cgtggattggaacagcttct-TATA-GCATTCTTTCTTGAGGAGGGCAGCAAACGGGAAGAG | 256 |
| P2B3-TtoC | B3 | Alexa 488 | | cgtggatcggaacagcttct-TATA-AAAGTCTAATCCGTCCCTGCCTCTATATCTCCACTC | 257 |
| P4B2 | B2 | Alexa 647 | | agcttgaacaccagtcgcaa-TATAAGCTCAGTCCATCCTCGTAAATCCTCATCAATCATC | 258 |
| P2B3 | B3 | Alexa 488 | FIGS. 5D and 5E, right panels | cgtggattggaacagcttct-TATA-AAAGTCTAATCCGTCCCTGCCTCTATATCTCCACTC | 259 |
| P2B1-TtoC | B1 | Alexa 594 | | cgtggatcggaacagcttct-TATA-GCATTCTTTCTTGAGGAGGGCAGCAAACGGGAAGAG | 260 |
| P4B2 | B2 | Alexa 647 | | agcttgaacaccagtcgcaa-TATA-AGCTCAGTCCATCCTCGTAAATCCTCATCAATCATC | 261 |

TABLE 5C

Sequences the constructs, barcodes, and/or probes used in Example 5. See FIGS. 5B, 5D-, 5E, 5G-5H, and related figures for results.

| Probe name | HCR initiator | Fluorophore | Related figure panel(s) | probe sequence (probe-LINKER-INITIATOR) | SEQ ID NO. |
|---|---|---|---|---|---|
| LP1-1A | B1 | Alexa 594 | FIG. 5G | cgtggattggaacagcttct-TATA-GCATTCTTTCTTGAGGAGGGCAGCAAACGGGAAGAG | 262 |
| LP1-1G | B3 | Alexa 488 | | cgtggatcggaacagcttct-TATA-AAAGTCTAATCCGTCCCTGCCTCTATATCTCCACTC | 263 |
| LP1-2A | B2 | Alexa 647 | | ttccacatccctctgcgatt-TATA-AGCTCAGTCCATCCTCGTAAATCCTCATCAATCATC | 264 |

TABLE 5C-continued

Sequences the constructs, barcodes, and/or probes used in Example 5. See FIGS. 5B, 5D-, 5E, 5G-5H, and related figures for results.

| Probe name | HCR initiator | Fluorophore | Related figure panel(s) | probe sequence (probe-LINKER-INITIATOR) | SEQ ID NO. |
|---|---|---|---|---|---|
| LP1-2G | B4 | Alexa 546 | | Ttccacacccctctgcgatt-TATAC-ACATTTACAGACCTCAACCTACCTCCAACTCTCAC | 265 |
| LP3-2A | B3 | Alexa 647 | FIG. 19 (pair 2) | ataccaatcccttcggcgat-TATA-AAAGTCTAATCCGTCCCTGCCTCTATATCTCCACTC | 266 |
| LP3-2G | B2 | Alexa 546 | | ataccaacccctttcggcgat-TATA-AGCTCAGTCCATCCTCGTAAATCCTCATCAATCATC | 267 |
| LP3-1A | B1 | Alexa 594 | | ttcaacatacgccaatgcgg-TATA-GCATTCTTTCTTGAGGAGGGCAGCAAACGGGAAGAg | 268 |
| LP3-1G | B4 | Alexa 488 | | ttcaacacacgccaatgcgg-TATA-CACATTTACAGACCTCAACCTACCTCCAACTCTCAC | 269 |
| LP3-1A | B2 | Alexa 594 | FIG. 19 (pair 3) | gtcaacatacacgccctgat-TATA-AGCTCAGTCCATCCTCGTAAATCCTCATCAATCATC | 270 |
| LP3-1G | B3 | Alexa 488 | | gtcaacacacacgccctgat-TATA-AAAGTCTAATCCGTCCCTGCCTCTATATCTCCACTC | 271 |
| LP3-2A | B1 | Alexa 647 | | ttagcgatacatccgaccca-TATA-GCATTCTTTCTTGAGGAGGGCAGCAAACGGGAAGAg | 272 |
| LP3-2G | B4 | Alexa 546 | | ttagcgacacatccgaccca-TATA-CACATTTACAGACCTCAACCTACCTCCAACTCTCAC | 273 |

TABLE 5D

Sequences the constructs, barcodes, and/or probes used in Example 5. See FIGS. 5B, 5D-5E, 5G-5H, and related figures for results.

| Barcode name | Barcode sequence | SEQ ID NO. |
|---|---|---|
| ZL1-barcode | cgacagcttgtctctccagatgctcttgggccatcttccacatcgtccgtagcagccttggcaatttgccatcactggcaaatacacataaatccaatgaatacggttaccaccatcacattaccatgcaggtacacagcaagaattgacgttggcatatcacatggtgtaataaccccacttgtgaaacaacccagaataaggtacaaggcggaaatgtcgtcattctaaaataaaaggcatggccaggaatttgtctaataccgggaacttaaattcagcttgaacaccagtcgcaaaaaaattcaaagaaagtgattcaggttcgggttcgtggattggaacagcttcttttgtttcagtgatgagagaatcctcctgtca | 274 |
| pair 1-AA barcode | TTCCACATCCCTCTGCGATTCGTGGCatcgtggatTggaacagcttcttt | 275 |
| pair 1-GG barcode | TTCCACACCCCTCTGCGATTCGTGGCatcgtggatCggaacagcttcttt | 276 |
| pair 2-AA barcode | TTCAACATACGCCAATGCGGACGCGGCCGCTGTTCAGATACCAATCCCTTCGGCGATTTCCCG | 277 |
| pair 2-GG barcode | TTCAACACACGCCAATGCGGACGCGGCCGCTGTTCAGATACCAACCCCTTCGGCGATTTCCCG | 278 |
| pair3-AA barcode | TTAGCGATACATCCGACCCAATCATACCCTGTGATTCGTCAACATACACGCCCTGATAAATAT | 279 |
| pair 3-GG barcode | TTAGCGACACATCCGACCCAATCATACCCTGTGATTCGTCAACACACACGCCCTGATAAATAT | 280 |

TABLE 6A

Sequences the constructs, barcodes, and/or probes used in Example 6. See FIGS. 6B-6D, and related figures for results.

| Barcode name | Barcode sequence | SEQ ID NO. |
|---|---|---|
| mL-1a | agatgctcctgagccatctt | 281 |
| mL-1b | cgtggattggaacagcttct | 282 |

TABLE 6A-continued

Sequences the constructs, barcodes, and/or probes used in Example 6. See FIGS. 6B-6D, and related figures for results.

| Barcode name | Barcode sequence | SEQ ID NO. |
|---|---|---|
| mL-1c | gaaagtgattcaggttcggg | 283 |
| mL-2a | agcttgaacaccagtcgcaa | 284 |

TABLE 6A-continued

Sequences the constructs, barcodes, and/or probes used in Example 6. See FIGS. 6B-6D, and related figures for results.

| Barcode name | Barcode sequence | SEQ ID NO. |
|---|---|---|
| mL-2b | gcatggccaggaatttgtct | 285 |
| mL-2c | ggcggaaatgtcgtcattct | 286 |
| mL-3a | ccacttgtgaaacaacccag | 287 |
| mL-3b | cgttggcatatcacatggtg | 288 |
| mL-3c | accatgcaggtacacagcaa | 289 |
| mL-4a | TTCCACATCCCTCTGCGATT | 290 |
| mL-4b | ATACCAATCCCTTCGGCGAT | 291 |
| mL-4c | ATCAGCGTGACAACTGTGCT | 292 |

with transcription by phage RNA polymerases, and therefore, should be avoided prior to the transcription step. Cells were then washed briefly first with 1× phosphate-buffered saline (PBS) and then with nuclease free water and subsequently were incubated with the transcription mix (MEGAscript Transcription Kit; Invitrogen, Carlsbad, CA) at 37° C. for 3 hours. All three RNA polymerases used in this study (T3, T7, and SP6) work at comparable levels. The choice of one polymerase over another in different experiments was mostly arbitrary. After transcription, cells were fixed with 4% formaldehyde solution in PBS for 20 minutes at room temperature followed by two washes with 5×SSC, for 5 minutes each, to remove traces of formaldehyde.

The samples were then pre-incubated in hybridization buffer at 37° C. for at least 10 minutes before overnight incubation, at 37° C., in hybridization buffer containing 4 nM of each probe. When the experiment involved probe competition or split initiator probes with 25 bp annealing region, 30% probe hybridization buffer (Molecular Technologies, Pasadena, CA) was used for hybridization and, the next day, samples were washed four times, 15 minutes each,

TABLE 6B

Sequences the constructs, barcodes, and/or probes used in Example 6. See FIGS. 6B-6D, and related figures for results.

| Probe name | Probe sequence (probe-LINKER-INITIATOR) | HCR initiator | Fluorophore | Hybridization round | SEQ ID NO. |
|---|---|---|---|---|---|
| mL-1a-B1 | agatgctcctgagccatctt-TATA-GCATTCTTTCTTGAGGAGGGCAGCAAACGGGAAGAG | B1 | Alexa647 | 1 | 293 |
| mL-1b-B2 | cgtggattggaacagcttct-TATA-AGCTCAGTCCATCCTCGTAAATCCTCATCAATCATC | B2 | Alexa594 | | 294 |
| mL-1C-B4 | gaaagtgattcaggttcggg-TATA-CACATTTACAGACCTCAACCTACCTCCAACTCTCAC | B4 | Alexa546 | | 295 |
| mL-4a-B3 | ttccacatccctctgcgatt-TATA-AAAGTCTAATCCGTCCCTGCCTCTATATCTCCACTC | B3 | Alexa488 | | 296 |
| mL-2a-B1 | agcttgaacaccagtcgcaa-TATA-GCATTCTTTCTTGAGGAGGGCAGCAAACGGGAAGAG | B1 | Alexa647 | 2 | 297 |
| mL-2b-B2 | gcatggccaggaatttgtct-TATA-AGCTCAGTCCATCCTCGTAAATCCTCATCAATCATC | B2 | Alexa594 | | 298 |
| mL-2c-B4 | ggcggaaatgtcgtcattct-TATA-CACATTTACAGACCTCAACCTACCTCCAACTCTCAC | B4 | Alexa546 | | 299 |
| mL-4b-B3 | ataccaatcccttcggcgat-TATA-AAAGTCTAATCCGTCCCTGCCTCTATATCTCCACTC | B3 | Alexa488 | | 300 |
| mL-3a-B1 | ccacttgtgaaacaacccag-TATA-GCATTCTTTCTTGAGGAGGGCAGCAAACGGGAAGAG | B1 | Alexa647 | 3 | 301 |
| mL-3b-B2 | cgttggcatatcacatggtg-TATA-AGCTCAGTCCATCCTCGTAAATCCTCATCAATCATC | B2 | Alexa594 | | 302 |
| mL-3c-B4 | accatgcaggtacacagcaa-TATA-CACATTTACAGACCTCAACCTACCTCCAACTCTCAC | B4 | Alexa546 | | 303 |
| mL-4c-B3 | atcagcgtgacaactgtgct-TATA-AAAGTCTAATCCGTCCCTGCCTCTATATCTCCACTC | B3 | Alexa488 | | 304 |

To establish Z1 and Z3 monoclonal cultures, approximately 1000 cells from the polyclonal population were cultured on a 10 cm plate, from which individual colonies were picked and expanded. Clones were then genotyped by polymerase chain reaction (PCR) to ensure that: the transgene was inserted properly in one of the ROSA26 loci, the other ROSA26 locus was intact, and there was no other integration of the transgene or Cas9 elsewhere in the genome.

Zombie Procedure for Cell Culture Samples

Cells were washed with 1×PBS before fixation by 3:1 (v:v) mix of methanol and acetic acid (MAA) at room temperature for 20 minutes. Cross-linking fixation interferes at 37° C. with 30% probe wash buffer (Molecular Technologies, Pasadena, CA) to remove excess probes, as previously described. For probes with 20 bp annealing region, in the absence of competition, 10% hybridization buffer (composed of 10% formamide, 10% Dextran Sulfate and 2× saline-sodium citrate (SSC) in RNAse-Free water) was used for overnight hybridization as previously described. These samples were then washed with a wash buffer, composed of 30% formamide, 2×SSC, and 0.1% Triton-X 100, at room temperature for 30 minutes, to remove excess probes, followed by a brief wash with 5×SSC.

HCR amplification was performed according to the manufacturer's instruction. Briefly, samples were first washed with 5×SSCT (5×SSC+0.1% Tween 20) for 5 minutes at room temperature and then incubated with amplification buffer (Molecular Technologies, Pasadena, CA) for at least 10 minutes at room temperature. Meanwhile, each fluorescently labeled hairpin was prepared by snap cooling (heating at 95° C. for 90 seconds and cooling to room temperature in a dark drawer for 30 minutes) in hairpin storage buffer. All the required hairpins were then added to the amplification buffer at the final concentration of 60 μM each. Cells were then incubated, in the dark, with amplification buffer containing the hairpins for 45 minutes at room temperature. Subsequently, excess hairpins were removed by five washes with 5×SSCT over one hour. 4',6-diamidino-2-phenylindole (DAPI) was added to the third wash to label nuclei. Nuclei could also be visualized using native fluorescent of Histone 2B protein-cyan fluorescent protein (H2B-CFP), when it was expressed in the cells (e.g. FIGS. 1C-1D). However, native fluorescence of cytoplasmically expressed fluorescent proteins could not be detected after the Zombie procedure. Samples were then kept in the dark at 4° C. until imaging.

When additional rounds of hybridization and imaging was required, samples were incubated first with 1× DNase I buffer (Roche (Basel, Switzerland) 4716728001) in nuclease free water at room temperature for 5 minutes and then with DNase I solution (2U/μl of the enzyme in 1× buffer) at 37° C. for 3 hours, to digest probes and HCR hairpins from the previous round. Subsequently, samples were washed three times with pre-warmed 30% wash buffer at 37° C. (first two washes for 5 min each and the third wash for 15 min). Another round of hybridization and HCR was then performed as described above.

The procedure described above was the main protocol used in the cell culture experiments described herein. See Table 7 and FIGS. 23-25, for details regarding the variations to this main protocol.

TABLE 7

List of experimental conditions and their effect on barcode detection efficiency.

| Condition | Description | Result |
|---|---|---|
| PFA fixation | Fixed with 1, 2, and 4% formaldehyde solution in PBS, followed by permeabilization by either 3:1 (v/v) mix of methanol and acetic acid or 70% ethanol. | Fixation with PFA prior to transcription step drastically reduced the detection efficiency (see FIG. 10) |
| Methanol and acetic acid fixation | Fixed with 100% methanol as well as 5, 15, 25, 35, and 50% acetic acid in methanol solutions. | Mix of acetic acid in methanol provides the best results (see FIGS. 11-12). |
| Clarke's fluid fixation | Fixed with 3:1 (v/v) mix of ethanol: Acetic Acid for 15 minutes at room temperature. | Observed a decrease in detection efficiency compared to 3:1 MAA fixation. |
| Methanol and acetone fixation | Fixed with 1:1 (v/v) mix of methanol and acetone for 15 minutes at room temperature. | Observed a drastic decrease in the detection efficiency. |
| Proteinase K treatment | Permeablized the cells initially using 1,5, and 10 ug/μl Proteinase K for 11 min at room temperature and in a subsequent experiment using 1 μg/μl of Proteinase K for 1, 2, 5, and 10 min at room temperature. | All of these treatments led to loss of most cells. |
| Triton X-100 | Washed the cells with 0.5% Triton X-100 for 10 minutes at room temperature after fixation by 3:1 MAA mix. | Observed no advantage over not washing the cells with this solution. |
| SDS | Washed with 0.1% SDS for 10 minutes at room temperature after fixation by 3:1 MAA mix. | It severely affected the cell morphology. |
| Histone wash | Washed with 2 mg/ml Dextran sulfate (MW 500,000), 0.2 mg/ml Heparin sodium salt, 0.1% IGEPAL CA-630, 10 mM EDTA, 10 mM Tris pH = 8.0 in nuclease free water for 10 minutes at room temperature after fixation by 3:1 MAA mix. | Observed a slight decrease in detection efficiency. |
| RNA polymerase concentration | Performed transcription with 2, 5, 10, 15, and 20 U/μl T7 RNA polymerase at 37° C. for 3 hours. | Observed no gain in efficiency for concentrations above 5 U/μl. |
| Duration of transcription reaction | Performed transcription with T7 RNA polymerase for 15, 30, 60, and 180 minutes at 37° C. | Duration of the transcription reaction only has a modest effect on detection efficiency (see FIG. 11) |

PFA, paraformaldehyde;
MAA, mix of methanol and acetic acid (v/v).

Design of the Synthetic Memory Arrays

Each unit of the memory arrays included a 20 bp probe site that partially overlapped with a 20 bp gRNA target site. gRNA target sites were followed by PAM sequence (NGG). To limit the possible outcome of base editing by ABE, gRNAs were designed so that from their position 2 to 10 there was only one "A" nucleotide, which occurred at position 5. Azimuth 2.0 software was used to choose gRNA candidates with high on-target and low off-target scores. Each probe sequence was designed so that its GC content was 50% and its predicted Tm, calculated using nearest neighbor method, was between 56 and 60° C. Sequences that form hairpins or dimers and homopolymeric tracts of 5 bp or longer were avoided in the probes. Recognition sites of some restriction enzymes (BsaI, BsmBI, BpiI, AarI, and XbaI) were avoided within the memory arrays to facilitate cloning. For design 1 array, probe sequences were chosen to differ from each other in at least 7 positions, to ensure specificity. For design 2, since all memory units were targeted with the same gRNA, 12 out of 20 bp was shared among all probes. The remaining 8 bp were chosen so that all probes were different from each other in at least 2 positions of the first 4 nucleotides and at least another 2 positions among the second 4 nucleotides. Furthermore, to facilitate discrimination, probes targeting all 12 design 2 barcodes were mixed together, at equimolar ratio, with the ones not being analyzed in any given experiment at an orthogonal channel (e.g., B5 HCR initiator). See tables herein for full sequence of the arrays and their corresponding probes.

The Combinatorial Barcode Library

Synthetic gene fragments containing 81 barcode combinations were obtained from Twist Bioscience (San Francisco, CA) and cloned into a lentiviral transfer plasmid by golden gate cloning, using Esp3I and T7 DNA ligase (see tables herein for the sequence of plasmids and barcodes). After transformation into NEB 10-beta chemical competent *E. coli* (C3019I), more than 10,000 colonies were scraped off the plates and used to prepare DNA for lentiviral packaging.

Lentiviral Delivery of Barcodes

Lentiviral vectors were produced and stored as previously described using the plasmids described above. The viral titer was determined by serial dilution. Only viral preparations with at least $10^7$ infectious units/μl were used. To establish stable cell lines, HEK293T cells were resuspended in the culture media, at a density of 500,000 cells per mL. 3 μL of lentiviral prep was mixed in with 97 μL of cell suspension. 10 μL of this mix was then added to another 90 μL of cell suspension in a separate tube. After mixing, the cells of the second tube were cultured in a 96-well plate for 3 days, without change of media. Subsequently, the cells were expanded in fresh media and used for the experiments.

To deliver barcodes to chicken embryos, fertilized eggs of white leghorn chickens were obtained from McIntyre Poultry & Fertile Eggs (Lakeside, CA) and incubated in a humidified atmosphere at 38° C. for 35 to 40 hours. The lentiviral prep was then injected in the neural tube of embryos ranging between stages HH10 and HH11. After injection, the eggs were closed with Parafilm and kept at 38° C. The embryos were analyzed 3 days after injection, at 5 days of incubation (stage HH27).

In mice, lentiviral injections were carried out stereotactically into the olfactory bulb of 3-month old male BL6 mice (JAX). Mice were anesthetized by single intraperitoneal injection with Ketamine/Xylazine solution. The stereotaxic coordinates were 5.5 mm anterior from bregma, 1.2 mm lateral from the midline, and 0.40 mm ventral from the brain surface. A single injection per olfactory bulb was performed using 0.3 μl of the lentiviral prep. The mouse brains were analyzed either 3 or 12 days after injection, as described in the text.

In some instances, different viral integration sites or chromatin states could potentially vary in their accessibility to phage polymerases. All the experimental procedures performed on animal models was approved by the Institutional Animal Care and Use Committee of California Institute of Technology.

Next Generation Sequencing gDNA was extracted from cells using DNeasy Blood & Tissue kit (Qiagen, Hilden, Germany) according to manufacturer instructions. Amplicon libraries containing the regions of interest (i.e., memory arrays or library barcodes) were then generated, from gDNA, with a two-step PCR protocol to add Illumina adapters and Nextera i5 and i7 combinatorial indices. Indexed amplicons were pooled and sequenced on the Illumina MiSeq platform with a 600-cycle, v3 reagent kit (Illumina, MS-102-3003). To analyze next generation sequencing data, raw FASTQ files were aligned to a FASTA-format reference file containing the expected amplicon sequences. Alignment was performed using the Burrows-Wheeler Alignment Tool (bwa-mem). For the combinatorial viral library (FIG. 6E), the number of reads aligning to each possible reference sequence was computed using a custom script in R, available here. For the base editing samples (FIG. 18), base calls were extracted from each read at the base editor target sites, as well as the quality scores at these sites. Paired-end reads were merged, accepting the base call with the highest quality score in overlapping regions. Reads with the quality score of more than 10, at the target site position, were included in the analysis.

Histology

After harvesting, adult mouse brain and embryonic chicken tissues were washed with cold RNase free 0.1M phosphate-buffered saline solution (PBS, pH 7.4) at 4° C. Fresh tissues were then immersed into the Tissue-Tek O.C.T. Compound (#4583; Electron Microscopy Sciences, Hatfield, PA) and were frozen immediately for 3 minutes in isopentane cooled to −70° C. in dry ice. Samples were then stored at −80° C. until sectioning. 20 μm thick sections were obtained using a Leica Cryostat, mounted on SuperFrost slides or coverslips coated with 2% v/v solution of (3-Aminopropyl)triethoxysilane in acetone. Sections were then stored at −80° C. until use.

Zombie Procedure for Tissue Sections

The slides were first left to dry at room temperature for about 5 minutes and then fixed with MAA at room temperature in a glass staining jar for 3 hours. Subsequently, the slides were washed, by transfer to a new jar filled with PBS, three times for 5 minutes each. After a brief wash in nuclease free water, SecureSeal hybridization chambers (SKU: 621501; Grace Bio-Labs, Bend, OR) were put on the slides and transcription mix (MEGAscript T7 or T3 Transcription Kit; Invitrogen) was added on the sections and incubated for 3 hours at 37° C. After transcription, samples were fixed with 4% formaldehyde in PBS overnight at 4° C. Formaldehyde was then removed by three washes with 5×SSC at room temperature for 10 minutes each.

Hybridization was performed similar to what is described above for cell culture samples. Sections were pre-hybridized with probe hybridization buffer for at least 30 minutes at 37° C., before overnight incubation with probe hybridization buffer containing 4 nM of each probe, at 37° C. When the experiment involved probe competition (e.g., FIGS. 5C-5H) or split initiator probes with 25 bp annealing region (e.g., FIGS. 5B and 22A-22D), 30% probe hybridization buffer (Molecular Technologies) was used for hybridization followed by 4×15 min wash at 37° C. with 30% probe wash buffer (Molecular Technologies). For probes with 20 bp annealing region, in the absence of competition (e.g., FIGS. 6A-6D), 10% hybridization buffer (composed of 10% formamide, 10% Dextran Sulfate and 2×SSC in RNAse-Free water) was used for overnight hybridization, followed by 2×30 min wash in 30% formamide, 2×SSC, and 0.1% Triton-X 100, at room temperature. Then, after three brief washes with 5×SSCT at room temperature, sections were incubated with amplification buffer for 20 minutes, which was then replaced by amplification buffer containing snap cooled fluorescently labeled hairpins (Molecular Technologies, Pasadena, CA), each at 60 μM. After one hour incubation in the dark at room temperature, excess hairpins were removed by five washes with 5×SSCT over one hour. DAPI was added to the third wash to label nuclei.

For samples that required only one round of hybridization (e.g., FIGS. 5B-5E), hybridization chambers were removed at this point and sections were mounted in Aqua-mount (14-390-5; Thermo Scientific) and kept in the dark at 4° C.

until imaging. For multiple rounds of hybridization, 5×SSCT was replaced with anti-bleaching buffer (50 mM Tris-HCl pH 8.0, 300 mM NaCl, 2×SSC, 3 mM Trolox (Sigma-Aldrich (St. Louis, MO) 238813), 0.8% D-glucose (Sigma-Aldrich (St. Louis, MO) G7528), 100-fold diluted Catalase (Sigma-Aldrich (St. Louis, MO) C3155), 0.5 mg/mL Glucose oxidase (Sigma-Aldrich (St. Louis, MO) G2133) and 0.02 U/mL SUPERase In RNase Inhibitor (Invitrogen (Carlsbad, CA) AM2694)) and samples were imaged as described below. After imaging, anti-bleaching buffer was washed first with 5×SSCT and then with 1× DNase I buffer (Roche 4716728001) in nuclease free water. Probes and HCR hairpins were then digested by 3 hours of incubation with DNase I solution (2U/µl of the enzyme in 1× buffer) at 37° C. for 3 hours. Subsequently, the samples were washed three times with pre-warmed 30% wash buffer at 37° C. (first two washes for 5 min each and the third wash for 15 min). Another round of hybridization and HCR was then performed as described above.

Imaging

Cell culture samples were imaged on a Nikon Eclipse Ti inverted fluorescence microscope with a Zyla 4.2 scientific Complementary metal-oxide-semiconductor (sCMOS) camera (Andor, Belfast, Northern Ireland). A 60× oil objective (1.4 NA) were used and 20 z-stacks were acquired with 0.5 micron spacing between them for each position. Positions were chosen solely based on DAPI channel to avoid bias. Imaging settings, including the exposure times, were kept the same for all the experiments involving cultured cells. Tissue sections were imaged either, using ZEN 2.3 (blue edition), on a Zeiss (Oberkochen, Germany) LSM800 confocal microscope with a 40× (Zeiss 1.2 NA), water immersion objective (FIGS. 5B-5E), or, using MetaMorph, on a Nikon (Tokyo, Japan) Eclipse Ti inverted microscope, equipped with a Yokogawa CSU-W spinning disc unit (Andor) and an EMCCD camera (Andor iXon Ultra), using a 40× (Nikon 1.3 NA) oil objective (FIGS. 6A-6D and 22A-22D) or a 60× (Nikon 1.4 NA) oil objective (FIGS. 5F-5H). The same imaging setting was used for related samples to facilitate comparison between images.

Image Analysis

Images were processed and analyzed using MATLAB and Fiji, mainly by custom scripts. For cell culture experiments, maximum intensity projection of the raw images was used in all analyses.

Segmentation. Segmentation of nuclei and dots was done automatically in MATLAB by filtering and thresholding of the images. However, the results were manually inspected to ensure accuracy. Segmentation of nuclei was done based on either CFP (FIGS. 1A-1G, 2A-2D, 3A-3D, 5A-5H, and their related figures) or DAPI (FIGS. 4A-4F, 6A-6D, 14, and 15-18) channel. When relevant to the analysis (e.g. for efficiency calculations) incorrectly segmented nuclei were manually identified and removed from the analysis. Active site dots were considered to belong to a cell if their center overlapped with the nuclear segmentation of that cell.

Intensity measurement. An estimate of dot intensity, used for FIGS. 4E, 5G-5H, 8, 23-25, and 15-19 was obtained by integration of pixel intensities over each dot's segment. A more precise measure of dot intensity was used for FIGS. 3D and 13, which was based on fitting a 2D Gaussian to each dot's filtered pixel intensity values and calculating the volume under the surface of the Gaussian.

Colocalization. Colocalization of dots was identified based on close proximity (less than 4 pixels) of the center of segmented dots in two or more channels.

Classification. For single nucleotide detection, where four probes compete for the same target site (FIGS. 3D and 13), to assign a nucleotide to each dot, the natural log of intensity values for that dot in each channel were normalized linearly between 0 and 1, using the intensity values from all the dots detected in that channel across the experiment. The nucleotide associated with the channel that had the highest normalized intensity was then assigned to the dot. Calling the base edits (FIGS. 4A-4H and their related figures) as well as A and G classification in vivo (FIGS. 5G-5H and 19), was done by clustering natural log of intensity values in two groups using k-means clustering with cosine distance metric (kmeans function, MATLAB).

Registration. Images of HEK293T cells transduced by the combinatorial viral library were registered initially based on CFP channel, using normalized cross-correlation method. A more refined registration was then achieved, using imregtform function in MATLAB, based on dots corresponding to different variant positions, regardless of their fluorescent channel, and using the CFP registration as the initial transformation.

Statistical Analysis

All experiments were performed in multiple distinct replicates, as indicated in the text and figure legends. Mutual information calculations in FIG. 9 were performed as previously described, by analyzing pairwise co-localization of barcodes in 564 cells across three replicates. Briefly, normalized mutual information (or uncertainty coefficient), U, between two barcodes, x and y, is defined as $$U(x|y) = \frac{H(x) - H(x|y)}{H(x)},$$

where H is the entropy calculated by the formula $H=-\Sigma_{i=1}^{I} p_i \ln(p_i)$.

Example 1

Phage RNA Polymerases can Transcribe Synthetic DNA Barcodes in Fixed Cells

This example demonstrates transcription of synthetic DNA barcodes by phage RNA polymerases in fixed cells.

To develop a method for specifically amplifying and detecting barcodes integrated in the genome (FIG. 1A), a construct, labeled Z1 (FIG. 1B), containing a 900 bp barcode sequence downstream of tandem SP6, T7, and T3 phage promoters, along with an H2B-Cerulean fluorescent protein under the control of the constitutive mammalian CAG promoter for imaging of cell nuclei was designed. Z1 site was integrated specifically at the ROSA26 locus in mouse embryonic stem (mES) cells. A similar cell line was also made with a control construct that lacks the phage promoters (FIG. 1B).

To detect the barcode, polyclonal populations of cells were grown, fixed, added with the phage RNA polymerases in each, and performed HCR with a set of split initiator probes to detect RNA transcripts (see Methods for details). Fluorescence imaging revealed two types of dots: bright fluorescent dots within cell nuclei and more numerous, but considerably dimmer, diffraction-limited dots scattered throughout the nucleus and cytoplasm (FIG. 1C). Neither type of dot was observed when either the phage promoters or polymerase were omitted (FIG. 1C). Parental cells lacking a barcode exhibited no dots when cultured alone but showed some overlapping dimmer dots when co-cultured with engineered cells (FIGS. 7A-7D). These results indicate that the bright dots reflect phage polymerase-dependent transcription at the integration site, whereas the dimmer dots reflect individual transcripts that can diffuse away from the cell in which they were produced. Together, this barcode design and analysis protocol enable in situ expression and detection of genomically integrated barcodes at integration sites.

Next, to quantify the efficiency of detection, a monoclonal line with exactly one integration per diploid genome, termed mES-Z1, was selected. Within the clone, 1 or 2 bright dots were consistently detected in the majority of cells, likely due to cell cycle phase variation at the time of fixing, with a small fraction of cells missing any bright dots (FIGS. 1D and 8). While the transcription active sites were detected efficiently with all three phage RNA polymerases, the average detection efficiencies of T3 (88%) and T7 (85%) were higher than that of SP6 (75%) (FIG. 1D). Variations in efficiencies may reflect the relative positions of the promoters in the construct, relative amounts of active enzymes, as well as intrinsic differences between the polymerases.

A lack of barcode detection could result if certain cells were impermeable to polymerases or otherwise do not permit in situ transcription. Alternatively, it could reflect intrinsic stochasticity in the polymerization reaction. To distinguish these possibilities, a second line containing a single integration of a construct termed Z3, in which three barcodes were each controlled by a separate set of phage promoters and can be detected using distinct fluorescence channels was engineered (FIG. 1E). If non-detection was a property of the individual cells, it was expected to predominantly detect either all three barcodes or no barcodes (strong correlation). By contrast, in a stochastic transcription model, it was expected that detection of one barcode would not affect the probability of detecting another barcode (weak correlation).

Analysis of active site co-localization in 564 cells revealed no significant correlation or pairwise mutual information between any pair of barcodes (chi-squared test, p-values 0.7970, 0.1917, and 0.1256 for the three pairs; FIG. 9). The chance of detecting each barcode in a cell was independent of detection of the other barcodes (FIG. 1F). Consistent with this observation, the fraction of cells with no detected active sites declined exponentially with the number of barcodes analyzed in the same cell at the rate expected from the single barcode detection frequencies (FIG. 1G). Together, these data suggest that detection was a stochastic event that occurred independently at each barcode. Therefore, although a fraction of barcodes failed to produce detectable signal, the false negative rate per cell can be reduced by increasing the barcode copy number. This property is valuable in the study of rare cell types, where capturing information from majority of cells is essential.

Altogether, these data indicate that phage RNA polymerases can transcribe synthetic DNA barcodes in fixed cells.

Example 2

Zombie Enables Reliable In Situ Detection of 20 bp DNA Barcodes

This example demonstrates reliable detection of short DNA barcodes using the Zombie method and system described herein.

Barcode transcription produces multiple RNA molecules from the same template in close proximity, which effectively amplifies the barcode target and could facilitate robust detection of short barcodes. To test this, fixed mES-Z1 cells after the in vitro transcription step were hybridized with three orthogonal 20 bp probes targeting regions downstream of the phage promoters (FIG. 2A). The binding of these probes, by both smFISH and HCR were then analyzed. In both analyses, easily detectable transcription active sites were observed in all three channels (FIGS. 2B and 10). For all three phage RNA polymerases, the active sites could be detected in a large fraction of cells (FIG. 2C), and most dots were redundantly detected in multiple channels (FIG. 2D).

RNA transcription sites contain multiple RNA molecules transcribed from the same template in close proximity, potentially reducing the number of probes required for detectable signal (FIG. 2A). To test this, fixed mES-Z1 cells after the in vitro transcription step were hybridized with 20 bp probes targeting regions downstream of the phage promoters. Three different probes each with a distinct (orthogonal) HCR initiator were designed, allowing simultaneous detection of each probe in a different fluorescent channel. Following HCR amplification, bright, easily detectable dots were observed at the transcription active sites in all three channels (FIG. 2E). Despite some differences in their efficiency, all three phage RNA polymerases showed high barcode detection rates ranging from 65 to 84 percent of cells (FIG. 2G). Because the monoclonal Z1 cell line contains one construct per diploid genome, one or two active sites per cell were expected to be observed, and cells without apparent active sites thereby represented false negative detection events. Analysis revealed that most dots were detected in multiple channels, suggesting that detection was reliable (FIG. 2H). Furthermore, HCR amplification was not necessary for in situ detection of short (20 bp) barcodes. The procedure was repeated but included only one of the two hairpins required for HCR amplification. This hairpin can bind to the initiator of the corresponding probes and generate a fluorescent signal, but cannot initiate a chain reaction. Nevertheless, individual transcription active sites were observed as distinct dots (FIG. 2F) and the detection was at rates similar to those obtained with HCR amplification (FIG. 2G; exact Wilcoxon rank sum test, $p>0.5$). However, co-localization of the detected active sites in three fluorescent channels was reduced in the absence of HCR amplification (FIG. 2H). Thus, HCR amplification increased detection reliability, but was not strictly necessary for analysis.

These results show that barcodes as short as 20 bp can be efficiently and reliably detected in situ.

Example 3

Zombie Enables In Situ Detection of Single Nucleotide Mismatches

This example demonstrates in situ detection of single nucleotide mismatches using the Zombie method and system disclosed herein.

Discrimination of small sequence differences could facilitate imaging-based barcoding applications. While structured and toehold probes can be used to detect single nucleotide variations by leveraging base pairing within the probe, traditional probes can bind to target sequences even when they contain a single nucleotide mismatch (FIG. 11). it was expected that simultaneously competing multiple probes, each containing a distinct nucleotide at a single site, for binding to the many transcripts present in an active site could lead to preferential binding of exact match probes over mismatch probes, and thereby enable nucleotide identification (FIG. 3A).

To test this idea, mES-Z1 cells, performed in vitro transcription were fixed with T7 RNA polymerase, and targeted a 20 bp region of the Z1 barcode with four probes, each containing a distinct nucleotide at a single position, and each detectable with orthogonal HCR initiators in different fluorescence channels (FIG. 3B). To control for systematic differences among fluorescent dyes, each analysis was performed with four different fluorescence channel permutations (FIGS. 3C and 12, columns) and quantified the relative fluorescence intensities of each channel for each active site. This analysis was performed four times, once for each possible nucleotide at the variable position (FIGS. 3C-3D and 12).

When targeting A, C, or G, a strong preference for the correct target nucleotide (FIG. 3D) across different color-HCR initiator permutations was observed, ranging between 92 to 96% for A, 79 to 93% for C, and 93 to 99% for G (percentages indicate the fraction of fluorescent dots that were 'called' correctly by the algorithm). Without being bound by any particular theory, it was believed that some inaccurate calls can be explained by non-specific background HCR amplification in a region that overlaps with the cell nuclei but was not a true active site. However, when targeting U, in addition to the matched A probes, detectable signal was also observed from the mismatched G probes (FIG. 12), consistent with wobble base pairing between U and G. Nevertheless, the base calling algorithm detected the correct match probe in three out of four permutations tested, with 90%, 97%, and 85% accuracy (FIG. 3D).

To investigate the dependence of single nucleotide variant (SNV) discrimination on the position of variant nucleotide within the probe, a similar analysis was performed with SNVs in positions 1 through 7 of the probes (FIG. 13). Positions 2 through 7 provided accurate SNV discrimination. Further, this analysis provided additional examples of accurate discrimination when U was the target (FIG. 13, position 6).

These results indicate that probe competition can enable accurate in situ identification of SNVs.

Example 4

Zombie Reads Out In Vivo Barcode Base Edits

This example demonstrates that the Zombie method and system disclosed herein are capable of reading out in vivo barcode base edits.

CRISPR base editors have recently emerged as powerful tools for precise and predictable genome editing. They can target and edit genomic DNA with single base pair resolution in a multiplexable manner. Heritable somatic mutations created by base editors could enable subsequent reconstruction of cell lineage and event histories. The ability to read out base edits by imaging, rather than sequencing, can enable lineage and event history recording approaches that preserve spatial information, operate in individual cells, and allow accurate recovery of sequence information from a high fraction of cells. As demonstrated herein, the Zombie method and system disclosed herein allow in situ detection of single nucleotide mismatches, this example shows that the Zombie method and system disclosed herein can be combined with base editors to read out single base pair changes in a synthetic memory unit.

A set of 12 memory units (FIG. 4B, left panel) that can each be edited by Adenine Base Editor (ABE) together with a unique gRNA was engineered. These units also incorporated phage promoters to enable readout. These 12 memory units were concatenated into a single ~500 bp cassette and inserted into a lentivirus, and the viruses were integrated into the genome of HEK293 cells to create the ZMEM cell line (FIG. 4A). Plasmids expressing ABE, a gRNA targeting one recording site, and a GFP transfection reporter were transiently co-transfected into Z-MEM cells, and the cells were cultured for five days. To analyze editing, cells were fixed, added with T3 polymerase to transcribe the barcodes, and analyzed for barcodes by HCR using competing probes with distinct HCR initiators, containing either a T or a C to probe the unedited A or edited G state, respectively. As a negative control, a second barcode that was not targeted by the gRNA was also probed. This procedure was then repeated, individually targeting each of the 12 units.

These experiments revealed that editing could be targeted to distinct memory units and read out with high fidelity. Individual memory units showed a binary response in imaging, appearing either in the A channel or in the G channel, but not both (left panel in FIGS. 4C-4E, and FIG. 14). Across ten memory units, the median edit rate was 12.7%. However, different units showed varying edit rates, ranging from 1.7% to 21.7% (The two remaining units each had one probe that failed to generate signal, and were not considered further). A broad range of edit rates, achieved here by using gRNAs with different efficiency to edit different memory units, has been shown to be advantageous for recording applications. Memory units that were not targeted by gRNA showed apparent edit rates close to 0 (FIG. 4F, left panel), consistent with both strong targeting specificity by ABE and accurate amplification and readout by Zombie. Together, these results show that Zombie can enable in situ readout of base edits in engineered memory elements.

31 bp barcodes that could be edited by the Adenine Base Editor (ABE) https://paperpile.com/c/kLgtra/XdWgp and a corresponding gRNA were engineered (FIG. 4A). These barcodes were concatenated into ~500 bp arrays, and preceded by phage promoters. Using lentiviral vectors, multiple array copies were incorporated into the genome of HEK293T cells to create the Z-MEM cell lines (FIG. 4A). Plasmids expressing the ABE (ABE7.10), the gRNA, and a fluorescent co-transfection marker (e.g., GFP) were transiently co-transfected into Z-MEM cells, and cells were cultured for five days. To analyze editing, cells were fixed, added with T3 RNA polymerase, and detected fpr transcribed barcodes using competing probes with distinct HCR initiators for edited and unedited states. This analysis was performed pair-wise, on adjacent barcodes. As a negative control, the analysis on cells that did not receive ABE or gRNA was also performed.

A key parameter for recording is the edit rate, defined as the probability of an edit occurring at a given unedited target site per unit time. To estimate the relative edit rates of different barcodes, the percentage of dots that were edited for each barcode in each design was tabulated (FIG. 4F). These values varied widely across ten distinct design 1 barcodes, from 1.6% to 19.7% with a median of 12.9% (Probes for the two remaining units failed to generate signal and were not considered in the analysis). A broad range of edit rates, such as that observed here, has been shown to be advantageous in recording applications. Similarly, design 2 units were edited at rates ranging from 15.5% to 51.5% with a median 31.3%. By contrast, memory units that were not targeted showed apparent edit rates close to 0 (FIG. 4F), consistent with both strong targeting specificity by ABE and accurate amplification and readout by Zombie. In a separate experiment, it was observed that the edit rates measured by Zombie were similar to those measured by next generation sequencing for the same set of barcodes, further validating the accuracy of Zombie in situ readout (FIG. 18).

Two types of synthetic memory arrays were designed (FIG. 4B). Design 1 enables independent addressing of different barcodes by distinct gRNAs, facilitating multichannel recording. By contrast, design 2 uses one gRNA to edit all 12 barcodes, allowing a single gRNA to generate greater sequence diversity. In both cases, editing should result in single base pair changes in corresponding barcodes.

In both designs, individual barcodes showed an approximately binary response in imaging, appearing in either the edited or unedited channel, but not both (FIG. 4C). Moreover, pairwise analysis of the adjacent barcodes verified independent addressing in design 1 and multiplexed addressing in design 2 (FIG. 4D). The signal intensity was quantified for each dot, in the edited and unedited channels, with or without co-transfection of ABE and gRNA (FIGS. 4E, 15, 16A-16B, and 17A-17B). Without ABE or gRNA most dots clustered in a single region (FIG. 4E, blue points). By contrast, when ABE and gRNA were both present a second cluster appeared, with a larger mean ratio of edited to unedited probe intensity (FIG. 4E, orange points), reflecting successful editing in a substantial fraction of cells (FIG. 4F). Similar behavior was observed with the other analyzed barcodes (FIGS. 16A-16B and 17A-17B). k-means clustering was then used to classify the active sites as edited or unedited, with bootstrap resampling allowing determination of confidence for each assignment (FIGS. 15, 16A-16B, and 17A-17B). In both designs, except for a small subpopulation (yellow dots in FIGS. 16A-16B and 17A-17B), active sites could be robustly classified based on their relative signal intensity.

Together, these results show that base editing can be targeted to distinct memory units and read out quantitatively in situ with high fidelity by Zombie.

Example 5

Zombie Identifies Compact Barcodes in Embryonic and Adult Tissues

This example demonstrates identification of compact barcodes in embryonic and adult animal tissues using the Zombie method and system disclosed herein.

Reconstructing lineage information in embryos, brains, and tumors requires the ability to discriminate among a set of distinct barcodes or barcode edits in complex spatially organized contexts. To test Zombie readout within tissues, a lentivirus, termed ZL1, containing probe target sequences downstream of phage promoters, along with a divergently oriented, constitutively expressed fluorescent protein reporter was engineered to enable identification of transduced cells (FIG. 5A). The lentivirus was first injected into the lumen of the developing chick neural tube at stage HH10, and embryos were analyzed 3 days later at stage HH27 (FIG. 5A, left). In a parallel study, Zombie readout was analyzed in adult mouse brain tissues, focusing on the olfactory bulb, which incorporates newly generated neurons in the adult stage. The ZL1 lentivirus was injected into the granular cell layer of the olfactory bulb and sacrificed the mice for analysis 3 days later (FIG. 5A, right). In both cases, robust, T7 polymerase-dependent in situ barcode transcription was observed within the transduced regions (FIG. 5B).

Together, these results show that Zombie can be used to detect viral barcodes in embryonic and adult tissues.

The ability to discriminate single base pair mismatches in the same chick and mouse contexts was tested next. Tissues with an equimolar mixture of perfect match and single base mismatch probes, along with a third reference probe targeting a distinct downstream region, each in a distinct color channel were tested (FIG. 5C). As a control, color channels were also swapped for the match and mismatch probes. Match probes strongly outcompeted mismatch probes, regardless of the color channel, in both organisms (FIGS. 5D-5E). Further, matching probes co-localized with reference probes, indicating that match-mismatch probe competition does not hinder detection efficiency (FIGS. 5D-5E). Taken together, these results demonstrate that Zombie can discriminate between single base pair mismatches in chick embryos and adult mouse brains.

Many in vivo barcoding and recording applications require simultaneous analysis of multiple barcode variants. To assess this capability, three pairs of distinctly barcoded lentiviruses were designed. Each virus contained two distinct 20 bp barcodes, each containing an A or a G at a designated variable position. These viruses were designed such that the identity of the variable base in one barcode matched that of the other barcode in the same virus (FIG. 5F). With this design, two barcodes on the same virus should appear strongly correlated in the variable base, while barcodes on different viruses should vary independently. A and G were selected to mimic possible base editing outcomes (FIG. 4A).

Mouse olfactory bulbs were co-injected with a mix of these three viral pairs. 12 days later, Zombie was used with three consecutive rounds of hybridization and imaging to read out all pairs of viral barcodes. Single nucleotide differences between barcodes were readily identifiable based on the relative signal intensity of competing probes (FIGS. 5G and 19). Further, as expected, a strong correlation between the state of two barcodes appearing on the same virus was observed, at each Zombie active site (FIGS. 5G-5H). Overall, 92% of sites were classified correctly as either A or G for both barcodes (FIG. 5H). Some of the remaining sites, classified as A for one barcode and G for another, might be explained by integration of both members of a lentivirus pair at sites too close to be spatially resolved (FIGS. 20A-20D). Together, these results indicate that Zombie permits multiplexed barcode readout with single base discrimination in brain tissue.

Combinatorial barcode libraries (FIG. 6A) can provide an exponentially increasing number of distinct barcodes with only a linear increase in the number of hybridization and imaging cycles needed to read them out. The ability to detect short (20 bp) DNA barcodes in situ should facilitate construction and delivery of such libraries. As a proof of principle, a lentiviral library containing 81 distinct combinations of 12 barcode sequences was constructed, each 20 bp long (FIG. 6A). HEK293T cells were transduced with this library and read out the library in 3 rounds of hybridization and imaging, each one probing 4 out of 12 barcodes with orthogonal color channels (FIG. 21). In this analysis, barcode combinations were detected at frequencies consistent with those measured by next generation sequencing (FIG. 6B), corroborating the accuracy of in situ readout.

In a parallel, in vivo study, the combinatorial library was injected into the lumen of the developing neural tube at stage HH11 chick embryos. Three days later (stage HH27), the embryos were frozen, performed with the Zombie procedure, and analyzed in three rounds of hybridization, as with the HEK293T cells (FIG. 6C). Cells with distinct combinations of barcodes were detected in both neural tube and retina of chick embryos (FIG. 6D). In many instances, cells labeled with the same barcode combination were observed close to each other and organized in a way that suggests clonal relationship (FIG. 6D, middle panel, clone 13). In other cases, despite relatively sparse labeling, cells with different barcode combinations were intermixed, indicating the necessity for high barcode diversity in establishing clonal relationships (FIG. 6D, left panel, clones 13, 16, and 11). These results demonstrate how Zombie can facilitate the use of combinatorial barcode libraries with imaging readout both in vitro and in vivo.

Finally, an ideal barcode readout system would be compatible with analysis of endogenous gene expression. To test this, gene expression was analyzed alongside barcode detection in the olfactory bulb of mice injected with the paired viruses (FIG. 5F). Using HCR, it was confirmed that Tbx21 (expressed by projection neurons) and Tyrosine hydroxylase (Th; expressed by periglomerular cells) could be detected alongside barcodes, in the mitral and glomerular layers, respectively, as expected (FIGS. 22A-22D).

This analysis demonstrates the suitability of Zombie for barcoding and recording applications that require readout of endogenous gene expression as well as barcodes in tissue samples.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of determining barcode sequences in situ, comprising:

providing a plurality of cells each comprising a barcode polynucleotide with a barcode sequence;

fixing the plurality of cells using a fixative to generate a plurality of fixed cells;

generating a plurality of barcode molecules comprising the barcode sequence of the barcode polynucleotide in each of the plurality of fixed cells;

contacting the plurality of fixed cells with a plurality of detection probes each comprising a barcode binding sequence and an initiator sequence, thereby each of the plurality of barcode molecules comprising the barcode sequence of the barcode polynucleotide in the fixed cell hybridizes to a detection probe, of the plurality of detection probes, comprising the barcode binding sequence reverse complementary to the barcode sequence, or a portion thereof;

contacting the plurality of fixed cells with a plurality of first amplifier probes each comprising a different fluorophore, thereby a first amplifier probe of the plurality of first amplifier probes hybridizes to (i) the initiator sequence of a detection probe of the plurality of detection probes hybridized to a barcode molecule in a fixed cell of the plurality of fixed cells;

detecting the fluorophore, or fluorescence thereof, of the first amplifier probe hybridized to the detection probe hybridized to the barcode molecules in each of the plurality of fixed cells using fluorescence imaging; and determining the barcode sequence in each of the plurality of fixed cells using the fluorophore detected, wherein the fluorophore detected indicates the barcode sequence of the barcode polynucleotide in the one or more fixed cells.

2. The method of claim 1, wherein providing the plurality of cells comprises: integrating the barcode polynucleotide into a genome of one, at least one, or each of the plurality of cells.

3. The method of claim 2, wherein integrating the barcode polynucleotide comprises: integrating the barcode polynucleotide into the genome of one, at least one, or each of the plurality of cells at a specific site of the genome.

4. The method of claim 2, wherein integrating the barcode polynucleotide into the genome of one, at least one, or each of the plurality of cells comprises: transfecting the cell with a donor plasmid comprising the barcode polynucleotide, a sequence thereof, a subsequence thereof, of a reverse complementary sequence of any of the preceding.

5. The method of claim 2, wherein integrating the barcode polynucleotide comprises: integrating the barcode polynucleotide into the genome of one, at least one, or each of the plurality of cells using a viral vector, wherein the viral vector comprises a polynucleotide comprising the barcode polynucleotide, a sequence thereof, a subsequence thereof, or a reverse complementary sequence of any of the proceeding.

6. The method of claim 1, wherein the barcode polynucleotide of one, at least one, or each of the plurality of cells comprises barcode sequences, and wherein a combination of the barcode sequences is selected from at least 500000, possible combinations of the barcode sequences.

7. The method of claim 6, wherein the barcode sequences are downstream of at least one promoter, and/or wherein two of the barcode sequences are downstream of different promoters, optionally wherein the different promoters comprise an identical promoter sequence.

8. The method of claim 1, wherein the barcode polynucleotides of at least two cells of the plurality of cells comprise an identical barcode sequence.

9. The method of claim 1, wherein the barcode polynucleotides of at least two cells of the plurality of cells comprise different barcode sequences.

10. The method of claim 8, wherein the at least two cells are cells of a cell type, cells of a cell subtype, and/or cells of an identical lineage.

11. The method of claim 8, wherein the at least two cells are cells of different cell types, cells of different cell subtypes, and/or cells of different lineages.

12. The method of claim 8, wherein a first cell of the at least two cells is a cell of interest, and/or wherein a second cell of the at least two cells is not a cell of interest.

13. The method of claim 1, wherein generating the plurality of barcode molecules comprises: transcribing the barcode polynucleotide in each of the plurality of fixed cell to generate the plurality of barcode molecules comprising the barcode sequence of the barcode polynucleotide in the fixed cell.

14. The method of claim 1, comprising: determining lineages of, and/or a clonal relationship between, two or more fixed cells of the plurality of fixed cells using the barcode sequence of the barcode polynucleotide in each of the two or more fixed cells.

15. The method of claim 1, comprising:

determining a spatial relationship of two or more fixed cells of the plurality of fixed cells; and correlating the barcode sequences of the barcode polynucleotide in each of the two or more fixed cells with a spatial relationship of the two or more fixed cells.

16. The method of claim 1, comprising: correlating gene expressions of two or more fixed cells of the plurality of fixed cells with the lineages of, the clonal relationship between, and/or the spatial relationship of, the two or more fixed cells.

17. The method of claim 1, wherein the plurality of cells is from a sample comprising a cell culture, a tissue, an organ, an embryo, an organism, a section thereof.

18. The method of claim 1, wherein the plurality of cells is from a sample comprising an in vivo sample and/or an in vitro sample.

19. The method of claim 1, wherein the plurality of cells comprises one or more tumor cells, one or more immune cells, one or more epithelial cells, one or more nervous cells, one or more blood cells, one or more bone cells, one or more fat cells, one or more muscle cells, and/or one or more sex cells.

20. The method of claim 1, wherein two, at least two, or each of the plurality of cells are cultured under an identical condition, and wherein the identical condition or each of the different conditions comprises a genetic perturbation, an environmental perturbation, or a combination thereof.

* * * * *